United States Patent
Trudeau et al.

(10) Patent No.: US 9,693,872 B2
(45) Date of Patent: Jul. 4, 2017

(54) INTERVERTEBRAL DISC IMPLANT

(71) Applicant: Pioneer Surgical Technology, Inc., Marquette, MI (US)

(72) Inventors: Jeffrey L. Trudeau, Marquette, MI (US); Brian Patrick Janowski, Marquette, MI (US); Thomas Kilpela, Marquette, MI (US); Michael R. Jackson, Hancock, MI (US); Qi-Bin Bao, Edina, MN (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 0 days.

(21) Appl. No.: 14/991,191

(22) Filed: Jan. 8, 2016

(65) Prior Publication Data

US 2016/0120657 A1 May 5, 2016

Related U.S. Application Data

(63) Continuation of application No. 14/270,076, filed on May 5, 2014, now Pat. No. 9,233,011, which is a
(Continued)

(51) Int. Cl.
*A61F 2/44* (2006.01)
*A61F 2/46* (2006.01)
*A61F 2/30* (2006.01)

(52) U.S. Cl.
CPC .............. *A61F 2/4425* (2013.01); *A61F 2/44* (2013.01); *A61F 2/442* (2013.01); *A61F 2/4611* (2013.01);
(Continued)

(58) Field of Classification Search
CPC ...... A61F 2/44; A61F 2/445; A61F 2002/443; A61F 2/4425
(Continued)

(56) References Cited

U.S. PATENT DOCUMENTS

| 3,867,728 A | 2/1975 | Stubstad et al. |
| 3,875,595 A | 4/1975 | Froning et al. |

(Continued)

FOREIGN PATENT DOCUMENTS

| CA | 2395609 | 2/2001 |
| CA | 2482403 | 9/2003 |

(Continued)

OTHER PUBLICATIONS

Bao et al., Artificial Disc Technology, Neurosurg. Focus 9(4)m Oct. 2000, 7pp.
(Continued)

*Primary Examiner* — Matthew Lawson
(74) *Attorney, Agent, or Firm* — Fitch, Even, Tabin & Flannery LLP

(57) ABSTRACT

Systems and tools for inserting and securing an implant within the intervertebral space. An intervertebral disc implant with upper and lower bearing members with an articulation interface between the members for providing relative motion therebetween. The implant may be provided with various securing members for fixing the implant within the intervertebral space. A tool may be used to insert the implant, which includes a plurality of shiftable implant engaging members that are shiftable between non-engaging and engaging configurations to alternatively release or hold the implant.

19 Claims, 78 Drawing Sheets

Related U.S. Application Data continuation of application No. 12/541,658, filed on Aug. 14, 2009, now Pat. No. 8,715,350, and a continuation-in-part of application No. 11/856,667, filed on Sep. 17, 2007, now Pat. No. 8,597,357.

(60) Provisional application No. 61/089,283, filed on Aug. 15, 2008, provisional application No. 60/912,138, filed on Apr. 16, 2007, provisional application No. 60/825,865, filed on Sep. 15, 2006.

(52) U.S. Cl.
CPC ........ *A61F 2/4684* (2013.01); *A61F 2/30965* (2013.01); *A61F 2002/305* (2013.01); *A61F 2002/3008* (2013.01); *A61F 2002/30112* (2013.01); *A61F 2002/30383* (2013.01); *A61F 2002/30387* (2013.01); *A61F 2002/30393* (2013.01); *A61F 2002/30485* (2013.01); *A61F 2002/30492* (2013.01); *A61F 2002/30571* (2013.01); *A61F 2002/30578* (2013.01); *A61F 2002/30579* (2013.01); *A61F 2002/30594* (2013.01); *A61F 2002/30601* (2013.01); *A61F 2002/30662* (2013.01); *A61F 2002/30677* (2013.01); *A61F 2002/30823* (2013.01); *A61F 2002/30841* (2013.01); *A61F 2002/30846* (2013.01); *A61F 2002/30884* (2013.01); *A61F 2002/30894* (2013.01); *A61F 2002/30899* (2013.01); *A61F 2002/30904* (2013.01); *A61F 2002/449* (2013.01); *A61F 2002/4627* (2013.01); *A61F 2002/4628* (2013.01); *A61F 2220/0025* (2013.01); *A61F 2230/0004* (2013.01); *A61F 2250/0098* (2013.01); *A61F 2310/00407* (2013.01); *A61F 2310/00796* (2013.01)

(58) Field of Classification Search
USPC .......................................... 623/17.11–17.16
See application file for complete search history.

(56) References Cited

U.S. PATENT DOCUMENTS

| | | |
|---|---|---|
| 3,975,778 A | 8/1976 | Newton, III |
| 4,021,382 A | 5/1977 | Stoy |
| 4,081,402 A | 3/1978 | Levy |
| 4,147,764 A | 4/1979 | Levy |
| 4,309,777 A | 1/1982 | Patil |
| 4,349,921 A | 9/1982 | Kuntz |
| 4,454,612 A | 6/1984 | McDaniel |
| 4,636,217 A | 1/1987 | Ogilvie |
| 4,650,490 A | 3/1987 | Figgie, III |
| 4,714,469 A | 12/1987 | Kenna |
| 4,728,561 A | 3/1988 | Crocker |
| 4,759,766 A | 7/1988 | Buettner-Janz |
| 4,759,769 A | 7/1988 | Hedman |
| 4,863,476 A | 9/1989 | Shepperd |
| 4,863,477 A | 9/1989 | Monson |
| 4,917,704 A | 4/1990 | Frey |
| 4,932,969 A | 6/1990 | Frey |
| 4,936,848 A | 6/1990 | Bagby |
| 4,946,378 A | 8/1990 | Hirayama |
| 4,997,432 A | 3/1991 | Keller |
| 5,002,576 A | 3/1991 | Fuhrmann |
| 5,035,716 A | 7/1991 | Downey |
| 5,047,055 A | 9/1991 | Bao |
| 5,071,437 A | 12/1991 | Steffee |
| 5,108,399 A | 4/1992 | Eitenmuller |
| 5,108,438 A | 4/1992 | Stone |
| 5,123,926 A | 6/1992 | Pisharodi |
| 5,127,920 A | 7/1992 | MacArthur |
| 5,133,759 A | 7/1992 | Turner |
| 5,133,772 A | 7/1992 | Hack |
| 5,147,404 A | 9/1992 | Downey |
| 5,171,281 A | 12/1992 | Parsons |
| 5,176,710 A | 1/1993 | Hahn |
| 5,192,326 A | 3/1993 | Bao |
| 5,258,031 A | 11/1993 | Salib |
| 5,258,043 A | 11/1993 | Stone |
| 5,273,742 A | 12/1993 | Gould |
| 5,306,308 A | 4/1994 | Gross |
| 5,306,309 A | 4/1994 | Wagner |
| 5,314,477 A | 5/1994 | Marnay |
| 5,320,625 A | 6/1994 | Bertin |
| 5,320,644 A | 6/1994 | Baumgartner |
| 5,401,269 A | 3/1995 | Buttner-Janz |
| 5,425,773 A | 6/1995 | Boyd |
| 5,443,512 A | 8/1995 | Parr |
| 5,458,642 A | 10/1995 | Beer |
| 5,458,643 A | 10/1995 | Oka |
| 5,462,362 A | 10/1995 | Yuhta |
| 5,480,449 A | 1/1996 | Hamilton |
| 5,507,816 A | 4/1996 | Bullivant |
| 5,514,180 A | 5/1996 | Heggeness |
| 5,522,899 A | 6/1996 | Michelson |
| 5,534,028 A | 7/1996 | Bao |
| 5,549,679 A | 8/1996 | Kuslich |
| 5,556,431 A | 9/1996 | Buttner-Janz |
| 5,556,433 A | 9/1996 | Gabriel |
| 5,562,736 A | 10/1996 | Ray |
| 5,562,738 A | 10/1996 | Boyd |
| 5,571,189 A | 11/1996 | Kuslich |
| 5,595,563 A | 1/1997 | Moisdon |
| 5,609,643 A | 3/1997 | Colleran |
| 5,645,596 A | 7/1997 | Kim |
| 5,645,597 A | 7/1997 | Krapiva |
| 5,658,336 A | 8/1997 | Pisharodi |
| 5,665,122 A | 9/1997 | Kambin |
| 5,674,295 A | 10/1997 | Ray |
| 5,674,296 A | 10/1997 | Bryan |
| 5,676,701 A | 10/1997 | Yuan |
| 5,676,702 A | 10/1997 | Ratron |
| 5,683,465 A | 11/1997 | Shinn |
| 5,693,100 A | 12/1997 | Pisharodi |
| 5,702,450 A | 12/1997 | Bisserie |
| 5,716,416 A | 2/1998 | Lin |
| 5,728,762 A | 3/1998 | Reich |
| 5,755,797 A | 5/1998 | Baumgartner |
| 5,755,798 A | 5/1998 | Papavero |
| 5,782,832 A | 7/1998 | Larsen |
| 5,800,547 A | 9/1998 | Schaefer |
| 5,824,093 A | 10/1998 | Ray |
| 5,824,094 A | 10/1998 | Serhan |
| 5,860,980 A | 1/1999 | Axelson, Jr. |
| 5,865,845 A | 2/1999 | Thalgott |
| 5,865,846 A | 2/1999 | Bryan |
| 5,888,223 A | 3/1999 | Bray, Jr. |
| 5,888,226 A | 3/1999 | Rogozinski |
| 5,888,227 A | 3/1999 | Cottle |
| 5,893,889 A | 4/1999 | Harrington |
| 5,895,428 A | 4/1999 | Berry |
| 5,899,941 A | 5/1999 | Nishijima |
| 5,919,235 A | 7/1999 | Husson |
| 5,964,807 A | 10/1999 | Gan |
| 5,969,020 A | 10/1999 | Shalaby |
| 5,976,186 A | 11/1999 | Bao |
| 5,980,572 A | 11/1999 | Kim |
| 6,001,130 A | 12/1999 | Bryan |
| 6,019,793 A | 2/2000 | Perren |
| 6,022,376 A | 2/2000 | Assell |
| 6,039,763 A | 3/2000 | Shelokov |
| RE36,758 E | 6/2000 | Fitz |
| 6,074,390 A | 6/2000 | Zucherman |
| 6,093,205 A | 7/2000 | McLeod |
| 6,093,207 A | 7/2000 | Pisharodi |
| 6,110,210 A | 8/2000 | Norton |
| 6,113,639 A | 9/2000 | Ray |
| 6,127,597 A | 10/2000 | Beyar |
| 6,136,031 A | 10/2000 | Middleton |
| 6,139,579 A | 10/2000 | Steffee |
| 6,143,031 A | 11/2000 | Knothe |

(56) References Cited

U.S. PATENT DOCUMENTS

| | | |
|---|---|---|
| 6,146,421 A | 11/2000 | Gordon |
| 6,146,422 A | 11/2000 | Lawson |
| 6,156,067 A | 12/2000 | Bryan |
| 6,162,252 A | 12/2000 | Kuras |
| 6,179,874 B1 | 1/2001 | Cauthen |
| 6,183,518 B1 | 2/2001 | Ross |
| 6,187,048 B1 | 2/2001 | Milner |
| 6,190,387 B1 | 2/2001 | Zucherman |
| 6,206,924 B1 | 3/2001 | Timm |
| 6,210,422 B1 | 4/2001 | Douglas |
| 6,210,442 B1 | 4/2001 | Wing |
| 6,224,630 B1 | 5/2001 | Bao |
| 6,240,926 B1 | 6/2001 | ChinGan |
| 6,251,140 B1 | 6/2001 | Marino |
| 6,264,695 B1 | 7/2001 | Stoy |
| 6,280,475 B1 | 8/2001 | Bao |
| 6,283,968 B1 | 9/2001 | Mehdizadeh |
| 6,283,998 B1 | 9/2001 | Eaton |
| 6,315,795 B1 | 11/2001 | Scarborough |
| 6,315,797 B1 | 11/2001 | Middleton |
| 6,348,071 B1 | 2/2002 | Steffee |
| 6,352,557 B1 | 3/2002 | Ferree |
| 6,368,350 B1 | 4/2002 | Erickson |
| 6,371,987 B1 | 4/2002 | Weiland |
| 6,371,990 B1 | 4/2002 | Ferree |
| 6,375,682 B1 | 4/2002 | Fleischmann |
| 6,395,032 B1 | 5/2002 | Gauchet |
| 6,402,784 B1 | 6/2002 | Wardlaw |
| 6,402,785 B1 | 6/2002 | Zdeblick |
| 6,419,704 B1 | 7/2002 | Ferree |
| 6,428,544 B1 | 8/2002 | Ralph |
| 6,428,575 B2 | 8/2002 | Koo |
| 6,428,579 B1 | 8/2002 | Valentini |
| 6,432,106 B1 | 8/2002 | Fraser |
| 6,432,107 B1 | 8/2002 | Ferree |
| 6,432,140 B1 | 8/2002 | Lin |
| 6,436,098 B1 | 8/2002 | Michelson |
| 6,436,101 B1 | 8/2002 | Hamada |
| 6,436,102 B1 | 8/2002 | Ralph |
| 6,436,140 B1 | 8/2002 | Liu |
| 6,436,141 B2 | 8/2002 | Castro |
| 6,436,142 B1 | 8/2002 | Paes |
| 6,436,146 B1 | 8/2002 | Hassler |
| 6,440,168 B1 | 8/2002 | Cauthen |
| 6,440,170 B1 | 8/2002 | Jackson |
| 6,478,822 B1 | 11/2002 | Leroux |
| 6,488,716 B1 | 12/2002 | Huang |
| 6,508,839 B1 | 1/2003 | Lambrecht |
| 6,517,580 B1 | 2/2003 | Ramadan |
| 6,527,803 B1 | 3/2003 | Crozet |
| 6,527,804 B1 | 3/2003 | Gauchet |
| 6,540,785 B1 | 4/2003 | Gill |
| 6,547,823 B2 | 4/2003 | Scarborough |
| 6,562,047 B2 | 5/2003 | Ralph |
| 6,579,320 B1 | 6/2003 | Gauchet |
| 6,579,321 B1 | 6/2003 | Gordon |
| 6,582,466 B1 | 6/2003 | Gauchet |
| 6,592,624 B1 | 7/2003 | Fraser |
| 6,602,291 B1 | 8/2003 | Ray |
| 6,610,091 B1 | 8/2003 | Reiley |
| 6,610,093 B1 | 8/2003 | Pisharodi |
| 6,620,091 B1 | 9/2003 | Zavell et al. |
| 6,679,915 B1 | 1/2004 | Cauthen |
| 6,682,562 B2 | 1/2004 | Viart |
| 6,743,257 B2 | 6/2004 | Castro |
| 6,767,367 B1 | 7/2004 | Michelson |
| 6,770,095 B2 | 8/2004 | Grinberg |
| 6,770,096 B2 | 8/2004 | Bolger |
| 6,783,550 B2 | 8/2004 | MacArthur |
| 6,793,678 B2 | 9/2004 | Hawkins |
| 6,899,716 B2 | 5/2005 | Cragg |
| 6,923,830 B2 | 8/2005 | Michelson |
| 6,926,737 B2 | 8/2005 | Jackson |
| 6,936,071 B1 | 8/2005 | Marnay |
| 6,981,975 B2 | 1/2006 | Michelson |
| 7,001,433 B2 | 2/2006 | Songer |
| 7,041,138 B2 | 5/2006 | Lange |
| 7,056,341 B2 | 6/2006 | Crozet |
| 7,074,240 B2 | 7/2006 | Pisharodi |
| 7,156,876 B2 | 1/2007 | Moumene |
| 7,235,079 B2 | 6/2007 | Jensen |
| 7,662,182 B2 | 2/2010 | Zubok |
| 7,682,397 B2 | 3/2010 | Berry |
| 7,794,465 B2 | 9/2010 | Marik |
| 7,819,920 B2 | 10/2010 | Assaker |
| 7,909,859 B2 | 3/2011 | Mosca |
| 8,038,678 B2 | 10/2011 | Schmieding |
| 8,303,660 B1 * | 11/2012 | Abdou .............. 623/17.14 |
| 2001/0010021 A1 | 7/2001 | Boyd |
| 2001/0012938 A1 | 8/2001 | Zucherman |
| 2001/0016733 A1 | 8/2001 | Frey |
| 2001/0016772 A1 | 8/2001 | Lee |
| 2001/0016773 A1 | 8/2001 | Serhan |
| 2001/0016776 A1 | 8/2001 | Zuckerman |
| 2001/0020476 A1 | 9/2001 | Gan |
| 2001/0027343 A1 | 10/2001 | Keller |
| 2001/0032019 A1 | 10/2001 | VanDyke |
| 2001/0032020 A1 | 10/2001 | Besselink |
| 2001/0047208 A1 | 11/2001 | Michelson |
| 2001/0051829 A1 | 12/2001 | Middleton |
| 2002/0013600 A1 | 1/2002 | Scribner |
| 2002/0022883 A1 | 2/2002 | Burg |
| 2002/0022888 A1 | 2/2002 | Serhan |
| 2002/0026244 A1 | 2/2002 | Trieu |
| 2002/0029082 A1 | 3/2002 | Muhanna |
| 2002/0029083 A1 | 3/2002 | Zucherman |
| 2002/0035400 A1 | 3/2002 | Bryan |
| 2002/0045942 A1 | 4/2002 | Ham |
| 2002/0045944 A1 | 4/2002 | Muhanna |
| 2002/0049498 A1 | 4/2002 | Yuksel |
| 2002/0082608 A1 | 6/2002 | Reiley |
| 2002/0082701 A1 | 6/2002 | Zdeblick |
| 2002/0087480 A1 | 7/2002 | Sauriol |
| 2002/0099444 A1 | 7/2002 | Boyd |
| 2002/0106393 A1 | 8/2002 | Bianchi |
| 2002/0107571 A1 | 8/2002 | Foley |
| 2002/0107572 A1 | 8/2002 | Foley |
| 2002/0107573 A1 | 8/2002 | Steinberg |
| 2002/0120269 A1 | 8/2002 | Lange |
| 2002/0120270 A1 | 8/2002 | Trieu |
| 2002/0120334 A1 | 8/2002 | Crozet |
| 2002/0120336 A1 | 8/2002 | Santilli |
| 2002/0156528 A1 | 10/2002 | Gau |
| 2002/0165612 A1 | 11/2002 | Gerber |
| 2002/0165613 A1 | 11/2002 | Lin |
| 2003/0009226 A1 | 1/2003 | Graf |
| 2003/0023311 A1 | 1/2003 | Trieu |
| 2003/0028197 A1 | 2/2003 | Hanson |
| 2003/0028251 A1 | 2/2003 | Matthews |
| 2003/0040799 A1 | 2/2003 | Boyd |
| 2003/0045939 A1 | 3/2003 | Casutt |
| 2003/0055427 A1 | 3/2003 | Graf |
| 2003/0074076 A1 | 4/2003 | Ferree |
| 2003/0100950 A1 | 5/2003 | Moret |
| 2003/0100951 A1 | 5/2003 | Serhan |
| 2003/0135276 A1 | 7/2003 | Eckman |
| 2003/0135277 A1 | 7/2003 | Bryan |
| 2003/0135278 A1 | 7/2003 | Eckman |
| 2003/0149484 A1 | 8/2003 | Michelson |
| 2003/0176921 A1 | 9/2003 | Lawson |
| 2003/0204260 A1 | 10/2003 | Ferree |
| 2003/0204261 A1 | 10/2003 | Eisermann |
| 2003/0220691 A1 | 11/2003 | Songer |
| 2003/0233146 A1 | 12/2003 | Grinberg |
| 2004/0006394 A1 | 1/2004 | Lipman |
| 2004/0024462 A1 | 2/2004 | Ferree |
| 2004/0030391 A1 | 2/2004 | Ferree |
| 2004/0044410 A1 | 3/2004 | Ferree |
| 2004/0082999 A1 | 4/2004 | Mathys |
| 2004/0093082 A1 | 5/2004 | Ferree |
| 2004/0102846 A1 | 5/2004 | Keller |
| 2004/0117019 A1 | 6/2004 | Trieu |
| 2004/0117022 A1 | 6/2004 | Marnay |
| 2004/0133278 A1 | 7/2004 | Marino |

(56) References Cited

U.S. PATENT DOCUMENTS

| | | |
|---|---|---|
| 2004/0143332 A1 | 7/2004 | Krueger |
| 2004/0153065 A1 | 8/2004 | Lim |
| 2004/0153157 A1 | 8/2004 | Keller |
| 2004/0158328 A1 | 8/2004 | Eisermann |
| 2004/0167536 A1 | 8/2004 | Errico et al. |
| 2004/0193272 A1 | 9/2004 | Zubok |
| 2004/0204760 A1 | 10/2004 | Fitz |
| 2004/0220670 A1 | 11/2004 | Eisermann |
| 2004/0243240 A1 | 12/2004 | Beaurain |
| 2005/0021042 A1 | 1/2005 | Marnay et al. |
| 2005/0021143 A1 | 1/2005 | Keller |
| 2005/0021149 A1 | 1/2005 | Borruto |
| 2005/0033437 A1 | 2/2005 | Bao |
| 2005/0038515 A1 | 2/2005 | Kunzler |
| 2005/0049590 A1 | 3/2005 | Alleyne |
| 2005/0055029 A1 | 3/2005 | Marik |
| 2005/0060034 A1 | 3/2005 | Berry |
| 2005/0071010 A1 | 3/2005 | Crozet |
| 2005/0071011 A1 | 3/2005 | Ralph |
| 2005/0080488 A1 | 4/2005 | Schultz |
| 2005/0085911 A1 | 4/2005 | Link |
| 2005/0085917 A1 | 4/2005 | Marnay |
| 2005/0107881 A1 | 5/2005 | Alleyne |
| 2005/0165485 A1 | 7/2005 | Trieu |
| 2005/0192671 A1 | 9/2005 | Bao |
| 2005/0216084 A1 | 9/2005 | Fleischmann et al. |
| 2005/0266581 A1 | 12/2005 | Droit |
| 2005/0273166 A1 | 12/2005 | Sweeney |
| 2006/0004453 A1 | 1/2006 | Bartish |
| 2006/0020341 A1 | 1/2006 | Schneid |
| 2006/0020342 A1 | 1/2006 | Ferree |
| 2006/0030860 A1 | 2/2006 | Peterman |
| 2006/0041614 A1 | 2/2006 | Oe |
| 2006/0085076 A1 | 4/2006 | Krishna |
| 2006/0095136 A1 | 5/2006 | McLuen |
| 2006/0116767 A1 | 6/2006 | Magerl |
| 2006/0136062 A1 | 6/2006 | Dinello |
| 2006/0178744 A1 | 8/2006 | de Villiers et al. |
| 2006/0178745 A1 | 8/2006 | Bartish |
| 2006/0195191 A1 | 8/2006 | Sweeney |
| 2006/0212122 A1 | 9/2006 | Perera |
| 2006/0235414 A1 | 10/2006 | Lim |
| 2006/0235527 A1 | 10/2006 | Buettner-Janz |
| 2006/0235528 A1 | 10/2006 | Buettner-Janz |
| 2006/0235531 A1 | 10/2006 | Buettner-Janz |
| 2006/0293752 A1 | 12/2006 | Moumene |
| 2007/0027547 A1 | 2/2007 | Rydell |
| 2007/0055376 A1 | 3/2007 | Michelson |
| 2007/0100454 A1 | 5/2007 | Burgess |
| 2007/0100455 A1 | 5/2007 | Parsons |
| 2007/0270961 A1* | 11/2007 | Ferguson ............... A61F 2/44 623/17.11 |
| 2007/0288005 A1* | 12/2007 | Arnin ............... A61F 2/4425 623/17.11 |
| 2008/0103598 A1 | 5/2008 | Trudeau |
| 2008/0288081 A1 | 11/2008 | Scrafton |
| 2009/0043390 A1 | 2/2009 | Meisel |
| 2009/0164023 A1 | 6/2009 | Devine |
| 2009/0185904 A1 | 7/2009 | Landberg |
| 2009/0240333 A1 | 9/2009 | Trudeau |
| 2009/0240336 A1 | 9/2009 | Vander Meulen et al. |
| 2010/0016974 A1 | 1/2010 | Janowski |
| 2010/0280619 A1 | 11/2010 | Yuan |

FOREIGN PATENT DOCUMENTS

| | | |
|---|---|---|
| CA | 2548780 A1 | 7/2005 |
| CN | 1697633 | 11/2005 |
| DE | 9000094 U1 | 1/1991 |
| DE | 29612269 | 9/1996 |
| DE | 29911422 U1 | 8/1999 |
| DE | 19816832 C1 | 1/2000 |
| DE | 10130825 | 3/2002 |
| DE | 202005005405 | 6/2006 |
| EP | 0179695 | 4/1986 |
| EP | 03346129 | 12/1989 |
| EP | 0773008 A1 | 5/1997 |
| EP | 0919209 A1 | 6/1999 |
| EP | 1104665 A1 | 6/2001 |
| EP | 1205160 | 5/2002 |
| FR | 2372622 | 6/1978 |
| FR | 2723841 | 3/1996 |
| FR | 2732841 | 10/1996 |
| FR | 2787014 | 6/2000 |
| FR | 2797179 | 2/2001 |
| FR | 2799116 | 4/2001 |
| FR | 2801782 A1 | 6/2001 |
| FR | 2805985 | 9/2001 |
| FR | 2824261 A1 | 11/2002 |
| JP | 63300758 A1 | 12/1988 |
| JP | 1308557 A1 | 12/1989 |
| JP | 01142293 | 4/1990 |
| JP | 02111358 | 4/1990 |
| JP | 2215461 A2 | 8/1990 |
| JP | 2224659 A1 | 9/1990 |
| JP | 2224660 A2 | 9/1990 |
| JP | 03275055 A | 12/1991 |
| JP | 03275056 A | 12/1991 |
| JP | 04303444 A | 10/1992 |
| JP | 05277141 A | 10/1993 |
| JP | 06285099 | 10/1994 |
| JP | 08098851 A2 | 4/1995 |
| JP | 08098850 A | 4/1996 |
| JP | 11009618 A | 1/1999 |
| JP | 11137585 A | 5/1999 |
| JP | 2008284348 A | 11/2008 |
| WO | 9011740 | 10/1990 |
| WO | 9105521 | 5/1991 |
| WO | 9116867 | 11/1991 |
| WO | 9316664 | 9/1993 |
| WO | 9500082 | 5/1995 |
| WO | 9601598 | 1/1996 |
| WO | 9611642 | 4/1996 |
| WO | 9627339 | 9/1996 |
| WO | 9805274 | 2/1998 |
| WO | 9819617 | 5/1998 |
| WO | 9855053 | 12/1998 |
| WO | 9911203 | 3/1999 |
| WO | 9922675 | 5/1999 |
| WO | 9930651 | 6/1999 |
| WO | 0013619 A1 | 3/2000 |
| WO | 0042953 | 7/2000 |
| WO | 0049977 A1 | 8/2000 |
| WO | 0059412 | 10/2000 |
| WO | 0115638 | 3/2001 |
| WO | 0132100 | 5/2001 |
| WO | 0168003 | 9/2001 |
| WO | 02087480 | 11/2002 |
| WO | 03035129 | 5/2003 |
| WO | 03099172 | 12/2003 |
| WO | 2005009298 | 2/2005 |
| WO | 2005041818 | 5/2005 |
| WO | 2005051240 | 6/2005 |
| WO | 2006016384 A1 | 2/2006 |
| WO | 2006061114 | 6/2006 |

OTHER PUBLICATIONS

Depuy Spine, Inc., Charite Artificial Disc Centreline TDR Instrumentation Surgical Technique, Dec. 2004, 20 pp.
Depuy Spine, Inc., Chardite Artificial Disc Product Catalog, Dec. 2004, 16 pp.
Depuy Spine, Inc., Charite Artificial Disc Product Catalog, Dec. 2004, 17 pp.
European Patent Office, Supplemental EPO Search Report for Application No. 03738960.8, Feb. 20, 2008, 6 pp.
European Patent Office, Supplementary European Search Report from corresponding International Patent Application No. PCT/US2007/078679, Jan. 28, 2013, 10 pp.
European Patent Office, Supplementary Partial Search Search Report issued corresponding to Application No. EP04796064, Mar. 22, 2012, 8 pp.

(56) References Cited

OTHER PUBLICATIONS

European Patent Office, Supplementary Search Report issued corresponding to Application No. EP 07 84 2616, Mar. 20, 2012, 7 pp.
European Search Report dated Feb. 20, 2008, corresponding to European Patent Application No. 03738960.8-2310.
Feder, B. When F.D.A. Says Yes, But Insurers Say No, The New York Times, Jul. 6, 2005, 2 pp.
Patent Cooperation Treaty, International Search Report from corresponding International Patent Application No. PCT/US2007/078679, Apr. 23, 2008, 3 pp.
Patent Cooperation Treaty, International Search Report from corresponding International Patent Application No. PCT/US2009/042882, Jun. 22, 2009, 2 pp.
The State Intellectual Property Office of China, First Notification of Office Action issued corresponding to Application No. 200780040650.7, Dec. 15, 2010, 9 pp.
Zdeblick, T. et al., Cervical Interbody Cages, An Animal Mode With and Without Bone Morphogenetic Protein, Spine 1998, vol. 23, No. 7, 11 pp.

\* cited by examiner

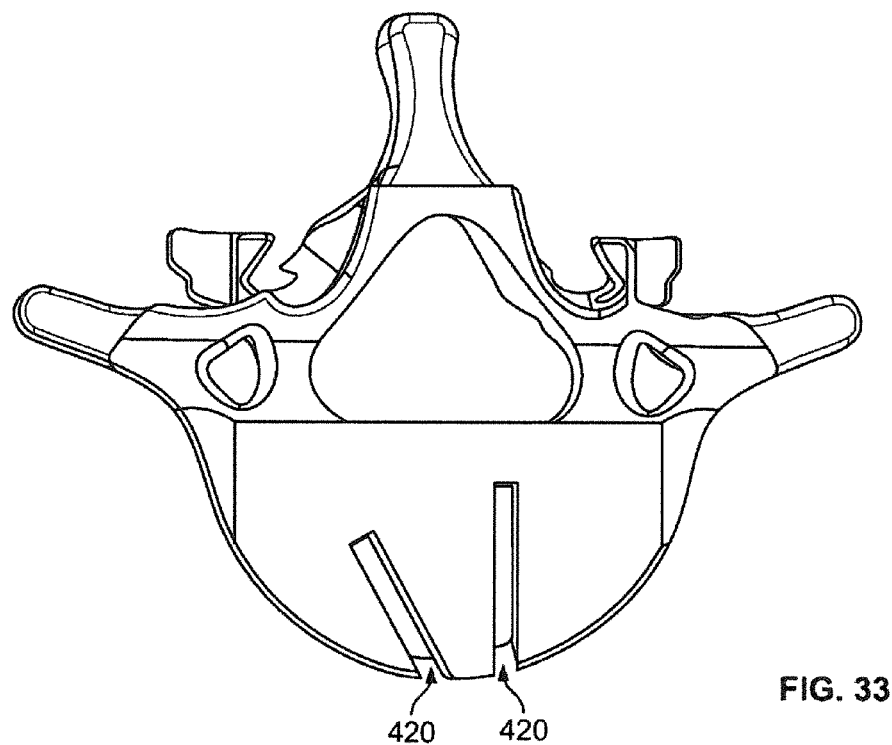
FIG. 33
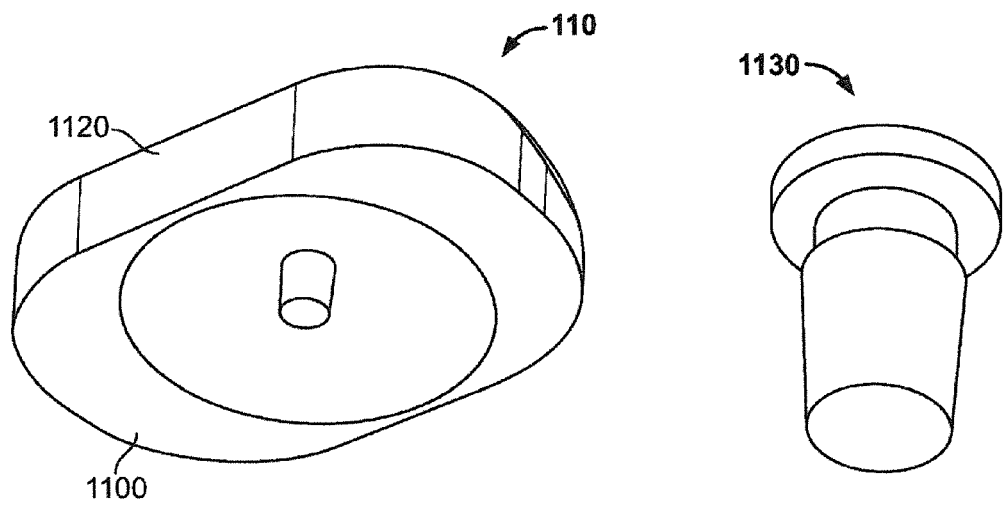
FIG. 34
FIG. 35

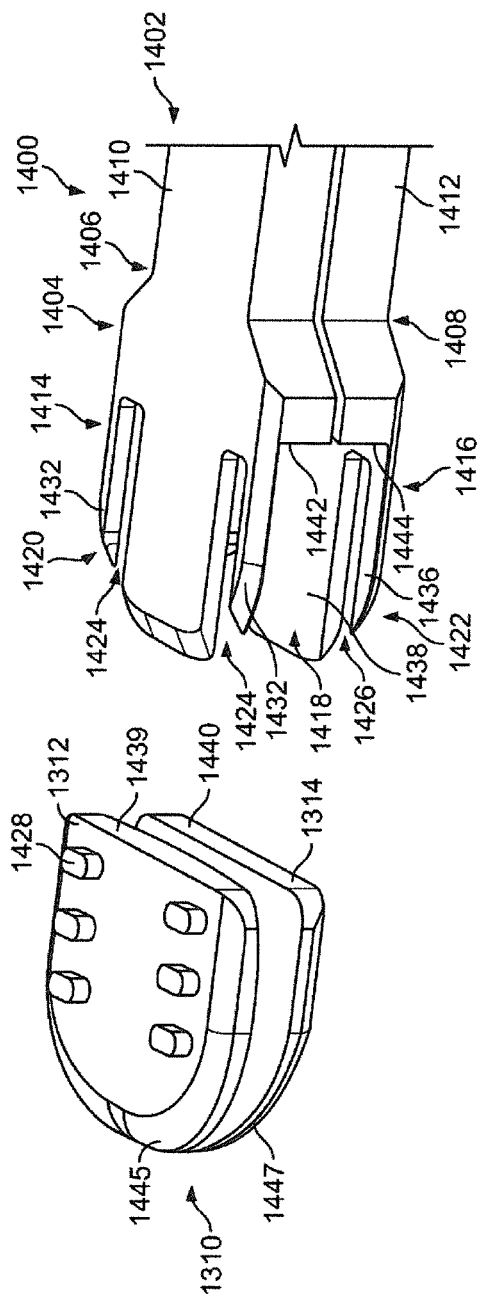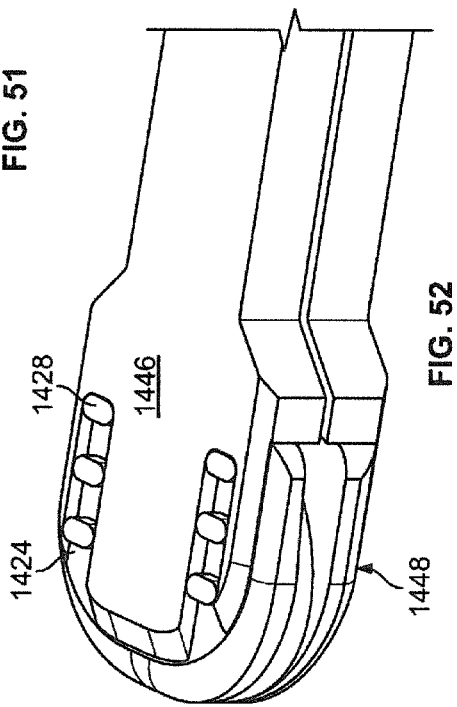
FIG. 51
FIG. 52

INTERVERTEBRAL DISC IMPLANT

RELATED APPLICATIONS

This application is a continuation of U.S. patent application Ser. No. 14/270,076, filed May 5, 2014, which is a continuation of U.S. patent application Ser. No. 12/541,658, filed Aug. 14, 2009, now U.S. Pat. No. 8,715,350, which claims the benefit of U.S. Provisional Patent Application No. 61/089,283, filed Aug. 15, 2008. U.S. patent application Ser. No. 12/541,658 is a continuation-in-part of U.S. patent application Ser. No. 11/856,667, filed Sep. 17, 2007, now U.S. Pat. No. 8,597,357, which claims the benefit of U.S. Provisional Patent Application No. 60/825,865, filed Sep. 15, 2006, and Provisional Application No. 60/912,138, filed Apr. 16, 2007. Each of the aforementioned applications are incorporated herein by reference in their entirety.

FIELD OF THE INVENTION

The invention relates to systems and apparatuses for securing an implant within a joint and, more particularly, to systems and apparatuses for securing an implant in the intervertebral space.

BACKGROUND OF THE INVENTION

Joint degeneration is a common problem that can occur in a variety of joints throughout the human body. The condition typically is more prevalent as the skeletal system ages and is often treated with medications and/or physical therapy. These conservative treatments sometimes meet only limited success. If unsuccessful, the patient typically will continue to experience ongoing pain and limited mobility.

Often the treatment progression leads to a total joint replacement. These replacements have been performed for years in joints such as the hip and the knee. The replacement devices usually comprise some form of a metallic structural component or endplate with an intermediate polyethylene core. It is not unusual for replacements such as these to give 15-20 years of service before requiring some degree of revision.

In the spine, the surgical treatment of choice has been fusion for the treatment of intervertebral disc degeneration. The spinal intervertebral disc is arguably the most important joint in the spine and is situated between the vertebral bodies. The spinal disc is comprised of a tough outer ring called the annulus, and a jelly-like filling called the nucleus. The belief has been that removing the diseased spinal disc(s) and fusing between affected levels will not make a significant difference in the overall mobility of the spine. However, spinal fusion has proved to cause an increase in degeneration at other vertebral levels that must compensate for the loss of motion at the fused level commonly causing the patient to relapse into more pain and limited mobility.

Recently, there has been a focus on the use of "motion preservation" implants over implants that promote spinal fusion. These motion preserving implants, in the form of joint replacements in the spine, hope to alleviate many of the problems associated with fusion devices in the spine. Intervertebral disc replacement devices are seen today typically comprising a pair of biocompatible metal plates with a polymer or elastomeric core, or a metal plate articulating on a metal plate.

Metal on metal implants have a history of failure in long term use, however, precision machining has spawned a reemergence of implants using these materials since it is believed that this change in manufacturing greatly improves the wear. Regardless, the metal implants are radiopaque and continue to frustrate surgeons due to the difficulty in imaging the affected area. Other implants, such as those using a polymer or elastomeric core between metallic plates suffer from the same radiopaque frustrations due to the metal components in addition to the added complexities of design due to the necessity of utilizing a multitude of materials for a single implant.

The prior art discloses a laundry list of biocompatible materials including metals, ceramics, and polymers, that can be used for the manufacture of these implants, yet historically many of these materials have failed when interfaced together and tested in an articulating joint. There is in particular an extensive history of failure when polymers articulate against polymers in weight bearing artificial joints. Due to this failure history, polymer combinations have naturally been excluded as an acceptable self-articulating material combination for use in weight bearing joint replacements.

PEEK (poly-ether-ether-ketone), for example, has been suggested as an appropriate material of manufacture for use in implant devices due in large part to its strength, radiolucent nature, and biocompatibility. This is particularly true in structural implants having no articulating component. PEEK on PEEK has been suggested for use in low wear non-weight bearing joints such as in finger joints. However, the prior art has been careful not to suggest self-articulating PEEK on PEEK as a suitable material combination in weight bearing joint replacement devices due to the failure history of biocompatible polymers articulating against themselves.

One important consideration in the design of an implant is ensuring that the implant remains at the implant site, and does not migrate. Migration of the implant away from the intended implant site can cause dangerous and even fatal complications. In the case of an intervertebral implant, the close proximity of vital blood vessels, nerves, the spinal cord, and other vital tissues makes securing the implant in place a vital concern. Many different ways to secure the implant to the adjacent bone of the joint have been proposed, including implementing protrusions or spikes, keels, screws, surface roughening, and bone-growth inducing coatings.

In one known form disclosed in Published U.S. Patent Application 2007/0270961, a spinal implant is provided with deployable and retractable barbs for securing the implant to a vertebra. In one embodiment, the barbs 130 have arcuate bodies having sharpened tips for protruding into the vertebral bone. The barbs 130 are disposed within recesses 120 in the implant body 110 and rotatably mounted on pins 140. The pins 140 are disposed transversely to channel 160, such that the barb rotates about the pin along the longitudinal axis of the channel. The barbs 130 are deployed via interaction with a rod 150 that is inserted into the channel 160 of the implant body 110. The rod 150 has a sloped end for engaging the barbs 130 and causing them to rotate upwards about the pins 140 and into engagement with the bone.

In another form according to U.S. Patent Application 2007/0270961 shown in FIG. 5A-5D of that application, the deployable barbs take the form of conical spikes 530 configured to be deployed into the adjacent vertebra for securing the implant thereto. The spikes 530 have lower edges 538 which engage with the tapered tip 552 of the rod 550, which propels the spikes through apertures 520 in the implant body 500. The implant is also supplied with a lock mechanism 548 in the form of annular washers that prevent the barb 530 from exiting the implant body 510.

One embodiment shown in FIG. 6 of U.S. Patent Application 2007/0270961 is described as having a nucleus portion 650 that may comprise a ball and trough arrangement to permit translational and rotational motion therebetween. However, the figures of the application do not disclose such a nucleus portion, and it is believed that the implants shown and described therein would be unable to incorporate such a configuration. Specifically, the implant bodies do not have sufficient material thickness to incorporate at least a trough portion for a ball and trough configuration.

In addition, in the configurations of the embodiments shown in 1A-4D of U.S. Patent Application 2007/0270961, the implant would be drawn further into the intervertebral space by the deployment of the barbs due to their shape and their axis of rotation about the pins. This pulling effect is believed to be counteracted by the protrusions 172 disposed on the end of the implant, such that an inner surface of the protrusions can bias against a surface of the adjacent vertebra, thereby preventing the implant from being pulled further into the intervertebral space. However, implants that have protrusions that extend outside of the intervertebral space are less preferred. For example, a cervical implant that protrudes from the intervertebral space between adjacent vertebrae may come into contact with the trachea, which can cause pain or difficulty in swallowing.

SUMMARY OF THE INVENTION

Testing in our laboratories however, told a different and unexpected story. In simulated weight bearing artificial joint configurations, PEEK against PEEK performed very favorably. PEEK articulating against PEEK demonstrated exceptional mechanical performance and biocompatibility characteristics required for load bearing artificial joints used in the human body and in other animals. PEEK may also be manufactured in a fiber reinforced form, typically carbon fiber, which also performs favorably against itself and against non-fiber reinforced PEEK.

Once PEEK was recognized as a viable option for self-articulation, it became clear that an entire articulating joint could be made from the material without the need for metallic structural or articulating components. This discovery substantially simplified the nature of weight bearing artificial joint replacement design and great benefits have emerged. A partial list of these benefits include artificial joints that; have less components due to integrating features into the same component that were previously separated due to the need for a plurality of materials to serve the function, will last longer due to favorable wear characteristics, are substantially radiolucent, have a modulus of elasticity closer to the bone tissue they are implanted in, and are ultimately less expensive. It is important to note that less components typically equates to fewer modes of failure, reduced inventory, and simplified manufacturing and assembly. Although less preferred, clearly one may choose to keep the metallic components of an implant system and utilize PEEK on each articulating surface of the artificial joint for a PEEK on PEEK articulation.

Two piece articulating PEEK on PEEK intervertebral implants have been presented in earlier applications by the same inventor. These implants perform exceptionally well for replacement of the spinal nucleus. However, many indications require implants of this nature to also comprise improved restraining features particularly in weight bearing applications.

For example, there is a need for a simplified radiolucent artificial disc device, with excellent wear characteristics and features that will secure the device to the vertebral endplates or otherwise restrain it between the vertebral bodies. An artificial disc such as this would be particularly useful as a lumbar disc replacement, and even more so as a cervical disc replacement. The cervical disc is much smaller than the lumbar disc as is the space the cervical disc occupies. For at least this reason, a simplified design utilizing fewer parts is beneficial.

The articulating joint surfaces are preferably a combination of PEEK articulating on PEEK, PEEK on carbon reinforced (CR) PEEK, or CR PEEK on CR PEEK. Boney integration of these implants may benefit from prepared osteo-conductive surfaces or coatings described elsewhere in this document.

It is preferable that the radiolucent implant includes one or more small radiopaque markers which will show on up an X-ray image to assist the surgeon in positioning the implant during surgery. The preferred material for these markers is tantalum. Typically these markers will be encased in predetermined locations in the implant at their periphery. Coatings which show up on imaging as a subtle outline of the implant device may also be used.

It is also preferable that the implants disclosed herein include a layer of osteo-conductive or osteo-inductive surfaces or coatings on those implant surfaces in contact with bone or tissue that will assist in securing the implant in a predetermined location. Typically this will occur through boney integration of the bone with the coating or implant surface. Examples of such coatings are hydroxyapatite, calcium phosphates such as tricalcium phosphate, or porous titanium spray.

The implant devices disclosed herein are particularly suited as intervertebral disc replacements for all or a portion of the natural intervertebral disc. In addition, the securing members disclosed herein are also suited for other spinal implants, such as vertebral body replacements, spinal cages, and other fusion promoting implants, as well as other known motion preserving implants. The devices have minimal structural parts and are preferably manufactured from specialized materials that are substantially radiolucent such as PEEK or Carbon-Fiber PEEK in both their structural and joint articulating portions.

Generally, the various systems and methods described herein allow for an implant, such as an artificial disc, to be properly sized, implanted and secured in an intervertebral space with the disc having a bearing interface that preserves motion between the upper and lower vertebrae between which the disc is implanted and secured. In each form described herein, a trial spacer may be used to assess the size of the intervertebral space so that an appropriately sized disc implant can be selected, and may also be used to assist in generating features in the vertebrae and/or end plates thereof for a securing member that holds and retains the disc implant in the intervertebral space.

An insertion tool may be used for inserting the implant within the intervertebral space between adjacent vertebrae. The insertion tool is generally comprised of a handle portion, an actuator, and a gripping mechanism. The gripping mechanism may include a plurality of shiftable implant engaging members for engaging with the implant. The implant engaging members may be shiftable prongs located at a distal end of the tool that are configured to shift between a non-engaging and engaging configurations to alternately release and hold the implant, respectively. The prongs preferably shift vertically, i.e., either inferiorly or superiorly when moving between the non-engaging and engaging configurations. The tool engages with the implant at tool engaging portions of the implant, such as a tool receiving recess formed in the inner facing surface of each of the upper and lower bearing members. The tool may include additional features such as tab members for engaging with tool engaging portions on the implant bearing members to grip the bearing members between the shiftable prongs and the tab members.

In some forms, the securing mechanism is associated with the implant to be inserted into the intervertebral space therewith. After the disc and securing mechanism are inserted in the intervertebral space, the securing mechanism can be deployed into the preformed features in the adjacent vertebral bodies from the disc implant. In one form, the insertion tool is used to engage the securing mechanism with the preformed features in the intervertebral bodies. In another form, the securing mechanism is actuated directly to engage the securing mechanism with the preformed features of the vertebral bodies.

In yet another form, the securing mechanism is inserted into the intervertebral space via the trial spacer prior to insertion of the disc implant. In this form, the securing mechanism is actuated directly to be deployed into the features in the adjacent vertebral bodies with the disc implant then inserted into the intervertebral space. Thereafter, the securing mechanism is actuated so as to engage both the implant and the vertebral body for securing the implant in the intervertebral space.

In any event, the level of restraint required for a particular orthopedic application will vary. This disclosure also describes examples of a variety of securing mechanisms or alternative features suitable for restraining the device in a predetermined location. The securing mechanisms generally possess structure which allow for dynamic fixation of the implant. Instead of relying solely on subsidence or boney ingrowth of the bone around the features of the implant, the securing mechanisms actively engage the bone for immediate and reliable fixation of the implant to the vertebrae. In one embodiment, a rotatable shaft with at least one bone engaging body is disposed on the implant for securing the implant within the intervertebral space. In an undeployed position, the bone engaging body is disposed within the implant body. When the shaft is rotated, the bone engaging body is deployed into the vertebra and thereby fixes the implant to the vertebra to prevent migration of the implant.

In addition, securing mechanisms according to the present invention may incorporate designs that transmit tactile feedback to the surgeon when the securing mechanism is being operated. As it is very difficult for the surgeon to visually ascertain the position of the implant and its securing features during operation, a surgeon will also use his hands to feel for tactile responses transmitted from the implant and through his tools. In one embodiment, the securing mechanism has a cammed surface for interacting with a corresponding cammed surface to cause the securing mechanism to be biased against the implant to provide resistance against the movement of the securing mechanism that can be felt through the surgeon's tools. In this manner, the surgeon can easily ascertain when the securing mechanism has been fully extended or deployed. The tactile feedback features of the securing mechanism also prevent the securing mechanism from being over- or under-actuated, i.e. deploying the securing mechanism beyond its intended range of motion, or failing to fully deploy the securing mechanism. This condition may result in improper fixation of the implant and cause damage to the implant, spine, nerves, vascular system, or other tissue in the area around the spine.

Another aspect of the current invention includes securing mechanisms for an implant having anti-retraction or derotation prevention means. Some securing mechanisms according to the present invention are deployed or extended into the bone by actuating the securing mechanism, for example, by rotating a shaft. However, it is possible for the securing mechanism to retract or derotate back to its undeployed position over time, due to forces exerted on the implant. Thus, to prevent such an event, a securing mechanism may be provided with means to prevent retraction or derotation. In one embodiment, derotation prevention means are provided in the form of a camming surface on the securing mechanism in combination with a corresponding camming surface on the implant. The camming surfaces are disposed to engage or interfere with one another when the securing mechanism is in a fully deployed position to prevent derotation of the securing mechanism.

In some forms, the securing member is associated with the implant to be inserted into the intervertebral space therewith. After the disc and securing member are inserted in the intervertebral space, the securing member can be deployed into the adjacent vertebral bodies from the disc implant. In one form, the insertion tool is used to engage the securing member with the intervertebral bodies. In another form, the securing member is actuated directly to engage the securing member with the vertebral bodies.

The securing members generally possess structure which allow for dynamic fixation of the implant. Instead of relying solely on subsidence or boney ingrowth of the bone around the features of the implant, the securing members actively engage the bone for immediate and reliable fixation of the implant to the vertebrae. In one embodiment, a rotatable shaft with at least one bone engaging body is disposed on the implant for securing the implant within the intervertebral space. In an undeployed position, the bone engaging body is disposed within the implant body. When the shaft is rotated, the bone engaging body is deployed into the vertebra and thereby fixes the implant to the vertebra to prevent migration of the implant.

In some forms, the securing member is disposed on the upper and lower surfaces of the upper and lower faces of the implant. However, in other forms, the securing member may be completely submerged within the body of the implant such that the upper and lower surfaces with the implant are relatively smooth or flat. When the securing member is securely submerged within the implant, the upper and lower vertebrae need not be prepared prior to the insertion of the implant, thereby simplifying the implantation procedure.

In another form, an implant according to the present invention may be provided with upper and lower bearing members having respective bodies and outer bearing surfaces. An articulation interface disposed between the upper and lower bearing members allows for relative movement therebetween. A securing member is disposed on one of the bearing members and has an elongate shaft portion and a bone-engaging member disposed on the shaft portion. The bone-engaging member is movable from an undeployed position, wherein the bone-engaging member is positioned out of engagement with an adjacent bone, and a deployed position, wherein the bone-engaging member is positioned in engagement with the adjacent bone via rotational displacement of the shaft portion. In some forms, the securing member is entirely disposed within the body of the bearing member when in an undeployed position.

In other forms, the securing member may include at least one bone engaging body disposed on the implant which is deployed into the vertebrae by the insertion of an elongate member into the implant body. The bone engaging body is disposed on the implant such that insertion of the elongate member causes the bone engaging body to be deployed from its initial position to a bone engaging position. Once the elongate member is inserted into the implant body, the bone engaging body is fully deployed and the elongate body is left within the implant to hold the bone engaging body in the deployed position.

The securing member in some forms includes an elongate shaft portion disposed within a channel of the bearing member and may have a plurality of bone engaging members. The bone engaging members may be lobe members having bodies orientated generally transversely to the elongate shaft portion. The lobe members may have a sharpened portion for easing insertion of the lobe member into the vertebral bone by either cutting or piercing the bone. In other forms, the lobe members may be sized and configured for engaging with prepared surfaces of the vertebra, wherein the surfaces are prepared prior to the insertion of the implant. The vertebra may be prepared using a cutting tool to form a securing member receiving portion by removing bone at the implant site. The bone may be prepared by cutting grooves or channels sized and configured to receive the securing member.

The securing member may be connected to the body of the bearing member via a retainer member for connecting the securing member to the bearing member body. In one form, the retainer securing member has opposing arms spaced from each other for receiving the elongate shaft member between the opposing arms by a friction fit.

The upper and lower bearing members may be sized and configured to fit entirely between inner surfaces of adjacent vertebrae when the deployable securing member is in an undeployed configuration. This configuration eases insertion of the implant, because the vertebrae need not be prepared prior to insertion. Moreover, in a preferred form, the implant fits entirely within the footprint of the intervertebral disc space such that the implant does not interfere with adjacent blood vessels, nerves, tissues, digestive or respiratory tracts and the like.

In another form according to the present invention, an intervertebral disc implant has a deployable securing member disposed on the implant body with a projection of the deployable securing member movably connected to the body having a head portion with an edge for engaging a bone, an actuation portion of the securing member having an actuator engagement portion thereon. The projection is deployable between an undeployed position, wherein the projection is remote from an adjacent vertebra, to a deployed position, wherein the projection is engaged with the adjacent vertebra through the interaction of the actuator with the projection when the actuator is inserted along an insertion axis into the body. The head portion of the deployable securing member is oriented in a generally transverse orientation with respect to the insertion axis when the securing member is in a deployed position.

The implant body has an outer bone engaging surface for non-invasive contact with an inner surface of the adjacent vertebra and a securing member mating portion of the implant body for mating with the securing member which protrudes outwardly beyond the bone engaging surface. The securing member mating portion comprises an elongate opening for receiving the projection and allowing the projection to travel from the undeployed position, wherein the projection is disposed within the opening, to a deployed position, wherein the projection protrudes from the opening and is brought into engagement with the adjacent vertebra.

The implant body may be part of a unitary implant, such as a spacer implant, or the implant body may be one member of a multiple-part implant, such as one of upper and lower bearing members. In a multi-part implant, the upper and lower bearing members may be provided with upper and lower inner arcuate bearing surfaces that slidingly engage one another. The sliding interface between the upper and lower bearing members between the upper and lower inner arcuate bearing surfaces allows the bearing members to articulate with respect to one another. In one form, the upper and lower inner arcuate bearing surfaces are sized and configured to allow the upper and lower bearing members to rotate with respect to one another over a range of approximately 13.7-22.5 degrees in flexion and 13.8-30 degrees in extension, depending on implant size.

In one form, the edge of the projection is deployed rostrally or caudally into engagement with the adjacent vertebra without substantial translation in another direction. For example, the projection may be a spade-like lobe that is driven straight up into the vertebral bone when it is actuated by an actuator. In other forms, the projection is connected to a pivot shaft connected to the implant body and oriented generally parallel to the insertion axis such that the projection pivots along with the shaft in a direction transverse to the insertion axis during deployment of the projection. Preferably, the projection and pivot shaft rotate about a pivot shaft axis parallel to the insertion axis during deployment of the projection.

In yet another form, the securing member may take the form of a bendable elongate member that may be inserted into a securing member receiving portion of the upper or lower face of the implant. The bendable elongate member is inserted into the securing member receiving portion which causes the bendable elongate member to flex or bend causing a projection to protrude into the adjacent vertebrae thereby fixing the implant to the vertebrae. The bendable elongate member may include preformed protrusions that are deployed upon compression of the elongate member.

The implant preferably includes an implant body having a securing member receiving portion. A bendable securing member for being inserted into the securing member receiving portion is provided to secure the implant to the vertebra. The bendable securing member is inserted into an opening of the securing member receiving portion to deploy a bone engaging member of the bendable securing member. The bone engaging member is movable from an undeployed orientation, wherein the bone engaging member is remote from an adjacent vertebra, and a deployed orientation, wherein the bone engaging member is brought into contact with the adjacent vertebra for securing the implant body to the adjacent vertebra. In some forms, the bone engaging member is deployed through the plastic deformation of the securing member upon insertion of the securing member into the opening of the securing member receiving portion. An abutment surface of the implant body is provided for engaging with the securing member to facilitate deformation of the securing member by compression of the securing member against the abutment surface. The bone engaging member may be a barb member disposed on the bendable securing member. In a preferred form, the barb member is disposed flush to an outer surface of the securing member prior to deployment of the barb. The bone engaging member may have a structurally weakened portion to promote plastic deformation thereof at a predetermined position to deploy the bone engaging member at a desired location. The bendable member preferably comprises a plurality of bone engaging members.

In some forms, the securing member receiving portion has an opening on an outer facing surface of the implant body which permits the bone engaging member to pass through the opening and engage the adjacent vertebra. The bone engaging member is preferably predisposed to bending at locations thereon that correspond to an opening or openings in the outer facing surface of the implant body.

BRIEF DESCRIPTION OF THE DRAWINGS

To understand the present invention, it will now be described by way of example, with reference to the accompanying drawings in which:

FIG. 33 is a top view of a vertebra end plate with grooves formed therein for mating with the securing mechanism of the implant of FIG. 31;

FIG. 34 is a perspective view of an implant component according to the present invention with a motion limiting component disposed on the articulating surface;

FIG. 35 is a perspective view of the motion limiting component of FIG. 34;

FIG. 51 is an anterolateral perspective view of the artificial disc implant of FIG. 41 with the implant inserter;

FIG. 52 is an anterolateral perspective view of the implant of FIG. 41 loaded in the inserter of FIG. 51;

FIG. 117 is an anterior view of the bearing member of FIG. 116 illustrating the deployable securing member in a deployed configuration, wherein the securing member protrudes above the upper bearing surface for engagement with a bone;

FIG. 118 is a plan view of the bearing member of FIG. 114 illustrating the deployable securing member in a deployed configuration;

FIG. 119 is a lateral cross-sectional side view of the bearing member of FIG. 114, illustrating the deployable securing member receiving portion, and the securing member in a deployed configuration;

FIG. 120 is a bottom view of the bearing member of FIG. 114, illustrating the concave articulation surface disposed on an inner surface of the bearing member;

FIG. 121 is a posterior view of the bearing member of FIG. 114, illustrating the deployable securing member in a deployed configuration and a centrally located marking member disposed in the bearing member body;

FIG. 122 is a partially exploded anterolateral perspective view of an alternate embodiment of an intervertebral implant according to the present invention illustrating a plurality of securing members of the securing member, an elongate actuating member, and a pair of prongs used for inserting the implant into the intervertebral space;

FIG. 123 is an exploded anterolateral perspective view of the intervertebral implant of FIG. 122;

FIG. 124 is an exploded posterolateral perspective view of the intervertebral implant of FIG. 122;

FIG. 125 is an anterolateral perspective view of the intervertebral implant of FIG. 122 illustrating the prongs secured to the upper bearing member for manipulation of the implant and the elongate actuating member positioned remotely from the deployable securing member prior to insertion thereof;

FIG. 126 is an anterolateral perspective view of the intervertebral implant of FIG. 122 showing the deployable securing member in a deployed orientation with the elongate actuating member inserted into the implant body;

FIG. 127 is an partially exploded anterolateral perspective view of an alternate embodiment of an intervertebral implant with a securing member according to the present invention illustrating a plurality of securing members, an elongate actuating member, and a pair of prongs used for inserting the implant into the intervertebral space;

FIG. 128 is an anterolateral perspective view of the implant of FIG. 126 illustrating the plurality of securing members in an undeployed configuration prior to insertion of the actuating member;

Figure 127:
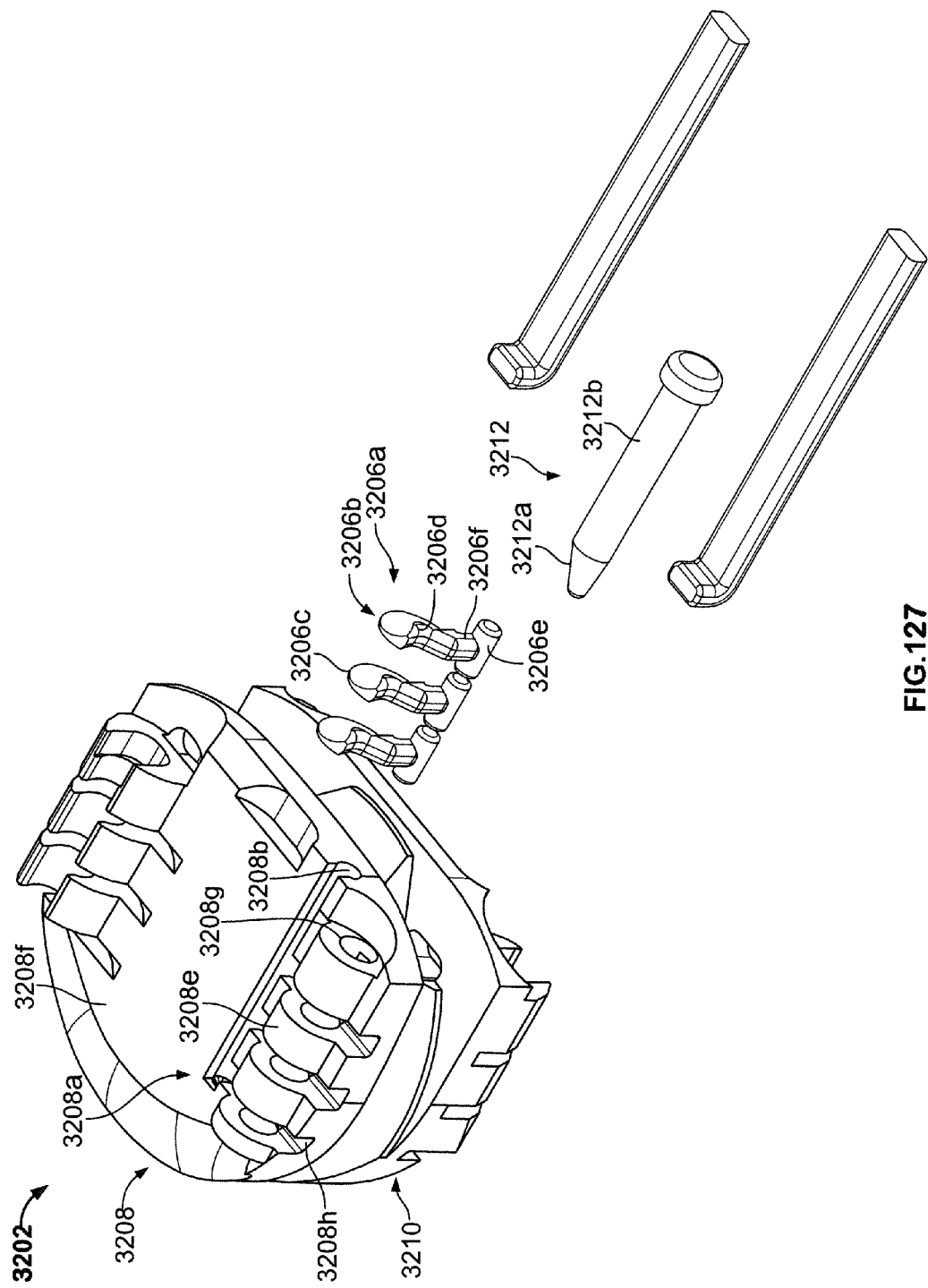
Figure 128:
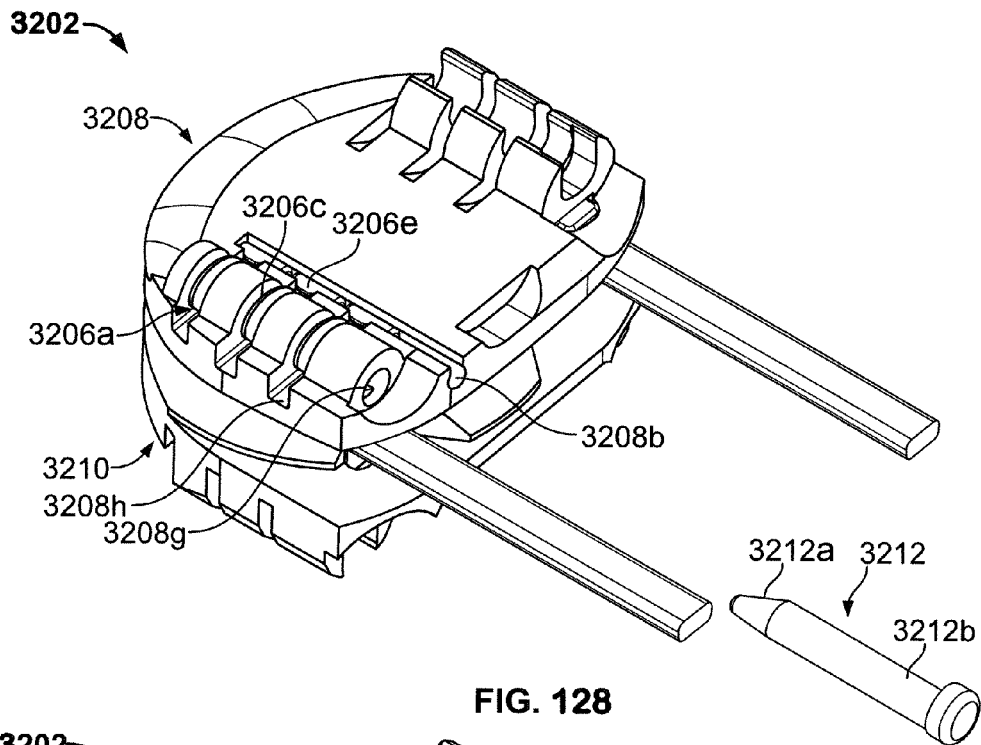
Figure 129:
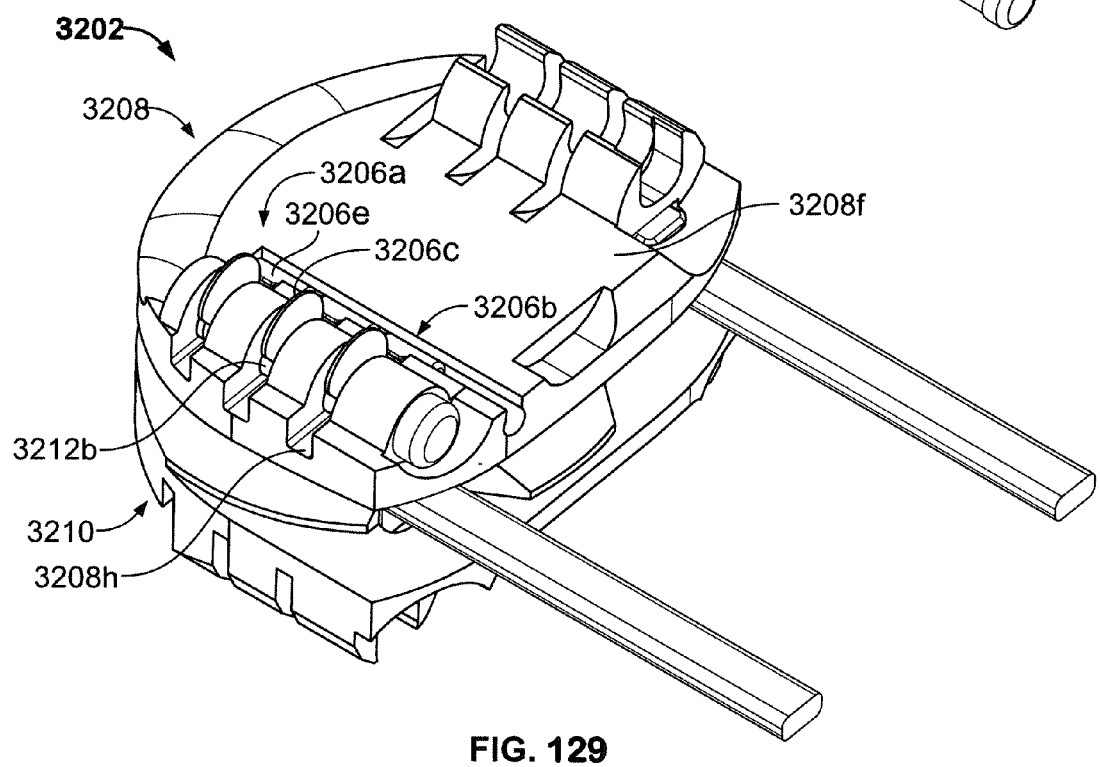
Figure 130:
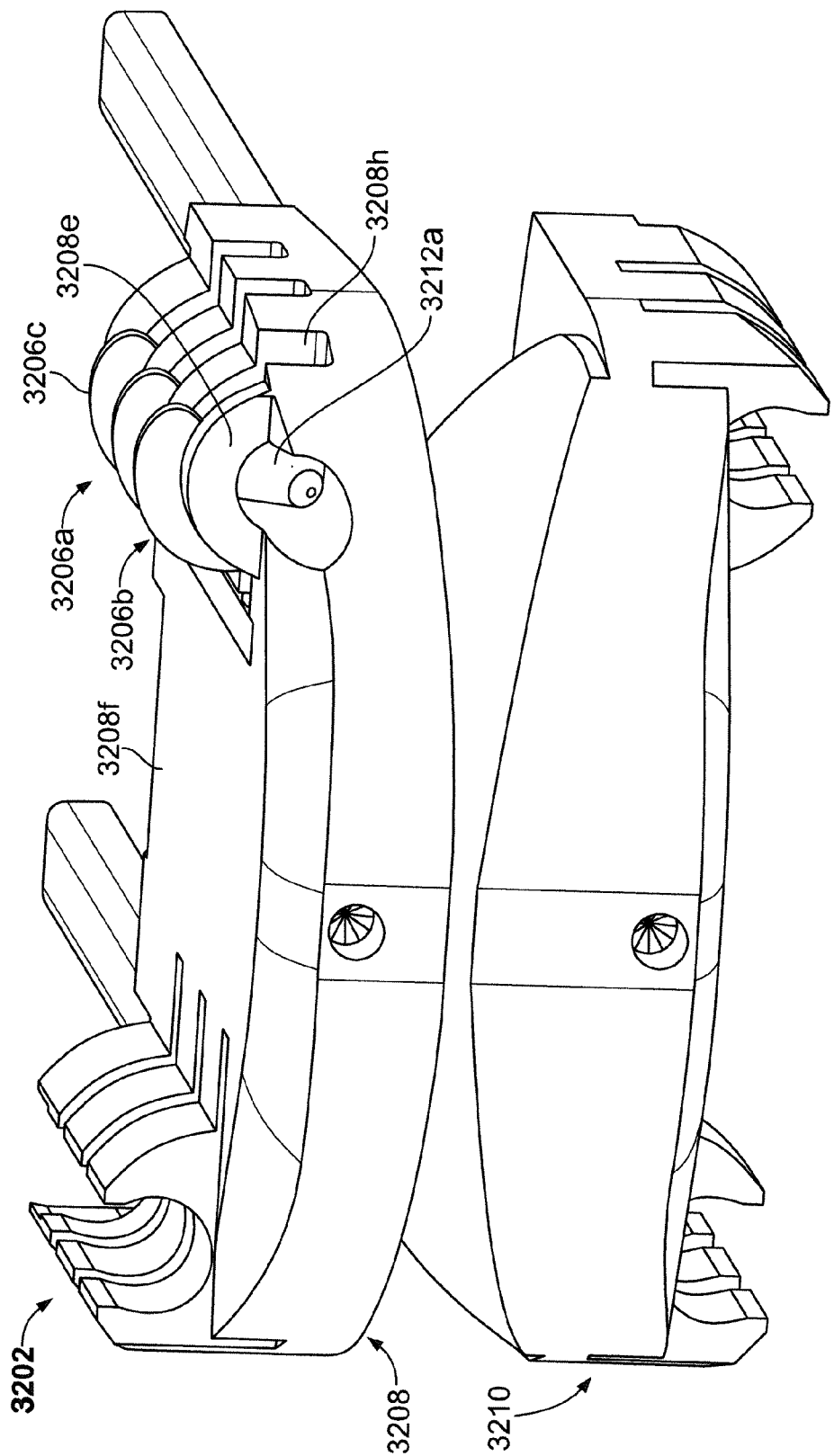
Figure 131:
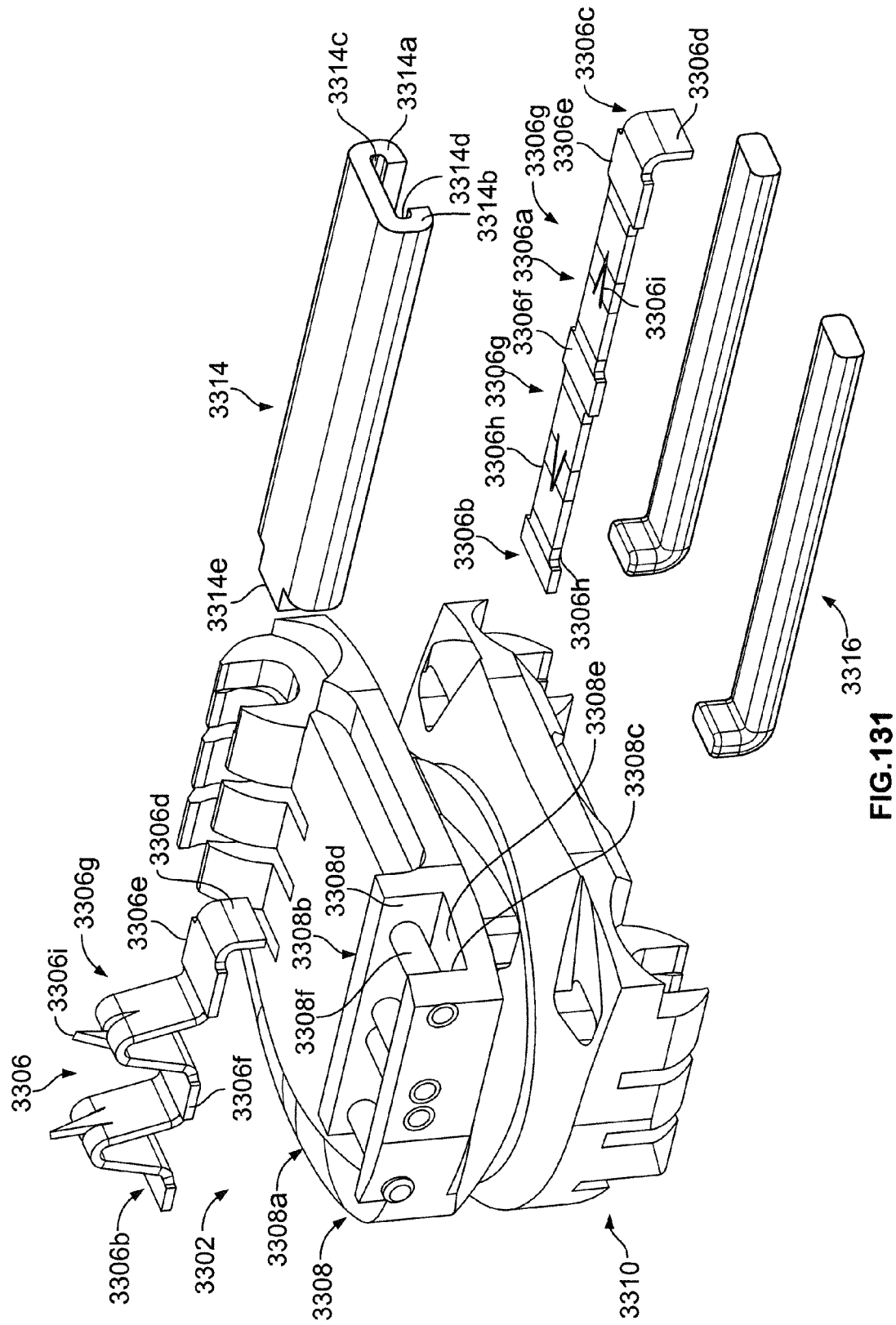
Figure 132:
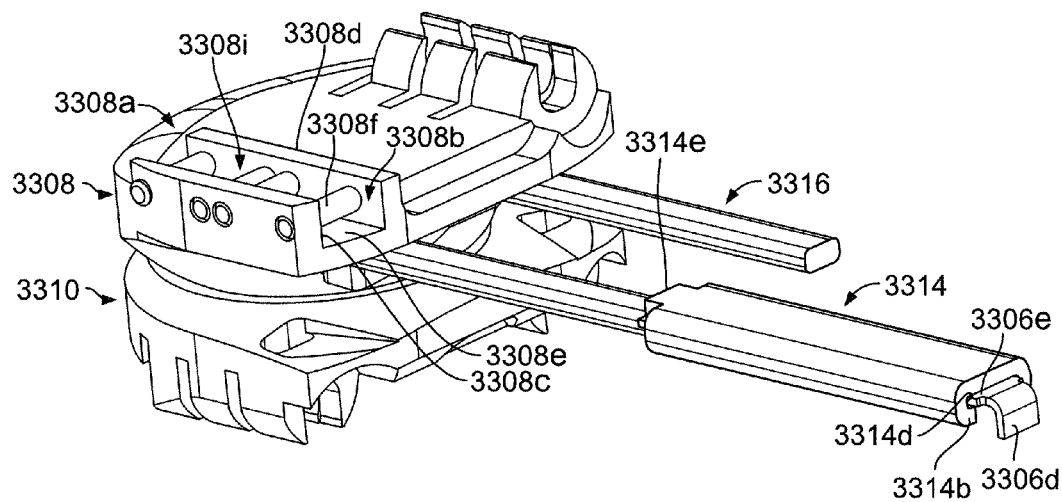
Figure 133:
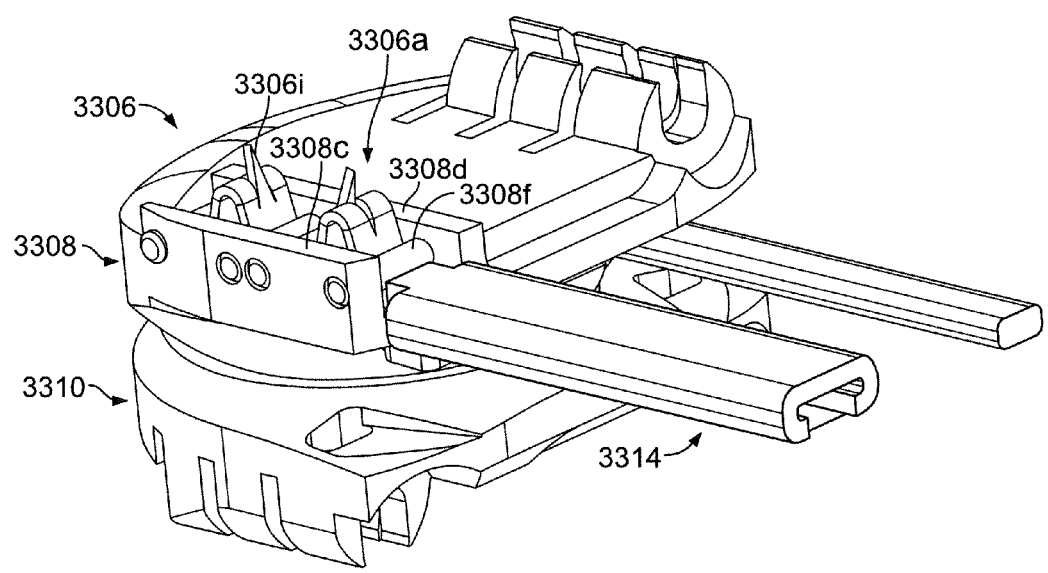
Figure 134:
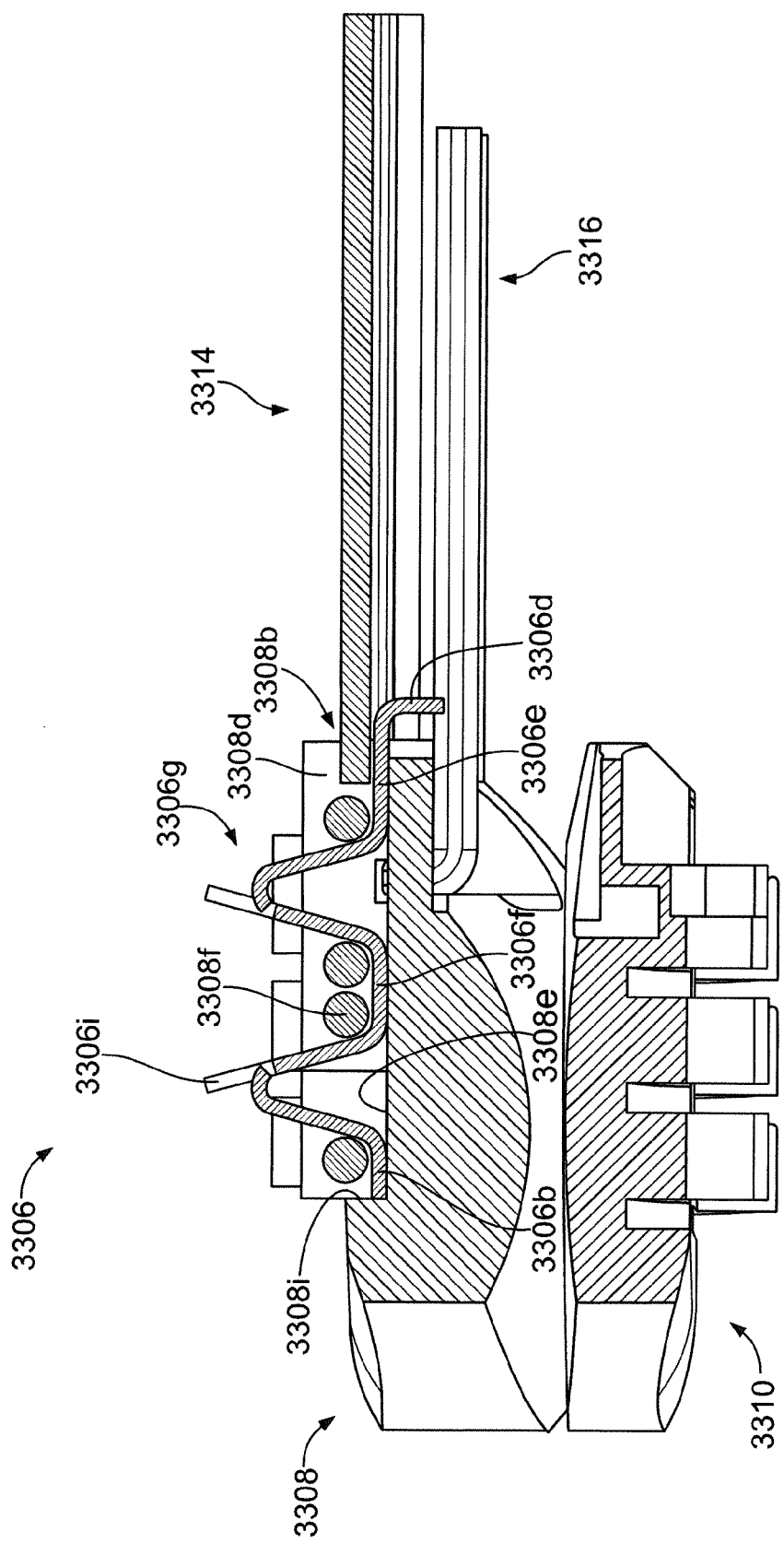

FIG. 129 is an anterolateral perspective view of the intervertebral implant of FIG. 127 showing the deployable securing member in a deployed configuration with the elongate actuating member inserted into the implant body;

FIG. 130 is a posterolateral perspective view of the implant of FIG. 127;

FIG. 131 is a partially exploded anterolateral perspective view of an alternate embodiment of an intervertebral implant with a securing member according to the present invention illustrating the securing member in a deployed and an undeployed configuration, a securing member inserter, and a pair of prongs used for inserting the implant into the intervertebral space;

FIG. 132 is an anterolateral perspective view of the intervertebral implant of FIG. 131 illustrating the securing member disposed within the securing member inserter;

FIG. 133 is an anterolateral perspective view of the implant of FIG. 131 illustrating the securing member in a deployed configuration; and FIG. 134 is a lateral cross-section along an anterior-posterior axis of the implant of FIG. 131 illustrating the securing member in a deployed configuration.

DETAILED DESCRIPTION OF PREFERRED EMBODIMENTS

In a preferred embodiment, such as illustrated in FIGS. 1-4, an artificial disc device 001 comprises an upper shell 100 and lower shell 110. The upper shell 100 comprises a substantially concave recess portion 120, and the lower shell 110 comprises a substantially convex portion 130. Although not preferred, the concave and convex portions may be switched such that the upper shell 100 may alternatively comprise the convex portion 130.

Figure 1:
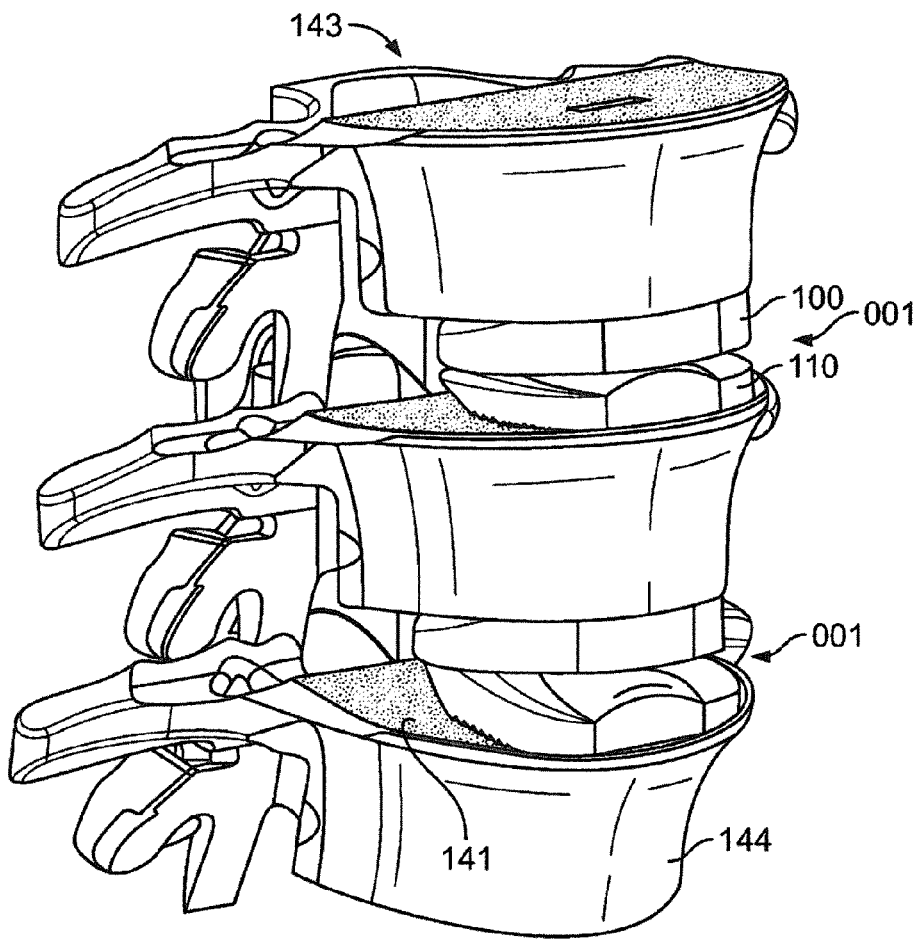
FIG. 1 is a perspective view of an anterior portion of the spine with two implants according to the present invention disposed within the intervertebral spaces.
Figure 2:
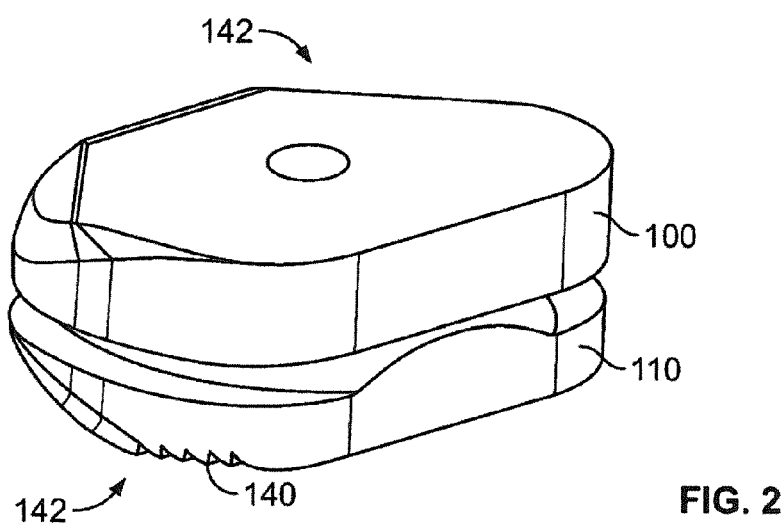
FIG. 2 is an anterolateral perspective view of an implant according to the present invention.
Figure 3:
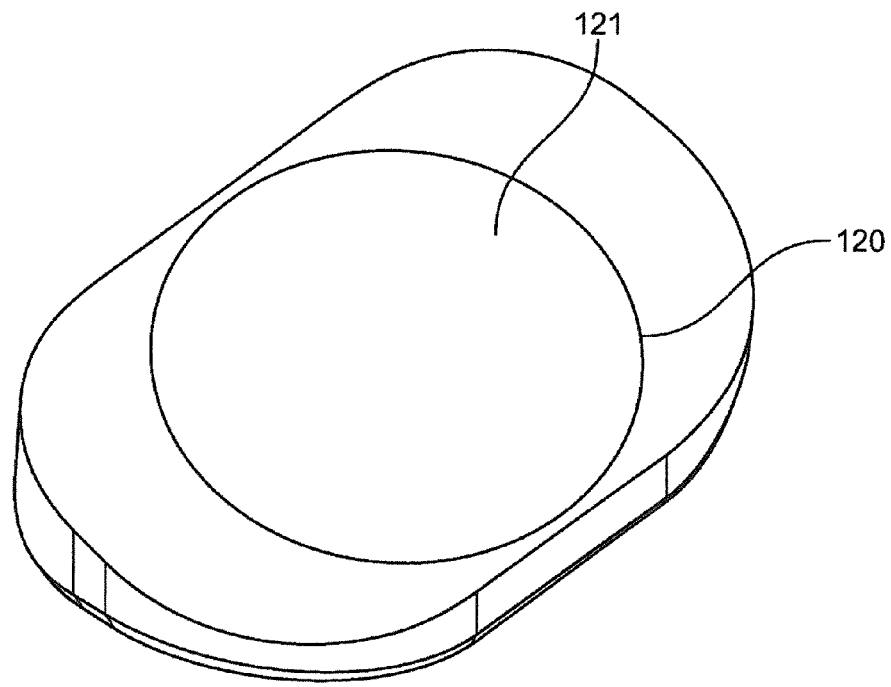
FIG. 3 is a perspective view of one part of a motion preserving implant with a concave articulation surface according to the present invention.
Figure 4:
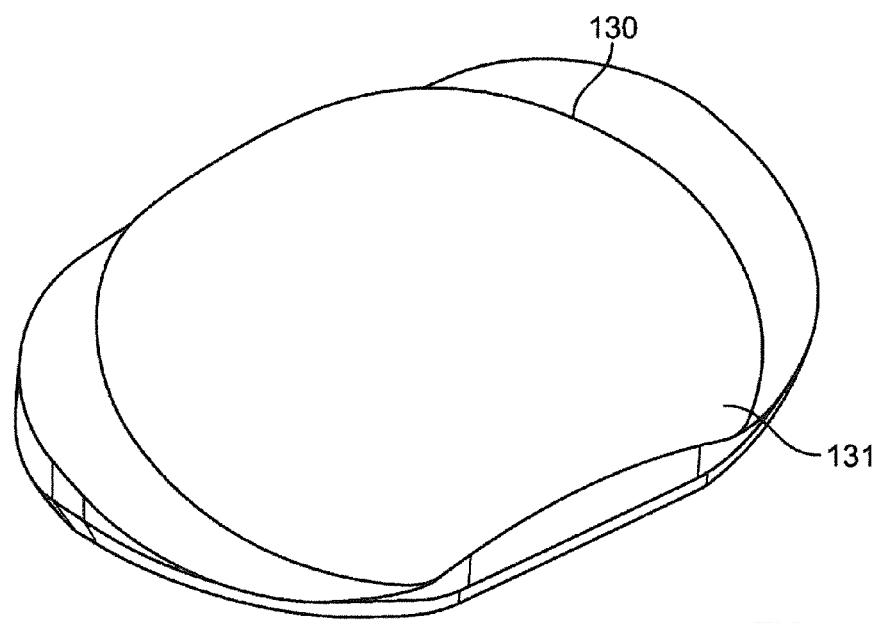
FIG. 4 is a perspective view of a corresponding part of the motion preserving implant of FIG. 3 with a convex articulation surface according to the present invention.

The convex portion 130 comprises a convex articulation surface 131, and the concave portion 120 comprises a concave articulation surface 121. It is preferred that the articulation surfaces 121 and 131 have substantially matching geometries or radiuses of curvature although some mismatch of curvature may be desired to provide a combination of rolling and sliding motion to occur between the articulation surfaces 120 and 121. The geometries may be complex in nature but preferably are ball and socket style. The convex portion 130 and concave portion 120 may extend substantially to the outer perimeter of the shell 100, 110 as illustrated in FIG. 4, or may be formed, typically with a smaller radius of curvature inward a predetermined distance from the outer perimeter of the shell 100, 110. Each shell 100, 110 is preferably manufactured from PEEK or fiber reinforced PEEK or other biocompatible polymer combination or radiolucent material demonstrating very low surface wear in high repetition wear testing.

The artificial disc device 001 preferably comprises one or more restraint portion(s) 220 or structure located on one or both of the shell members 100, 110 to help prevent the shells 100, 110 from becoming dislodged or migrating across the boney endplate 141 of the vertebrae 143 after insertion. For example, the restraining portion 220 may be located on one of the shells 100, 110 on the endplate facing surface 142 in the form of directional teeth 140.

It is preferred that the footprint of the artificial disc device 001 be similar to the footprint of the endplate although generally smaller to fit within the intervertebral space. The endplate facing surfaces 142 are preferably contoured to match the contour of the endplates 141. For example, if the surgeon prepares the endplates to be flat, it is preferred that the endplate facing surfaces 142 are also flat. Likewise, if the endplates 141 are prepared to be concave, it is preferred that the endplate facing surfaces 142 are similarly convex. It should be noted that endplates 141 that are concave will generally retain the artificial disc device 001 better since the device 001 becomes cupped between the vertebrae.

Additional restraining features may be needed to assist holding the artificial disc device 001 in the predetermined position. Described in this application are various securing mechanisms, coatings, or surface preparations that can be used on the endplate facing surfaces 142 to restrain an implant.

Figure 5:
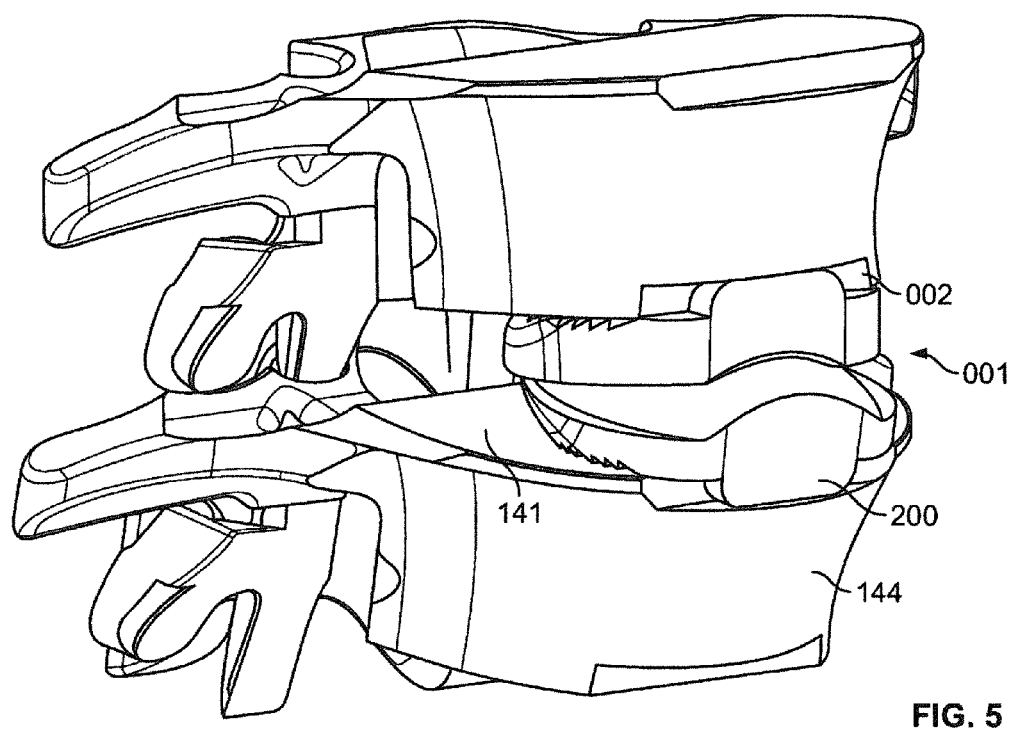
FIG. 5 is an anterolateral perspective view of an implant with securing means according to the present invention implanted within the intervertebral space.

An additional embodiment of a restraint is illustrated in the artificial disc device 001 shown in FIG. 5. In this embodiment, the surgeon may choose to form a recess 002 in the anterior edge of the facing upper and lower vertebrae to accommodate the restraint boss 200. The restraint boss 200 is preferably an extended wall or lip from the endplate facing surface 142 and is of a thickness suitable to block further posterior motion. If the recess 002 is suitably formed into a pocket, the restraint boss 200 will also assist in unwanted lateral motion of the shell 100 or 110. Alternatively, the restraint boss may sit on the anterior bone surface of the vertebral body without the recess 002. The restraint boss 200 may be included on one or both of the shells 100, 110.

Upon insertion of the artificial disc device 001, the restraint boss 200 acts as a stop to the shell 100, 110 as it is guided to the predetermined position. The boss 200 also assures the device is unable to migrate posteriorly towards the spinal cord and cause injury. It is preferred the recess 002 is generally the thickness of the boss 200 such that the boss 200 may be generally flush with the anterior surface of the vertebral body 144.

Figure 6:
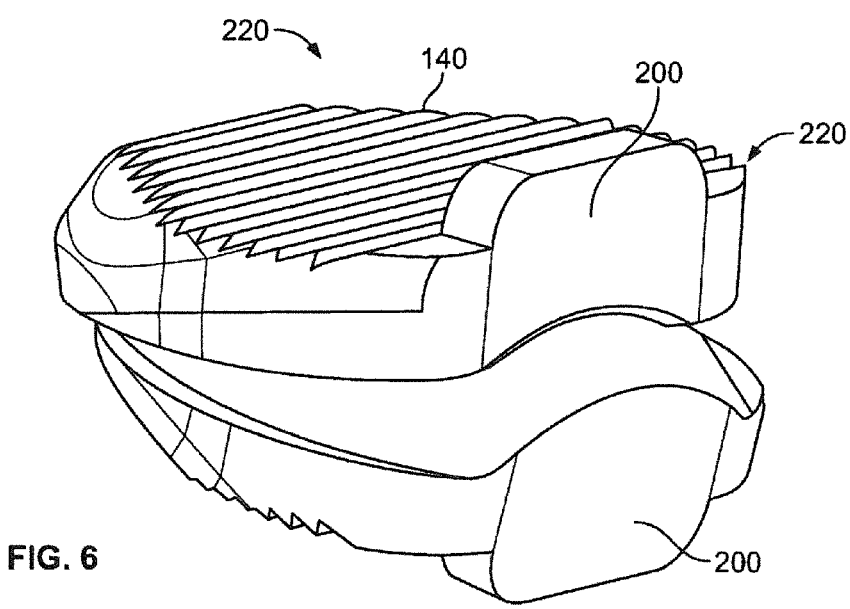
FIG. 6 is an anterolateral perspective view of an implant with securing means according to the present invention.
Figure 6A:
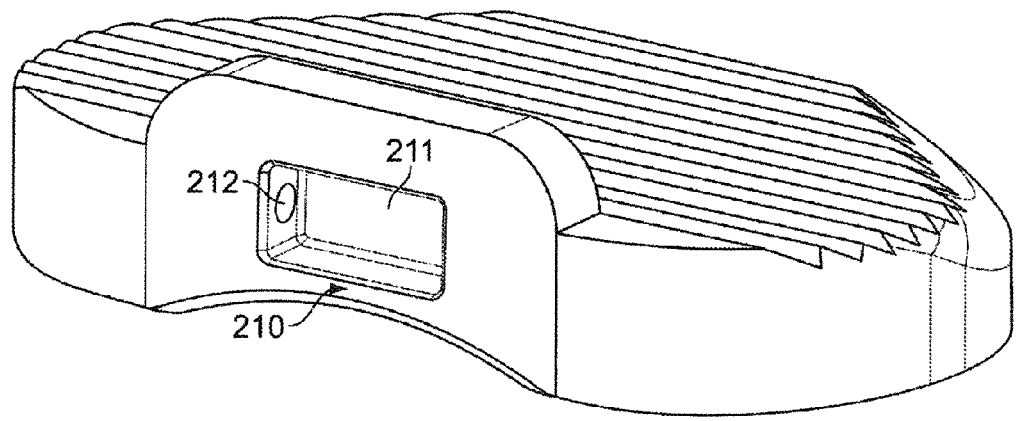
FIG. 6A is an anterolateral perspective view of an implant component with securing means and inserter tool docking means according to the present invention.
Figure 7:
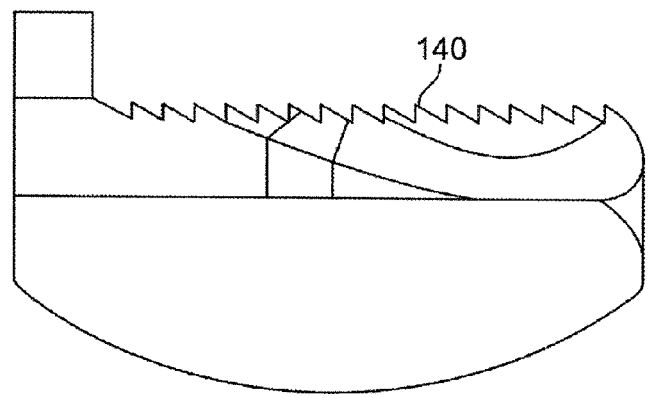
FIG. 7 is a side view of an implant component with securing means according to the present invention.

The shell 100, 110 preferably includes an attachment portion 210 which may be in the form of a boss, hole, post, recess, ridge, flange or other structure for securing of an implant insertion or removal instrument to assist with inserting or removing the implant from the intervertebral space. For example, in the embodiment in FIG. 6A, the attachment portion 210 comprises a window 211 for insertion of the head of an insertion or removal instrument and connection holes 212 for occupation by deployable pins on each end of the window 211 situated in the instrument.

As described earlier, the restraint portion 220 on the endplate facing surfaces 142 may be in the form of directional teeth 140 which are angled like saw teeth to encourage eased insertion across the boney endplate 141 and resist anterior migration to help retain the shell members 100, 110 in the predetermined location between the intervertebral bodies. The actual form of the restraint portion 220, i.e. directional teeth 140 or a surface coating, may be found on one or both shell 100, 110 members. The restraint portion 220 may include different forms of restraint on each shell 100, 110. In addition, more than one form of restraint may be used on each restraining portion 220. For example, the shell 100 may include a restraint portion 220 which comprises both directional teeth 140 with an osteo-conductive surface coating such as hydroxyapatite.

The shell 100, 110 may include apertures for the placement of fasteners such as bone screws to secure the shell 100, 110 to the endplate 141 after insertion. It is preferable that the fasteners are also manufactured from a radiolucent material such as PEEK, however the surgeon may choose to use fasters made of a biocompatible metal such as from the family of titaniums or stainless steels. It is preferable that these apertures are counter bored when possible to reduce the profile of the screw head outside the periphery of the shell 100, 110. If the device is equipped with a restraint boss 200, the anterior facing surface of this boss is a preferred location for these apertures 520 wherein the apertures 520 are preferably directed towards the center of the vertebral body.

Figure 16:
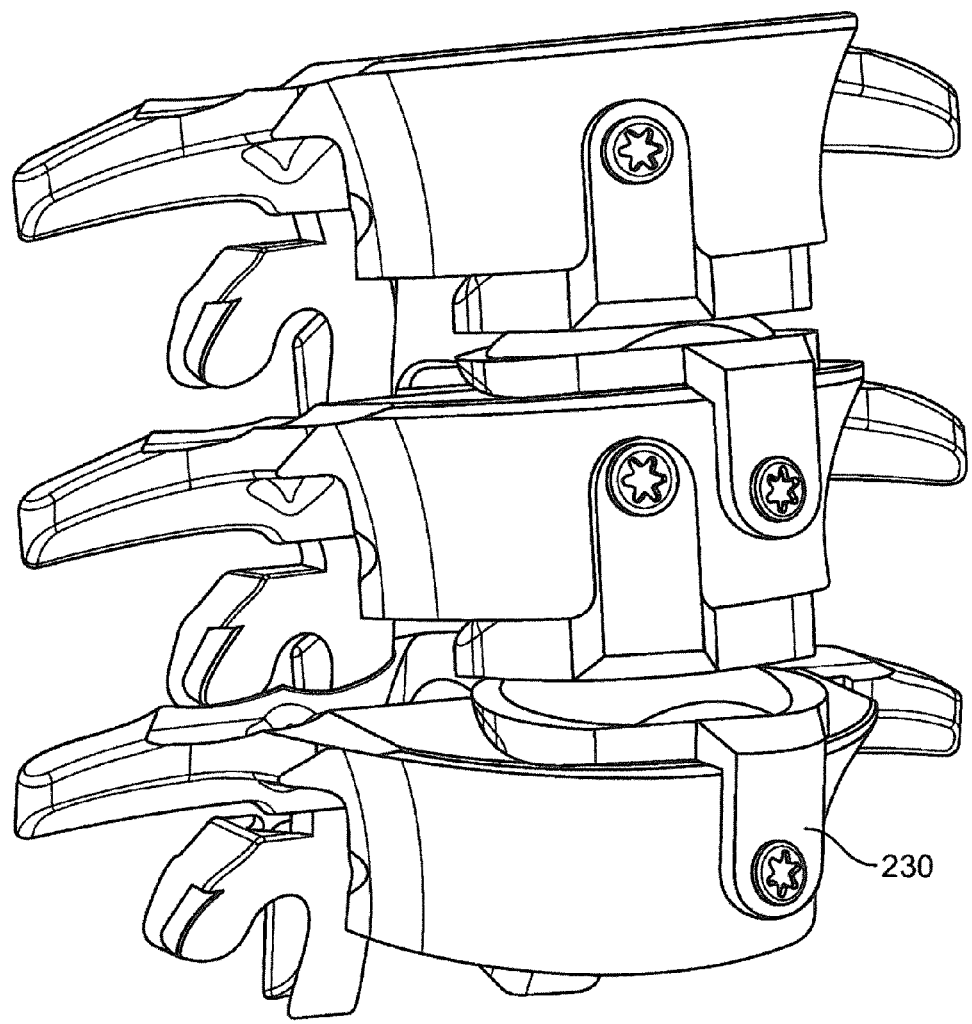
FIG. 16 is an anterolateral perspective view of two implants with securing mechanisms according to the present invention implanted within the intervertebral space.
Figure 17:
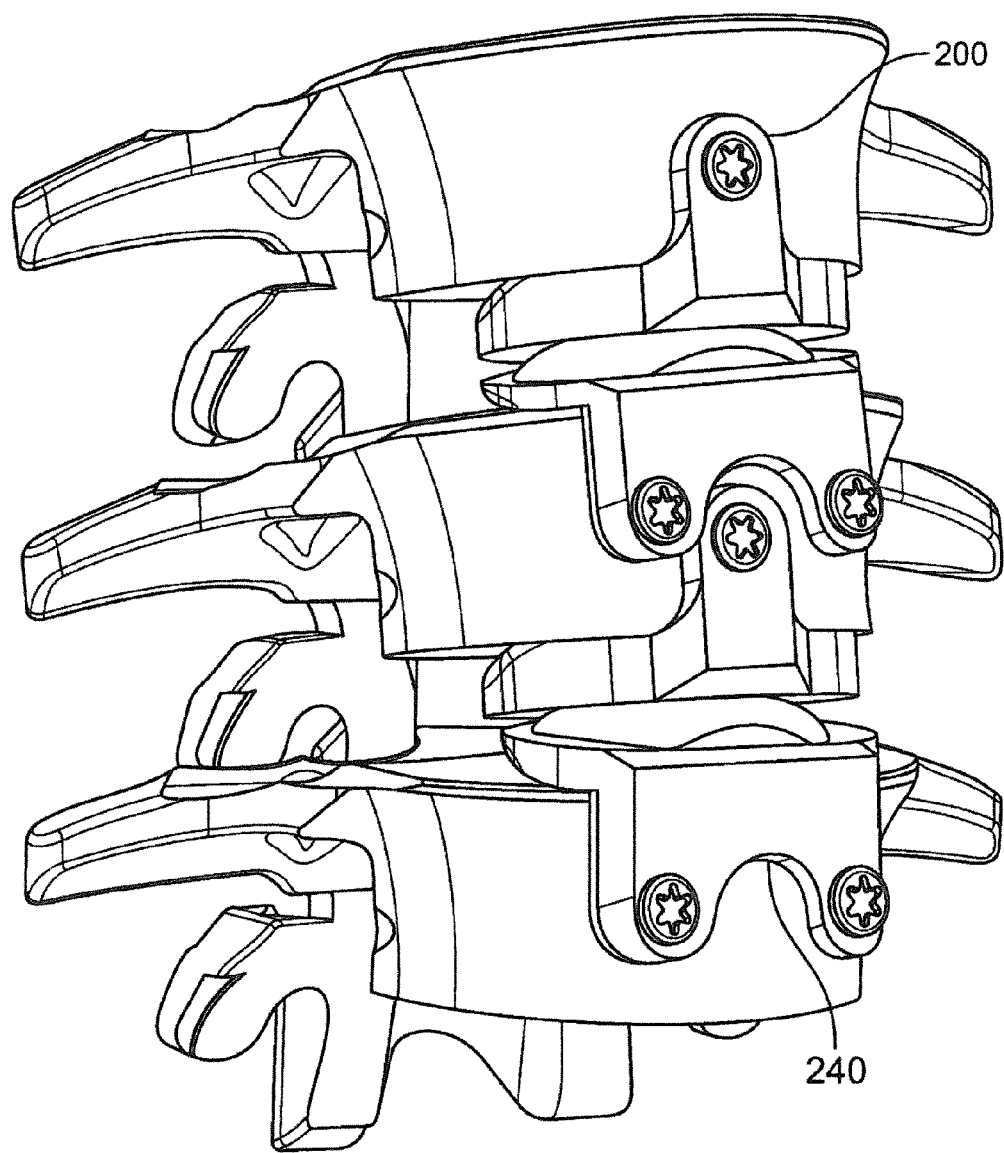
FIG. 17 is an anterolateral perspective view of two implants with securing mechanisms according to the present invention implanted within the intervertebral space.
Figure 18:
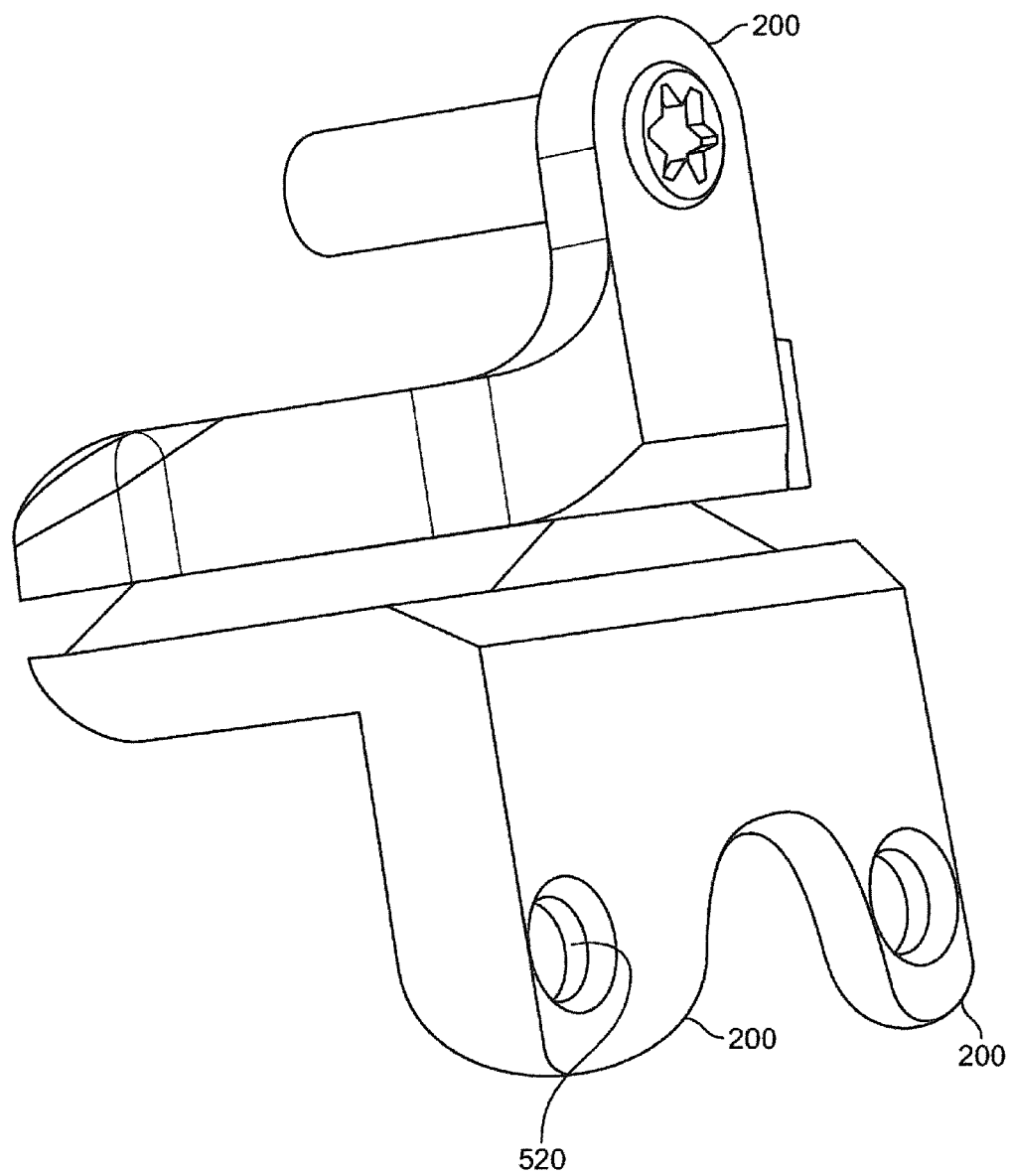
FIG. 18 is an anterolateral perspective view of the implant of FIG. 17.

In some forms, the restraint boss 200 may be offset to the left or the right as illustrated in FIG. 16. In this fashion, the artificial disc device 001 can be utilized at multiple adjacent vertebral levels without interference of an adjacent restraint boss 200. Similarly, the restraint boss 200 may be contoured to accommodate an adjacent restraint boss 200 through a boss recess 240. Again, this orientation provides utilization of the artificial disc device at multiple adjacent vertebral levels without interference of an adjacent restraint boss 200. FIG. 18 further illustrates this embodiment.

In other forms, the restraint boss 200 may not be integral to the shell 100, 110. Instead the boss 200 may be configured as a small plate, fastened to the anterior surface of the vertebral body and extending just past the endplate to block back-out of the shell 100, 110 and lateral movement of the shell 100, 110 if the boss 200 is so equipped with interlocking geometry. Further, the disc device may be blocked from backing out by a broad flexible mesh, preferably made of a polymer such as PEEK, fastened from the anterior surface of one vertebral body to the other.

Figure 8:
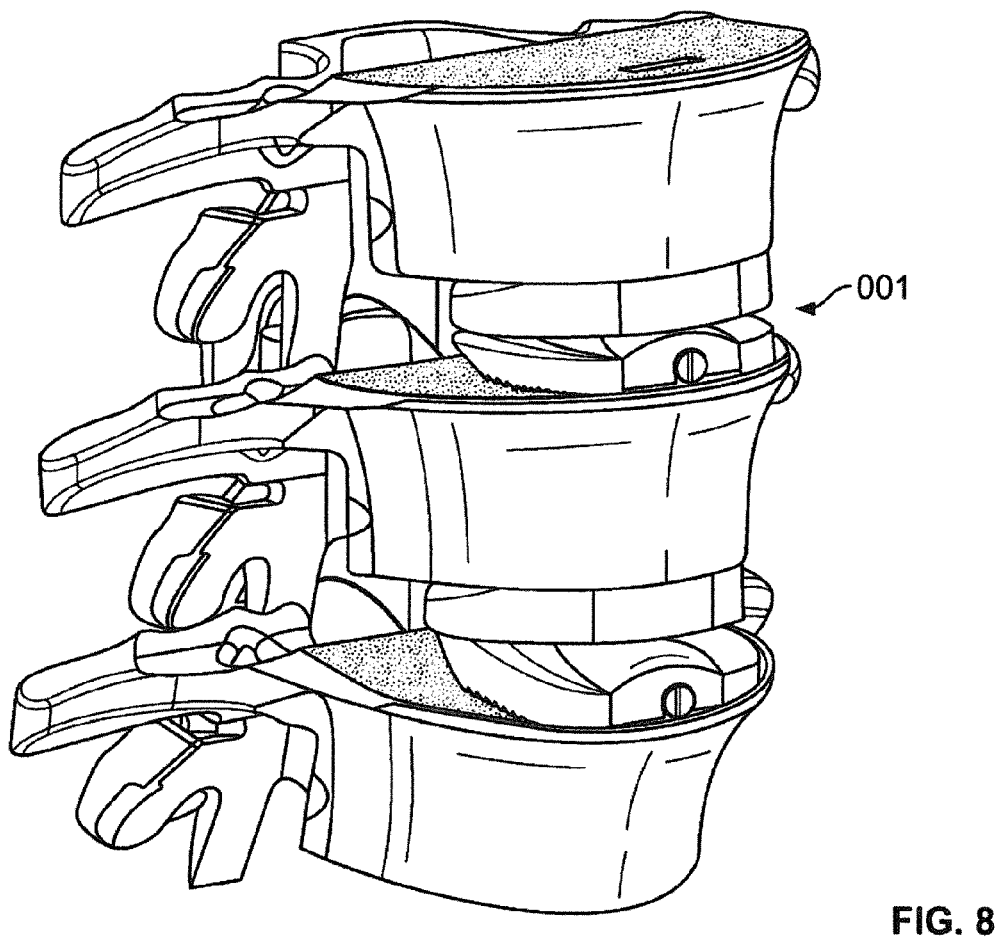
FIG. 8 is an anterolateral perspective view of an implant with a securing mechanism according to the present invention implanted within the intervertebral space.
Figure 9:
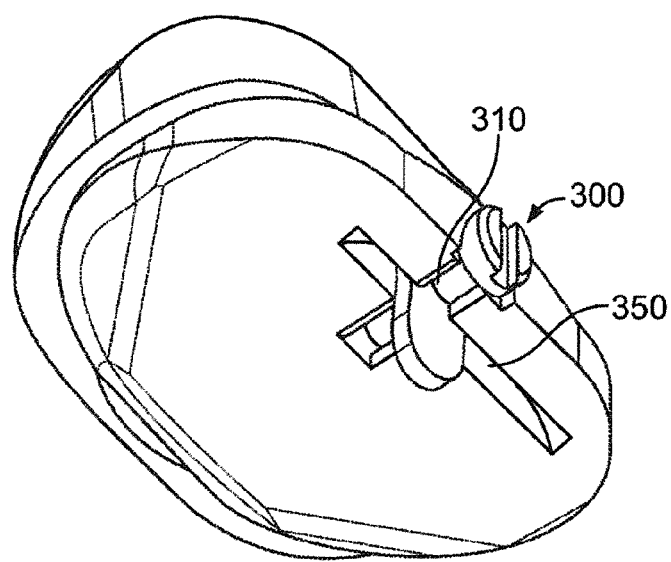
FIG. 9 is a perspective view of a bearing surface of an implant component with a securing mechanism according to the present invention.
Figure 10:
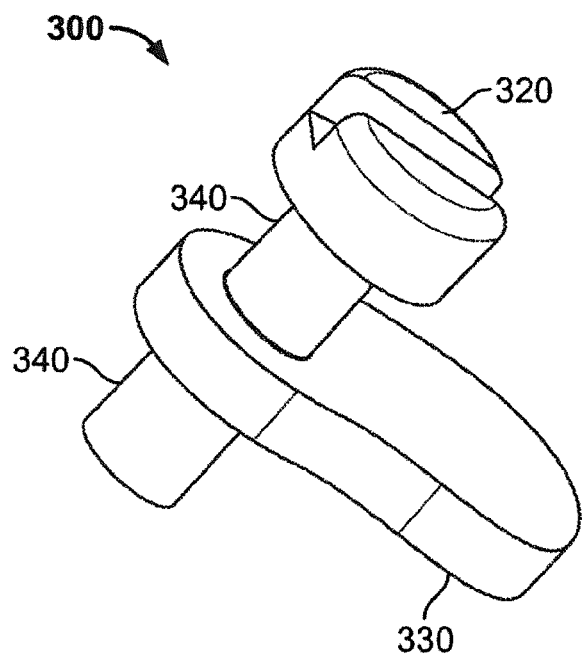
FIG. 10 is a perspective view of a securing component in the form of a deployable paddle or cam according to the present invention.
Figure 11:
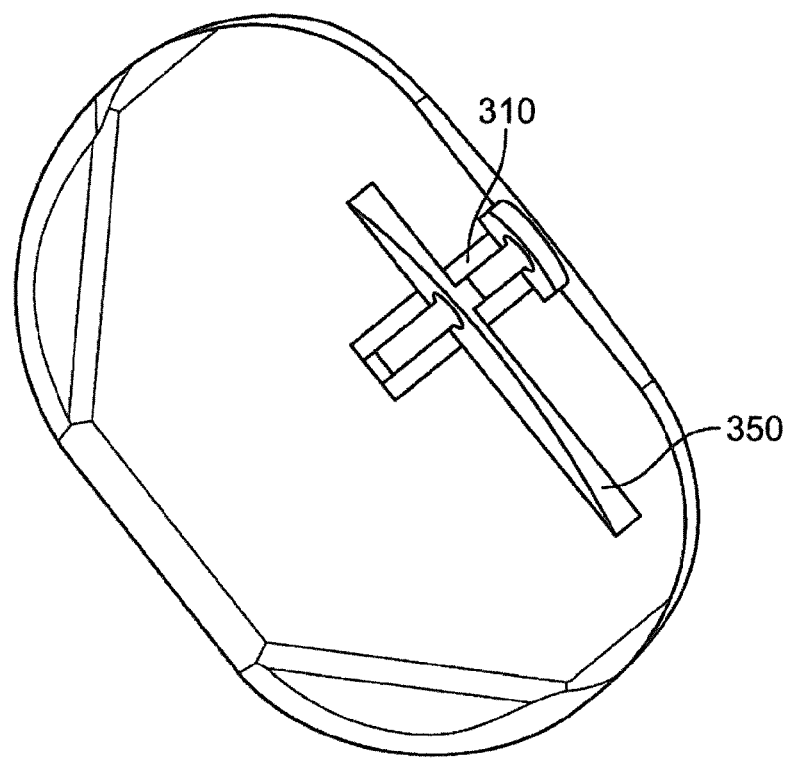
FIG. 11 is a perspective view of a bearing surface of an implant component with a deployable securing mechanism according to the present invention.
Figure 12:
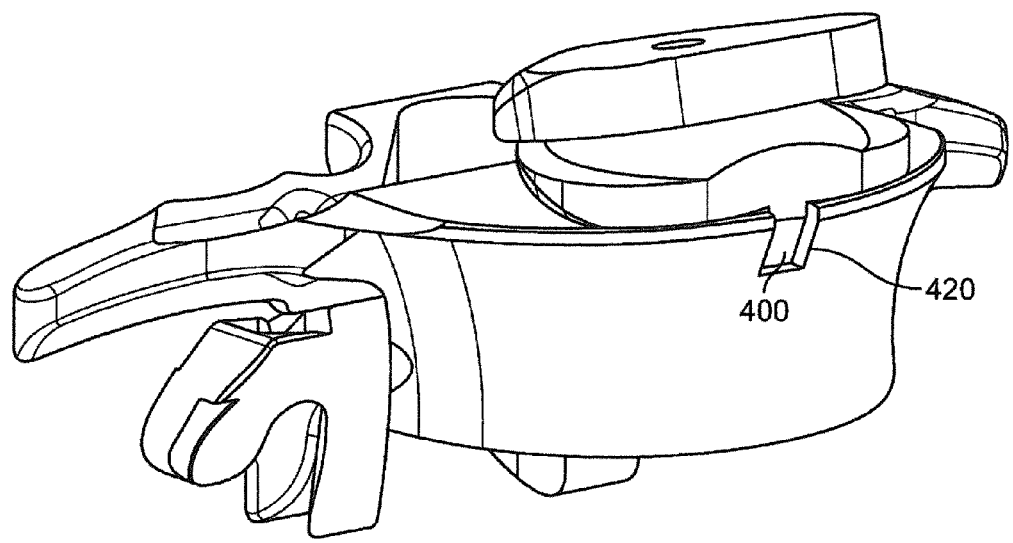
FIG. 12 is an anterolateral perspective view of an implant with a securing mechanism according to the present invention implanted within the intervertebral space.

In an alternative embodiment, the artificial disc device 001 shown in FIG. 8 comprises a restraint portion 220 in the form of a deployable paddle 300. The paddle 300 is housed within one of the shell members 100, 110 as illustrated in FIG. 9. The paddle 300 may be manufactured from an array of biocompatible materials including but not limited to polymers such as PEEK or metals such as titanium or stainless steel alloys although radiolucent materials are preferred. In a preferred orientation, the paddle 300 is secured within the body of a shell 100, 110 by a paddle restraint 310 in this case in the form of a snap joint. The paddle comprises a restraint arm 330 that may be deployed into the endplate 141 of the vertebrae 143 upon rotation of the drive head 320 with the proper instrument. The restraint arm 330 may include a sharpened edge if so desired. The neck portion 340 of the paddle 300 is held by the paddle restraint 310 and is preferably configured with a profile suitable for rotation. The restraint arm 330 may include apertures or slots to encourage bone growth through the restraint arm 330.

The endplate facing surface 142 comprises a restraint recess 350 to accommodate the paddle 300 and the restraint arm 330 during implant insertion. Once the disc device 001 is inserted, the restraint arm 330 may be deployed into the endplate to secure the device 001 in the desired location between the vertebrae. Several of the disclosed embodiments may require the surgeon to prepare the vertebral body 144 to accept restraint portions 220 that are intended to become integrated into the bone. In most cases, this preparation involves removing bone and creating restraint access 420 typically in the form of a recess, channel, slot or profile similar to the restraint feature. Obviously, the size of the restraint portion 220 will affect the size of the restraint access 420. Therefore it is beneficial that restraint portions 220 that interfere with the bone are suitably sized to prevent an oversized restraint access 420 that compromises the vertebrae 143 and risks vertebrae 143 fracture. It is preferable that both the restraint access 420 and restraint portion 220 have radiused edges to reduce stress concentrations in the vertebral body.

Figure 13:
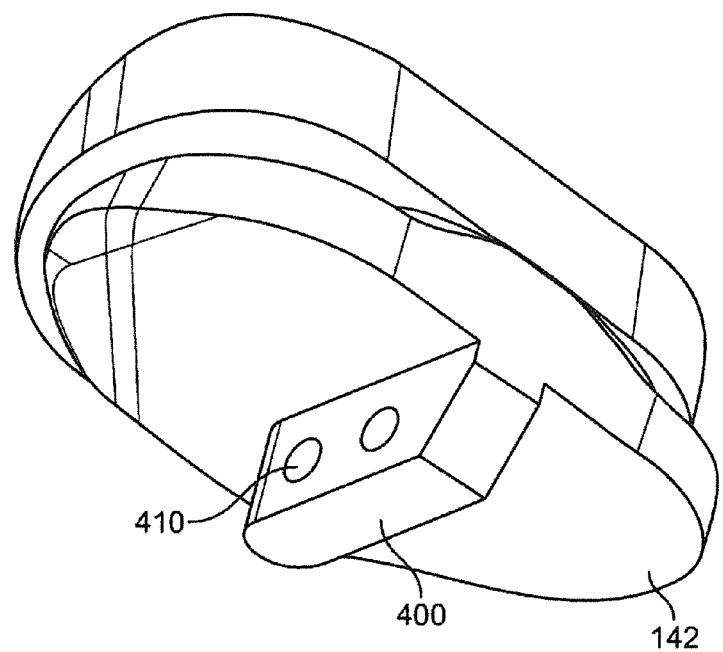
FIG. 13 is a perspective view of an implant with a securing mechanism according to the present invention.
Figure 13A:
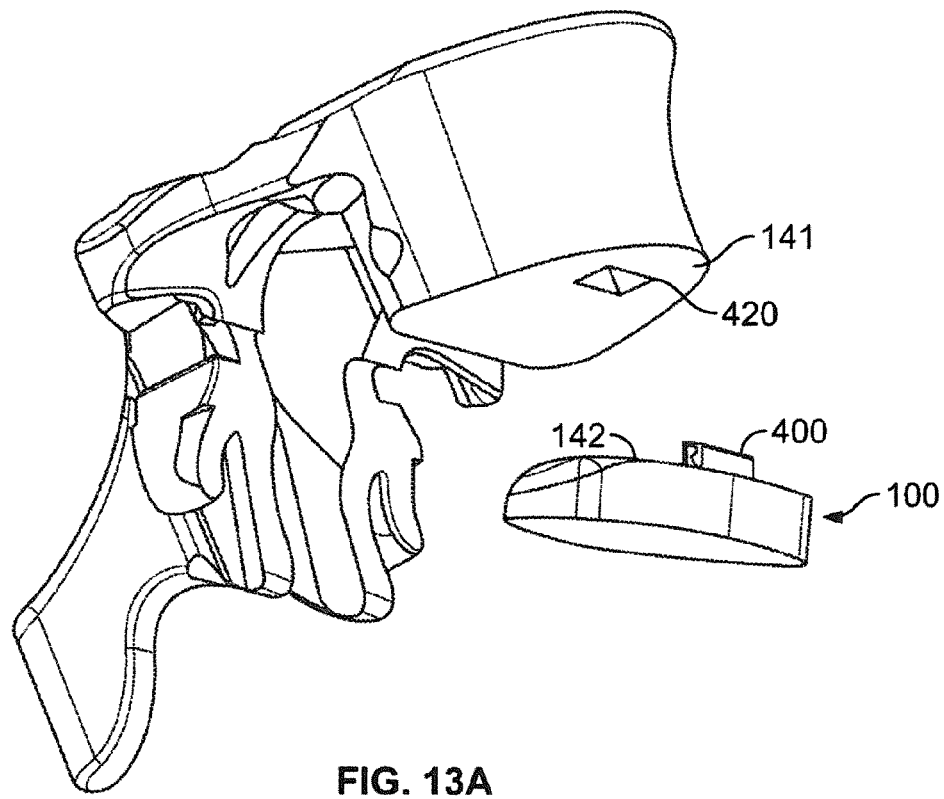
FIG. 13A is a perspective view of an implant component with a securing mechanism according to the present invention shown adjacent a vertebra.
Figure 15:
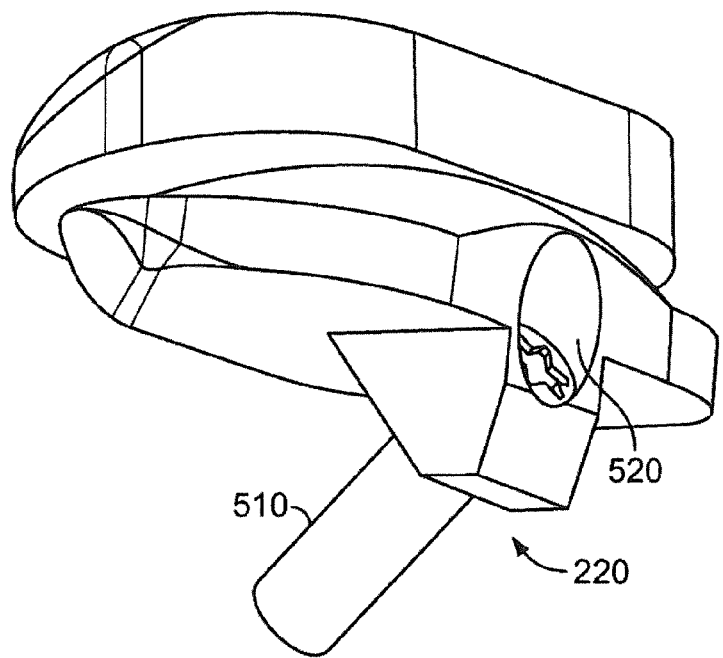
FIG. 15 is an anterolateral perspective view of an implant with a securing mechanism according to the present invention.

In another alternative embodiment, such as shown in FIG. 13, an artificial disc device 001 comprises a restraint portion 220 in the form of an integrated fin 400 extending from the endplate facing surface 142. The fin 400 may vary in thickness and length as needed to assist in restraining the artificial disc device 001 in a predetermined intervertebral position. The fin 400 may include bone growth apertures 410, slots, or other structure to facilitate bone growth through the fin and thereby provide additional restraint to the device. Again, the restraint portion 220 may be found on one or both of the shells 100, 110. Alternatively, although the implant is typically inserted from an anterior to posterior approach, the fin 400 may not necessarily be oriented in this same direction. For example, the fin 400 in FIG. 13A illustrates a fin 400 that extends laterally across the endplate facing surface 142. In this embodiment, a restraint access 420 is also cut laterally across the endplate 141. There is no entry into the restraint access 420 from the peripheral edge of the vertebral body. Therefore, the surgeon may choose to first distract or over stretch the intervertebral space, making room for the addition height of the fin 400 until the fin 400 can fall into the restraint access 420 to secure the implant in the predetermined position. The fin 400 may be equipped with a ramped lead-in wherein the lead-in can be utilized to help distract the vertebrae.

Figure 14:
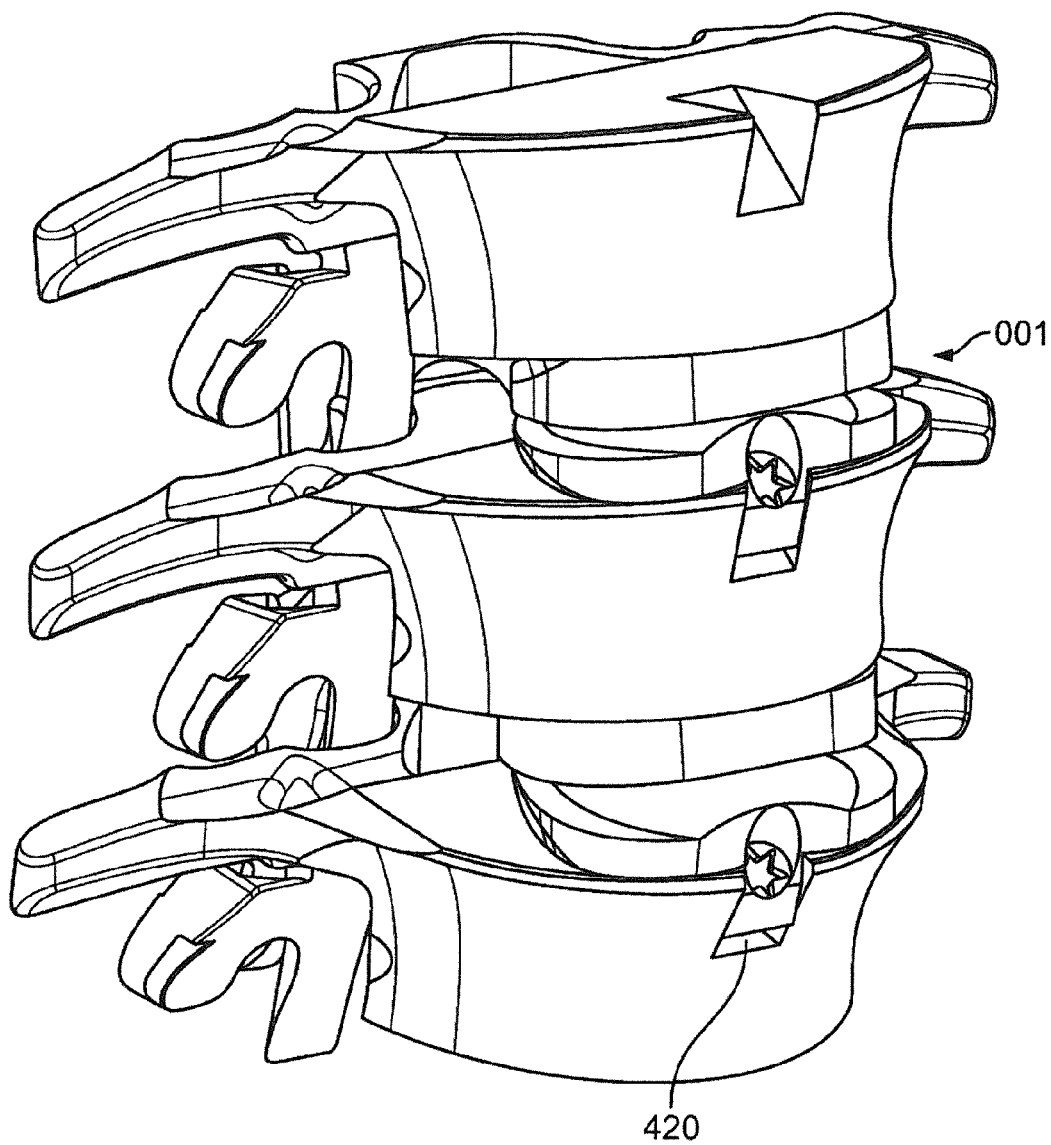
FIG. 14 is an anterolateral perspective view of two implants with a securing mechanism according to the present invention implanted within the intervertebral space.

In an alternative embodiment, the artificial disc device 001 as illustrated in FIG. 14 may comprise a restraint portion 220 in the form of a fin 400 which accommodates a bone fastener 510 therein. It is preferable that the bone fastener 510 is in the form of a bone screw and is manufactured from a radiolucent material such as PEEK, however the surgeon may choose to use bone fasteners 510 made of a biocompatible metal such as from the family of titaniums or stainless steels. It is preferable that the fastener aperture 520 is counter bored when possible to reduce the profile of the screw head outside the periphery of the shell 100, 110. The fastener aperture 520 may include fastener restraint such as an interference spring to prevent fastener 510 back-out. For example, the fastener aperture 520 may have a groove inscribed therein to house a spring that expands out of the way of the fastener 510 while driving the fastener and closes over the head of the fastener once the head passes the spring.

Figure 19:
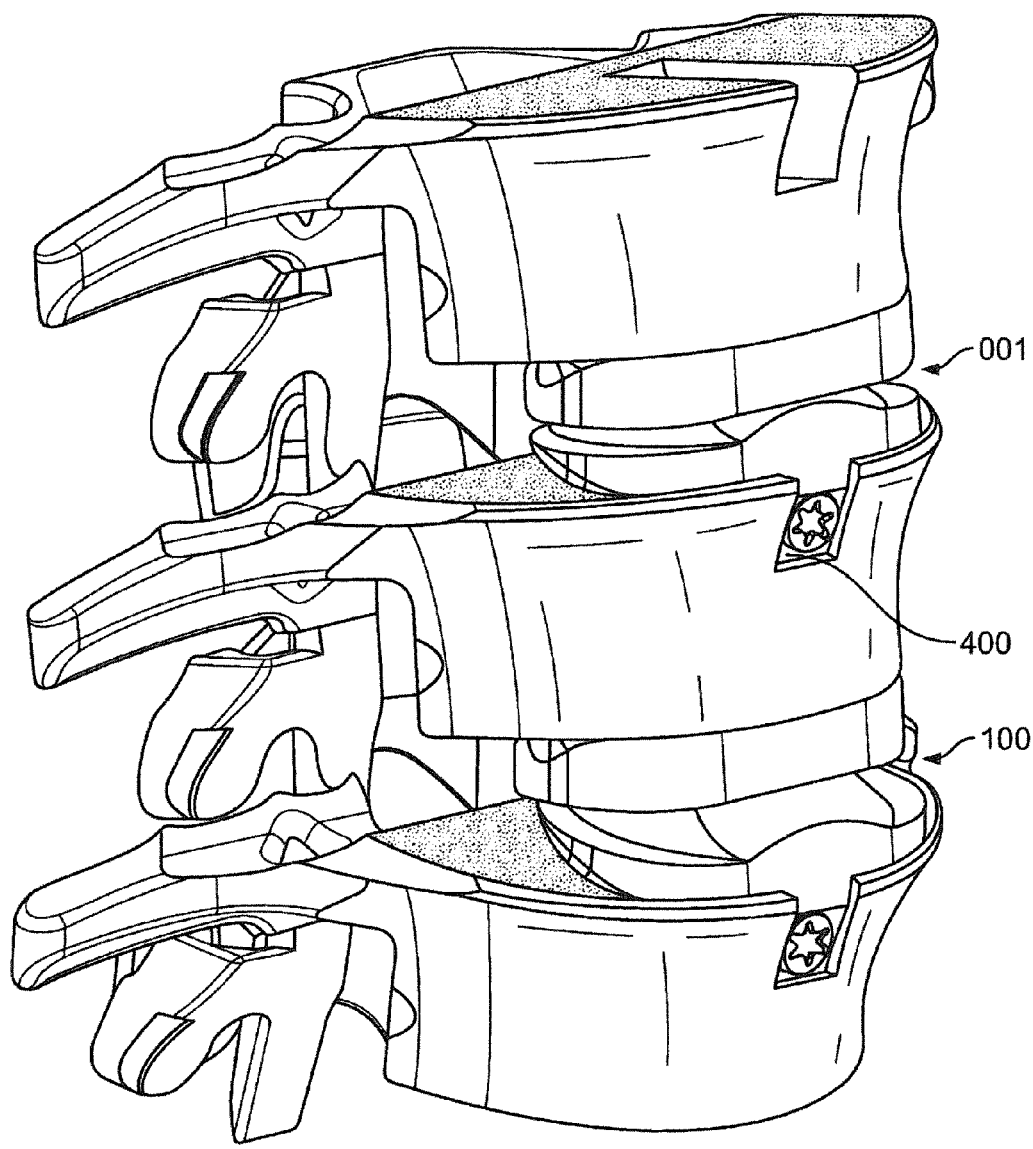
FIG. 19 is an anterolateral perspective view of two implants with securing mechanisms according to the present invention implanted within the intervertebral space.
Figures 20, 21:
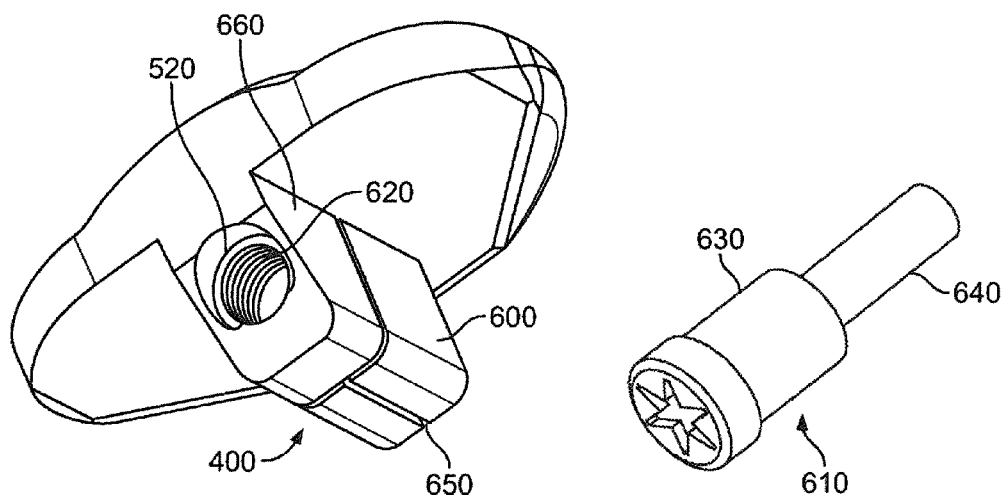
FIG. 20 is a perspective view of the lower implant member of FIG. 19.
FIG. 21 is a perspective view of a fastener implemented in the securing mechanism of FIG. 20.

An additional alternative embodiment of the artificial disc device 001 is illustrated in FIGS. 19-21 and comprises a restraint portion 220 in the form of a fin 400 wherein the fin 400 comprises one or more deflectable wall portions 600. The fin 400 again comprises a fastener aperture 520 to house an expansion fastener 610. In the preferred form, the expansion fastener 610 comprises a threaded shaft 630, to drive the fastener 610 down the aperture 520 when rotated, and an expansion shaft 640 to drive apart the deflectable wall portions 600 as the fastener 610 is driven forward. The aperture 520 in this configuration preferably comprises threads 620 to complement the threaded shaft 630. As the expansion fastener 610 is driven and causes the wall portion 600 to deflect outward a predetermined amount, these wall portions 600 will interfere within the restraint access 420 securely holding the disc device 001 in position. Deflection cuts 650 facilitate the deflection of the wall portion 600 with respect to the fastener block 660. The deflection cuts 650 may be orientated in different directions wherein, for example, the wall portion may deflect laterally along a vertical plane or laterally along a horizontal plane. Since the disc device 001 will typically be inserted from a generally anterior surgical approach, it is preferred that the fin 400 also be orientated generally anterior to posterior.

Figure 22:
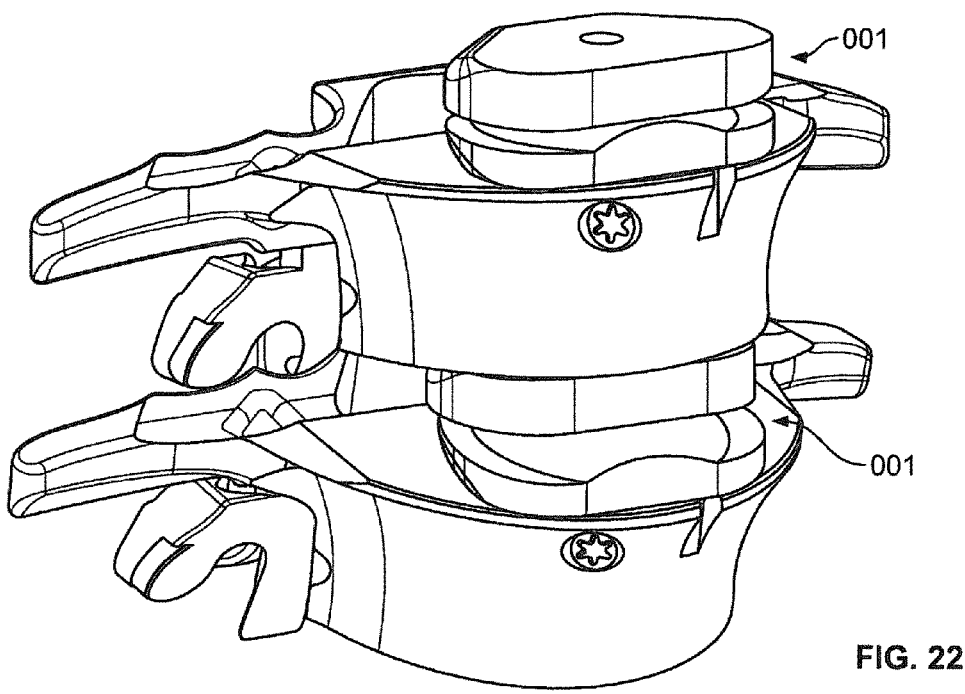
FIG. 22 is an anterolateral perspective view of two implants with securing mechanisms according to the present invention implanted within the intervertebral space.
Figure 23:
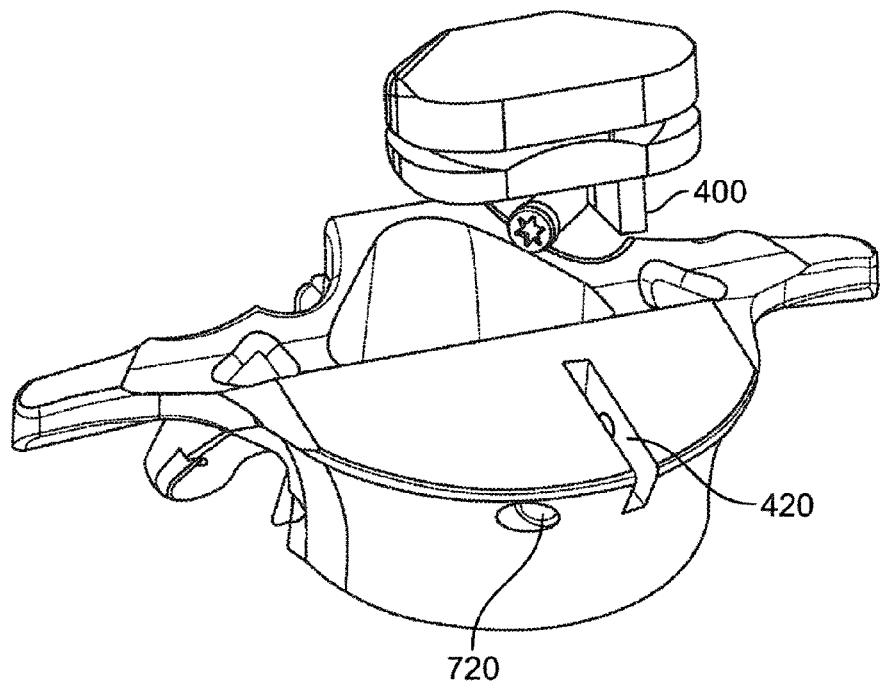
FIG. 23 is an anterolateral perspective view of the implant of FIG. 22 adjacent a vertebrae having a groove and angled bore formed therein for engaging with the securing mechanism.
Figure 24:
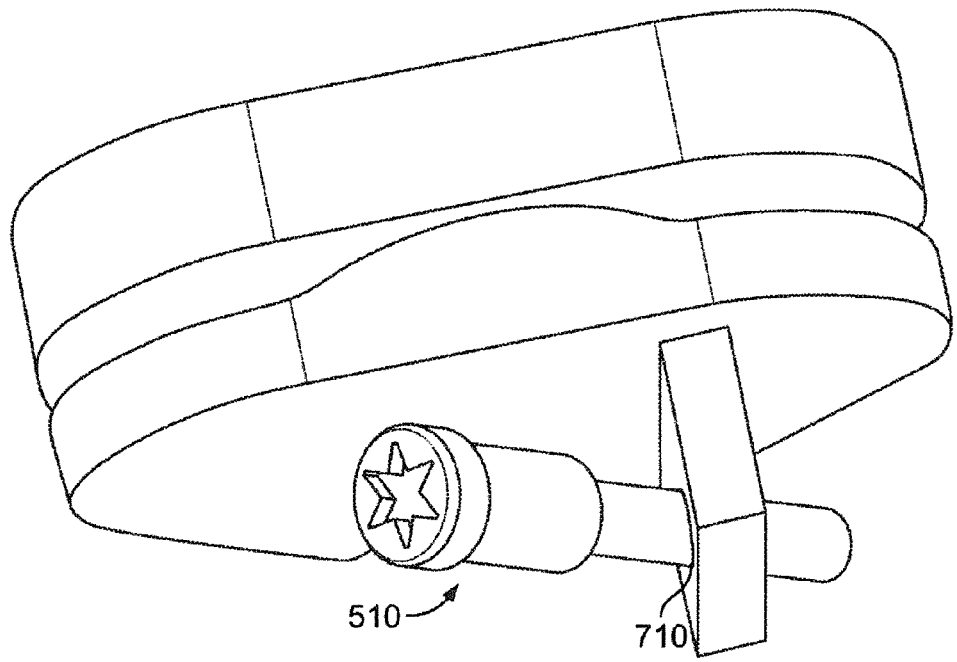
FIG. 24 is a perspective view of the implant of FIG. 22.

Another embodiment of an artificial disc device 001 is illustrated in FIGS. 22-24 and comprises a restraint portion 220 in the form of a fin 400. The fin 400 in this embodiment is preferably laterally offset to one side or the other. The fin 400 preferably comprises an interference portion 710, typically in the form of a threaded or unthreaded hole or recess. After the shell 100, 110 having this feature is inserted into the predetermined position, an alignment instrument (not shown), comprising a drill guide orientated to the implant may be utilized to create a pilot hole 720 through the vertebrae that is directed at the interference portion 710. A bone fastener 510, preferably in the form of a bone screw, is then driven into the pilot hole 720, and in interfering relation with the interference portion 710, secures the disc device 001 in a predetermined position. The fastener 510 in this embodiment is preferably threaded where it contacts the bone, and may interfere with the fin 400 by threading through it, extending through it, abutting it, or any other interference method. In embodiments wherein a fastener 510 is threaded or otherwise engaged into a deformable implant material, (i.e. an implant manufactured from PEEK), the material itself may serve as adequate protection against fastener 510 back-out.

Figure 25:
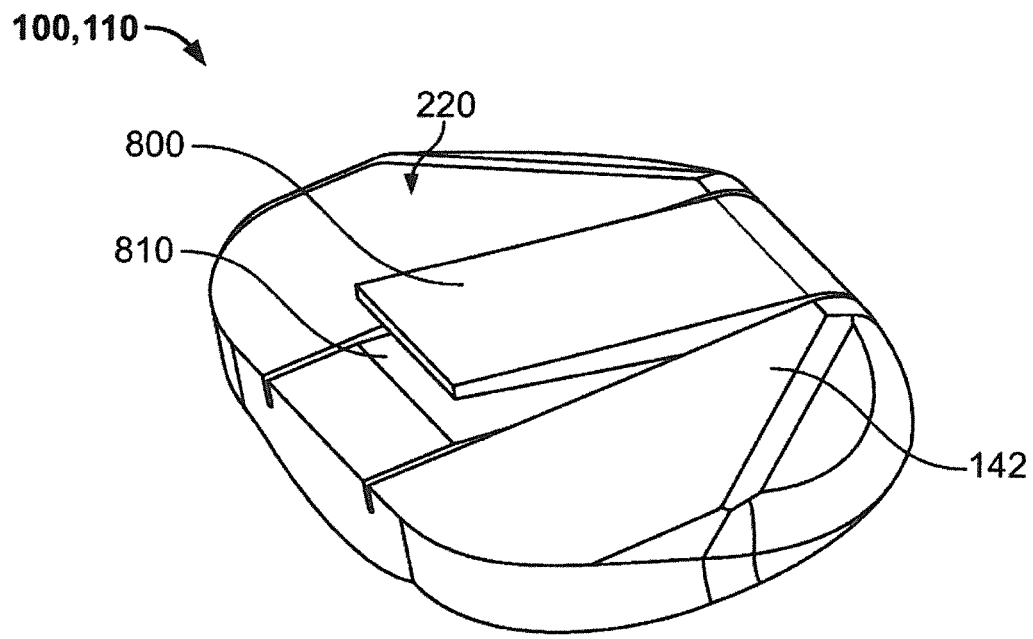
FIG. 25 is an anterolateral perspective view of an implant member with a deflectable stop according to the present invention.
Figure 26:
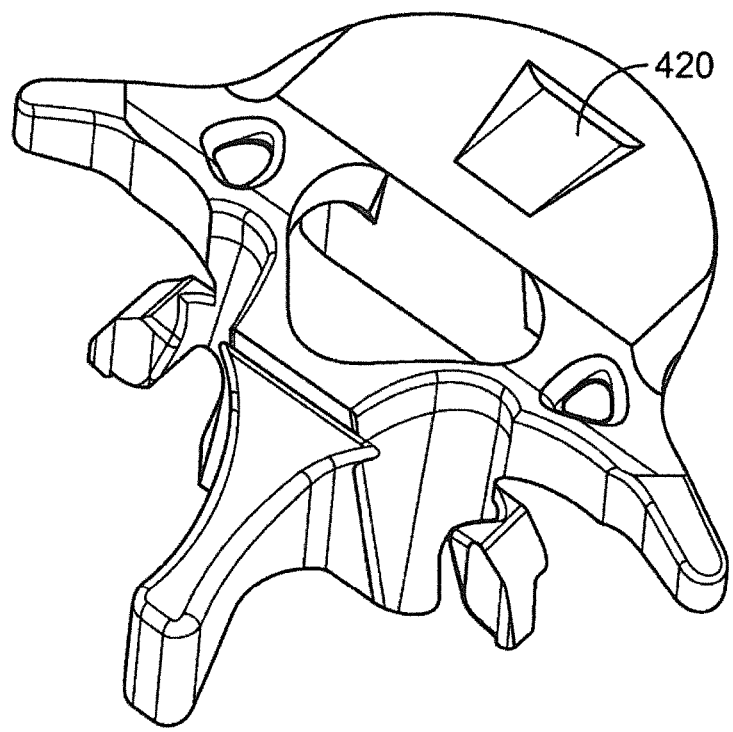
FIG. 26 is a posterolateral perspective view of a vertebrae with a formed recess for engaging with the deflectable stop of FIG. 25.

In an alternative embodiment, a shell 100, 110 is illustrated in FIG. 25 comprising a restraint portion 220 in the form of a deflectable stop 800. The deflectable stop 800 is preferably integrated into the endplate facing surface 142 adjacent the posterior end of the shell 100, 110. In the undeflected orientation and from this point of integration, the deflectable stop 800 gradually extends anterior and away from the endplate facing surface 142. As the shell 100, 110 is inserted between the vertebrae, the deflectable stop 800 may deflect into the stop recess 810 as the shell passes over the complementary profiled restraint access 420 created by the surgeon as illustrated in FIG. 26. Once the shell 100, 110 is positioned in its predetermined location, the deflectable stop 800, and the restraint access 420 are aligned such that the stop 800 will spring back into the restraint access 420 securely retaining the shell 100, 110 in position.

Figure 27:
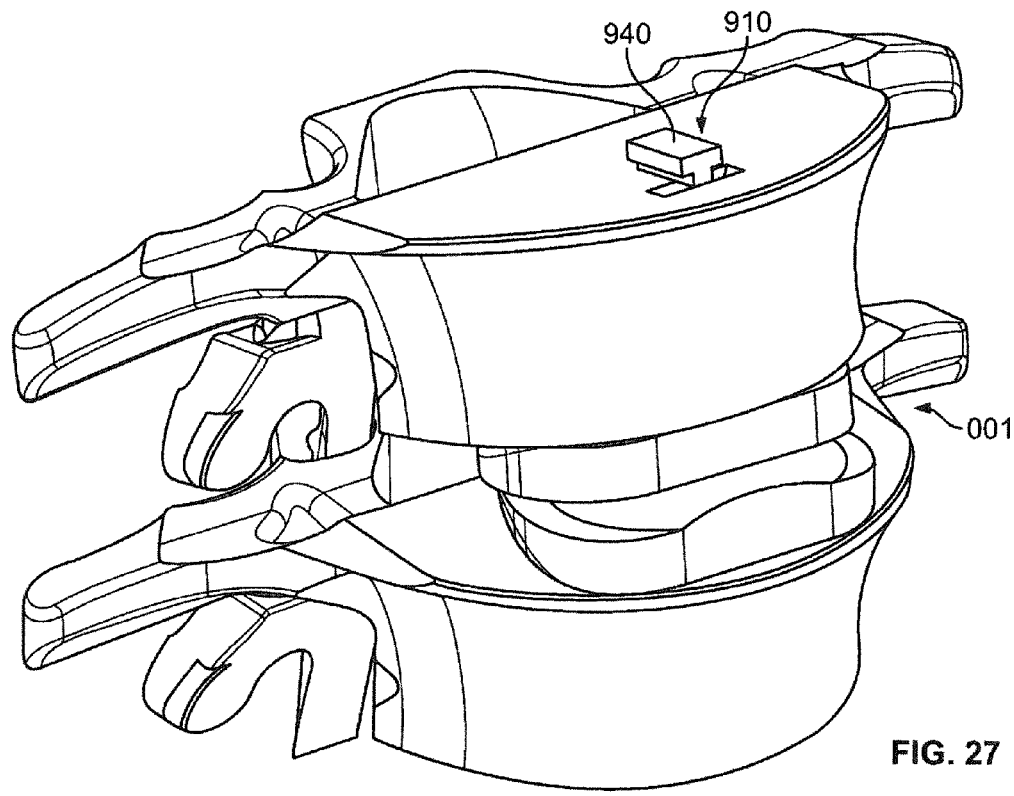
FIG. 27 is an anterolateral perspective view of an implant with a securing mechanism according to the present invention implanted within the intervertebral space.
Figure 28:
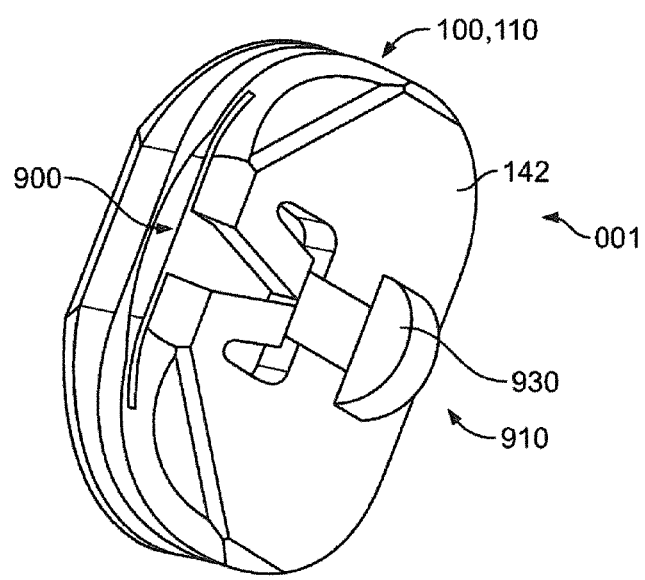
FIG. 28 is a perspective view of the implant of FIG. 27.
Figure 29:
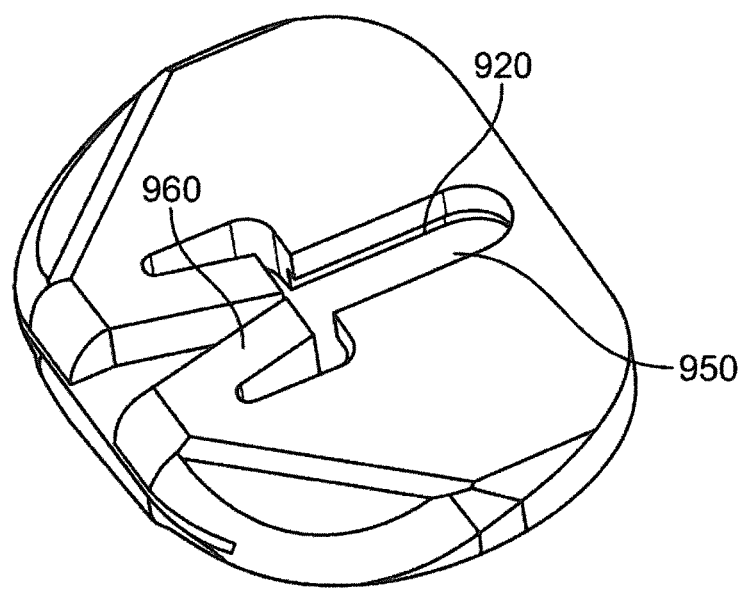
FIG. 29 is a perspective view of an implant member of the implant of FIG. 27.
Figure 30:
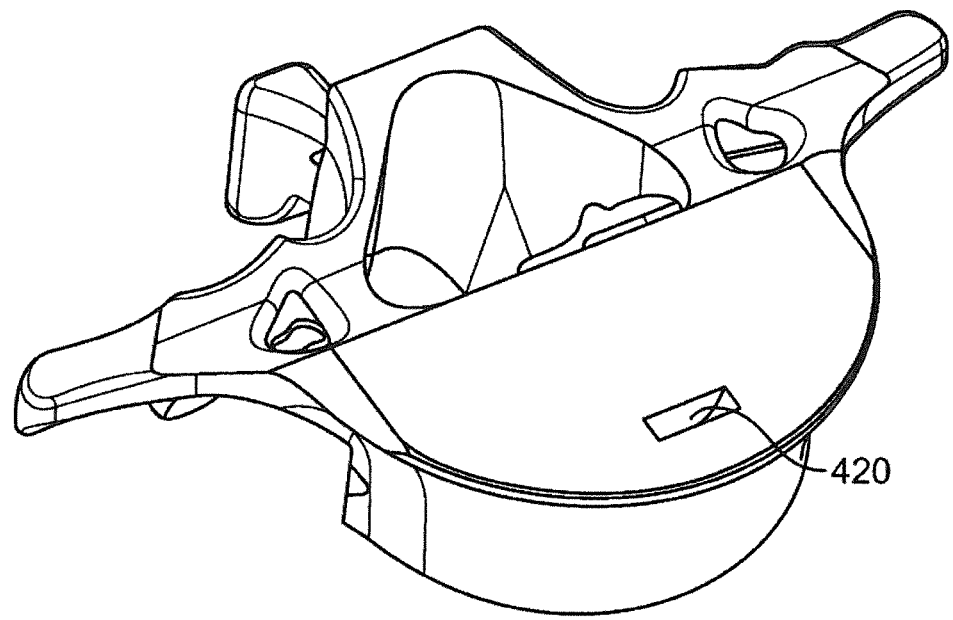
FIG. 30 is an anterolateral perspective view of a vertebra with a formed recess for interacting with a securing mechanism.

Similarly, and in a further alternative embodiment, an artificial disc device 001 is illustrated primarily in FIGS. 27-29 comprising a restraint portion in the form of a deflectable capture 900 preferably integrated into the endplate facing surface 142 adjacent the posterior end of the shell 100, 110. An interlock key 910, comprising a bone boss 930 and a connection pod 940 with interlock structure complementary to the interlock key 910, is situated in a preformed restraint access 420 such as shown in FIG. 30. As the shell 100, 110 is inserted across the vertebral endplate 141, the deflection arms 960 are pushed open by the connection pod 940 until the pod 940 is seated in the pod canal 950 and the deflection arms 960 are able to spring back into a pod 940 locking position. The pod canal 950 may include complementary structure, such as a tongue and groove arrangement 920, to secure the pod 940 to the shell 100, 110.

Figure 31:
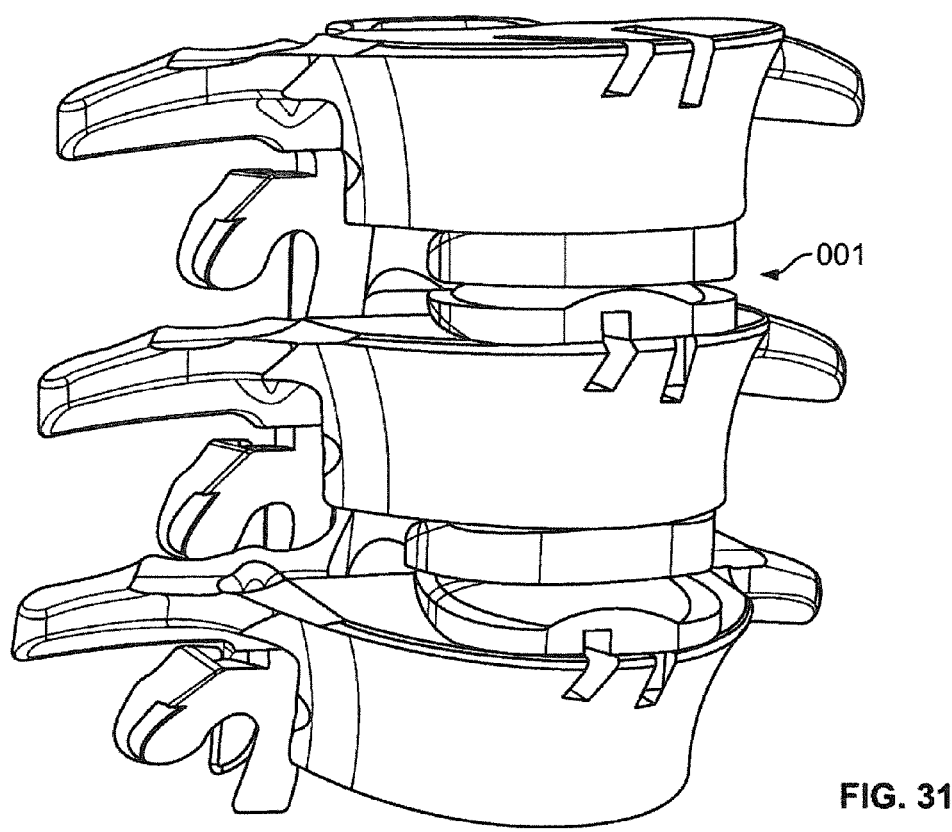
FIG. 31 is an anterolateral perspective view of two implants with securing mechanisms according to the present invention implanted within the intervertebral space.
Figure 32:
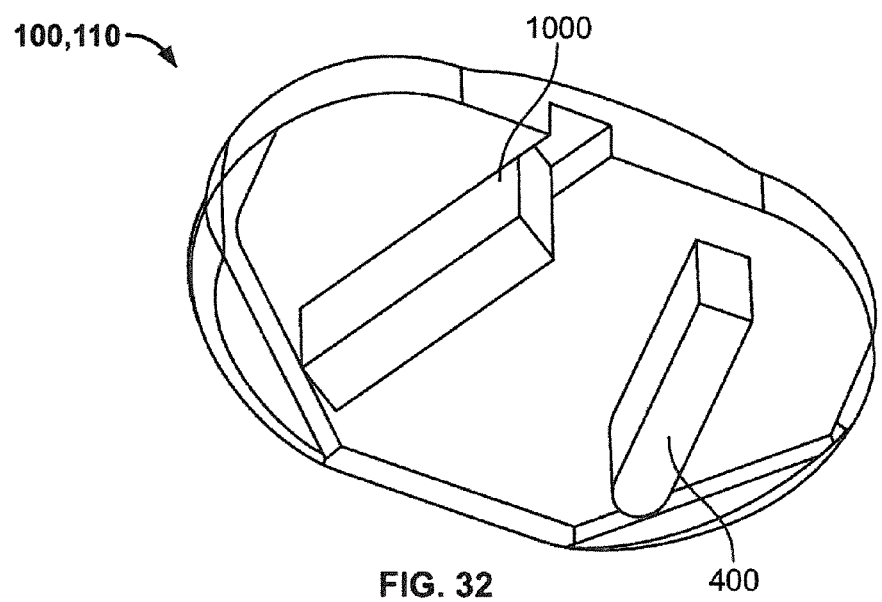
FIG. 32 is a perspective view of a bearing surface of the lower implant member of the implant of FIG. 31.

Another alternative embodiment is illustrated in FIG. 31 wherein an artificial disc device 001 comprises a restraint portion 220 in the form of a fixed fin 400, and an insertable locking fin 1000. Restraint access 420 is formed in the vertebral endplate 141 complementing the position of the fixed fin 400 and the locking fin 1000 on the shell 100, 110 as illustrated in FIG. 33. The shell 100, 110 is inserted, with the locking fin 1000 removed, to its predetermined position between the intervertebral endplates. The locking fin 1000 preferably comprises a friction fit interlocking architecture such as tongue and groove with the shell 100, 110 to secure the locking fin to the shell 100, 110 and restrict back-out. The locking fin 1000 and the fixed fin 400 are orientated non-parallel to each other such that once the locking fin 1000 is inserted, the corresponding shell is restrained to the desired position on the endplate 141.

The artificial disc device 001 can take a form of a non-constrained articulating joint wherein the device 001 has no built in features to limit motion between the articulation surfaces 121 and 131. In some cases, this can be problematic if the anatomy of the user, by hard or soft tissue, does not perform this function since it is possible that a shell 100, 110 can dislocate off the other shell 100, 110 and potentially become jammed. In addition, excessive unnatural motion at the device 001 may cause injury to the user. For these reasons it may be advantageous to limit the motion occurring between the articulation surfaces 121 and 131.

Figure 36:
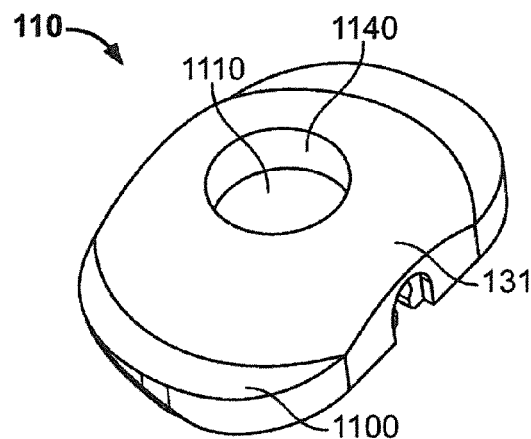
FIG. 36 is a perspective view of a corresponding implant component of the implant component of FIG. 34 with a motion limiting recess.

The artificial disc device may include a motion-limiting portion. In the shell 110 embodiment shown in FIG. 36, this motion-limiting portion is in the form of a motion-limiting stop 1100 that is a protruding surface discontinuous with the curvature of the convex articulating surface 131. Alternately, the stop may instead be formed on the shell 100, or on both shells 100, 110. As one shell articulates against the other, the stop will limit the freedom of motion that can occur.

The motion limit portion may take numerous forms. For example, one of the shells 100, 110 may comprise a limiter holder 1120 to house a limit post 1130. Alternatively the limit post 1130 may be integrated into the articulating surface of the shell 100, 110. The limit post 1130 extends into a limit recess 1110 preferably bound by a limit wall 1140. As the shells 100, 110 articulate against each other, interference between the limit post 1130 and the limit wall 1140 limit the motion that can occur between the shells 100 and 110. Clearly, by adjusting the shape and/or size of the limit recess 1110, motion can be limited in varying amounts in different directions. For example, motion can be limited to 10 degrees of flexion but only 5 degrees of lateral bending at the joint.

Figure 37:
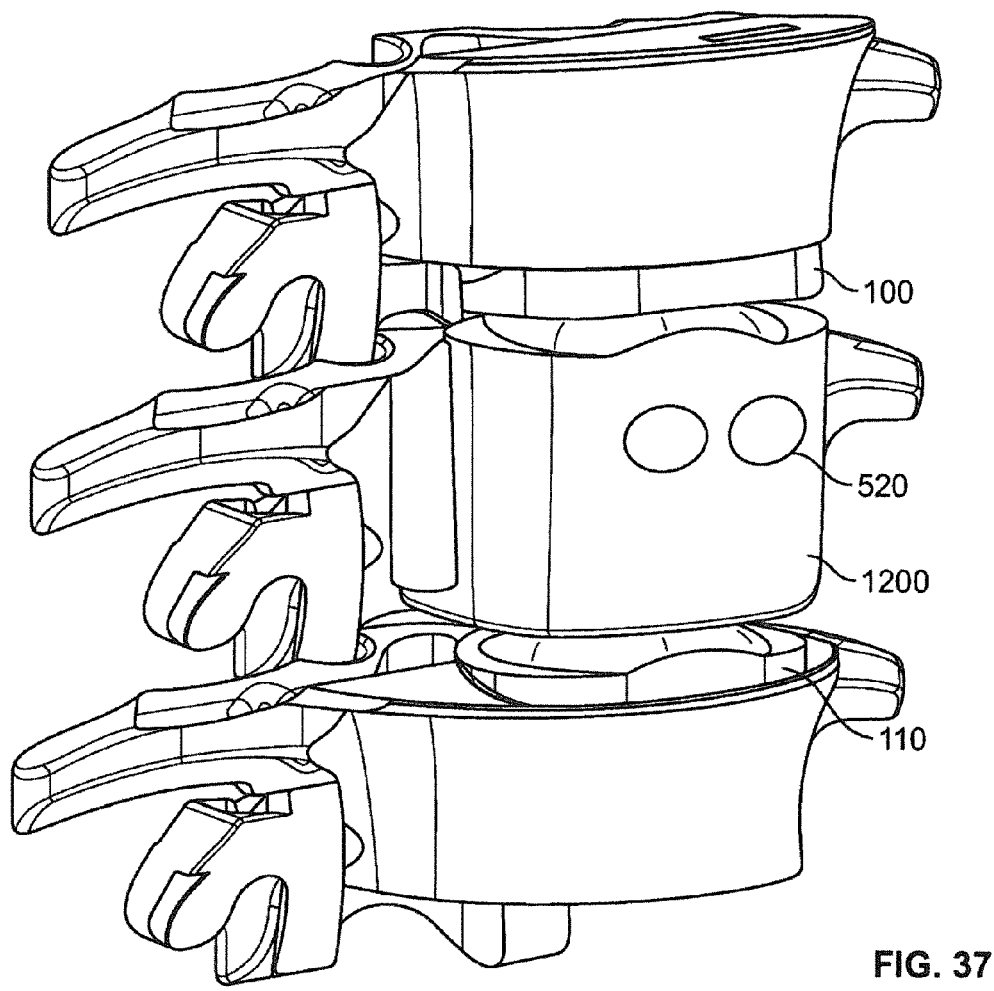
FIG. 37 is an anterolateral perspective view of a strut implant according to the present invention implanted within spine.
Figure 38:
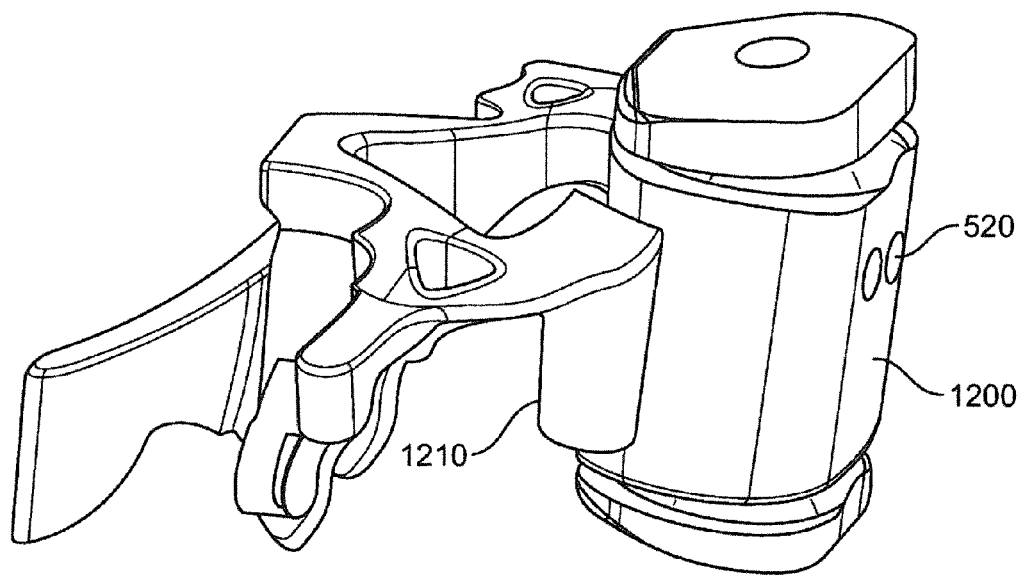
FIG. 38 is a lateral perspective view of the implant of FIG. 37.
Figure 39:
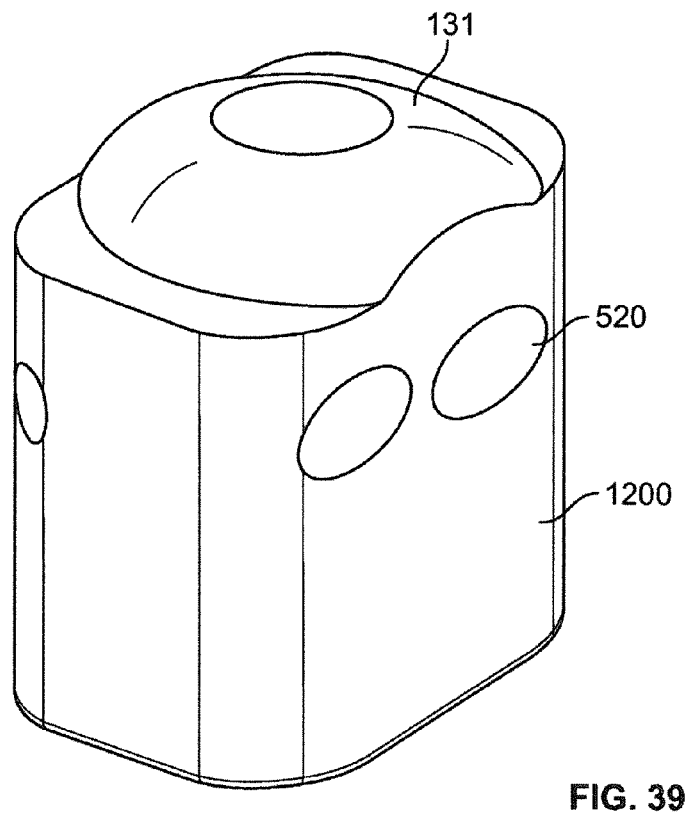
FIG. 39 is an anterolateral perspective view of an implant member of the implant of FIG. 37.
Figure 40:
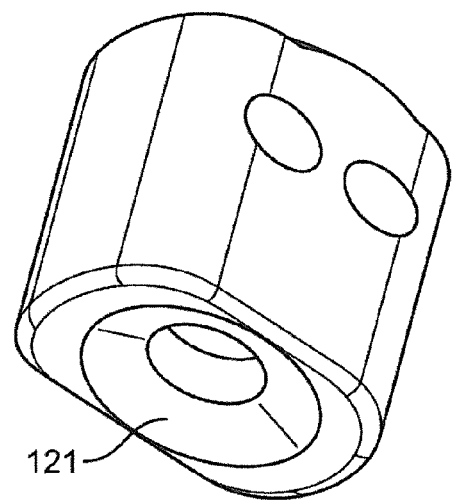
FIG. 40 is bottom perspective view of the implant member of FIG. 39.

The artificial disc device 001 may be configured for use when all or a portion of the vertebral body 144 is removed such as in a corpectomy surgery. As seen in FIGS. 37 and 38, the majority of a vertebral body 144 is removed and replaced with a vertebral strut 1200. The strut 1200 comprises any combination of convex articulation surfaces 131 and/or concave articulation surfaces 121. In addition, the body of the strut 1200 preferably comprises fastener apertures 520 to house bone fasteners 510 (not shown) secured into the remaining bone 1210 of the vertebrae 143 securing the vertebral strut 1200 in the predetermined position. Complementary shells 100, 110 articulate with the vertebral strut 1200. The vertebral strut may also comprise apertures for boney ingrowth or other osteo-conductive coatings or surfaces.

Figure 41:
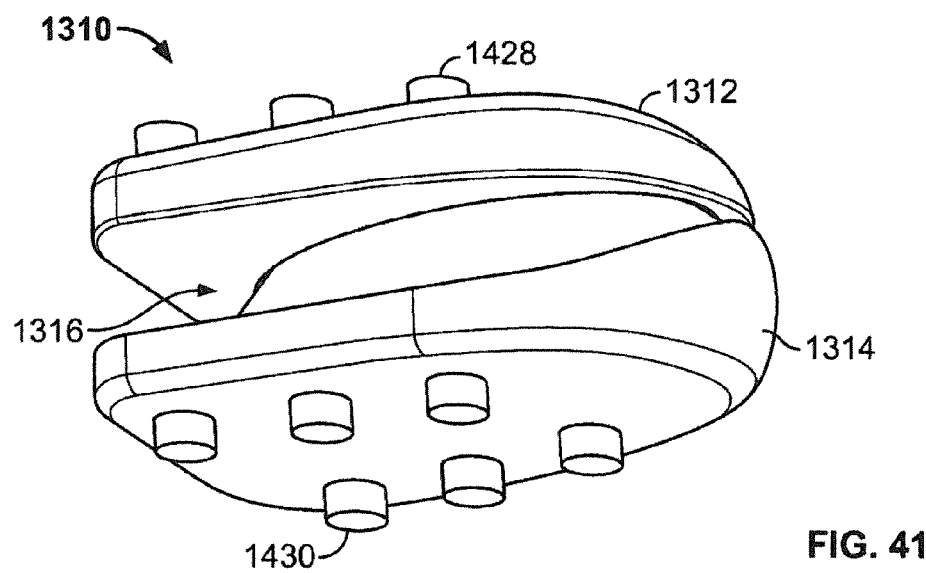
FIG. 41 is a posterolateral perspective view of an artificial disc implant according to the present invention.
Figure 42:
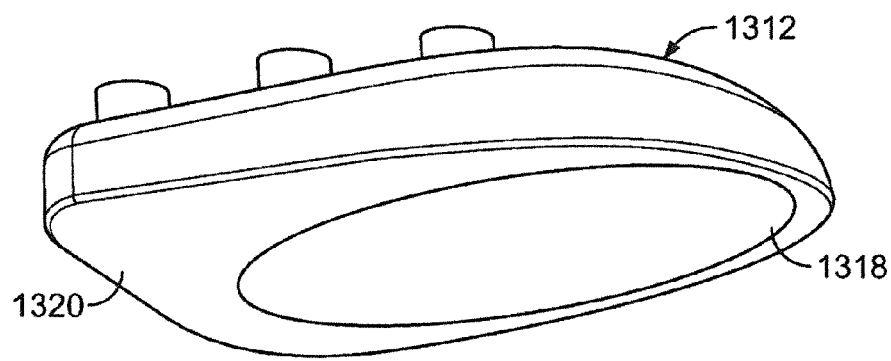
FIG. 42 is a posterolateral perspective view of the upper artificial disc implant member of FIG. 41.
Figure 43:
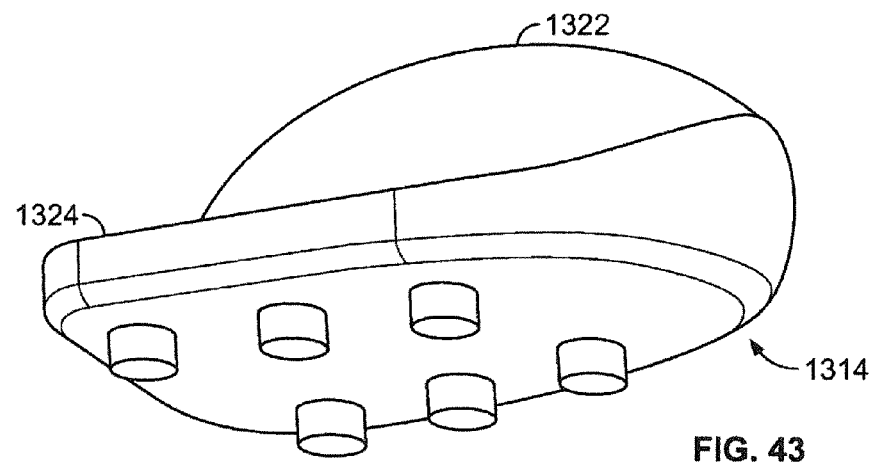
FIG. 43 is a posterolateral perspective view of the lower artificial disc implant member of FIG. 41.

FIG. 41 shows an artificial disc implant 1310 having an upper component or member 1312 and a lower component or member 1314 with the members 1312 and 1314 having a bearing interface 1316 therebetween that allows the members 1312 and 1314 to shift or articulate relative to each other when implanted and secured in an intervertebral space. The bearing interface 1316 can be in the form of a concave recess 1318 formed in the inner or lower surface 1320 of the upper disc member 1312 (FIG. 42), and a convex dome 1322 that projects up from inner or upper surface 1324 of the lower disc member 1314 (FIG. 43). Manifestly, the orientation of the bearing interface 1316, and specifically the concave recess 18 and convex dome 1322 can be reversed such that the recess 18 would be formed on the lower implant member 1314 while the dome 1322 would be formed on the upper member 1312. Preferably, the radius of curvature of the concave recess 1318 and convex dome 1322 are the same for smooth sliding engagement therebetween, although differences in the radius of curvature can also be utilized if desired.

Preferably, both the upper and lower disc members 1312 and 1314 are formed of a PEEK (polyetheretherketone) material which has been found to provide the disc implant 1310 with excellent strength and wear characteristics that are desirable for a joint that is intended for motion preservation such as the artificial disc implants described herein.

Figure 44:
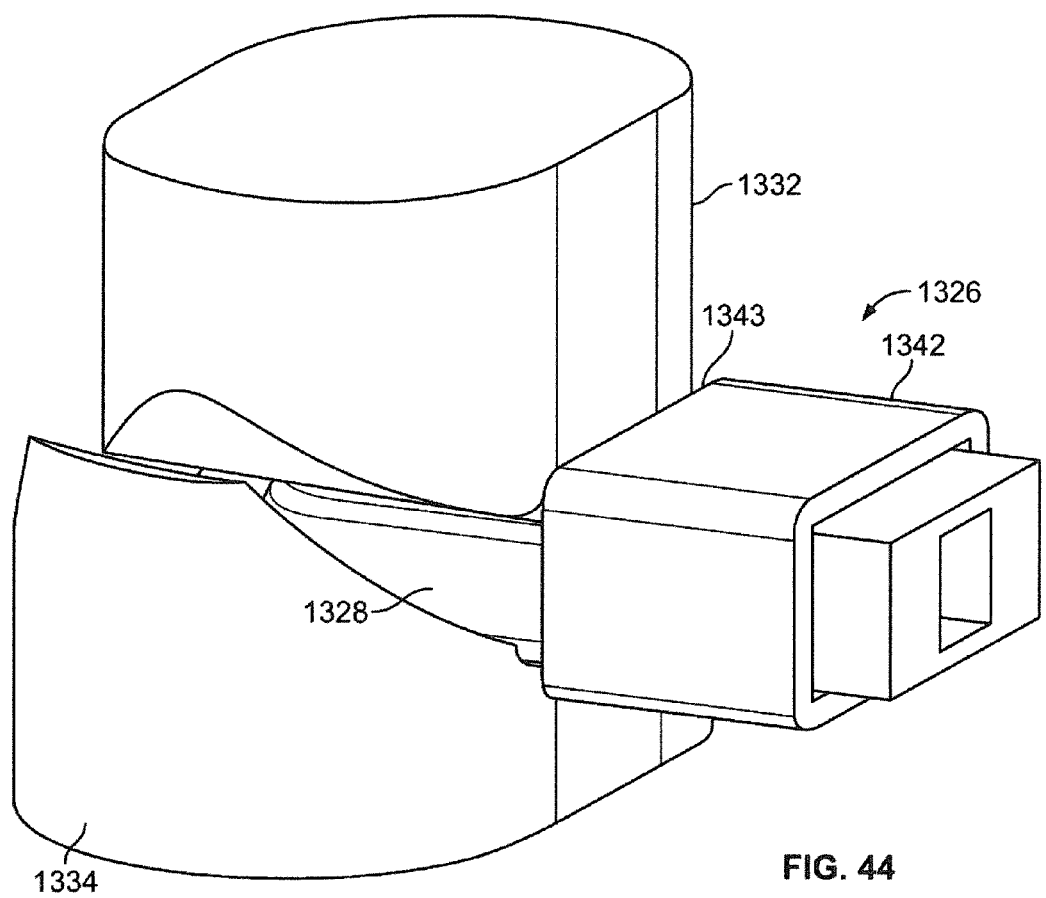
FIG. 44 is an anterolateral perspective view of a trial spacer assembly according to the present invention inserted between two adjacent vertebrae.
Figure 45:
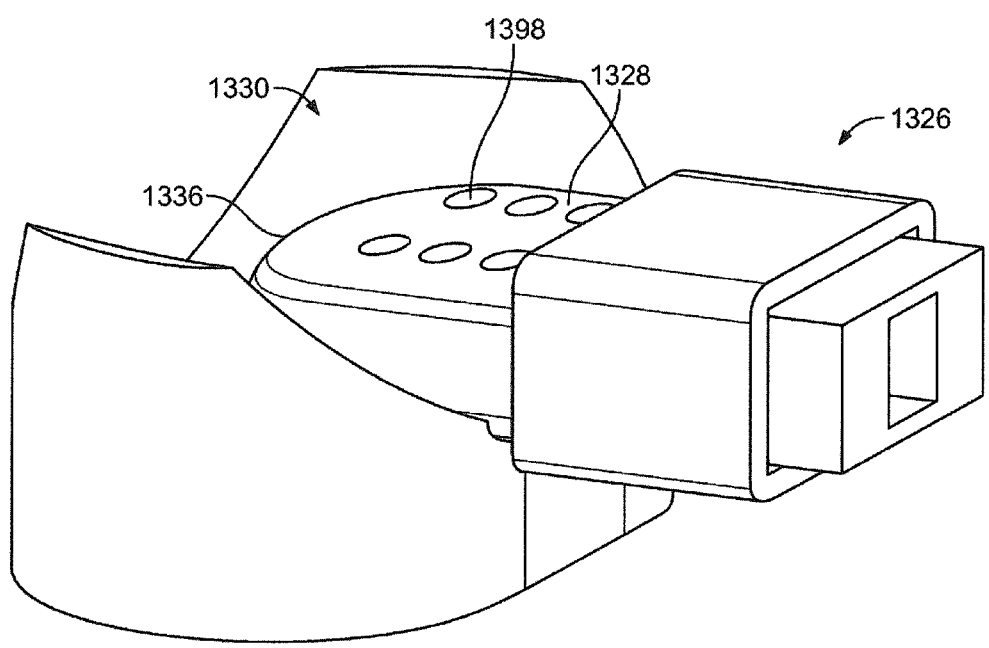
FIG. 45 is an anterolateral perspective view of the trial spacer assembly of FIG. 44 with the upper vertebra hidden for illustration purposes.
Figure 46:
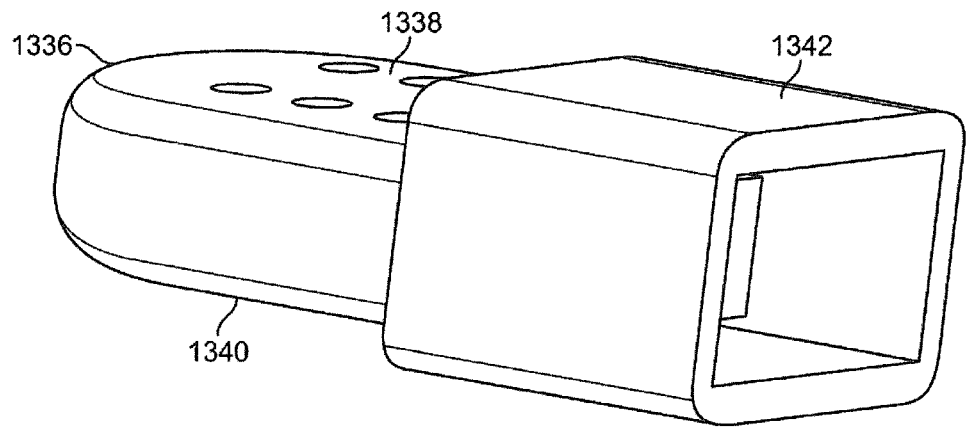
FIG. 46 is an anterolateral perspective view of the trial spacer assembly of FIG. 44.

Referring to FIG. 44, a trial spacer assembly 1326 is shown that includes a forward, trial spacer portion 1328 that is inserted into the intervertebral space 1330 between adjacent, upper and lower vertebral bodies 1332 and 1334. The trial spacer portion 1328 has a generally tongue-shaped configuration including a rounded distal end 1336 and generally flat upper and lower surfaces 1338 and 1340, as best seen in FIGS. 45 and 46. The outer surfaces of the trial spacer portion 1328 present a generally smooth, continuous periphery of the trial spacer portion 1328 for smooth insertion thereof into the intervertebral space 1330. This smooth tongue configuration for the trial spacer portion 1328 substantially corresponds to the peripheral configuration of the disc implant 1310 less the integrated securing mechanism thereof, as will be described hereinafter.

The forward trial spacer portion 1328 is connected to an enlarged rear portion 1342 that remains outside the intervertebral space 1330 after the trial spacer portion 1328 is fully inserted therein, as shown in FIG. 44. The trial spacer portion 1328 and rear portion 1342 have a hollow interior with the rear portion 1342 having a generally rectangular box-like configuration. As shown, there is a transverse shoulder surface 1343 between the trial spacer portion 1328 and rear portion 1342 that acts as a stop to engage the vertebral bodies 1332 and 1334 with the trial spacer portion 1328 fully inserted into the intervertebral space 1330.

Figure 47:
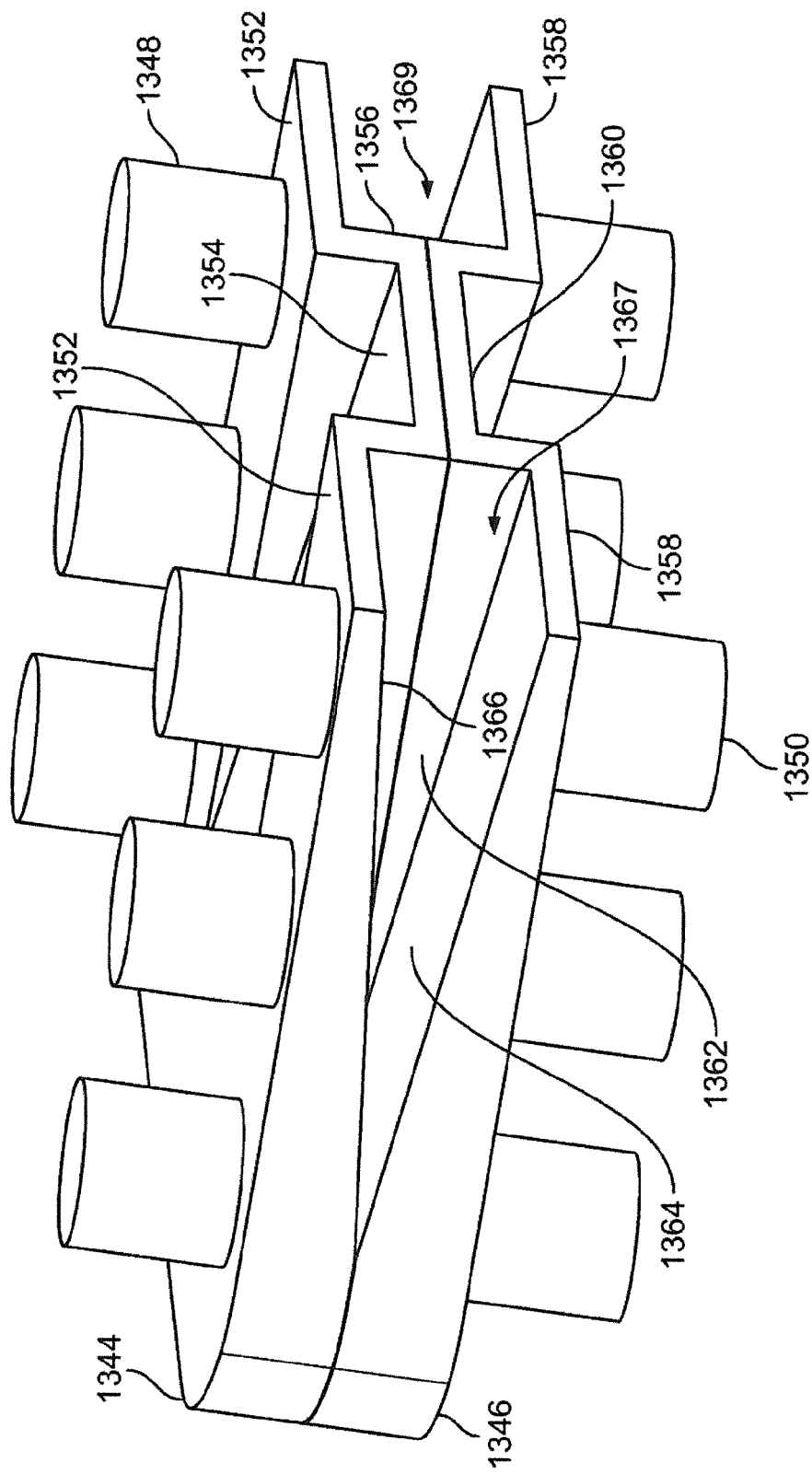
FIG. 47 is an anterolateral perspective view of the internal components of the trial spacer of FIG. 44.
Figure 48:
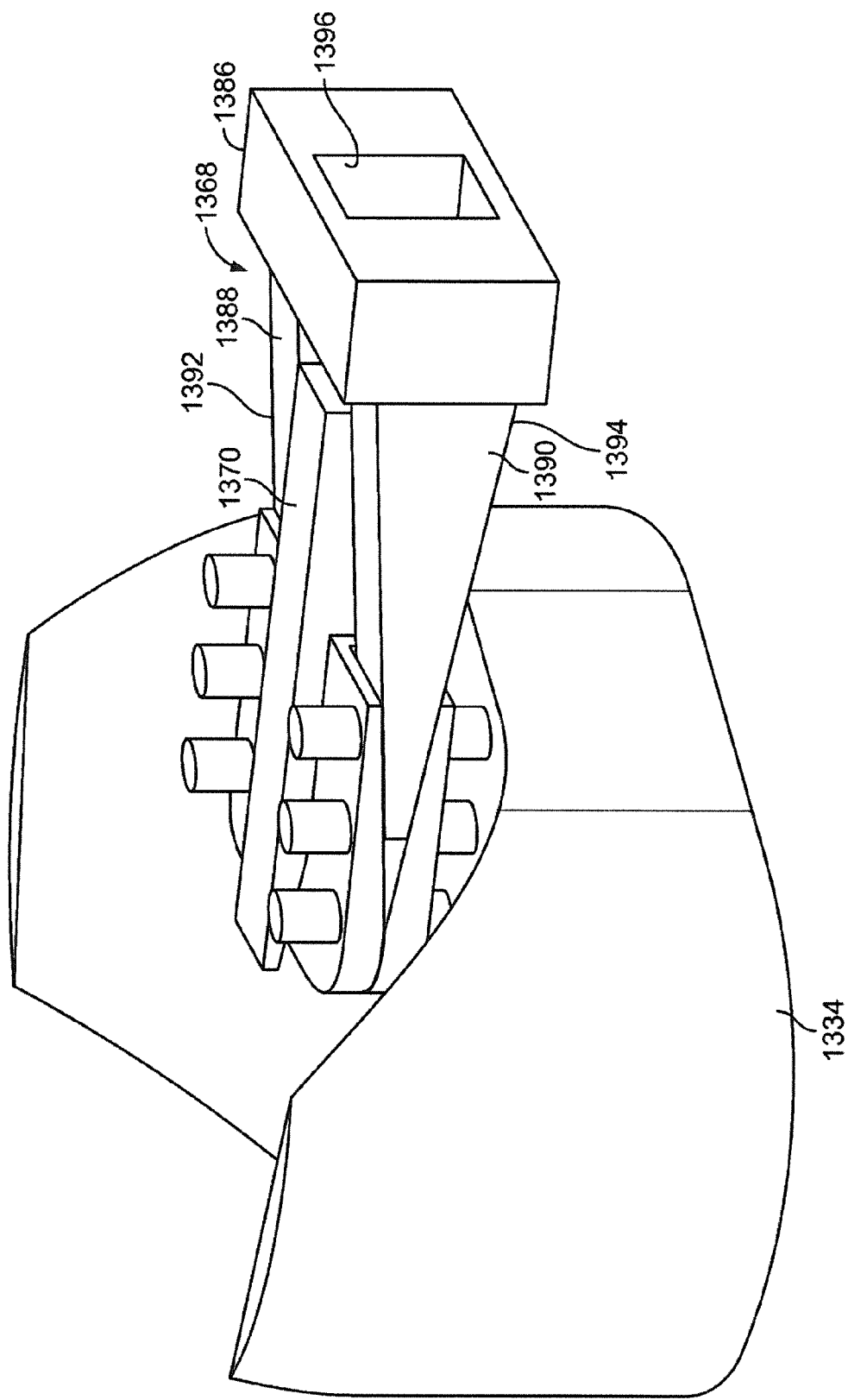
FIG. 48 is an anterolateral perspective view of the components of FIG. 47 including a spreader device disposed between the vertebrae.
Figure 49:
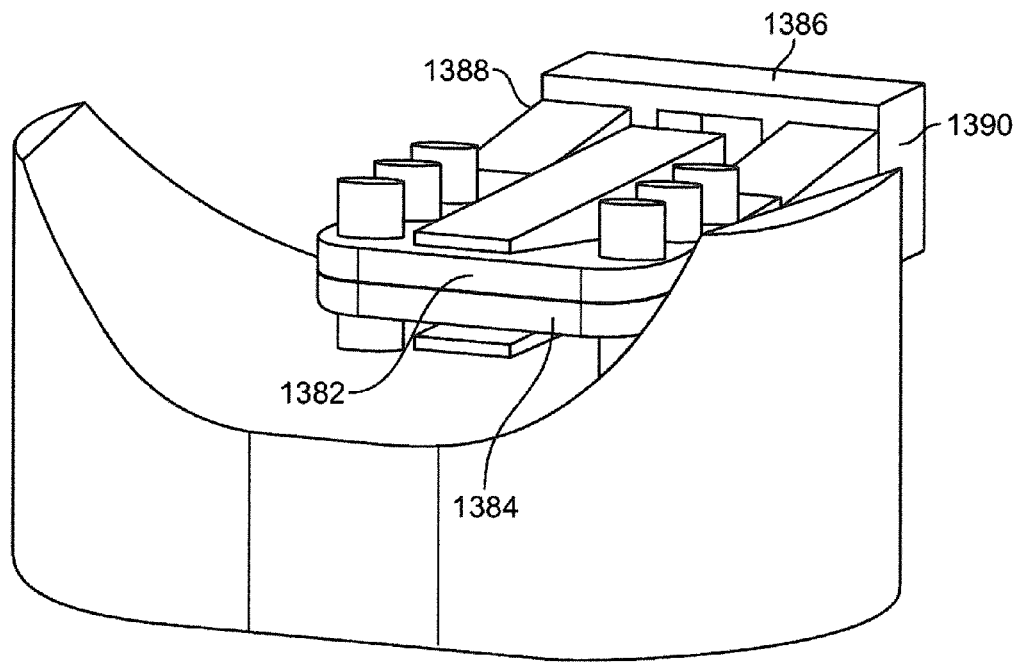
FIG. 49 is a posterolateral perspective view of the trial spacer internal components of FIG. 47.

The hollow portion of the tongue 1328 contains a pair of plates 1344 and 1346 with the upper plate 1344 including several upstanding posts 1348 and the lower plate 1346 including several depending posts 1350 corresponding in positioning to the posts 1348, as can be seen in FIGS. 47-49. The posts 1348 and 1350 are used to form correspondingly spaced openings in the facing surfaces of the vertebral bodies 1332 and 1334. As shown, the posts 1348 and 1350 have blunt end surfaces, although other configurations for these ends can also be used to ease driving of the posts 1348 and 1350 into the bone surfaces.

Referring to FIG. 47, the upper plate 1344 includes raised side platform portions 1352 each having three posts 1348 equally spaced therealong and upstanding therefrom. A central ramp portion 1354 is recessed from the raised side portions 1352 at its rear end and extends at an incline upwardly and forwardly toward the forward end 1382 of the upper plate 1344. Intermediate vertical wall portions 1356 extend along either side of the ramp portion 1354 to interconnect the ramp portion 1354 and the side platform portions 1352 of the upper plate 1344. The lower plate 46 has a similar configuration to the upper plate 1344 in that it also has lowered, side platform portions 1358 that each include three posts 1350 equally spaced therealong and depending therefrom. A central ramp portion 1360 extends between the side portions 1358 and is raised at its rearward end and extends at an incline downwardly and forwardly toward the forward end 1384 of the lower plate 1346. Intermediate vertical wall portions 1352 interconnect the side platform portions 1358 and the central ramp portion 1360.

The corresponding platform portions 1352 and 1358 of the plates 1344 and 1346 cooperate to form a wedge-shape elongate openings or channels 1367 and 1369 by way of their facing inclined surfaces 1364 and 1366. More specifically, the corresponding wall portions 1356 and 1362 and the inclined surfaces 1364 and 1366 cooperate to form wedge-shaped side channels 1367 and 1369 which are used to drive the plates 1344 and 1346 apart for creating the indentations or pocket openings in the vertebral bodies, as described further hereinafter.

Figure 50:
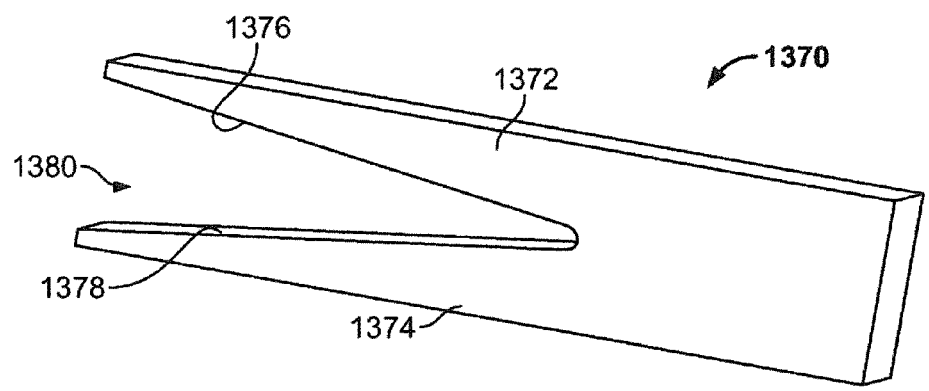
FIG. 50 is a perspective view of the closing device of the trial spacer assembly.
Figure 53:
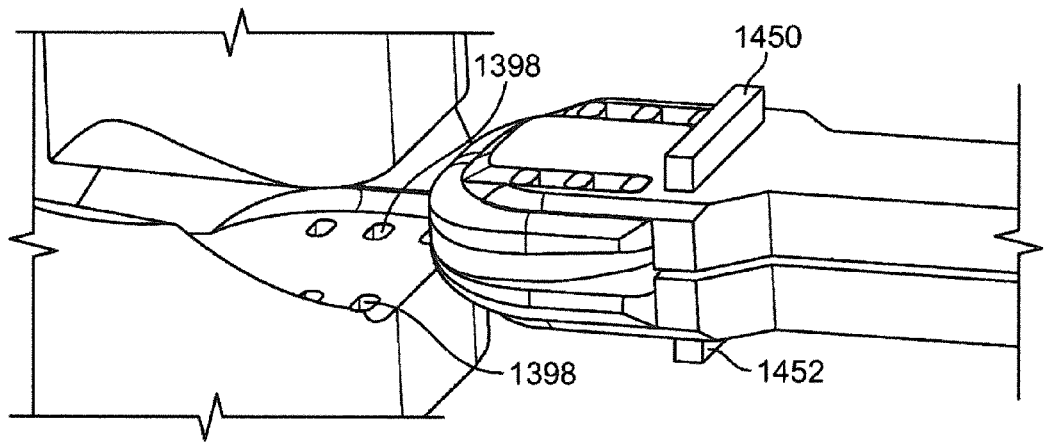
FIG. 53 is an anterolateral perspective view of the implant of FIG. 41 loaded in the inserter of FIG. 51 adjacent the intervertebral space prior to insertion.

Referring to FIG. 48, in addition to the upper and lower plates 1344 and 1346, the internal components of the trial spacer assembly 1326 include a spreader device 1368, and a generally block-shaped, closing device 1370 shown in their compact or insertion/removal configuration. Referring to FIG. 50, the closing wedge device 1370 has upper and lower projecting arms 1372 and 1374 including inclined facing surfaces 1376 and 1378, respectively. The surfaces 1376 and 1378 cooperate to form a V-shaped opening 1380. In the insertion configuration, the closing device 1370 has the ramp portions 1354 and 1360 of the plates 1344 and 1346 fully received in the V-shaped opening 1380 with the surfaces 1376 and 1378 fully engaged on the ramp portions 1354 and 1360, as shown in FIGS. 48 and 49. In this manner, the plates 1344 and 1346 are held together with the respective forward ends 1382 and 1384 in engagement, as is best seen in FIG. 49.

The spreader device 1368 has an enlarged rear, box-shaped portion 1386 that fits in the hollow space defined by a box-shaped portion 1342 of the trial spacer assembly 1326. The spreader device 1368 also includes forwardly projecting arms 1388 and 1390 laterally spaced so that the wedge device 1370 fits therebetween, as can be seen in FIGS. 48 and 49. As best seen in FIG. 48, the arms 1388 and 1390 have a wedge configuration so that they fit into the corresponding wedge channels 1367 and 1369 formed on either side of the plates 1344 and 1346. In this regard, each of the wedge arms 1388 and 1390 have inclined surfaces 1392 and 1394 that extend from their rear ends at the portion 1386 and taper down toward each other at their forward ends in the channels 1367 and 1369.

Accordingly, to drive the plates 1344 and 1346 apart, the spreader device 1368 and wedge device 1370 are moved in opposite directions with the wedge device 1370 being advanced forwardly so that the inclined surfaces 1392 and 1394 cam against the corresponding plate inclined surfaces 1364 and 1366 to drive the upper plate 1344 in an upward direction toward the vertebral body 1332 and the lower plate 1346 downwardly toward the vertebral body 1334. The rear portion 1386 of the spreader device 1368 has a window opening 1396 to allow the closing device 1370 to fit therethrough so that as the spreader device 1368 is advanced, the wedge device 1370 can be retracted off of the ramp portions 1354 and 1360 of the plates 1344 and 1346 and through the window opening 1396 to allow the plates 1344 and 1346 to be spread apart. In addition, the trial spacer portion 1328 is provided with through openings 1398 so that the posts 1348 and 1350 can be driven therethrough and into the facing surfaces of the vertebral bodies 1332 and 1334. As can be seen in FIG. 45, openings 1398 are shown in the upper portion of the trial spacer portion 1328 through which the upper posts 1350 are driven. Similar openings are provided in the lower portion of the trial spacer portion 1328 for the lower posts 1350.

To remove the trial spacer portion 1328 from the intervertebral space 1330, the trial spacer assembly 1326 is shifted back from its spread or expanded configuration to its insertion/removal or compact configuration with the plates 1344 and 1346 held together with the closing device 1370. For this purpose, the operation of the spreader device 1368 and the closing device 1370 is reversed with the closing device 1370 being advanced forwardly through the window opening 1396 of the spreader device 1368 and the spreader device 1368 being retracted rearwardly until the plate ends 1382 and 1384 are brought together as shown in FIG. 49 with the surfaces 1376 and 1378 of the closing device 1370 once more fully engaged on the ramp surfaces 1354 and 1360. As the trial spacer assembly 1326 is shifted back to its compact configuration, the posts 1348 and 1350 are retracted back through their corresponding openings 1398 in the trial spacer portion 1328 and into the hollow space therein.

After the trial spacer assembly 1326 is utilized as described above to form openings or indentations 1398 in the facing surfaces of the vertebral bodies 1332 and 1334, the implant 1310 is inserted into the intervertebral space 1330 via inserter tool 1400. The inserter tool 1400 has an elongate shaft 1402 and an enlarged head 1404 at its end in which it carries the disc implant 1310 for insertion thereof. Shaft 1402 and the head 1404 are formed by an upper elongate tool member 1406 and a lower elongate tool member 1408 having shaft portions 1410 and 1412, respectively, and an associated head portion 1414 and 1416 at their respective ends. The upper and lower tool members 1406 and 1408 are able to slidingly reciprocate relative to each other for removal of the disc 1310 from the intervertebral space 1330, as will be described more fully hereinafter.

As shown in FIG. 51, the tool head 1404 has a forward opening 1318 between upper and lower plate portions 1420 and 1422 of the respective upper and lower head portions 1414 and 1416. The opening 1418 between the plate portions 1420 and 1422 is sized to receive the implant 1310 therein. In this regard, each plate portion 1420 and 1422 has respective side slots 1424 and 1426 formed therein. The slots 1424 and 1426 allow the securing mechanism, in the form of upstanding posts 1428 that are integral with and project up from the upper disc member 1312, and depending posts 1430 that are integral with and project downwardly from the lower disc member 1314, to fit therein. The slots 1424 and 1426 are defined by side prongs that extend along either side of a central projection of each of the tool member head portions 1414 and 1416. More specifically, the upper head portion 1414 has side prongs 1432 on either side of central projection 1434, and the lower head portion 1416 has side prongs 1436 on either side of central projection 1438. The posts 1428 are formed in two rows of three equally spaced posts 1428 on either side of the upper disc member 1312, and the lower posts 1430 are formed similarly in two rows of three equally spaced lower posts 1430 on lower disc member 1314 so that the posts 1428 and 1430 correspond to the spacing and positioning of the posts 1348 or 1350 of the plates 1344 and 1346, and the openings 1398 that they form in the vertebral bodies 1332 and 1334.

As shown in FIG. 51, the implant 1310 is arranged so that the straight upper and lower ends 1438 and 1440 thereof are facing rearwardly so that they abut against the shoulder abutment walls 1442 and 1444 at the rear end of the disc receiving opening 1418 in the tool head 1404. In this regard, the upper and lower actuator ends 1445 and 1447 are arranged forwardly so as to be at the trailing end of the disc implant 1310 as it is inserted into the tool head opening 1418. So that the upper plates 1420 and 1422 substantially match the configuration of the upper and lower disc members 1312 and 1314, the prongs 1432 and 1436 do not extend as far forwardly as the adjacent central projection 1434 and 1438, respectively. In addition, the peripheral edges of the side prongs 1432 and 1436 and the respective central projections 1434 and 1438 have an actuate chamfer to match that of the ends 1445 and 1447 of the disc members 1312 and 1314, respectively. In this manner, with the disc 1310 fully received in the tool head opening 1418 as shown in FIG. 52, the projecting ends 1445 and 1447 of the disc implant 1310 present a substantially smooth, continuous surface in combination with the corresponding, adjacent edges of the prongs 1432 and 1436 and central projections 1434 and 1438.

Referring to FIG. 52, the implant posts 1428 and 1430 are received in the respective slots 1424 and 1426. As shown, the rearmost posts 1428 abut against the end of the slots 1424 with the upper and lower disc member ends 1439 and 1440 engaged against the shoulder walls 1442 and 1444 with the disc implant 1310 fully received in the tool head opening 1418. Similarly, the rearmost lower posts 1430 are engaged at the end of lower slots 1426 with the upper and lower disc ends 1439 and 1440 engaged against the shoulder walls 1442 and 1444 with the disc implant 1310 fully received in the tool head opening 1418. As shown, the spacing the plates 1420 and 1422 is such that with the posts 1428 and 1430 received in the slots 1424 and 1426, the upper ends of the posts 1428 and 1430 will be substantially flush with the top and bottom surfaces 1446 and 1448 of the plate portion 1420 and 1422, respectively. In this manner, the disc implant 1310 is smoothly inserted into the intervertebral space 1330 with the inserter tool 1400. Also, the inserter tool plates 1420 and 1422 are spaced so as to distract the vertebral bodies 1332 and 1334 apart for fitting the disc implant 1310 therebetween. In other words, the spacing between the surfaces 1446 and 1448 of the respective plates 1420 and 1422 is slightly greater than the spacing between the surfaces 1338 and 1340 of the trial spacer portion 1328 of the trial spacer assembly 1326. This allows the disc posts 1428 and 1430 to be fit into the openings 1398.

More specifically, the upper and lower tool members 1406 and 1408 preferably include respective, laterally extending stop members 1450 and 1452 that are spaced slightly rearwardly of the rear ends of the slots 1424 an 1426. The tool 1400 is advanced forwardly to fit the tool head 1404 and artificial disc 1310 carried thereby into the intervertebral space 1330. The tool 1404 continues to be advanced forwardly until the stops 1450 and 1452 abut against the vertebral bodies 1332 and 1334 to provide the user an indication that the tool head 1404 and the artificial disc 1310 carried thereby are fully received in the intervertebral space 1330. With the stops 1450 and 1452 engaged against the respective vertebral bodies 1332 and 1334, the posts 1428 and 1430 are now properly aligned with the pocket openings 1398 formed in each of the vertebral bodies 1332 and 1334.

Figure 54:
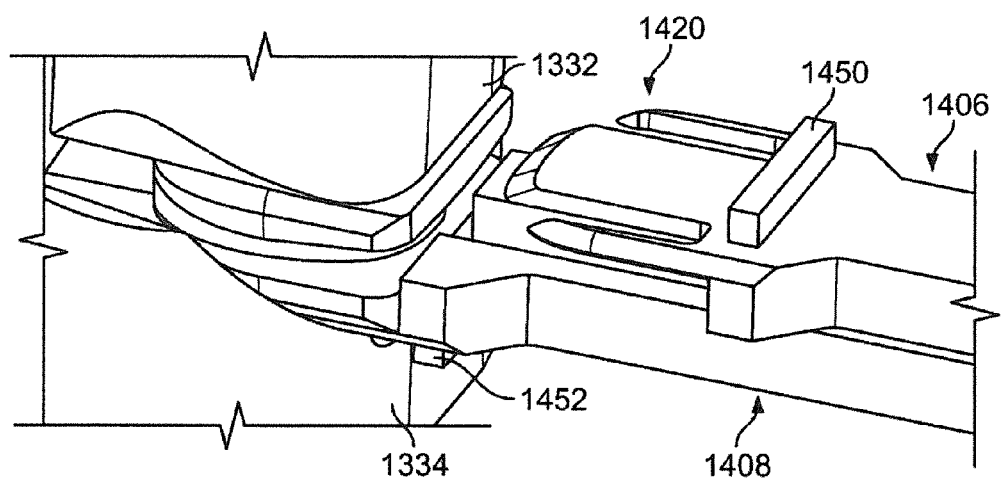
FIG. 54 is an anterolateral perspective view of the implant and inserter of FIG. 53 with the upper arm of the inserter retracted from the implant.
Figure 55:
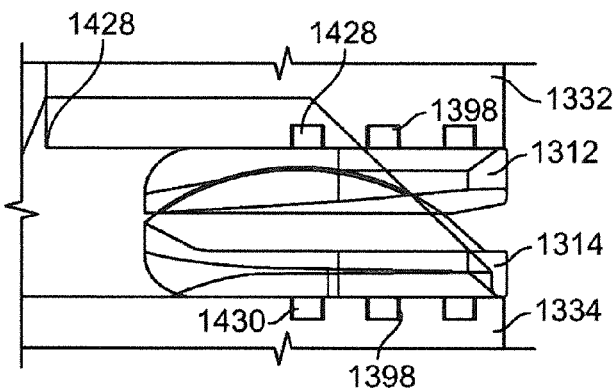
FIG. 55 is a side view of the implant of FIG. 41 implanted within the intervertebral space.

As previously mentioned, the tool members 1406 and 1408 are slidable relative to each other so that one of the members 1406 and 1408 can be retracted while the other member 1406 or 1408 remains in its advanced position with the corresponding stop 1450 or 1452 engaged against the corresponding vertebral body 1332 or 1334. As shown in FIG. 54, upper tool member 1406 is retracted while the lower tool member 1408 remains in its advanced position with the stop 1452 thereof engaged against the vertebral body 1334. With the plate 1420 retracted out from the intervertebral space 1330, the distracted vertebral body 1332 will shift down toward the vertebral body 1334 causing the posts 1428 of the disc upper member 1312 to be received in the corresponding preformed pocket openings 1398 in the vertebral body 1332. Thereafter, the lower tool member 1408 is retracted to pull the plate member 1422 out from the intervertebral space 1330 so that the posts 1430 can fall into the corresponding preformed pocket openings 1398 formed in the vertebral body 1334, as shown in FIG. 55. With the disc implant 1310 secured to the vertebral bodies 1332 and 1334 in the intervertebral space 1330 therebetween via the fitting of the posts 1428 and 1430 into the pocket openings 1398, the risk that the disc 1310 will be extruded out from the intervertebral space 1330 is substantially minimized as the vertebral bodies 1332 and 1334 move relative to each other via the bearing interface 16 between the secured upper and lower disc members 1312 and 1314.

Figure 56:
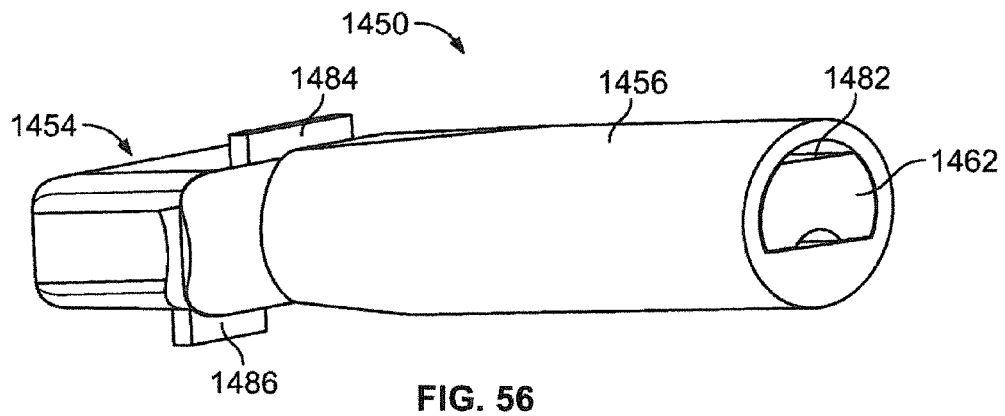
FIG. 56 is an anterolateral perspective view of a trial spacer assembly according to the present invention.

In the next trial spacer and disc implantation and securing system, a trial spacer assembly 1450 as shown in FIG. 56 is employed. The trial spacer assembly 1450 also is utilized to form features in the vertebral bodies 1334 and 1336 for receipt of the securing mechanism that is associated with the artificial disc implant 1452 (FIG. 52). The disc implant 1452 only varies from the disc implant 1310 in the securing mechanism employed so that the common features between the disc implants 1310 and 1452 will not be described in detail hereinafter.

Figure 58:
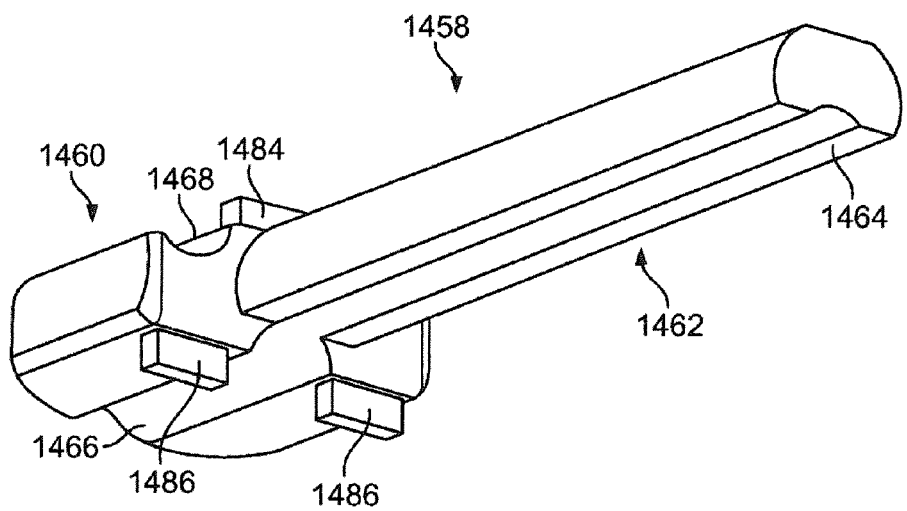
FIG. 58 is a anterolateral perspective view of the trial spacer assembly of FIG. 56 with the shaft handle removed.
Figure 59:
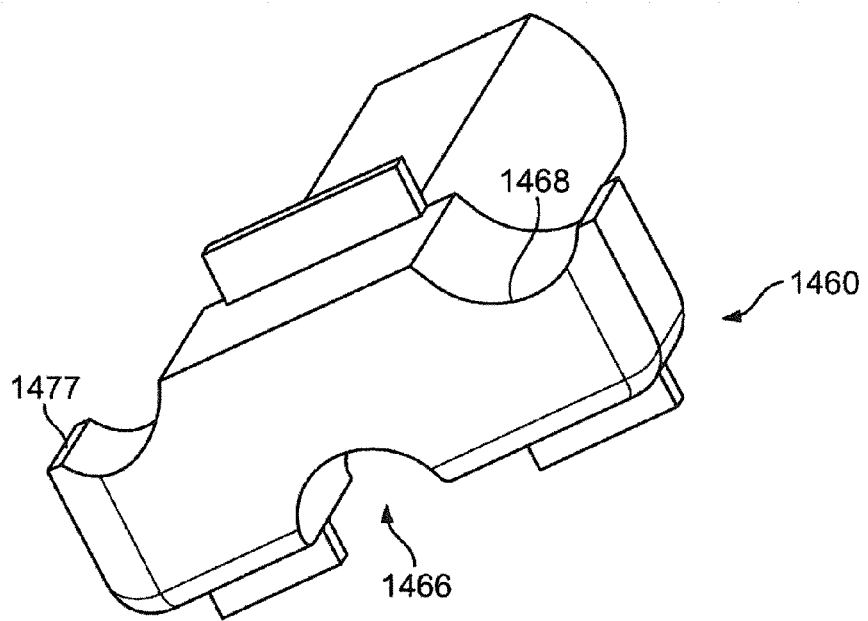
FIG. 59 is a posterolateral perspective view of the trial spacer assembly of FIG. 58.

The trial spacer assembly 1450 has a forward, trial spacer portion 1454 that has an outer, peripheral configuration substantially matching that of the disc implant 1452 less the securing mechanism thereof. The trial spacer assembly 1450 also includes a rearwardly extending shaft portion 1456. The trial spacer assembly 1450 is formed from two components. As shown in FIG. 58, the main trial spacer member 1458 includes a head trial spacer portion 1460 and a rearwardly extending shaft portion 1462. The shaft portion 1458 has an elongate lower groove 1464 formed along its entire length, and the head portion 1460 also includes an elongate lower groove 1466 aligned with the shaft groove 1464, as shown in FIG. 58. In addition, the head portion 1460 has a pair of upper grooves 1468 and 1470 on either side thereof. The grooves 1464-1470 are used to form features in the vertebral bodies 1332 and 1334 for receipt of the securing mechanism of the disc implant 1452, as described more fully hereinafter.

Figure 60:
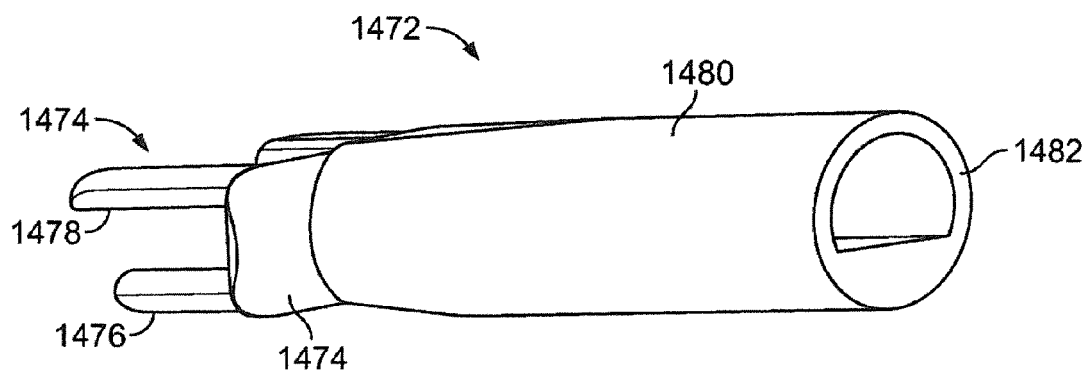
FIG. 60 is an anterolateral perspective view of the shaft handle of the trial spacer assembly of FIG. 56.
Figure 61:
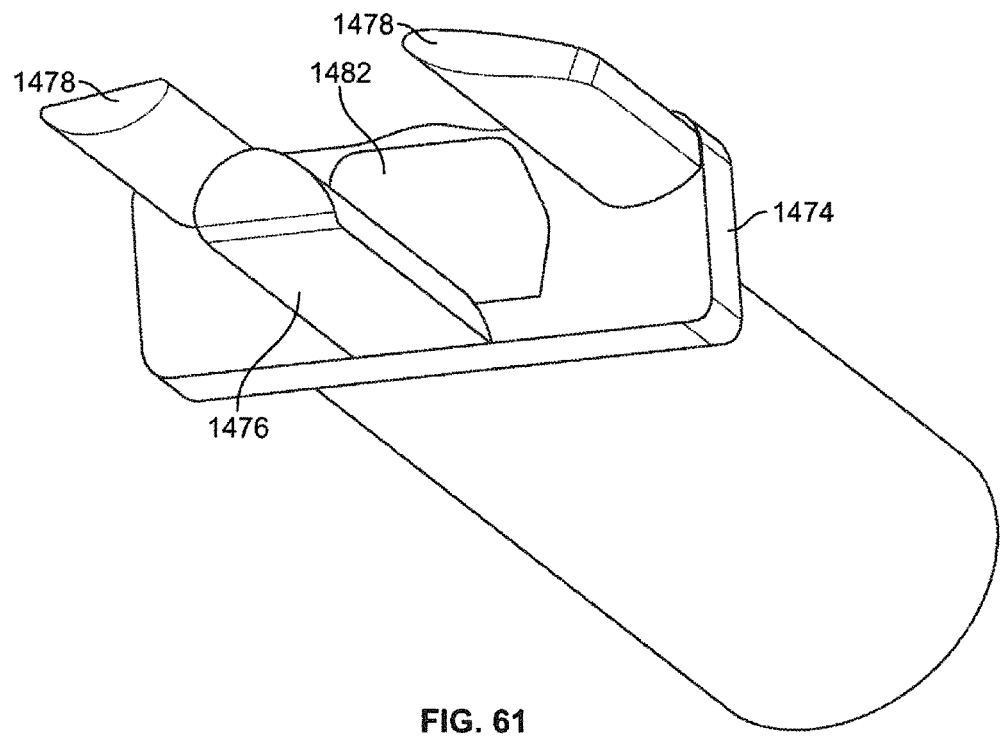
FIG. 61 is an posterolateral perspective view of the shaft handle of the trial spacer assembly of FIG. 56.

The second component of the trial spacer assembly 1450 is a head cover and handle member 1472. The member 1472 includes a head cover portion 1474 that consists of a laterally extending, rear flange portion 1474 from which a central lower prong 1476 and a pair of upper prongs 1478 extend forwardly. Shaft handle portion 1480 extends rearwardly from the flange portion 1474 and has a hollow throughbore 1482 extending therethrough opening to the flange portion 1474, as seen in FIGS. 60 and 61.

Figure 57:
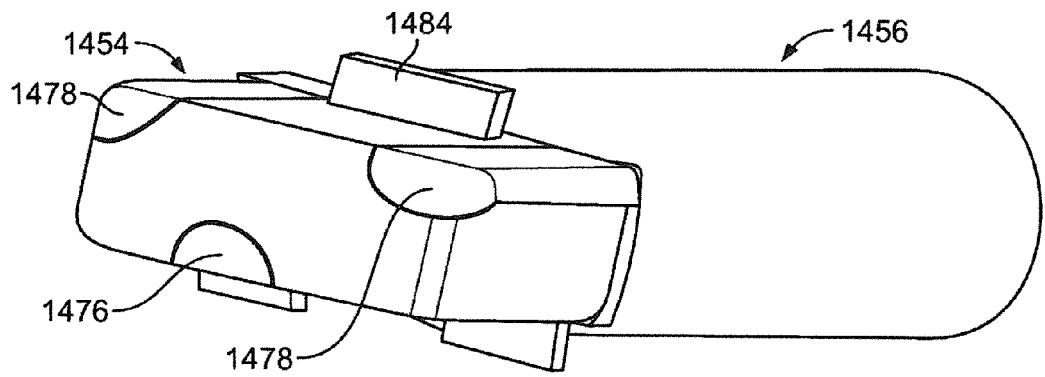
FIG. 57 is a posterolateral perspective view of the trial spacer assembly of FIG. 56.

The trial spacer assembly 1450 is assembled by sliding the head cover and handle member 1472 over the trial spacer member 158 with the shaft portion 1462 fitting into the throughbore 1482 and the prongs 1476 and 1478 fitting into the corresponding grooves 1466-1470 of the trial spacer head portion 1460. Referring to FIG. 56, the throughbore 1482 has a generally D-shaped configuration so that the shaft portion 1462 is non-rotatably received therein. Further, as can be seen in FIG. 57, the prongs 1476 and 1478 fit into the corresponding grooves 1466-1470 such that the outer, peripheral surface of the trial spacer portion 1454 has no sharp or discontinuous surfaces that might otherwise gouge the vertebral bodies 1332 and 1334 during insertion of the trial spacer portion 1454 into the intervertebral space 1330. Also, the trial spacer portion 1460 is provided with three laterally extending stop members including central, upper stop member 1484 that extends laterally between the upper grooves 1468 and 1470, and side, lower stop members 1486 that extend laterally on either side of the central lower groove 1466 with all three stop members 1484 and 1486 being adjacent the rear end of the trial spacer portion 1460.

Figures 62, 63:
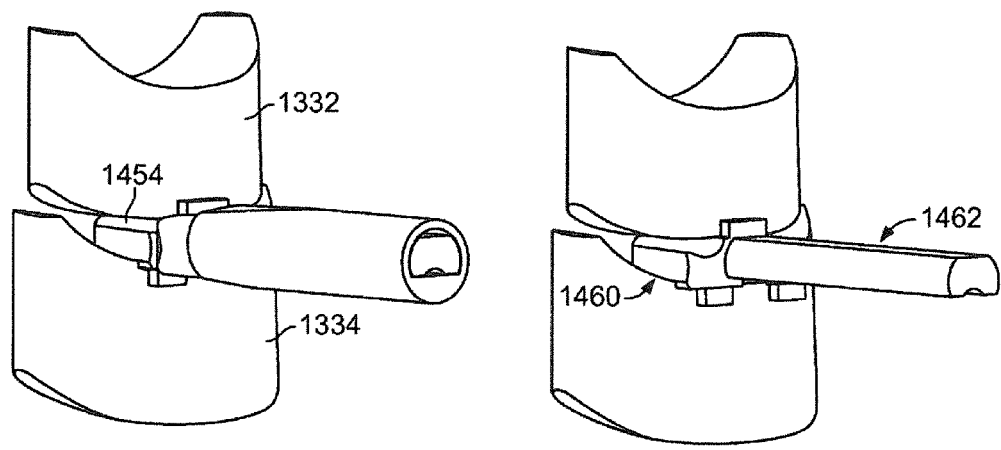
FIG. 62 is an anterolateral perspective view of the trial spacer assembly of FIG. 56 inserted into the intervertebral space.
FIG. 63 is an anterolateral perspective view of the trial spacer assembly of FIG. 56 inserted into the intervertebral space with the handle portion removed.

FIG. 62 shows the trial spacer portion 1454 inserted into the intervertebral space 1330 between adjacent vertebral bodies 1332 and 1334 for assessing the size of the intervertebral space 1330 so as to be able to accurately select an appropriately sized artificial disc 1452 for implantation therein. As shown in FIG. 62, the trial spacer portion 1454 is fully received in the intervertebral space 1330 with the stops 1484 and 1486 engaged against the vertebral bodies 1332 and 1334 and the shaft portion 1462 extending outside the intervertebral space 1330 and away therefrom. Thereafter, the head cover and handle member 1472 are slid off and removed from the trial spacer member 1458 leaving the grooved trial spacer portion 1460 in the intervertebral space 1330 with the shaft portion 1462 extending rearwardly therefrom, as shown in FIG. 63.

Figure 64:
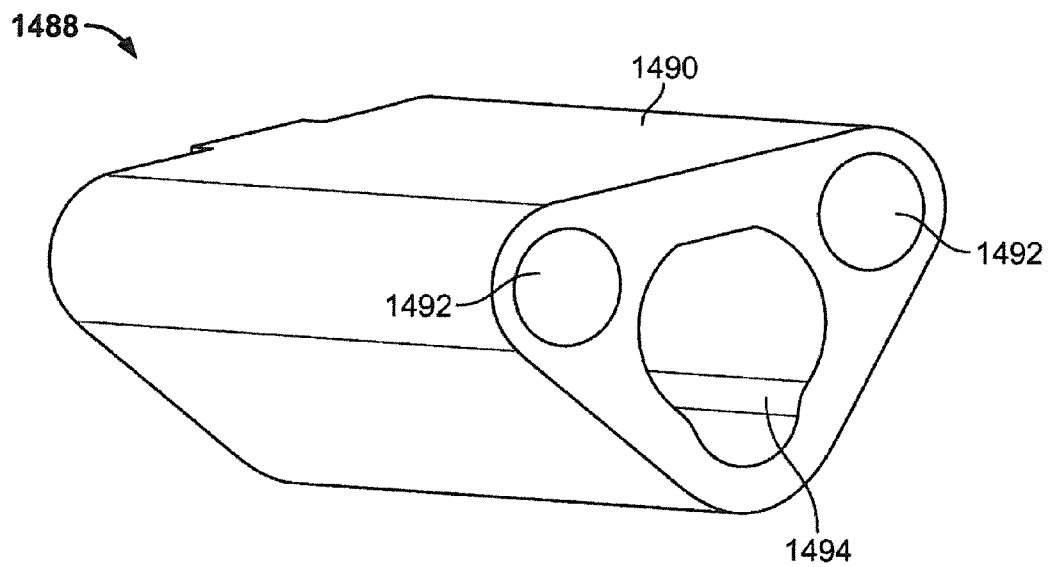
FIG. 64 is an anterolateral perspective view of a drill guide according to the present invention.
Figure 65:
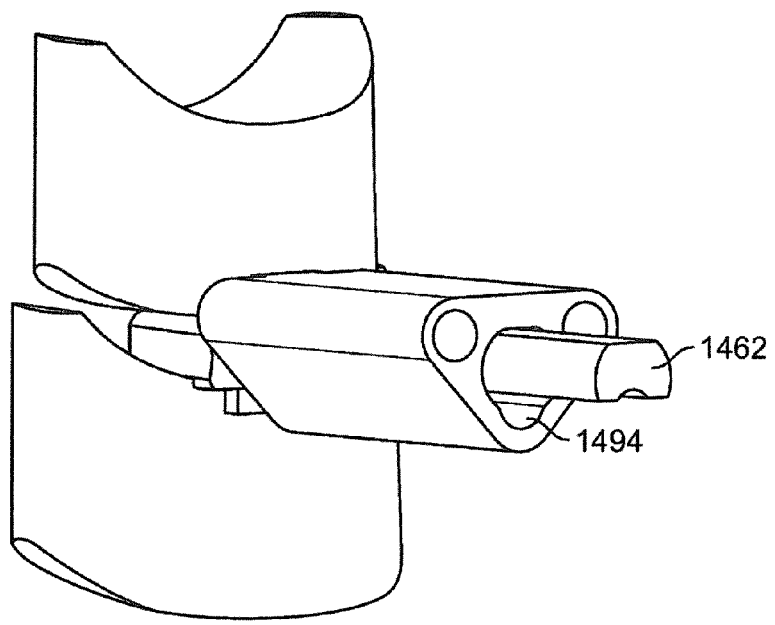
FIG. 65 is an anterolateral perspective view of the drill guide of FIG. 64 inserted over the trial spacer assembly.
Figure 66:
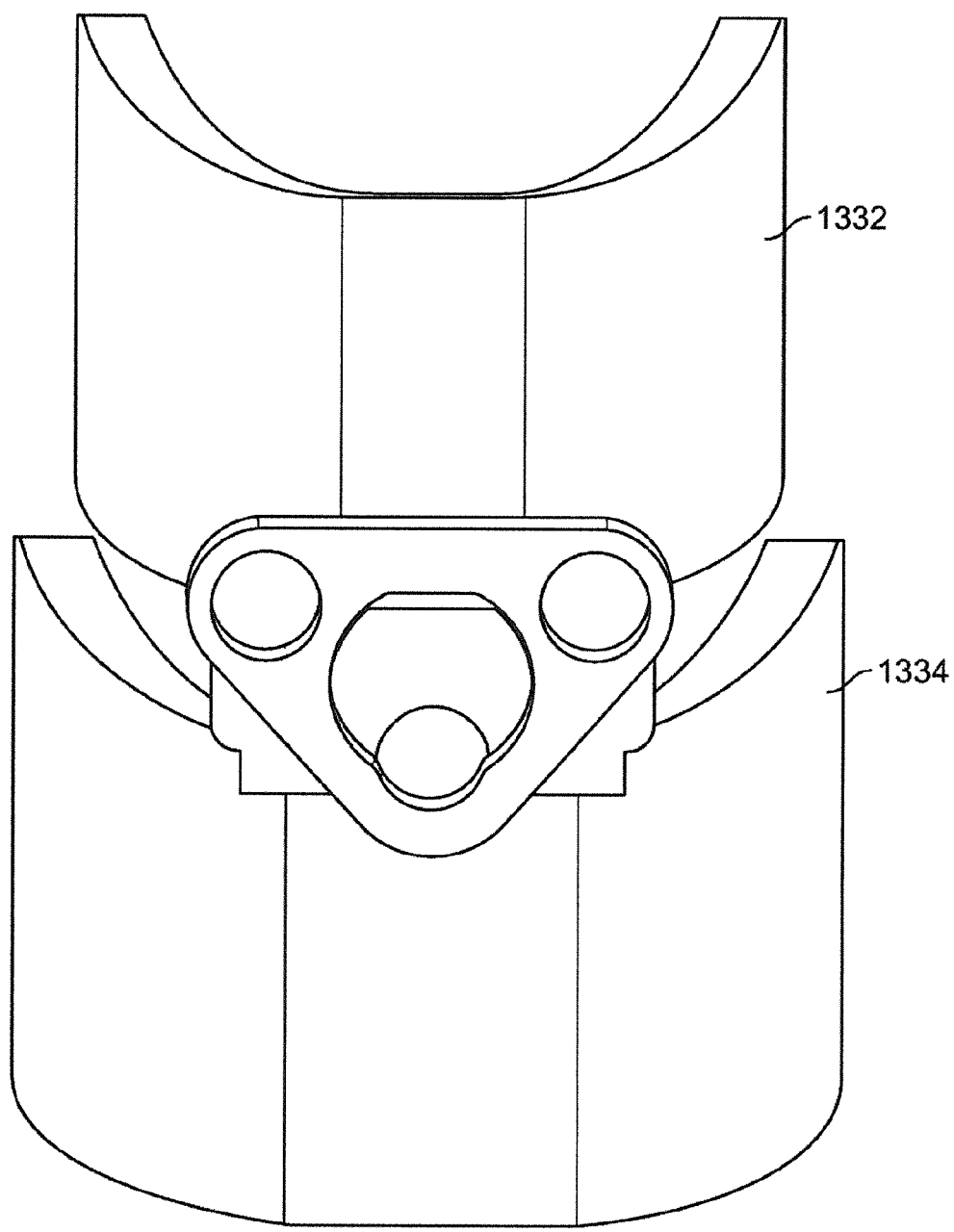
FIG. 66 is an anterior view of the trial spacer and drill guide of FIG. 65.
Figure 67:
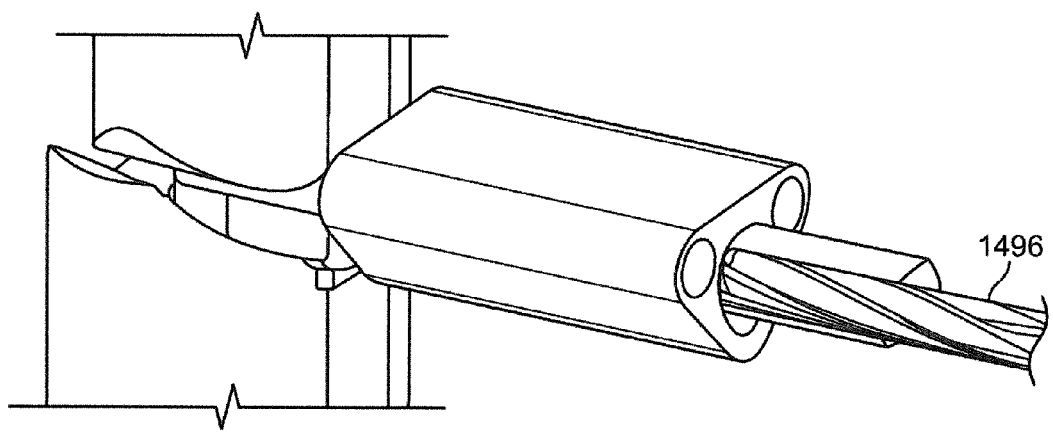
FIG. 67 is an anterolateral perspective view of the trial spacer and drill guide of FIG. 65 with a drill.
Figure 68:
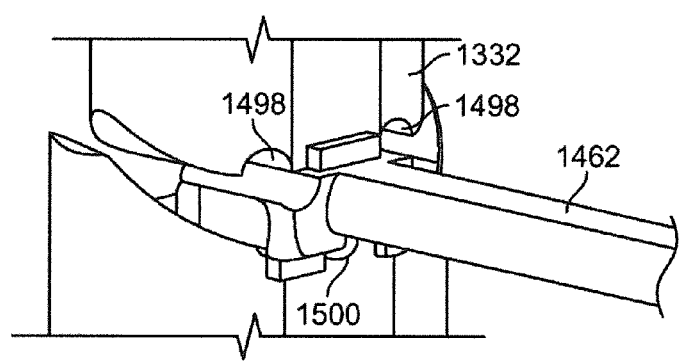
FIG. 68 is an anterolateral perspective view of the trial spacer of FIG. 67 after the grooves have been drilled and the drill guide is removed.

At this point, the trial spacer member 1458 is used in cooperation with a drill guide 1488 for drilling grooves in the vertebral bodies 1332 and 1334 at the facing surfaces thereof. Referring to FIG. 64, the drill guide 1488 has a triangular-block body 1490 with a pair of upper throughbores 1492 extending through the body 1490, and an irregularly-shaped, enlarged central throughbore 1494 between and below the upper, side throughbores 1492. The enlarged, central throughbore 1494 is sized so that the drill guide 1488 can be slid along the trial spacer member 1458 with the shaft portion 1462 fitting in the upper portion of the central throughbore 1494, as shown in FIG. 65. Referring next to FIG. 66, it can be seen that the upper side throughbores 1492 are aligned with the upper grooves 1468 and 1470 in the trial spacer portion 1460 to cooperate therewith in guiding a drill 1496 (FIG. 67) for cutting grooves in the upper vertebral body 1332. Similarly, the lower portion of the central throughbore 1494 of the drill guide 1488 cooperates with the lower groove 1464 in the shaft portion 1462 and lower groove 1466 in the trial spacer portion 1460 to form an opening through which the drill bit 1496 is guided for cutting a groove in the lower vertebral body 1334. FIG. 68 shows the pair of upper grooves 1498 formed along either side of the facing surface of the vertebral body 1332 and the lower groove 1500 formed centrally in the facing surface of the lower vertebral body 1334 with the drill guide 1488 removed from the shaft portion 1462 for purposes of illustrating the grooves 1490 and 1500.

Figure 70:
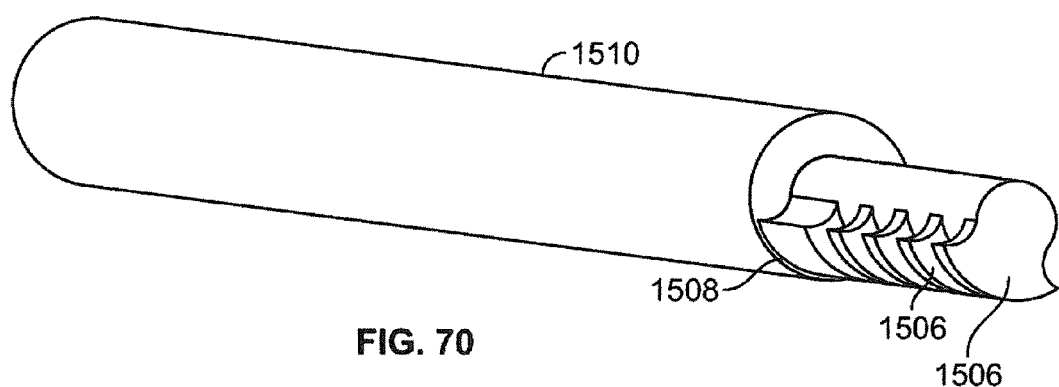
FIG. 70 is a perspective view of the cam cutter of FIG. 69.

Next, a cam cutter 1502 is advanced through the bores 1492 and 1494 in a manner similar to the drill bit 1496. The cam cutter 1502 has a reduced size, radially offset cutting end 1504 including several cutting blade portions 1506, and a counter bore cutting portion 1508 at the rear thereof. An enlarged shaft 1510 extends rearwardly from adjacent to the counter bore cutting portion 1508. The shaft 1510 is sized to fit into the openings through the drill guide 1488 formed in cooperation with the trial spacer member 1458, as previously described with respect to the drill bit 1496. FIG. 70 is a view of the cam cutter 1502 showing the bell-shaped configuration of the cutting blade portions 1506 and counter bore cutting blade portion 1508. The cam cutter 1502 is operable to cut radially enlarged recesses 1512 in the grooves 1498 and 1500 as well as enlarged counter bore portion 1514 at the rear end of the grooves 1498 and 1500. Alternately, the drill bit 1496 can be provided with a stepped configuration to form the counter bore 1514 simultaneously with the drilling of the grooves 1498 and 1500. Similarly, the cam cutter 1502 can be avoided altogether if the securing mechanism for the artificial disc implant 1452 is provided with cutting-type cams, as will be described hereinafter.

Figure 72:
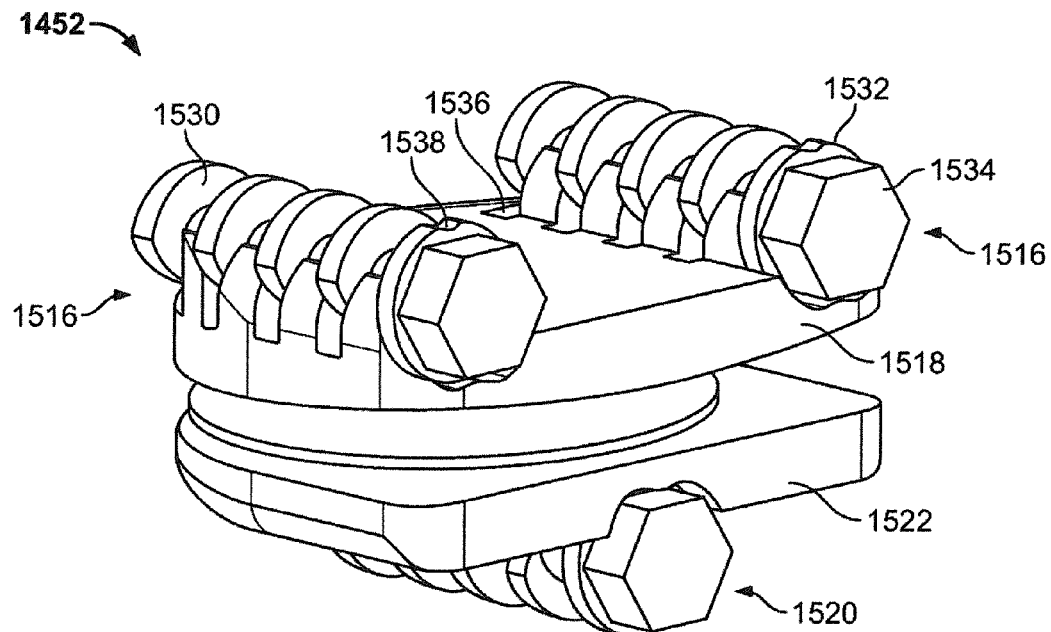
FIG. 72 is an anterolateral perspective view of an artificial disc implant according to the present invention including a securing mechanism in the form of three cam shafts with deployable cam lobe members.
Figure 73:
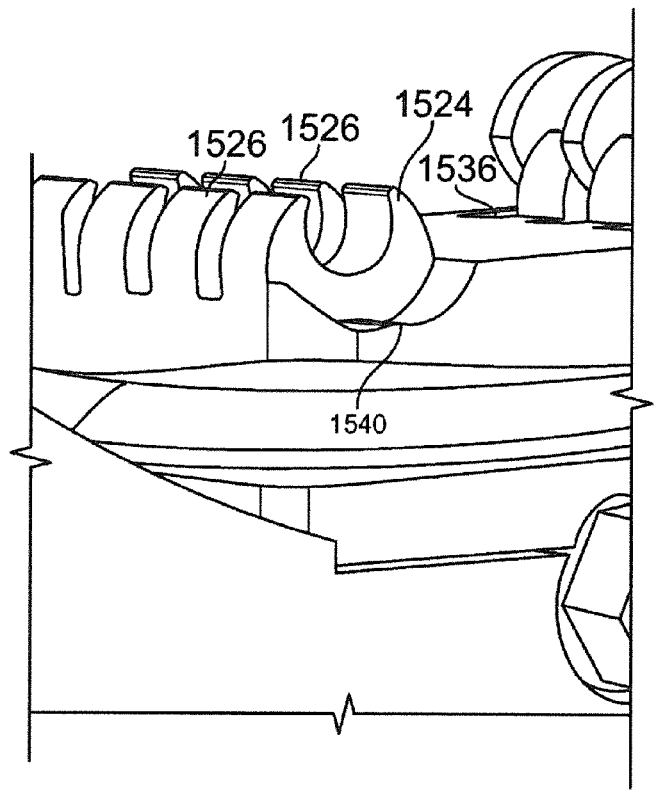
FIG. 73 is an enlarged anterolateral perspective view of the artificial disc implant of FIG. 72 with one cam shaft removed to show the retainer members.

Referring to FIG. 72, the securing mechanism of the disc implant 1452 takes the form of upper cam shafts 216 secured on either side of upper disc implant member 1518, and lower cam shaft 1520 secured centrally to the lower disc implant member 1522. To hold the cam shafts 1516 and 1520 to the respective disc members 1518 and 1522, each is provided with a plurality of spaced upwardly open, U-shaped retainer members 1524. The retainer members 1524 have upwardly extending arms 1526 that are spaced from each other so that the shaft portion 1528 of the cam shafts 1516 and 1520 will be received by a friction fit therebetween. In this regard, the preferred PEEK material from which the disc members 1518 and 1522 including the retainer members 1524 thereof are formed will provide the arms 1526 with sufficient strength and resiliency to provide a secure friction fit with the shaft portions 1528 snap-fit therebetween while allowing for the shaft portions to be rotated to secure the disc members 1518 and 1522 to the corresponding vertebrae 1332 and 1334.

Figure 74:
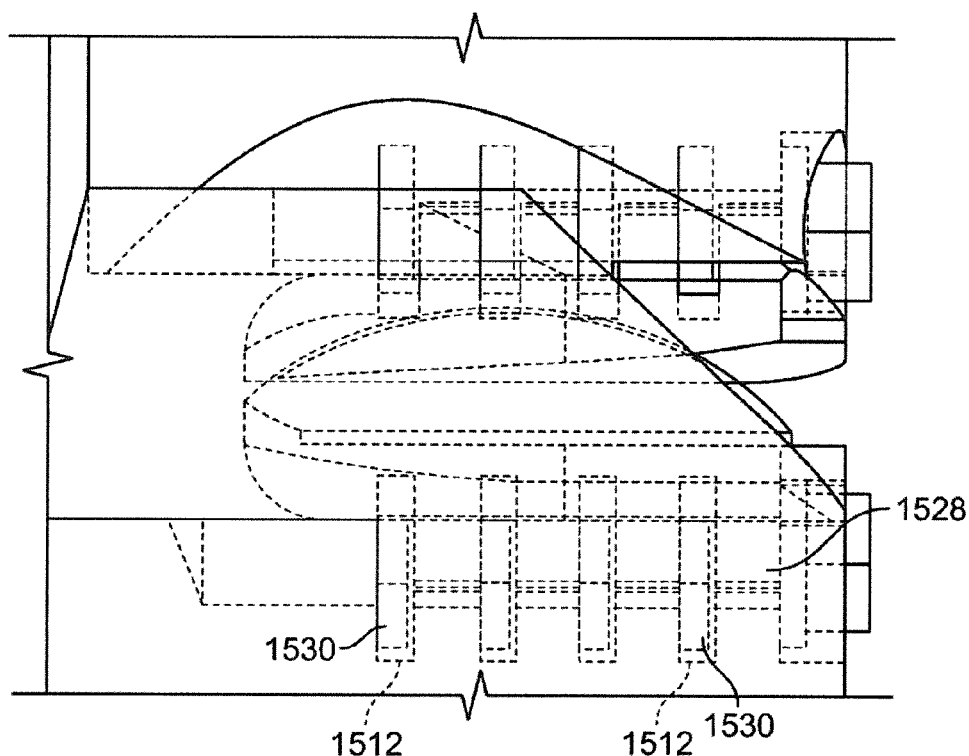
FIG. 74 is lateral view of the implant of FIG. 72 as implanted in the intervertebral space.

More specifically, the cam shafts 1516 and 1522 each include several cam lobe members 1530 spaced along the length thereof and a proximate disc indicator member 1532 adjacent drive head 1534. Initially, the cam shafts 1516 and 1520 are oriented 1480 degrees from their orientation shown in FIG. 72 for insertion of the artificial disc 1452 into the intervertebral space 1330 with the cam shafts 1516 and 1520 received in the corresponding grooves 1498 and 1500 of the vertebral bodies 1332 and 1334. In this regard, the cam lobes 1530 are rotated down into recessed slots 1536 formed in the upper surface of the upper disc member 1518. Rotating the cam shafts 1516 and 1520 via the hex drive heads 1534 thereof by 1480 degrees from their insertion orientation to their secured orientation shifts the cam lobes 1530 into the recesses 1512 cut into the vertebral body grooves 1498 and 1500, as shown in FIG. 74. In this manner, the artificial disc implant 1452 is secured in the intervertebral space 1330 against extrusion out therefrom during articulation of the upper and lower disc members 1518 and 1522 relative to each other as the upper and lower vertebrae 1332 and 1334 shift via the arcuate bearing interface formed between the members 1518 and 1522. The disc indicator member 1532 is sized to be received in the counter bore portion 1514 of the grooves 1498 and 1500. The disc member 1532 can be provided with a pair of diametrically opposite notches 1538 about its periphery that cooperate with a raised nub 1540 on the disc member 1518 so that the user is provided with a tactile indication that the cam shafts 1516 and 1520 have been rotated by 1480 degrees from their insertion orientation to shift the cam lobes 1530 so that they are substantially fully received in the groove recesses 1512.

Figure 75:
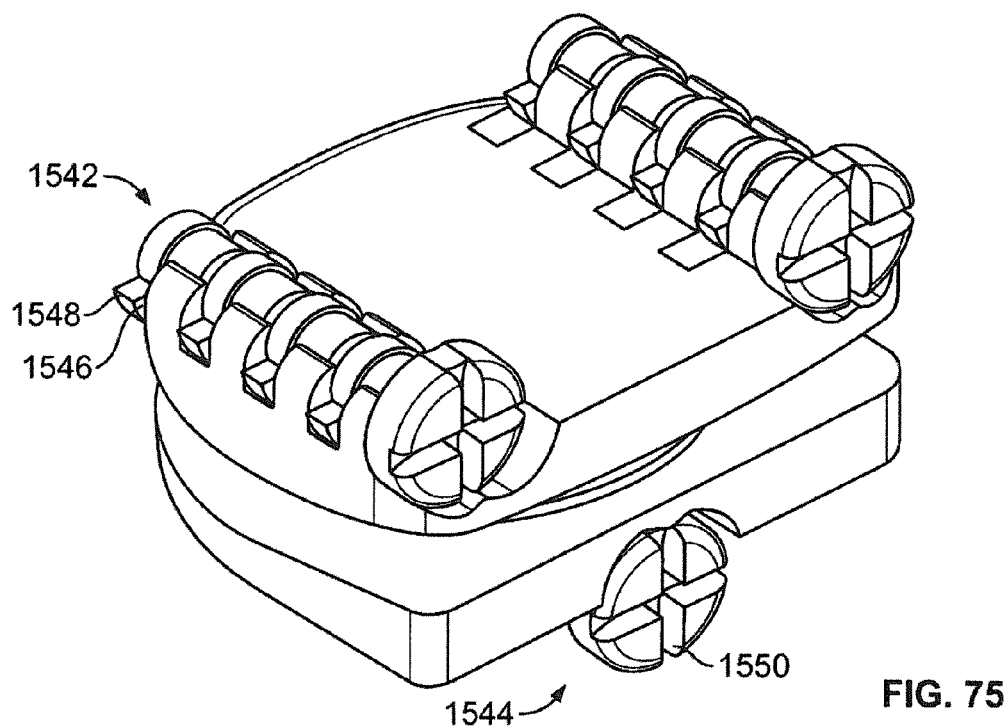
FIG. 75 is an anterolateral perspective view of the implant of FIG. 72 with cam members with sharpened edges for cutting into bone when deployed into the vertebrae.
Figure 76:
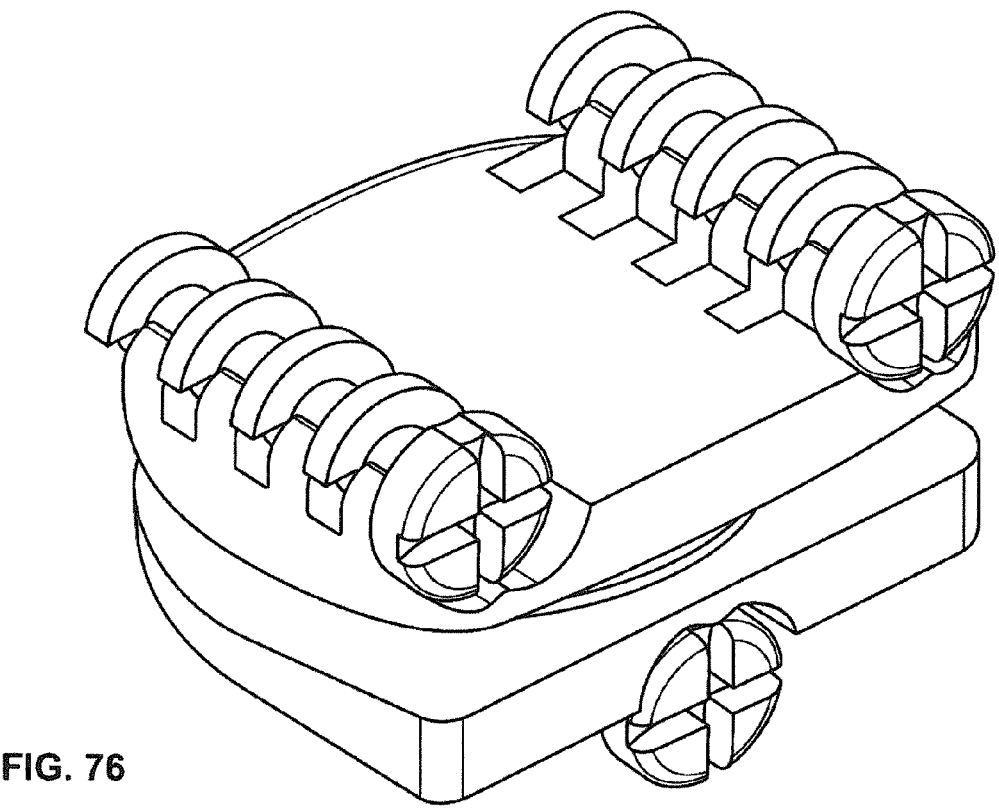
FIG. 76 is an anterolateral perspective view of the implant of FIG. 75 with the cam members fully deployed.

FIGS. 75 and 76 show alternative upper cam shafts 1542 and an alternative lower cam shaft 1544. In this form, the cam members 1546 have more of a flat mushroom-like configuration with sharp corner edges 1548 for cutting into the vertebral bodies 1332 and 1334. In this manner, the separate cam cutter 1502 need not be used for cutting the recesses 1512 in the vertebral body grooves 1498 and 1500. Also, it can be seen that the drive head 1534 can have a cruciform drive recess 1550 rather than having the hex drive configuration of the drive head 1534.

Figure 77:
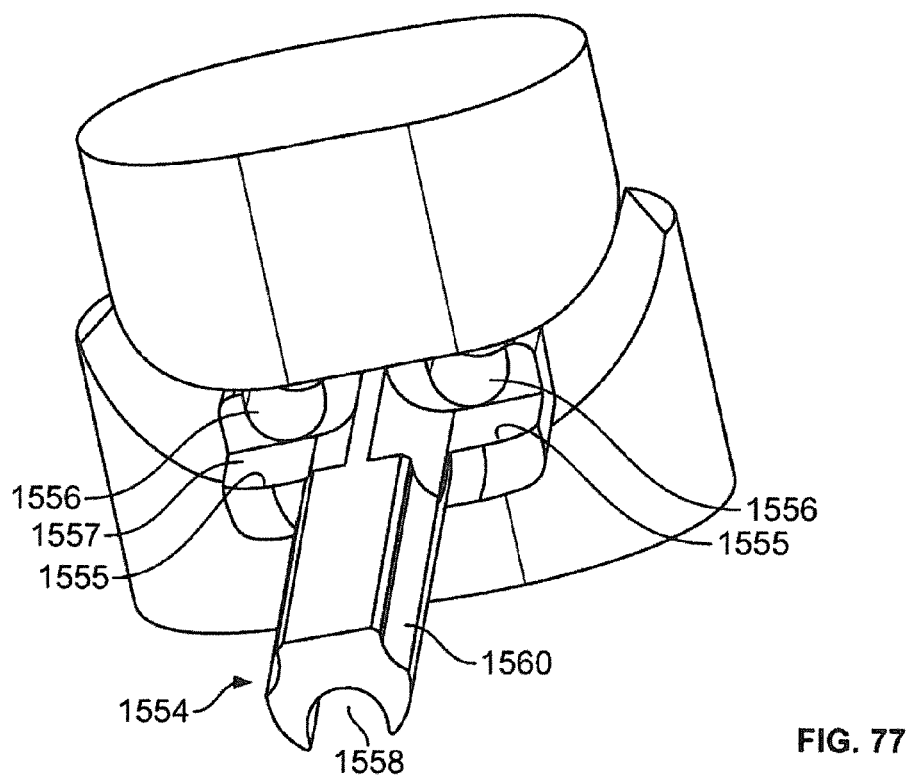
FIG. 77 is an anterior perspective view of a trial spacer member according to the present invention inserted into the intervertebral space.
Figure 85:
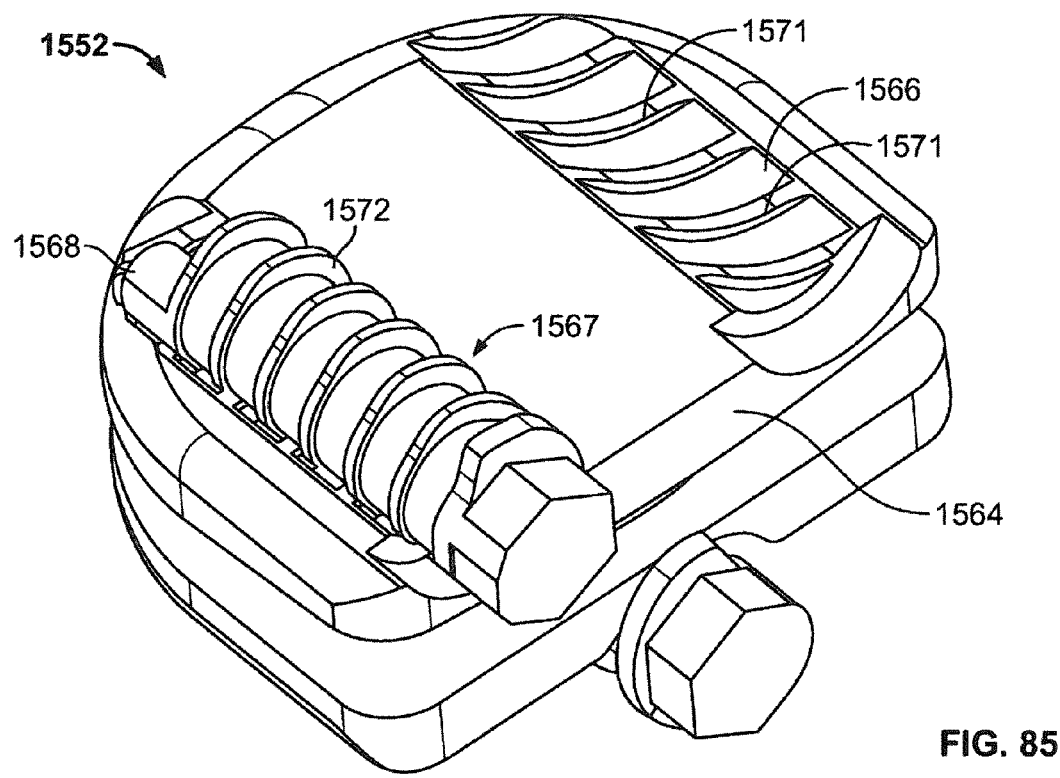
FIG. 85 is an anterolateral perspective view of an artificial disc implant according to the present invention with one cam shaft hidden, wherein the cam shafts are first imbedded into the vertebrae before the implant is inserted.
Figure 86:
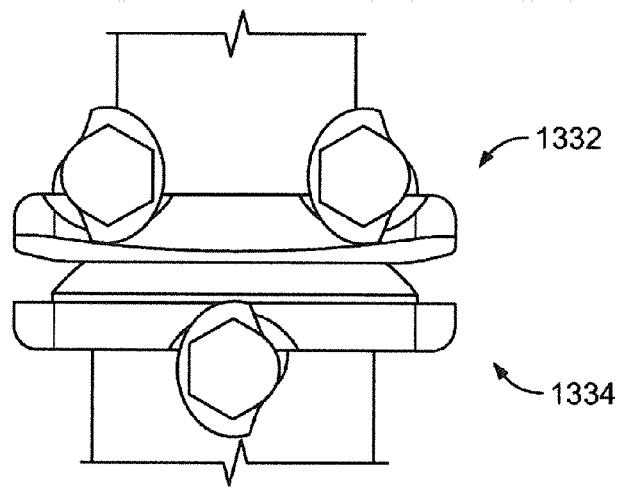
FIG. 86 is an anterior view of the artificial disc implant of FIG. 85 wherein the cam shafts have been rotated 90 degrees to secure the implant with respect to the vertebrae.
Figure 87:
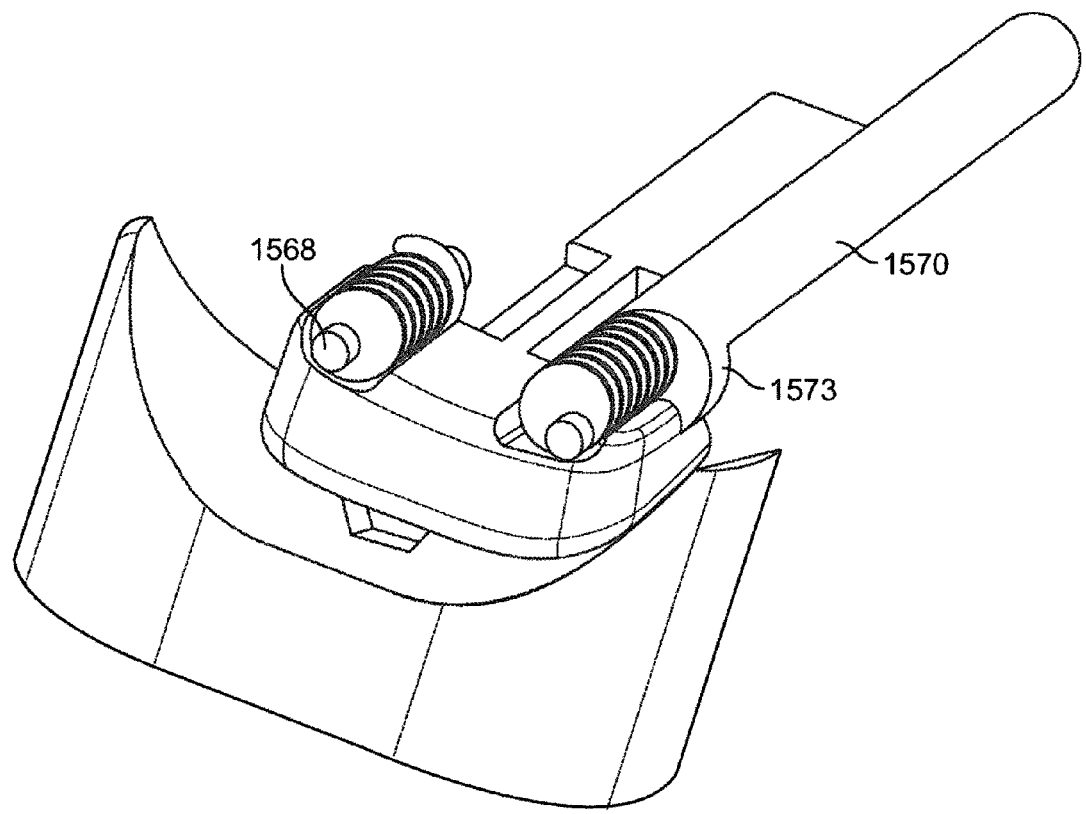
FIG. 87 is a posterolateral view of the trial spacer of FIG. 79 with the cam shaft driver driving one of the cam shafts up into the upper vertebrae, which is hidden for illustration purposes.

The next trial spacer and artificial disc implantation and securing system is similar to the previous system except that the securing mechanism is not associated with the artificial disc as it is inserted into the intervertebral space 1330, but rather is first inserted into the preformed features formed in the vertebral bodies 1332 and 1334 and thereafter deployed therefrom to interconnect the vertebral bodies and the artificial disc implant 1552 (FIG. 85). Referring to FIG. 77, a trial spacer member 1554 is shown having upper side grooves 1556 in the forward head portion 1557 thereof and a lower central groove 1558 that extends in the rear shaft portion 1560 thereof as well as in the forward head portion 1557. The cover and handle member for the trial spacer member 1554 is not shown for illustration purposes but otherwise is similar to the previously described cover and handle member in that it is configured to ensure that the forward trial spacer portion including the grooved head portion 1557 can be inserted smoothly into the intervertebral space 1330 without gouging the vertebral bodies 1332 and 1334.

Figure 78:
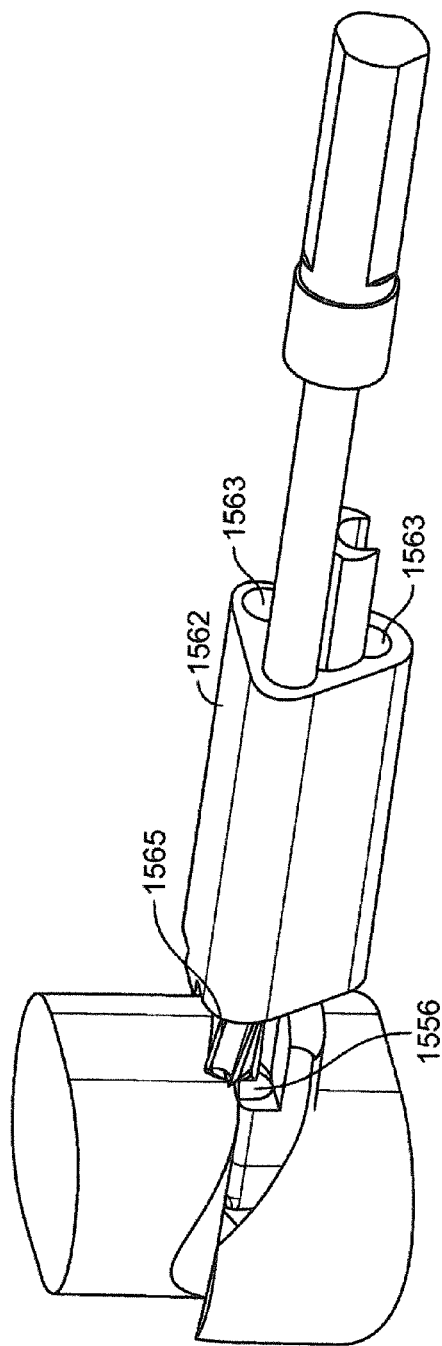
FIG. 78 is an anterolateral perspective view of a trial spacer member of FIG. 77 with a drill guide inserted over the trial spacer for drilling offset grooves into the vertebrae for installing cam shafts directly into the vertebrae.

As shown in FIG. 78, the shaft member 1560 receives a drill guide 1562 thereon which has throughbores 1563 that are slightly offset from the corresponding grooves 1556 and 1558 of the trial spacer member 1554. Accordingly, drill 1565 is guided through the bores 1563 to drill grooves 1569 into the vertebral body 1332 that are slightly offset upwardly from the upper grooves 1556 of the trial spacer member and a groove 1569 into the vertebral body 1334 that is slightly offset downwardly from the lower groove 1558 of the trial spacer member 1554.

Figure 79:
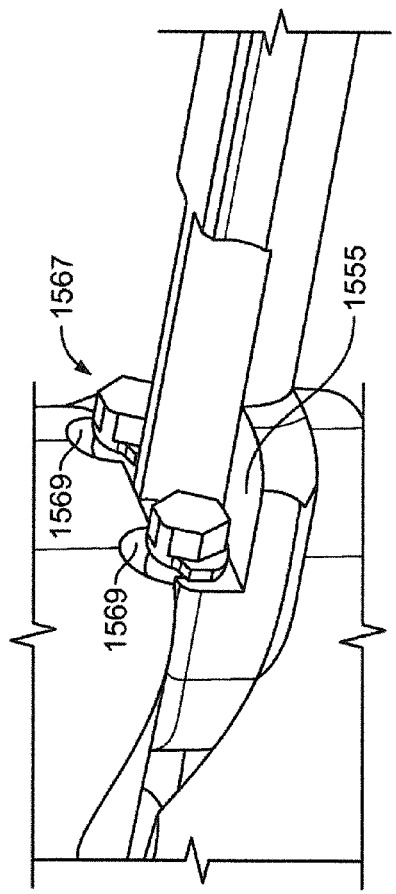
FIG. 79 is an anterolateral perspective view of a trial spacer member of FIG. 77 with the cam shafts inserted into the trial spacer for being imbedded in the vertebra prior to insertion of the implant.
Figure 80:
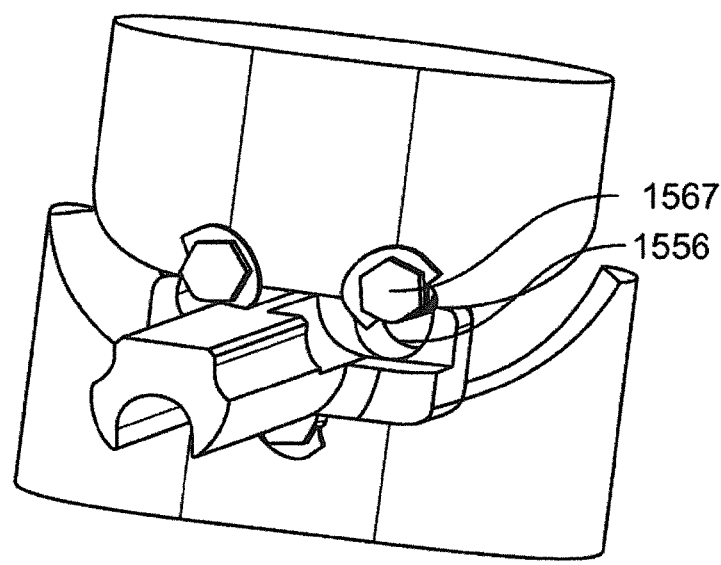
FIG. 80 is an anterolateral perspective view of a trial spacer of FIG. 79 with the cam shafts imbedded into the offset grooves in the vertebrae.

Next, cam shafts 1567 are inserted into the intervertebral space 1330 guided by the grooves 1556 and 1558 of the trial spacer member 1554, and then they are rotated and cammed up into the offset grooves 1569 formed in the upper vertebral body 1332 and down into the offset groove 1569 formed in the lower vertebral body 1334, as shown in FIGS. 79 and 80. The camming action of the cam shafts 1567 is shown in FIGS. 81-84.

Figure 81:
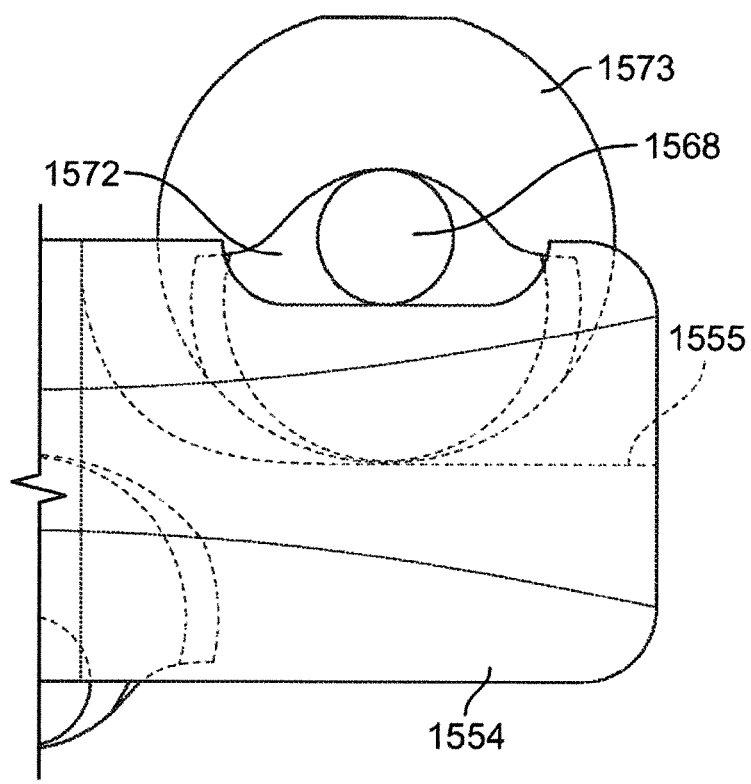
FIGS. 81-84 show a sequence from a posterior viewpoint detailing the operation of the cam shafts from an initial resting point on the trial spacer in FIG. 81 to being cammed up into the vertebrae in FIGS. 82 and 83, and being imbedded into the vertebrae in FIG. 84 so that the trial spacer may be removed and the implant may be inserted.
Figure 82:
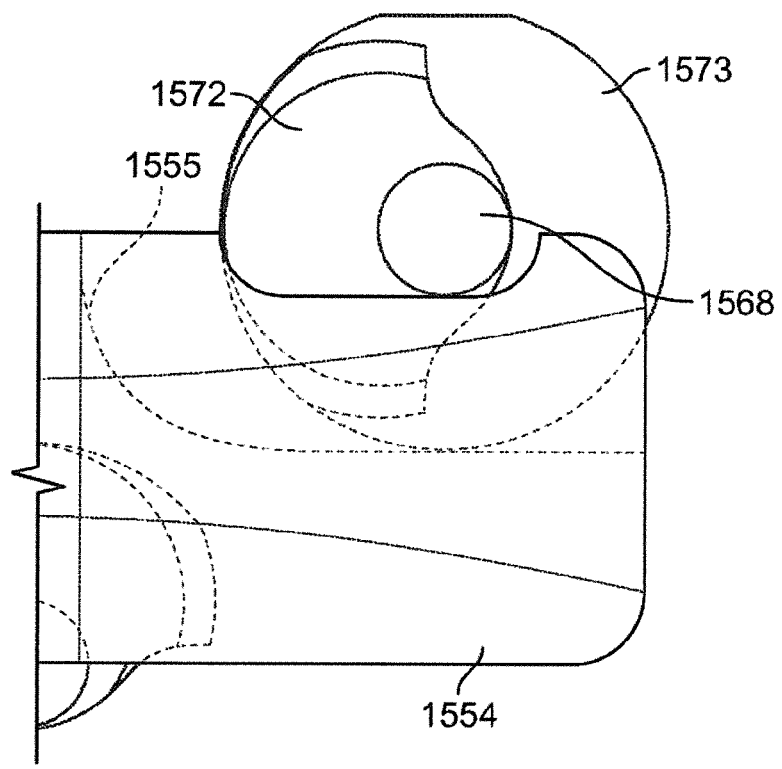
Figure 83:
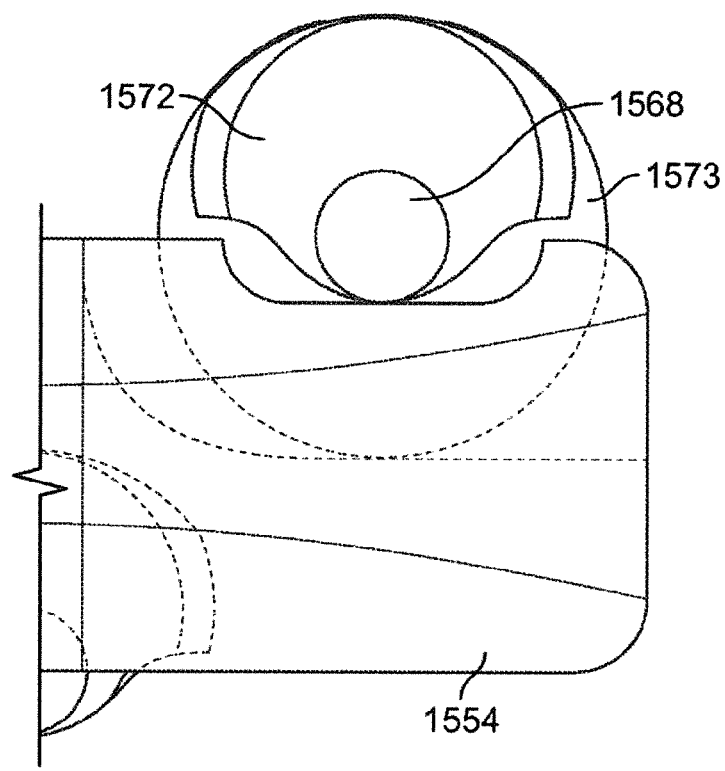
Figure 84:
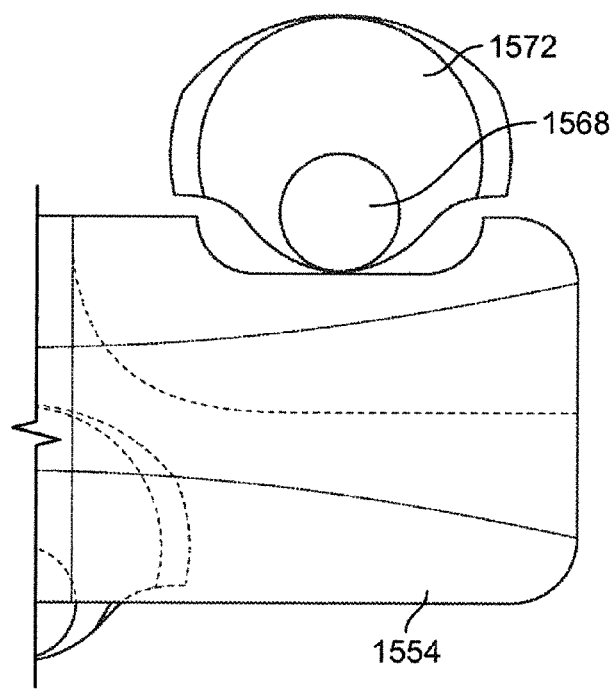

In FIG. 81, a cam shaft 1567 is shown from a posterior viewpoint in its initial position resting in the groove 1556 of the trial spacer member 1554. The head of the cam shaft is engaged by the drive tool 1570 having an eccentric cam 1573 (FIG. 87) for camming against an anterior platform or ledge 1555 (FIGS. 77 and 79) on the trial spacer member 1554. The cam shafts 1567 are cammed at both their distal shaft ends 1568 as shown in FIGS. 81-85 and 87, as well as at their proximate ends where they interface with drive tool 1570. In FIG. 82, the drive tool 1570 has been rotated clockwise 90 degrees along the anterior platform 1555 of the trial spacer member 1554. This causes the cam shaft 1567 to rotate 90 degrees and the cam lobes 1572 begin to engage and imbed themselves the upper vertebra. In FIG. 83, the cam shaft 1567 is shown fully rotated 180 degrees from its initial position in FIG. 81. At this point, the cam lobes 1572 are embedded into the vertebra, and are held in place due to the frictional engagement between the cam lobes 1572 and the bone. Finally, the driver 1570 may be removed, as is shown in FIG. 84. Once the cam shafts 1567 have been fully rotated 180 degrees, the cam lobes 1572 are completely removed from the body of the trial spacer member 1554. Thus, the trial spacer 1554 may be removed.

With the cam shafts 1567 rotated as shown in FIG. 84 so that the sharp cam lobes 1572 thereof are rotated up (or down) into the vertebral bodies via a cutting action generated by the cams during such rotation, the disc implant 1552 is then inserted into the intervertebral space 1330. As shown in FIG. 85, the upper disc member 1564 has spiral cutouts 1566 in the upper surface thereof so that rotating the cam shafts 1562 again causes the cam lobes 1572 to be engaged in both the grooves of the vertebral bodies 1332 and 1334 as well as tightly engaged or embedded into the raised ribs 1571 defining the spiral cutouts 1566 so that the implant 1552 is securely held and retained in the intervertebral space 1330 during articulation thereof.

Figure 88:
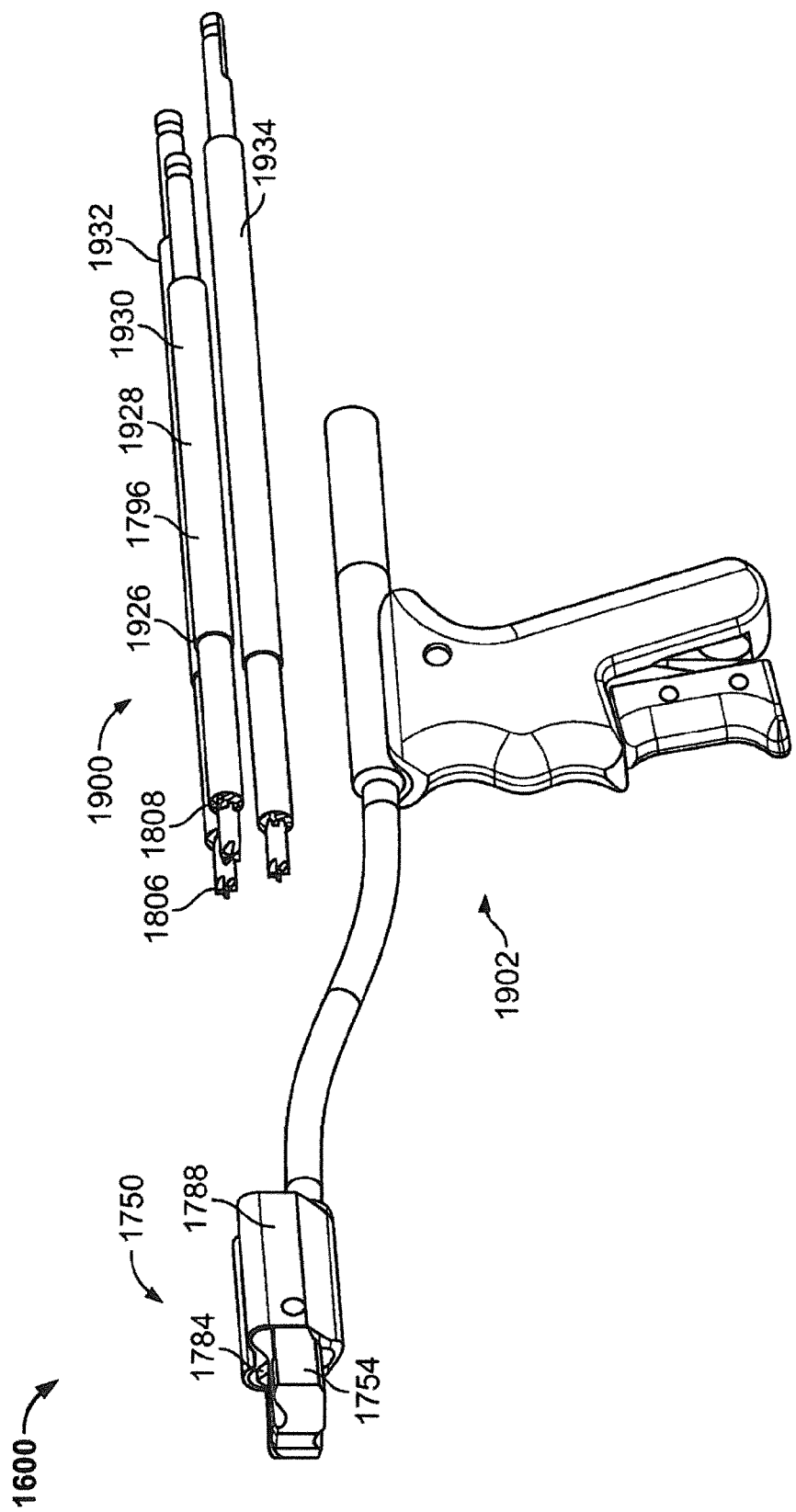
FIG. 88 is a side perspective view of the trial spacer system comprised of a trial spacer assembly, a drill set, and a trial spacer inserter tool.

In another form, a trial spacer system 1600 is shown in FIG. 88 is employed for sizing and preparing an implantation site for an implant. The trial spacer system 1600 includes a trial spacer assembly 1750, a drill set 1900, and an insertion tool 1902. As in the embodiment disclosed in FIG. 56, the trial spacer assembly 1750 is utilized to form features in the vertebral bodies 1330, 1332 for receipt of the securing mechanism that is associated with the artificial disc implant 1752. A principal difference between the trial spacer assembly 1450 of FIG. 56 and the present trial spacer assembly 1450 is that present assembly eliminates the shaft portion 1462 and integrates the drill guide 1488 together with the trial spacer portion 1454. Additional features that vary from the previous embodiment of the trial spacer assembly 1450, including the insertion tool 1902, will be described below.

Figure 89:
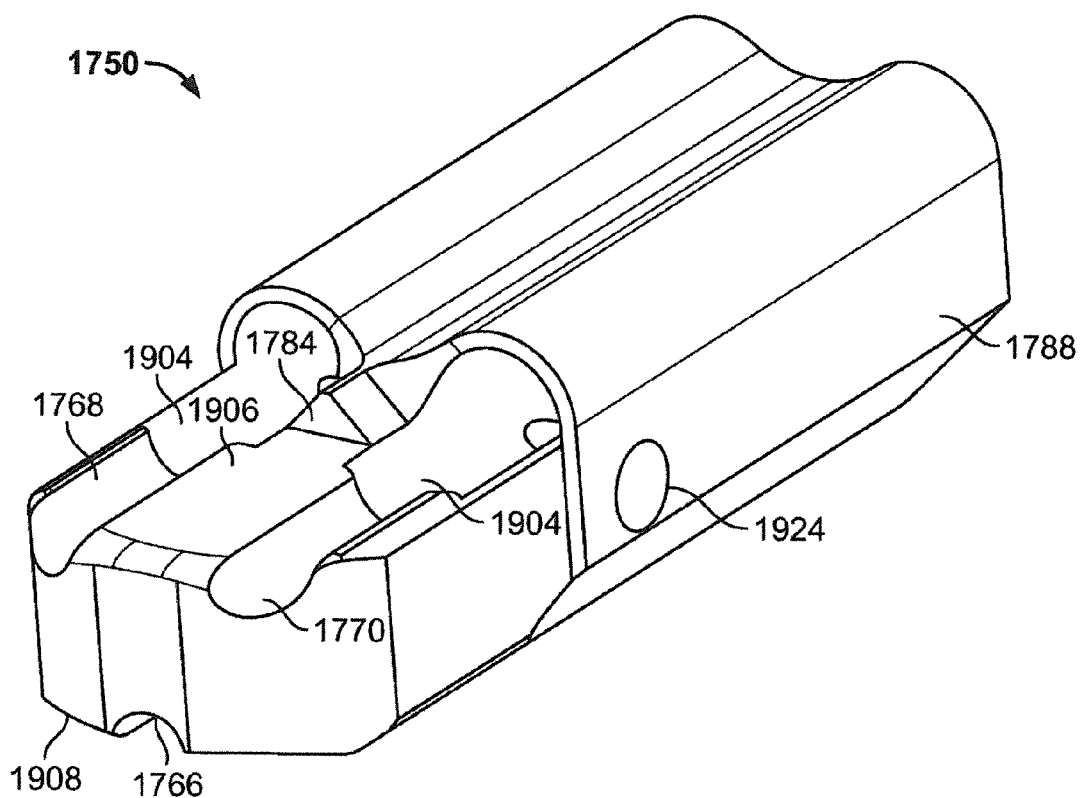
FIG. 89 is a posterolateral perspective view of the trial spacer assembly of FIG. 88.

The trial spacer assembly 1750 generally has a forward trial spacer portion 1754 for insertion into the intervertebral space 1330 and rearward drill guide 1788 integrated with the forward trial spacer portion 1754. The forward trial spacer portion 1754 varies little from the previously described embodiment in FIG. 56, and therefore will not be described in full detail here. However, one feature notably different in geometry from the previous embodiment is the upper stop member 1784, shown in FIG. 89 located on the upper surface of the trial spacer portion between the upper grooves 1768, 1770. In addition, both the upper grooves 1768, 1770 and the lower groove 1766 have a rearward counterbored portion 1904 for accommodating drill bits 1930, 1932, 1934 having a forward cutting portion 1806 and a rearward counterbored portion 1808. Also, the upper and lower faces 1906, 1908 of the trial spacer portion 1754 may be skewed with respect to one another to mimic the lordotic angle of the spine to improve the fit of the trial spacer 1754. Preferably, the angle between the upper and lower faces 1906, 1908 is about 5 degrees. The trial spacer assembly 1750 is preferably made out with titanium or stainless steel. In addition, the assembly is preferably colorized using an anodization process, such that different sized trial spacer assemblies are color coded for ease of identification.

Figure 90:
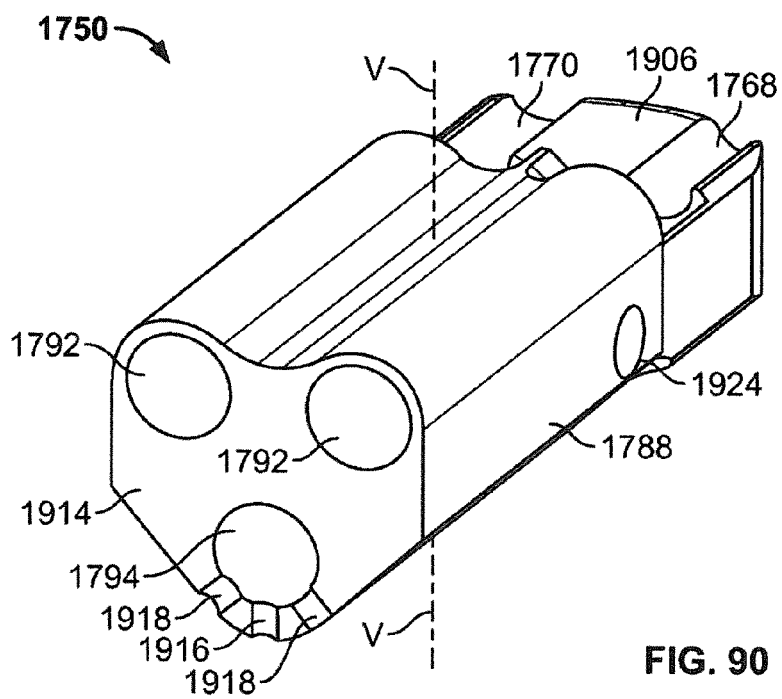
FIG. 90 is an anterolateral perspective view of the trial spacer assembly of FIG. 88.
Figure 91:
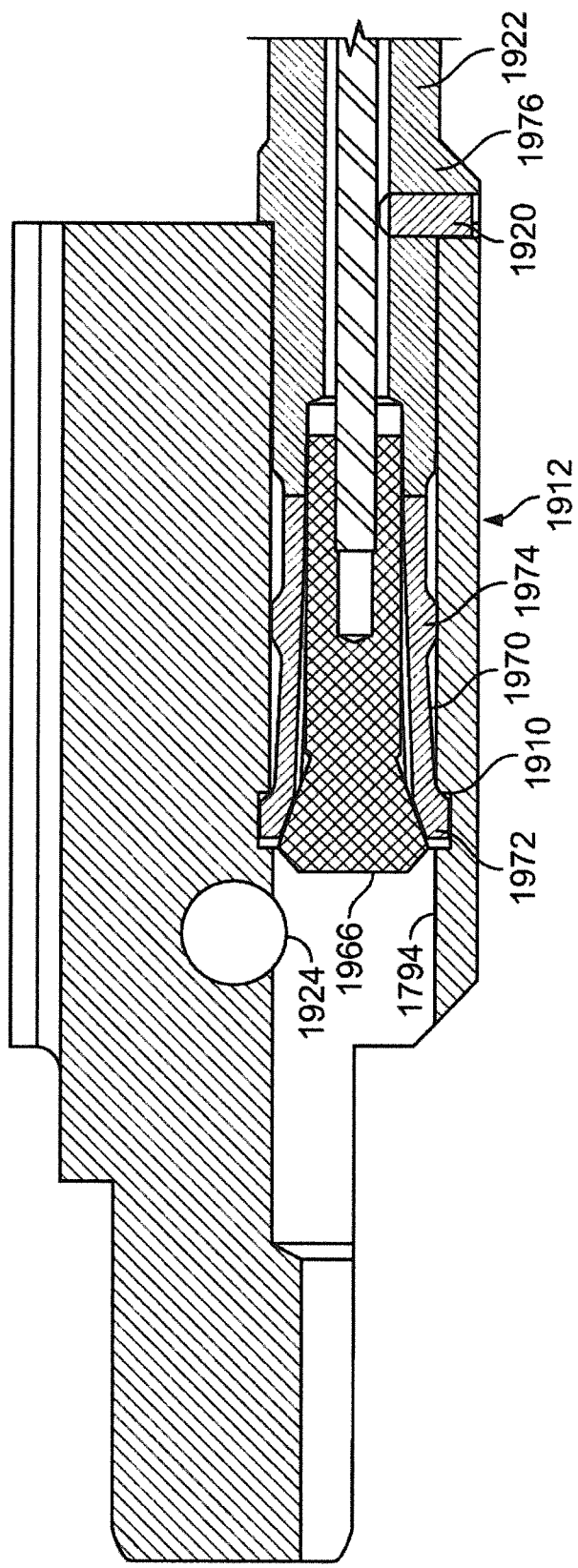
FIG. 91 is an enlarged longitudinal cross-sectional view of the trial spacer assembly of FIG. 88 with the gripping mechanism of the inserter tool inserted therein.

The drill guide portion 1788 of the of the trial spacer assembly 1750 is similar from the drill guide 1488 of FIG. 64, except for a few notable features. For instance, the present drill guide portion 1788 replaces the irregularly-shaped throughbore 1494 with a lower throughbore 1794 similar in diameter to the upper throughbores 1792, as shown in FIG. 90. As shown in FIG. 91, the lower throughbore 1794 has an annular recessed portion 1910 for accepting the gripping mechanism 1912 of the insertion tool 1902 to allow the tool 1902 to securely attach to the trial spacer assembly 1750. Now referring to FIG. 90, the drill guide portion 1788 has a rear face 1914 wherein each throughbore 1792, 1794 terminates. On the face 1914 adjacent to the lower throughbore 1794 are a set of three recesses 1916, 1918 for providing three positions at which the inserter tool 1902 may engage the trial spacer assembly 1750. Each recess 1916, 1918 is sized to mate with a single corresponding guide pin 1920 on the barrel 1922 of the inserter tool 1902. When the middle recess 1916 is engaged by the pin 1920 of the inserter tool 1902 (as in FIG. 91), the trial spacer assembly 1750 is held at a neutral angle, with the vertical axis (denoted with a "v") of the assembly parallel with the vertical axis of the inserter tool 1902. The two remaining recesses 1918 to either side of the middle recess 1916 allow the user to grip the trial spacer assembly 1750 at 45 or −45 degrees with respect to the vertical axis. This allows the surgeon to manipulate the trial spacer 1750 in multiple positions, and gives the tool 1902 greater flexibility. Accordingly, the tool 1902 has a plurality of relative positions between the tool barrel 1922 and the trial spacer assembly 1750. The drill guide portion 1788 also defines a lateral bore 1924 for providing a point of reference for the surgeon when viewing the trial spacer 1750 using fluoroscopy to help position the assembly 1750 once inserted into the patient's body. A bore 1924 is used because the trial spacer assembly 1750 is preferably made out of stainless steel or titanium.

Now referring to FIG. 88, each drill bit 1930, 1932, 1934 of the set 1900 has identical cutting surfaces 1806, 1808 on the forward end of the shaft 1928. The forward cutting portion 1806 consists of a cutting surface at the tip of the bit 1796 suitable for cutting an elongate groove 1498 in the vertebra 1332, 1334 for the forward portion of the securing mechanism of the implant 1752. At the rear end of the first cutting portion 1806 begins the counterbore cutting portion 1808 for creating a counterbore in the vertebra to provide clearance for the head of the securing mechanism.

Each drill bit 1796 has a collar 1926 for providing an abutment surface to restrict the distance the bit 1796 may be inserted into the trial spacer assembly 1750. The collar 1926 is an enlarged portion of the drill bit shaft 1928 and abuts the rear face 1914 of the trial spacer assembly 1750 when the drill bit 1796 is fully inserted. This keeps the surgeon from unintentionally drilling too far and damaging surrounding tissue, bone, nerves, and other vital areas.

As shown in FIG. 88, the drill set 1900 is comprised of three drill bits 1930, 1932, 1934 having shafts 1928 of differing lengths. The length of each shaft 1928 is different so the bits 1930-34 may be left in the drill guide 1788 and used sequentially, from shortest to longest, without interfering with the drill. The first and shortest bit 1930 is used to create the first groove 1798 in the upper vertebra 1332, the second and intermediate bit 1932 to create the second groove 1798 in the upper vertebra 1332, and the third and longest bit 1934 to create the groove 1800 in the lower vertebra 1334. This way, the first and second drill bits 1930, 1932 need not be removed from the trial spacer assembly 1750 prior to insertion of the third drill bit 1934. Once the first and second drills have cut grooves 1798 into the upper vertebra 1332, they remain in place to act as placeholders in the newly formed grooves 1798. In this manner, the drill bits 1900 help to secure the trial spacer 1750 in place to prevent movement of the trial spacer assembly 1750 with respect to the vertebrae 1332, 1334 while the other grooves are being cut and while the inserter tool 1902 is being removed. Advantageously, no other fixation means, such as bone screws, are necessary to secure the trial spacer 1750 to the vertebrae 1332, 1334.

Figure 92:
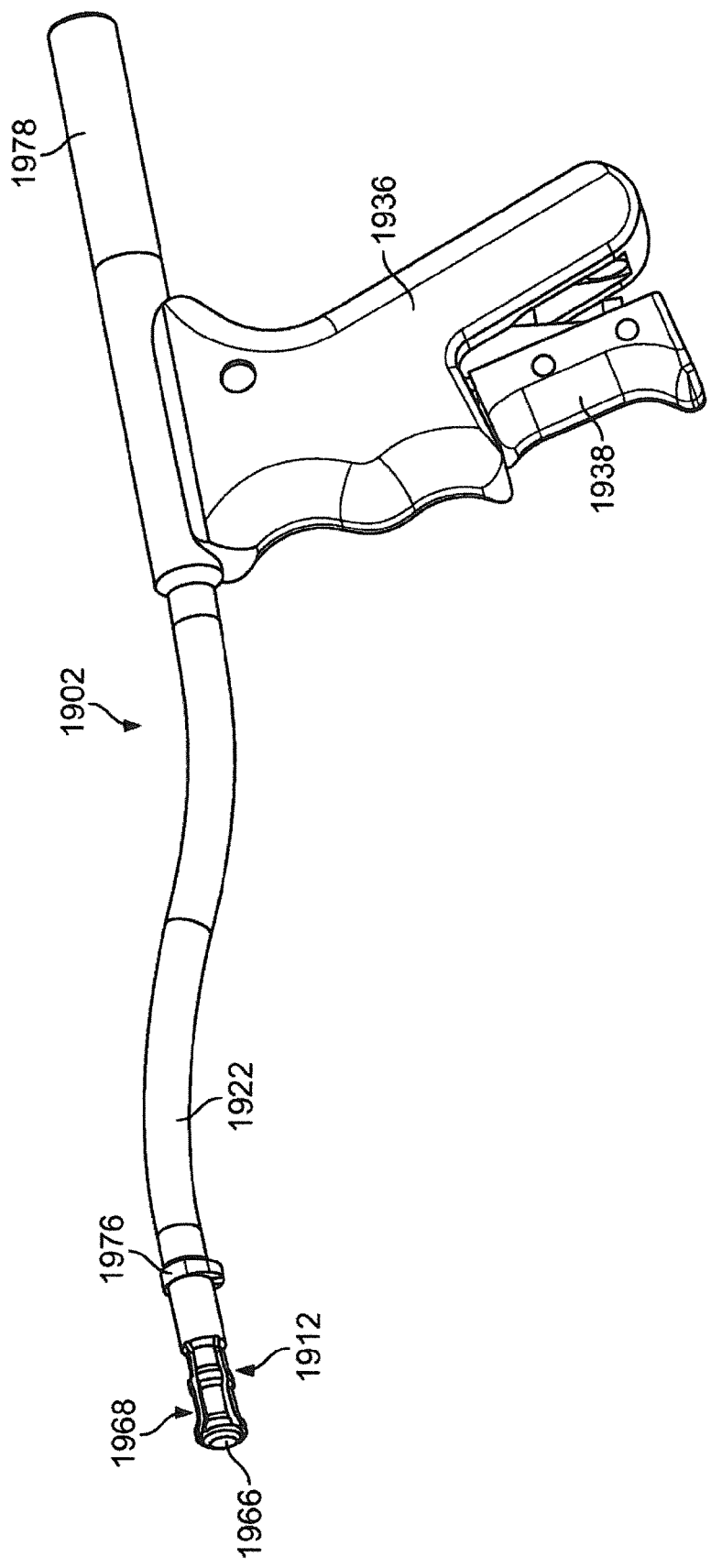
FIG. 92 is a side perspective view of the inserter tool of FIG. 88.
Figure 93:
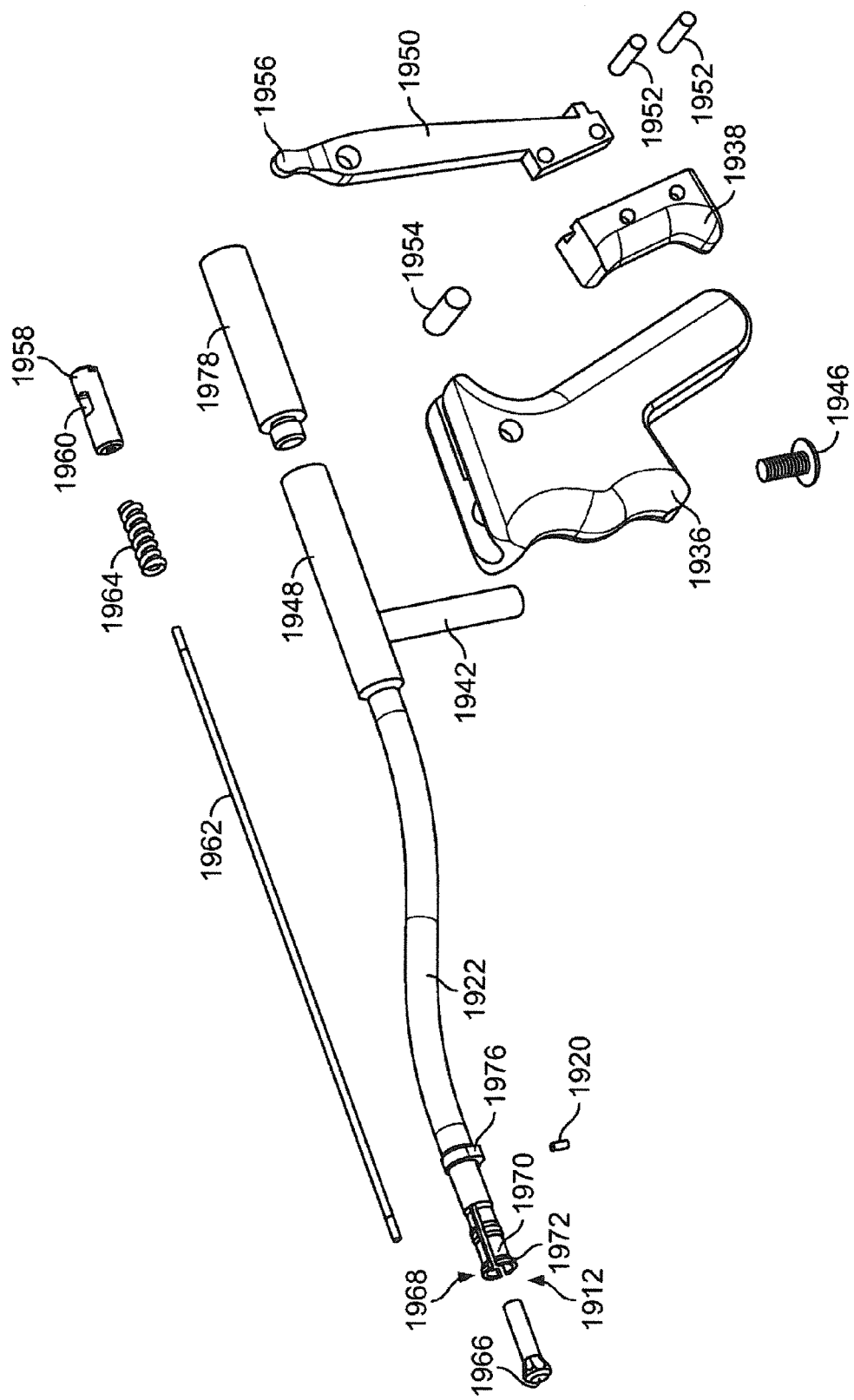
FIG. 93 is an exploded view of the inserter tool of FIG. 88.
Figure 94:
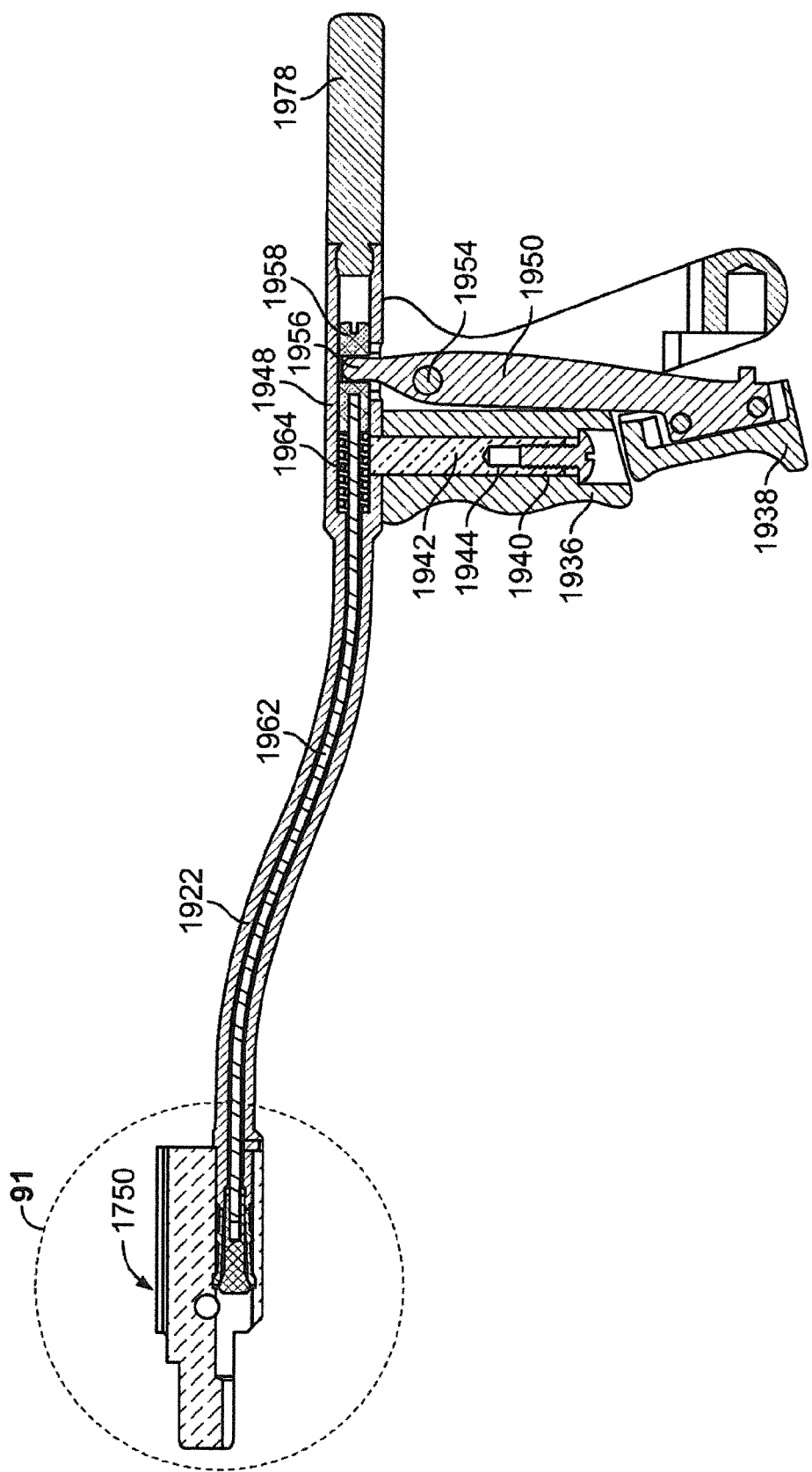
FIG. 94 is a longitudinal cross-sectional view of the inserter tool and trial spacer assembly of FIG. 88.
Figure 95:
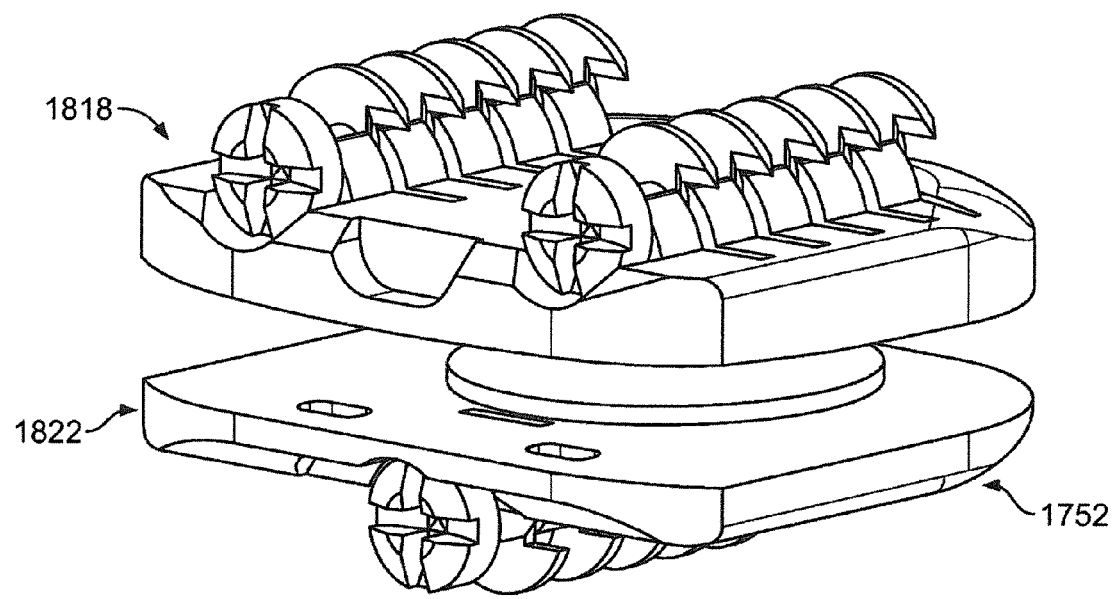
FIG. 95 is an anterolateral perspective view of an artificial disc implant according to the present invention with the securing mechanisms fully deployed.

Now referring FIG. 92, the trial spacer inserter 1902 comprises a gripping assembly 1912 connected by a barrel 1922 to a handle 1936 and an actuator in the form of a trigger 1938. As shown in FIGS. 93 and 94, the handle 1936, preferably made of a polymer, such as Radel®, has a partially hollow interior including an annular recess 1940 for accepting a downwardly extending handle shaft 1942 having a threaded recess 1944 at the bottom. A fastener 1946 affixes the handle 1936 to the downwardly extending handle shaft 1942 by threading the fastener 1946 into the threaded end 1944. The handle shaft 1942 is welded or otherwise integrated into the yoke housing 1948 of the inserter 1902. The trigger 1938 is attached to an elongate trigger link 1950 at the link's lower end with two pins 1952. The trigger link 1950 is disposed partially within the interior of the handle 1936 and pivots about a hinge pin 1954 which protrudes through the trigger link 1950 and is captured within the handle 1936. At its upper end, the trigger link 1950 has an actuating head portion 1956 for actuating the gripping mechanism 1912.

Specifically, the head portion 1956 of the trigger link 1950 directly engages the yoke 1958 to move it within the yoke housing 1948 to actuate the gripping mechanism. The yoke 1958 is a cylindrical body having a bore 1960 for accepting the head portion 1956 of the trigger link 1950 and is directly propelled thereby. The yoke 1958 is attached to the push rod 1962 at the rear portion of the yoke's forward end. A spring 1964 disposed between the yoke 1958 and the internal end wall of the yoke housing 1948 provides a biased resistance to the trigger 1938 when the yoke 1958 is actuated by the trigger link 1950.

The yoke housing 1948 is connected to the barrel 1922, which defines an internal bore 1960 for guiding the push rod 1962 through the barrel 1922. The push rod 1962 is preferably made of a flexible material, such as Nitinol. The push rod 1962 extends through the internal bore 1960 within the barrel 1922 from the yoke 1958 to the gripping mechanism 1912. The gripping mechanism 1912 includes a wedge shaped plunger 1966 connected to the push rod 1962 and an expandable flared end 1968. The flared end 1968 has a plurality of flexible tabs 1970 each having a protrusion 1972 at the forward end of the tab 1970 for engaging the recessed portion 1910 within the lower throughbore 1794 of the trial spacer assembly 1750 as shown in FIG. 91. The tabs 1970 also have a stabilizing ridge 1974 for engaging the internal surface of the lower throughbore 1974 to further stabilize the trial spacer assembly 1750 to prevent unwanted movement between the assembly 1750 and the inserter tool 1902. The flared end 1968 is sized to fit within the lower throughbore 1794 when the plunger 1966 is not retracted. The flexible tabs 1970 are splayed radially outwards by the wedge-shaped plunger 1966 when the plunger 1966 is pulled inwards towards the rear. When the plunger 1966 is retracted, the flexible tabs 1970 engage the internal surfaces of the lower throughbore 1794.

The barrel 1922 includes an insertion guide 1976 disposed on the barrel 1922 near the gripping mechanism 1912 for abutting the rear face 1914 of the drill guide portion 1788 to prevent inserting the barrel 1922 too far into the lower throughbore 1794. In addition, the insertion guide 1976 comprises a guide pin 1920 as described above for engaging the recesses 1916, 1918 in the rear face 1914 of the drill guide portion 1788 to increase maneuverability and stability of the trial spacer assembly 1750.

A solid cylindrical end cap 1978 at the rear end of the tool 1902 is connected to the yoke housing 1948 to provide a contact surface for the surgeon to strike during insertion of the trial spacer assembly 1750.

Figure 69:
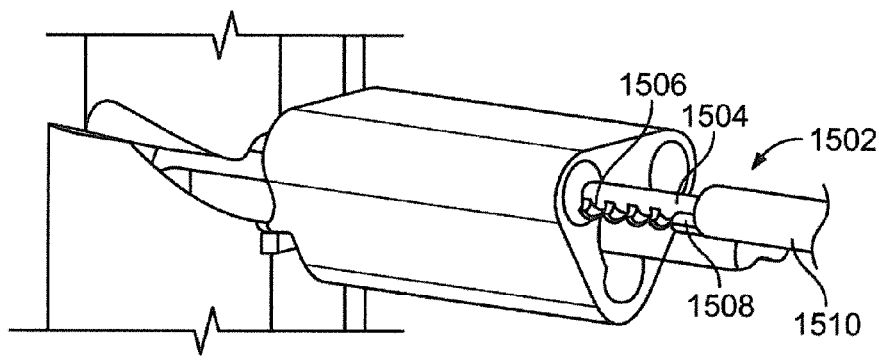
FIG. 69 is an anterolateral perspective view of the trial spacer of FIG. 68 with the cam cutter guide slid over the shaft and a cam cutter prior to cutting cams into the vertebrae.
Figure 71:
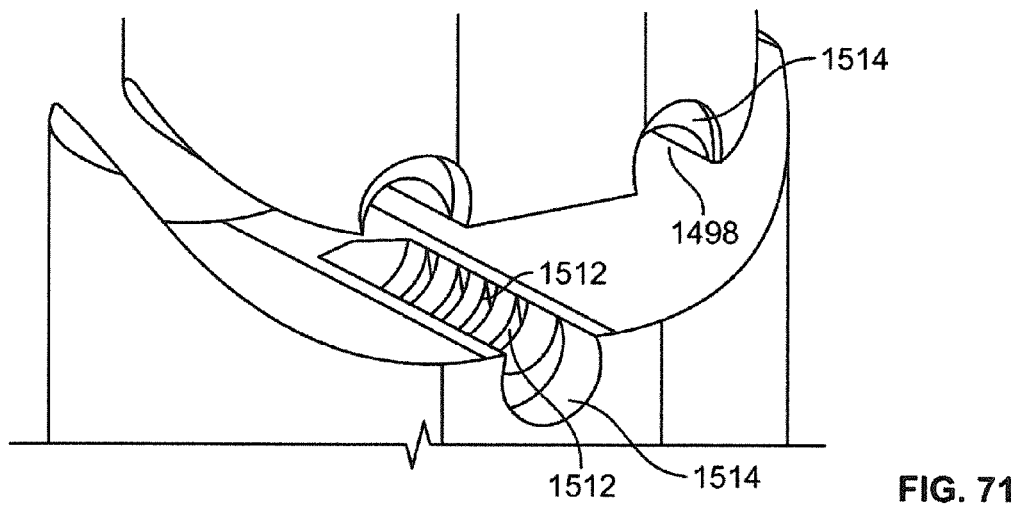
FIG. 71 is an anterolateral perspective view of the intervertebral space after the grooves and cams have been cut by the drill and the cam cutter.

In operation, the gripping mechanism 1912 is inserted into the lower throughbore 1794 of the trial spacer assembly 1750 with the trigger 1938 depressed to push the plunger 1966 forward to disengage the flexible tabs 1970 of the gripping mechanism 1912. Once the inserter end is fully inserted into the trial spacer assembly 1750, the trigger 1938 is released, causing the plunger 1966 to be pulled back and splaying the flexible tabs radially outward. The flexible tabs 1970 are forced into gripping engagement with the internal surfaces of the lower throughbore 1794, and the guiding pin 1920 engages one of the recesses 1916, 1918 in the rear face 1914 of the drill guide portion 1788 for providing additional stability and control. The trial spacer 1750 is then inserted into the intervertebral space 1330. If the spacer 1750 is the appropriate size, the surgeon will then prepare the vertebrae 1332, 1334 for the implant 1752. While continuing to hold the trial spacer assembly 1750 in place with the trial spacer inserter 1902, the first drill bit 1930 is affixed to the drill, and then inserted into one of the upper throughbores 1792 of the trial spacer assembly 1750. The first groove 1798 is drilled. While the drill bit 1930 is still fully within the trial spacer assembly 1750, the drill bit 1930 is released from the drill and left in place. Next, the second intermediate drill bit 1932 is attached to the drill and the second upper groove 1798 is then drilled. Again, the second drill bit 1932 is left in place. The inserter 1902 is then removed from the trial spacer assembly 1750. This is done by pulling the trigger 1938 to disengage the gripping mechanism 1912 and pulling the inserter 1902 away. The inserter tool 1902 is then removed and the lower groove 1800 is drilled, using the third and longest drill bit 1934. Once all of the grooves have been drilled, all three of the drill bits 1930-34 are removed by hand. In a preferred embodiment, the cam cutting step described in FIGS. 69-71 is omitted because the artificial disc implant 1752 is provided with cutting-type cams 1846 as previously described. Then, to remove the trial spacer assembly 1750, the insertion tool 1902 is reinserted into the lower throughbore 1794, the trigger 1938 is released to grip the trial spacer assembly 1750, and the assembly 1750 is pulled out using the insertion tool 1902. The surgical site is then preferably irrigated in preparation for insertion of the implant 1752.

The artificial disc implant 1752 of the present embodiment varies in only a few respects compared with the artificial disc implant shown in FIGS. 72-76. For instance, the present embodiment has a different form of disc indicator member 232. The following embodiments provide tactile feedback regarding the position of the securing mechanism to the surgeon as the securing mechanism is deployed. Because the bone is relatively soft compared to the projections being deployed into the bone, the bone provides little resistance to the projections as they are deployed into the bone. Therefore, it is important to provide the surgeon with tactile feedback so that he does not over or under deploy the projections, causing the implant 1752 to be improperly affixed to the bone. In addition, it is important to provide the securing mechanism with positive retraction blocking structure. Because the vertebral bone provides only a limited amount of resistance to the deployable projections, the projections may be prone to retract, derotate, or otherwise begin to return to their original undeployed position over time. Thus, retraction blocking structures are provided on the disc implant 1752 to avoid this condition.

Figure 96:
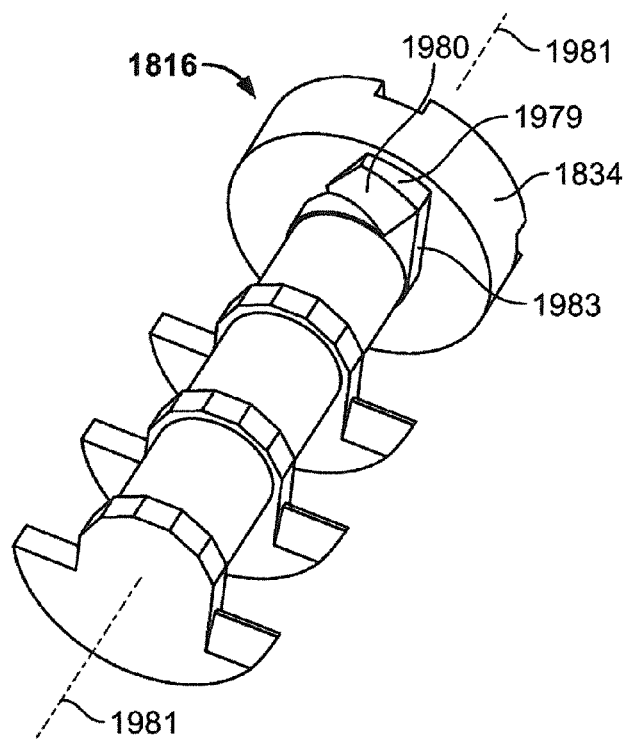
FIG. 96 is a posterolateral perspective view of a cam shaft securing mechanism according to the present invention illustrating a camming surface.
Figure 97:
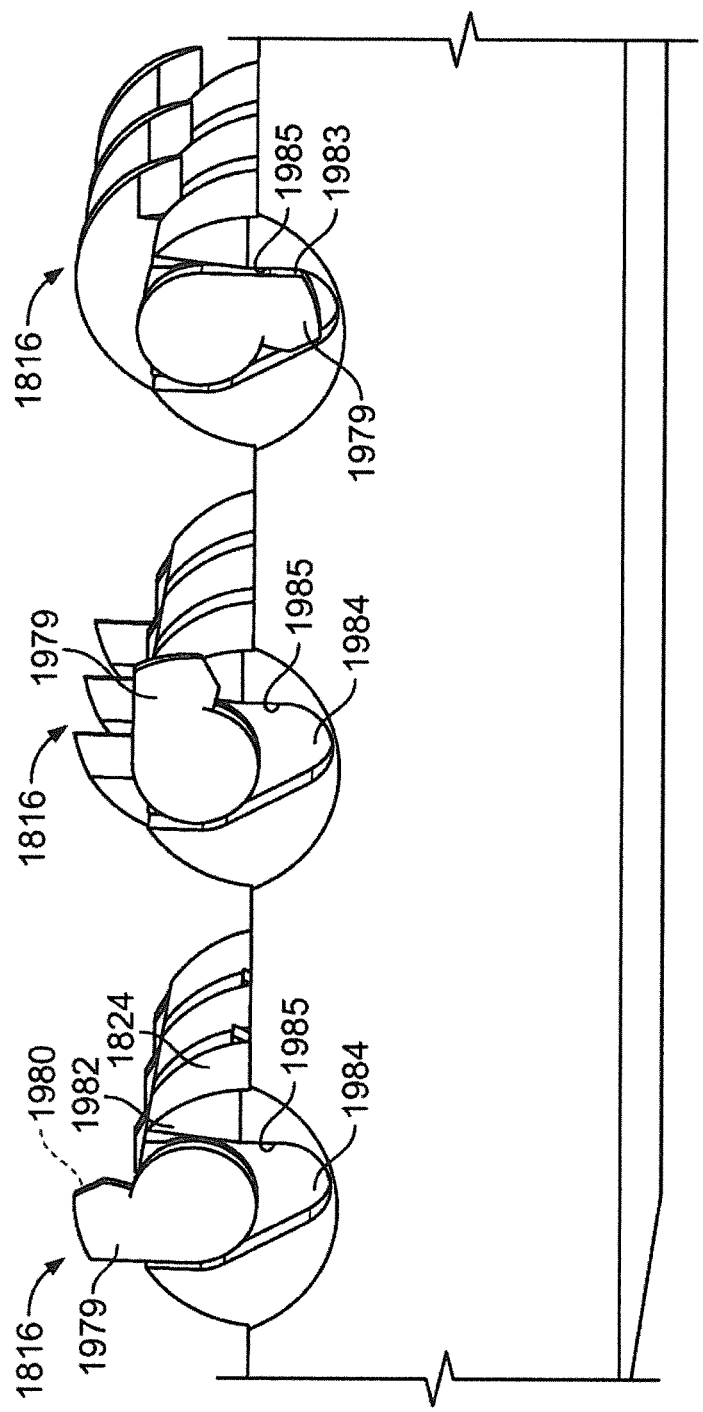
FIG. 97 is an anterolateral perspective view of the cam shaft of FIG. 96 with the head hidden disposed in a test block mimicking a securing mechanism for an implant for illustration of the operation of the cam shaft. The cam shaft is shown in an undeployed position, a partially deployed position, and fully deployed, from left to right.

The securing mechanism may take many forms. In one embodiment according to FIG. 96, the securing mechanism takes the form of a cam shaft 1816. The cam shaft 1816 has a radially extending cam projection 1979 including a tactile feedback creating surface in the form of a wedge-shaped camming surface 1980 adjacent the drive head 1834. The camming surface 1980 frictionally engages a corresponding camming surface 1982 disposed on the adjacent retainer member 1824 shown in FIG. 97 (in a test block for demonstrative purposes with heads 1834 of the cam shafts 1816 hidden) as the cam shaft 1816 is rotated from its undeployed starting position (on left side of FIG. 97), to a partially deployed position, and then to its fully deployed position 180 degrees from its starting position. The camming surfaces 1980 and 1982 are inclined relative to the longitudinal axis 1981 so that as the camming surfaces 1980, 1982 engage and cam against each other, the cam shaft 1816 is shifted axially towards the anterior direction (as installed in the spine).

This frictional interaction between the camming surfaces 1980, 1982 and a biasing force exerted by the retainer members 1824 on the cam shaft 1816 caused by the deformation of the retainer members 1824 provides tactile feedback to the surgeon. The deformation of the retainer members is preferably elastic, such that the retainer members 1824 will return to their original shape when the cam shaft 1816 is in its fully deployed position. Alternatively, the deformation could be plastic, wherein the retainer members 1824 undergo some irreversible deformation. This is acceptable when the securing mechanism is not deployed and retracted repeatedly.

Once the cam shaft 1816 is turned a full 180 degrees, the cam shaft camming surface 1980 snaps into a recess 1984 formed in the adjacent retainer member 1824, due to the biasing force exerted on the cam shaft 1816 by the flexed retainer members 1824. The recess 1984 and cam shaft camming surface 1980 is formed such that the camming surface 1980 becomes trapped in the recess 1984 and blocks derotation of the cam shaft 1816. More specifically, the cam projection 1979 has a straight, trailing edge surface 1983 that is turned toward the straight edge surface 1985 of recess 1984. Once the trailing edge surface 1983 clears the recess surface 1985, the cam surface 1980 will have traveled past the corresponding camming surface 1982 so that the cam surfaces 1980 and 1982 are disengaged from one another. This removes the axial biasing force that their camming engagement generates, so that the cam projection 1979 travels or snaps axially back into the recess 1984. In this orientation, the flat edge surfaces are in confronting relation to each other so that the cam projection 1979 cannot be moved back out of the recess 1984.

Figure 98:
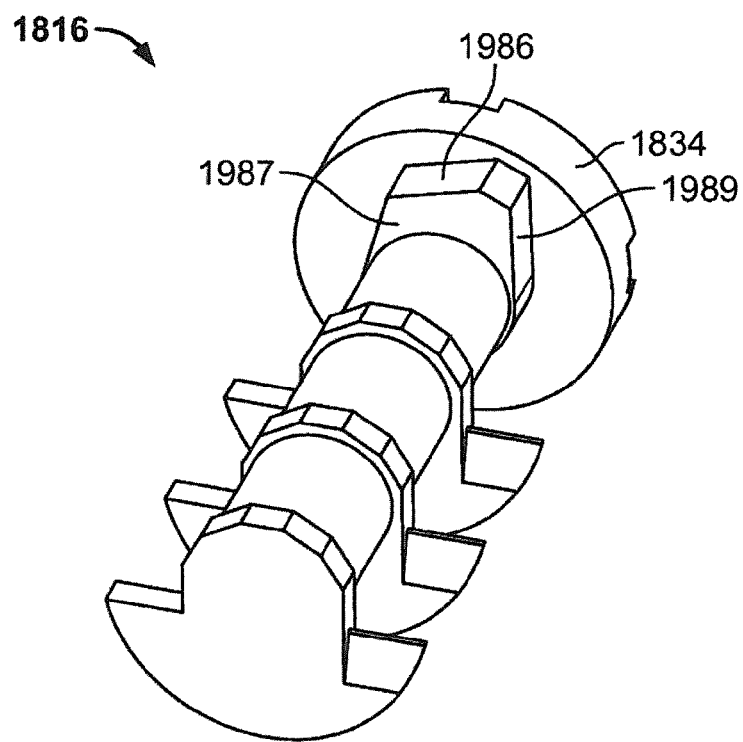
FIG. 98 is a posterolateral perspective view of a cam shaft securing mechanism according to the present invention illustrating a flat camming surface.
Figure 99:
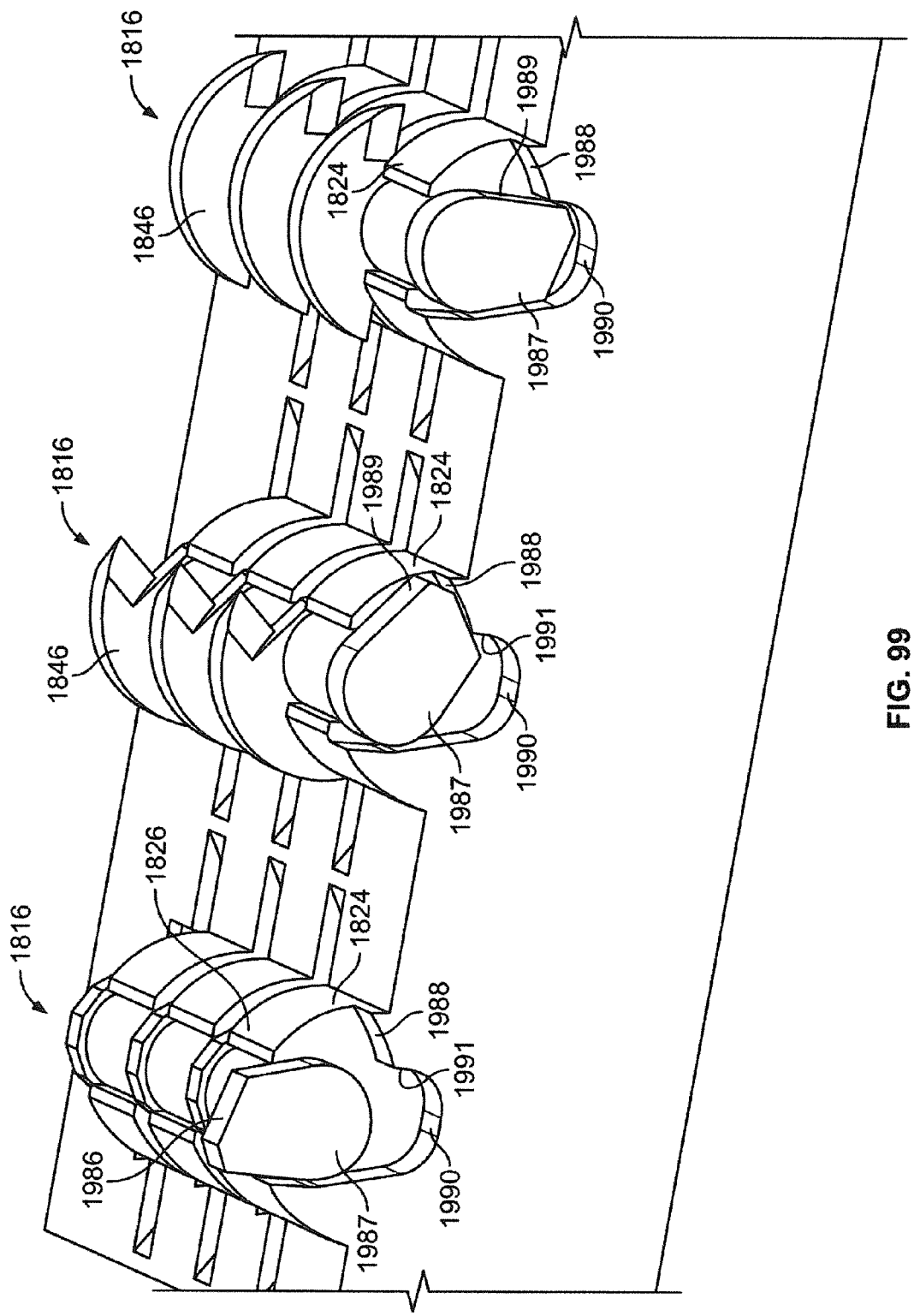
FIG. 99 is an anterolateral perspective view of the cam shaft of FIG. 98 with the head hidden disposed in a test block mimicking a securing mechanism for an implant for illustration of the operation of the cam shaft. The cam shaft is shown in an undeployed position, a partially deployed position, and fully deployed, from left to right.

Now referring to FIGS. 98 and 99, another embodiment of the securing mechanism for providing tactile feedback to the surgeon and preventing retraction of the securing mechanism is disclosed. The cam shaft 1816 has a flat camming surface 1986 adjacent the drive head 1834. As shown in FIG. 99 (in a test block arrangement similar to FIG. 97), the flat camming surface 1986 frictionally engages a corresponding camming surface 1988 formed in the adjacent retainer member 1824. The camming surfaces 1986, 1988 operate similarly to the wedge shape camming surface 1980 and corresponding camming surface 1982, except that instead of biasing the cam shaft 1816 axially, they bias the cam shaft 1816 generally vertically. As the cam shaft 1816 is rotated from its starting position to the fully deployed position (at 180 degrees from its undeployed starting position), the flat camming surface 1986 of the cam shaft 1816 engages the corresponding camming surface 1988 of the retainer member 1824. This pushes the cam shaft 1816 generally upward away from the retainer members 1824, which biases the cam shaft 1816 against the upwardly extending arm 1826 of the retaining members 1824, providing tactile feedback to the surgeon in the form of increased resistance to the rotation of the cam shaft 1816 until the shaft is almost turned a full 180 degrees. The resistance dissipates quickly as the camming surfaces begin to disengage each other. In fact, the deformation of the retaining members 1824 may help to propel the cam shaft into a fully deployed position. This propulsion and dissipation of resistance constitutes additional tactile feedback which varies during the deployment of the securing mechanism and informs the surgeon that the cam members 1846 are fully deployed. Once the cam shaft 1816 is turned a full 180 degrees, the flat camming surface 1986 snaps into a recess 1990 formed in the adjacent retainer member 1824, due to the generally vertical biasing force exerted by the flexed retainer members 1824. The recess 1990 and cam shaft camming surface 1986 are formed such that the camming surface 1986 becomes trapped in the recess 1990 and prevents derotation of the cam shaft 1816.

More specifically, the cam projection 1987 has a straight, trailing edge surface 1989 that is turned toward the straight edge surface 1991 of recess 1990. Once the trailing edge surface 1989 clears the recess surface 1991, the cam surface 1986 will have traveled past the corresponding camming surface 1988 so that the cam surfaces 1986 and 1988 are disengaged from one another. This removes the vertical biasing force that their camming engagement generates, so that the cam projection 1987 travels or snaps axially down into the recess 1990. In this orientation, the straight edge surfaces 1989, 1991 are in confronting relation to each other so that the cam projection 1987 cannot be moved back out of the recess 1990.

Figure 100:
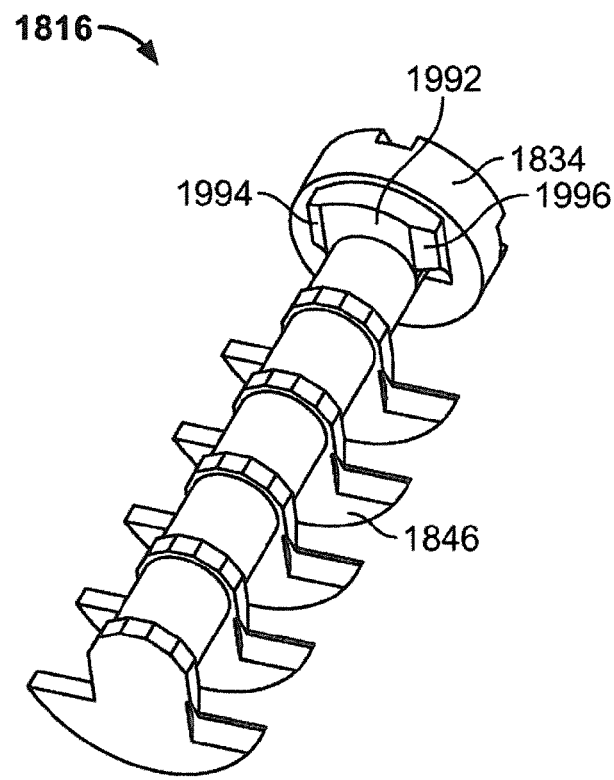
FIG. 100 is a posterolateral perspective view of a cam shaft securing mechanism according to the present invention illustrating a dual chamfered camming surface.
Figure 101:
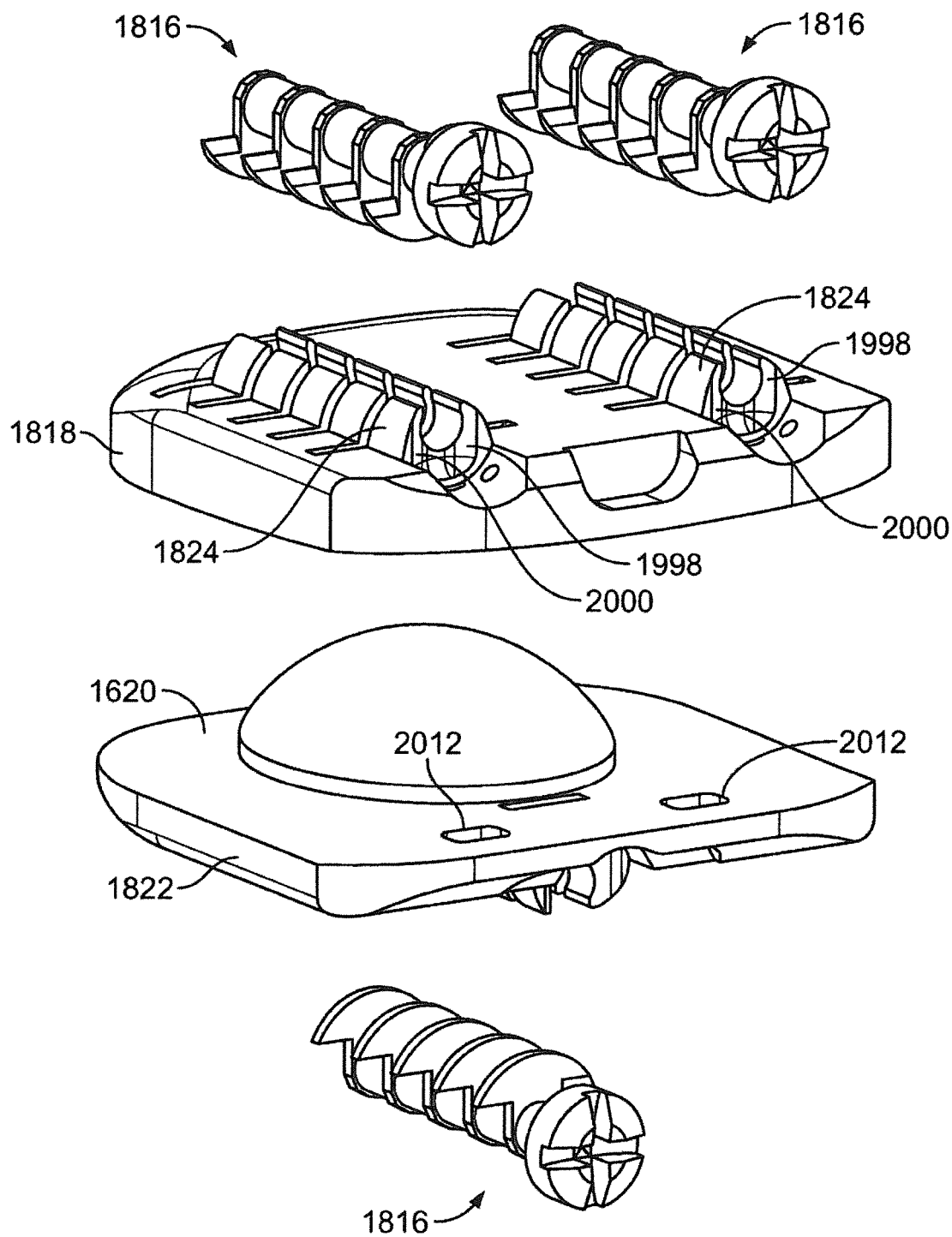
FIG. 101 is an anterolateral exploded view of the artificial disc implant of FIG. 95.

In another form shown in FIGS. 100 and 101, the cam shaft 1816 has a dual chamfered camming surface 1992 for providing tactile feedback to the surgeon and preventing derotation of the cam shaft 1816. In this embodiment, a chamfered surface 1994 for providing resistive feedback during deployment of the cam lobes 1846 is provided on one side of the camming surface 1992, which is engaged when the cam shaft 1816 is rotated in a clockwise direction. Another chamfered surface 1996 is provided on the other side of the camming surface 1992 for providing resistive feedback during retraction of the cam lobes 1846, which is engaged when the cam shaft 1816 is rotated in a counterclockwise direction. Like the embodiments described directly above, the camming surface 1992 engages a corresponding generally concave camming surface 1998 formed in the adjacent retainer member 1824. The corresponding camming surface 1998 is formed such that the chamfered camming surface 1992 adjacent the drive head engages the corresponding camming surface 1998 causing the cam shaft 1816 to bias against the retainer members 1824 and provide tactile or resistive feedback as described above. Unlike the embodiments above, the cam 1816 may be manually retracted by turning the cam shaft 1816 back 180 degrees in the counterclockwise direction. This is desirable if the surgeon wishes to adjust the implant 1752 or prepare the implantation site further. Over-rotation and rotation in the wrong direction is prevented by leaving a raised surface 2000 on the opposite side of the corresponding camming surface 1998 such that it is virtually impossible to turn the cam shaft 1816 in the wrong direction due to interference between the camming surface 1992 on the cam 1816 and the raised surface 2000.

Figure 102:
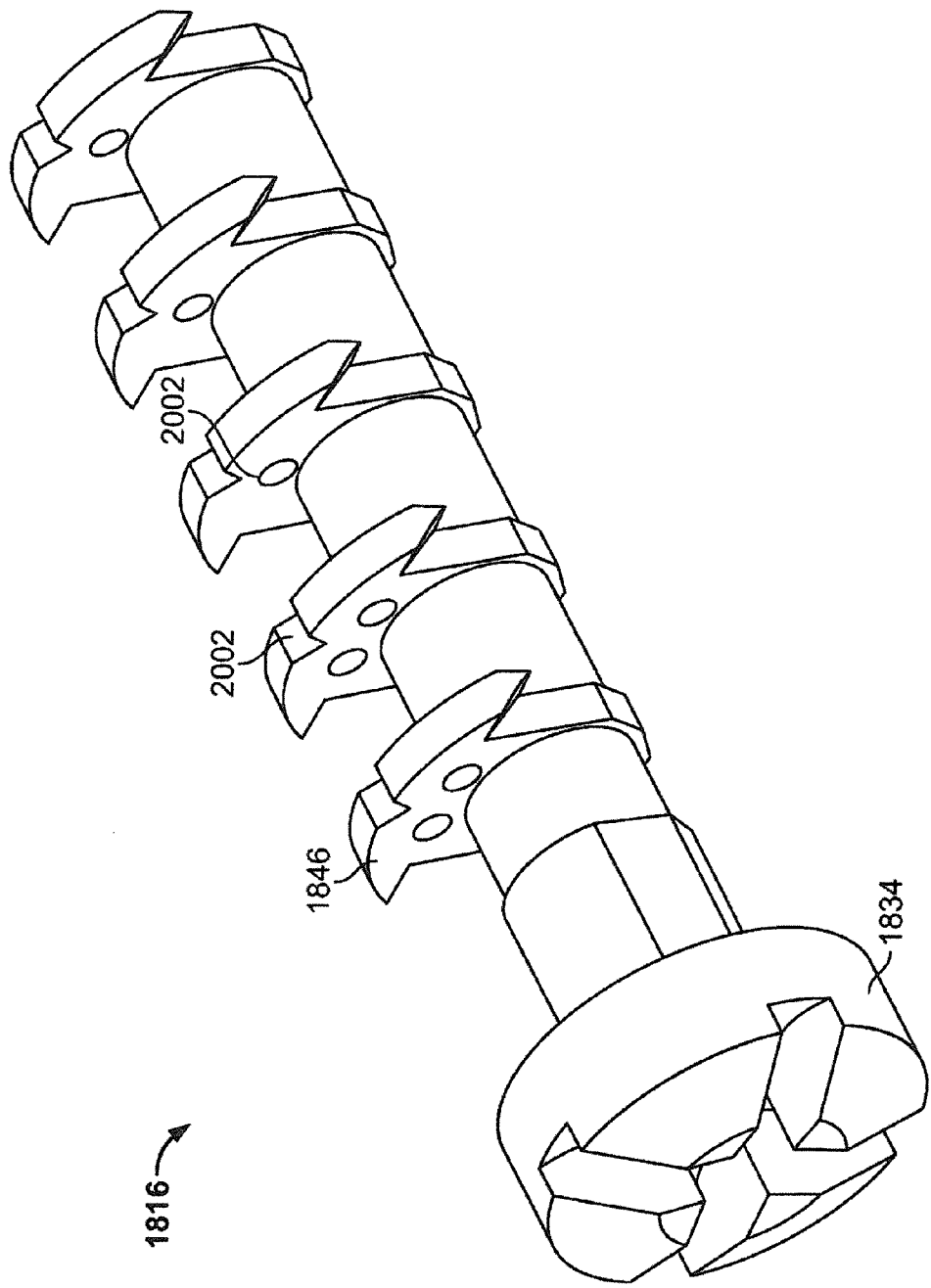
FIG. 102 is an anterolateral perspective view of an alternate embodiment of a cam shaft securing mechanism according to the present invention.
Figure 103:
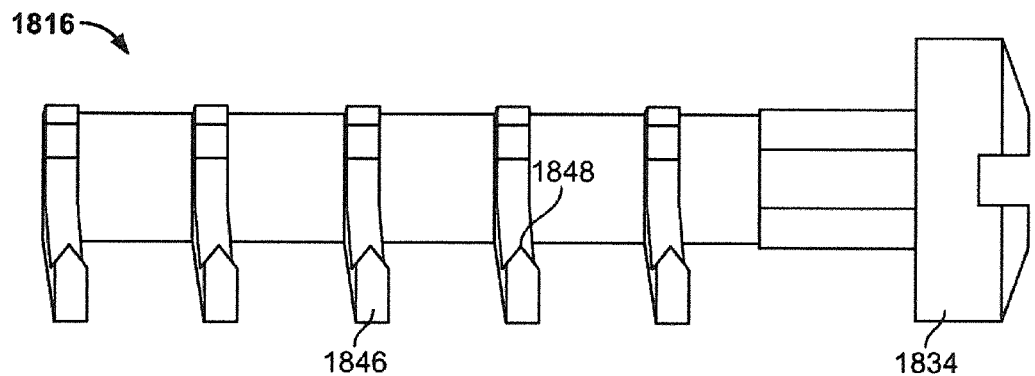
FIG. 103 is a side view of an alternate embodiment of a cam shaft securing mechanism according to the present invention illustrating cupped cam members.
Figure 104:
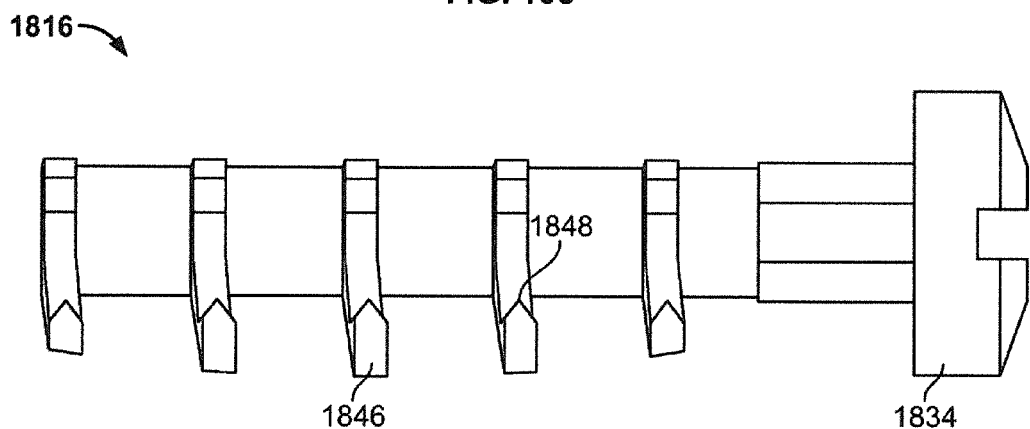
FIG. 104 is a side view of an alternate embodiment of a cam shaft securing mechanism according to the present invention illustrating contoured cam members.
Figure 105:
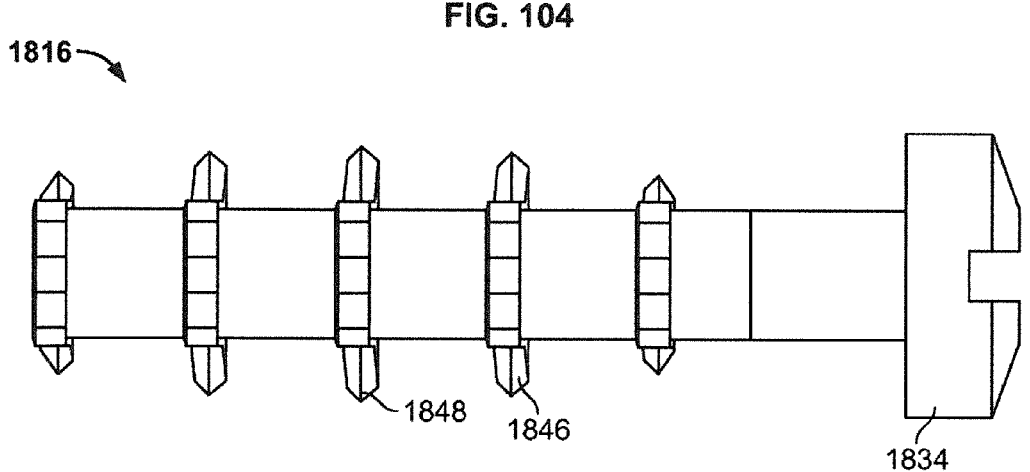
FIG. 105 is a top view of an alternate embodiment of a cam shaft securing mechanism according to the present invention illustrating contoured cam members.

The cam shafts 1816, cam members, lobes, or fins 1846 may take on different geometries and orientations to improve performance of the securing mechanism. For example, the camming fins may include serrations 2002, as shown in FIG. 102, divots, or recesses 2002 to promote boney ingrowth. The serrations 2002 may also help to cut the bone when the cam 1816 is rotated. In addition, the camming fins 1846 may be cupped or slanted, as shown in FIG. 103, to further promote anchoring of the implant 1752 to the vertebrae 1332, 1334. In a preferred embodiment, the camming fins 1846 are cupped about 8 degrees. Further, as shown in FIGS. 104 and 105, the camming fins 1846 may have an outside contour, such that shape or size of the cam fins 1846 varies from one end of the cam shaft 1816 to the other. The contour may match the profile of the endplates to take advantage of the softer bone in the center of the vertebrae 1332, 1334 as opposed to the harder-denser bone at the periphery of the vertebrae 1332, 1334. Further, the cam shafts 1816 may have any number of cam members 1846. In a preferred embodiment, each cam shaft 1816 may have between three and five cam members 1846. Larger implants may have five members 1846 per cam shaft 1816, while smaller implants may have only three. The cam shafts 1816 are preferably made from titanium or stainless steel, and may be coated with a bone-growth promoting substance, such as hydroxyapatite, tricalcium phosphates, or calcium phosphates.

Cam members 1846 that cut or imbed themselves into the bone provide advantages over other securing mechanisms. For instance, securing mechanisms that use static projections such as spikes and keels may rely on the subsidence of the bone around the securing mechanism to secure the implant. Static securing mechanisms are less desirable because they may not properly secure the implant to the bone until the bone begins to subside around the securing mechanism. Thus, the implant may tend to migrate prior to bone subsidence. However, dynamic securing mechanisms like cam members 1846 with cutting surfaces 1848 actively cut into or imbed themselves into the bone, instead of relying on the subsidence of the bone. In this manner, dynamic securing mechanisms create a much more reliable and stable connection between the implant 1752 and the vertebra 1332, 1334. These benefits translate into a more robust and reliable implant 1752, which means quicker recovery times and increased mobility for the patient.

Figure 106:
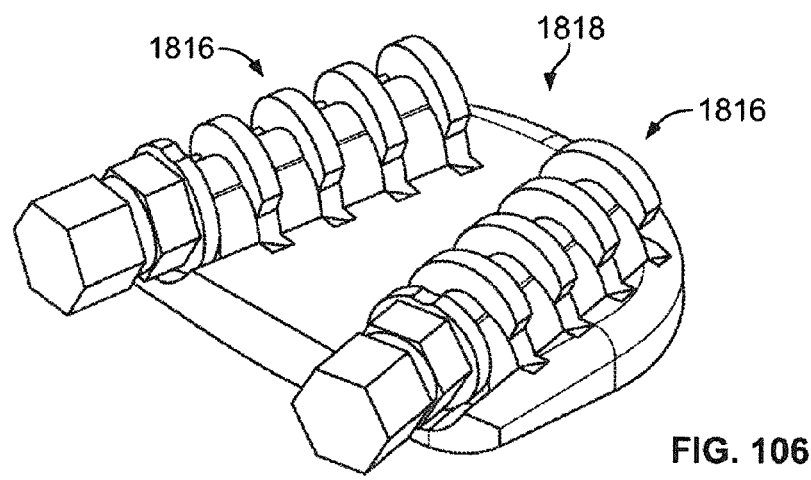
FIG. 106 is an anterolateral perspective view of an alternate embodiment of the artificial disc implant according to the present invention.

In another form, the cam shafts 1816 on the upper disc implant member 1818 may be disposed at converging or diverging angles, such as shown in FIG. 106. This orientation prevents migration of the implant 1752 not only in an anterior/posterior direction, but also substantially in the lateral direction as well. Naturally, the lower disc implant member 1822 may employ such a configuration.

It should be noted that the cam shafts 1816 provide certain advantages over other securing mechanisms, such as screws. For instance, screws do not provide a significant level of tactile feedback. It is very difficult for a surgeon to determine how far a screw has been turned, and therefore he may over- or under-rotate the screw, increasing the risk of implant migration and failure. In addition, metal screws may damage the implant if over-tightened. If the implant is made of a relatively soft material, such as PEEK, the metal screws will easily strip and damage the implant if over-tightened. Moreover, a surgeon is more likely to over-tighten a screw housed within a polymer because the screw is so much harder than the polymer that he will not be able to feel when the screw has been over-tightened. To alleviate this problem, the implant 1752 may be fabricated with a metal portion for housing the screw combined with a polymer, but this greatly increases the difficulty in manufacturing the implant 1752, as well as its cost, and is therefore less desirable. In addition, over-rotation of a screw may advance the screw beyond its intended range of motion, and may cause it to protrude from the implant and cause damage to vital areas in and around the spine. Because the cams do not advance or retreat as they are rotated, there is no danger that the cams 1846 will be accidentally projected into other vital areas.

Figure 107:
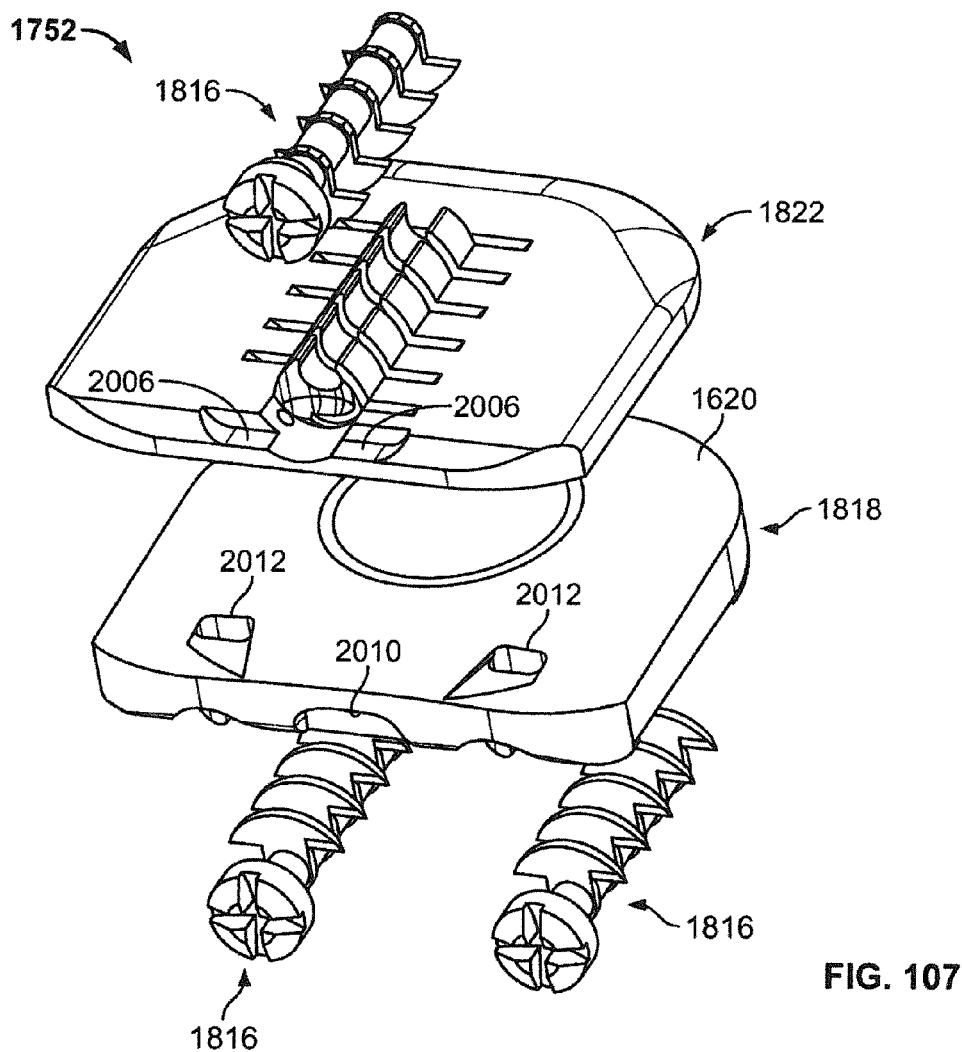
FIG. 107 is an inverted anterolateral exploded view of the artificial disc implant of FIG. 95.
Figure 108:
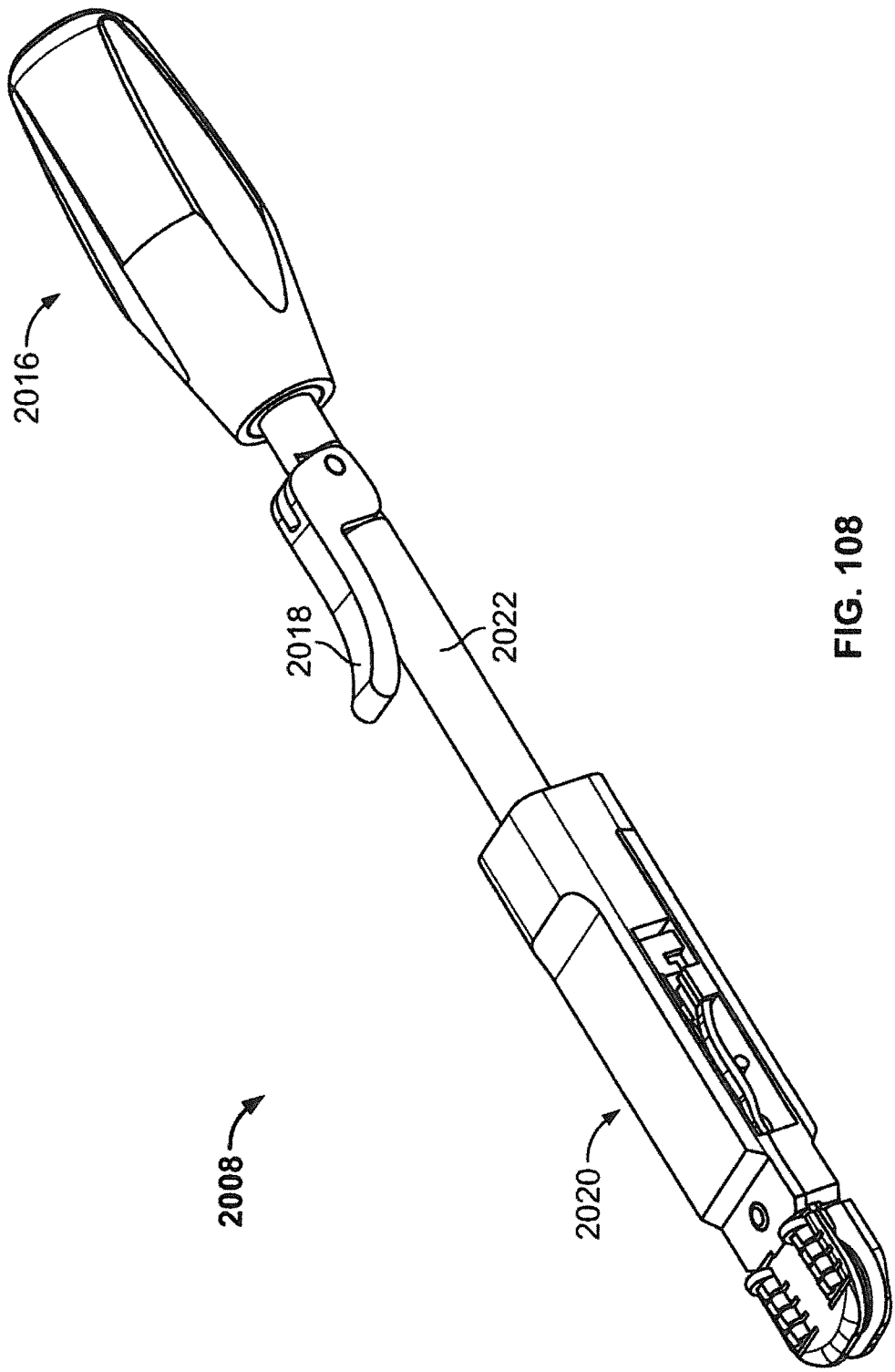
FIG. 108 is a perspective view of the implant inserter tool and artificial disc implant according to the present invention.
Figure 109:
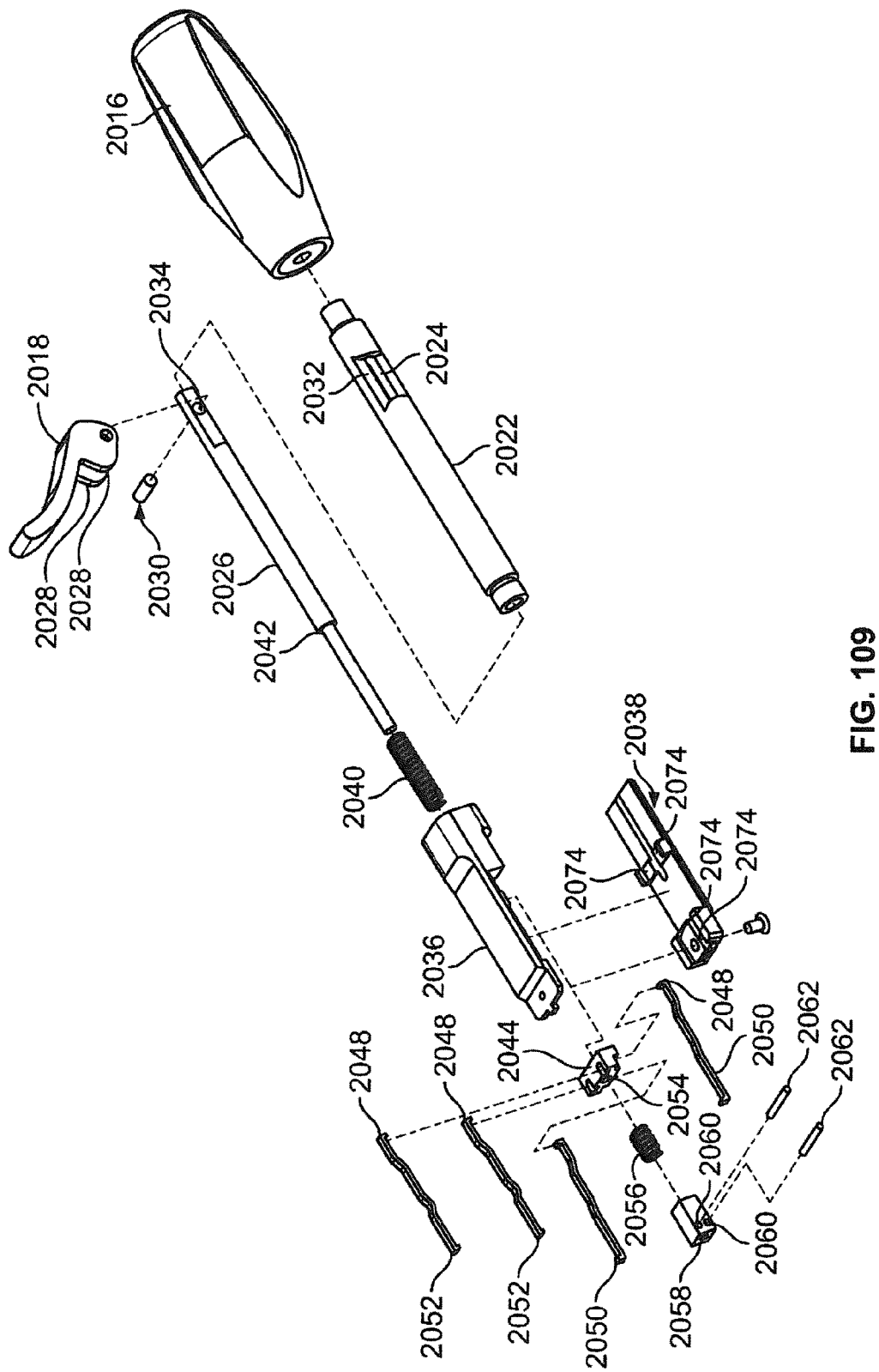
FIG. 109 is an exploded view of the implant inserter tool of FIG. 108.
Figure 110:
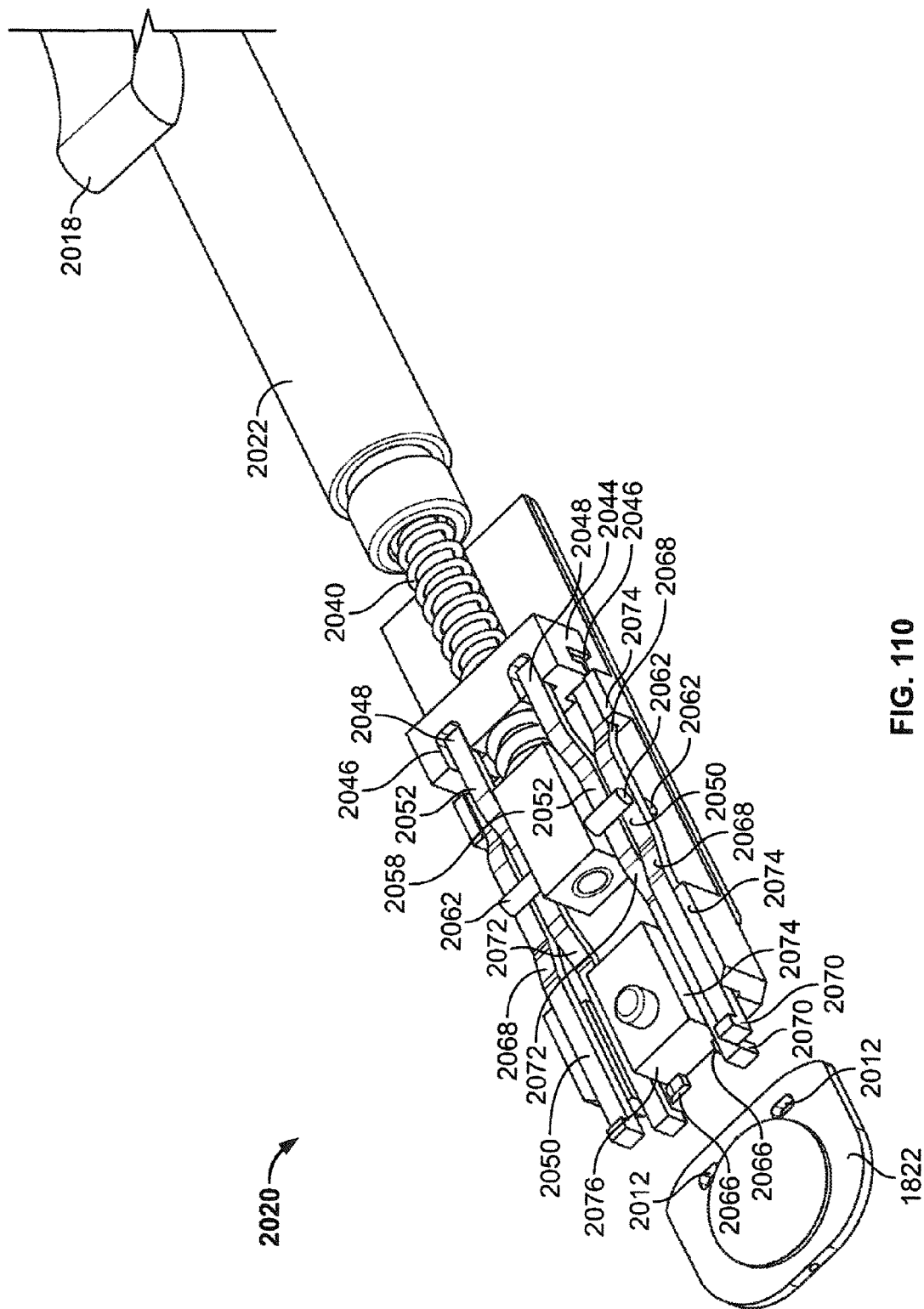
FIG. 110 is an enlarged perspective view of the implant and implant inserter tool of FIG. 108 with the upper disc member and upper housing member of the tool hidden for illustration purposes.

The disc implant 1752 according to the present embodiment has docking features for attaching with the implant insertion tool 2008, as shown in FIGS. 101, 107, and 108. The lower disc implant member 1822 has a shelf-like platform 2006 along its rear face on either side of the cam shaft 1816 for providing a contact surface for the implant insertion tool 2008. Similarly, the upper disc implant member 1818 has a shelf 2010 on its anterior face between the two upper cam shafts 1816 for providing a contact surface for the insertion tool 2008. The internal facing surfaces 1620 of both disc members 1818, 1822 each have a pair of generally rectangular recesses 2012 disposed therein to accept the gripping members 2014 of the insertion tool 2008. These docking features are advantageous because the insertion tool 2008 manipulates the implant 1752 substantially within the overall footprint of the implant 1752. This prevents trauma to the surrounding tissue and bone during insertion of the implant 1752 and removal of the inserter 2008 after the implant 1752 is inserted.

An insertion tool 2008 according to the present invention is shown in FIGS. 108-113B. The insertion tool 2008 is generally comprised of a handle portion 2016, an actuator, and a gripping mechanism 2020. Specifically, the handle portion 2016 is attached to a handle shaft 2022. The handle shaft 2022 has an annular bore 2024 therethrough for slidingly housing the push rod 2026. An actuator in the form of a cam lever 2018 with opposed camming surfaces is attached to the handle shaft 2022 and push rod 2026 with a pin connection 2030 extending between the camming surfaces 2028 and through opposed openings 2032 in the handle shaft 2022 and a bore 2034 in the push rod 2026. The handle shaft 2022 is attached at its forward end to upper and lower housing members 2036, 2038 which house the gripping mechanism 2020. A rear spring 2040 surrounds push rod 2026 and is biased between a collar 2042 on the handle shaft 2022 and the prong holder 2044. The prong holder 2044 is a rectangular shaped block with four L-shaped recesses 2046 (see FIG. 110), two on the upper face and two on the lower face for capturing the L-shaped anchoring ends 2048 of four prongs 2050, 2052. The prong holder 2044 has a cylindrical bore 2054 extending between the front and rear face for allowing the push rod 2026 to pass therethrough. The end of the push rod 2026 extends through a forward spring 2056, which is captured between the prong holder 2044 and a compression block 2058, which is attached to the end of the push rod 2026. The compression block 2058 is a rectangular block having an aperture in the rear face for attaching to the push rod 2026. In addition, the block 2058 has a pair of vertically aligned bores 2060 extending laterally through the side walls of the block 2058 for holding two pins 2062 operable to actuate the prongs 2050, 2052 into a disengaged position by temporarily deforming the prongs 2050, 2052 between the two pins.

Figure 111A:
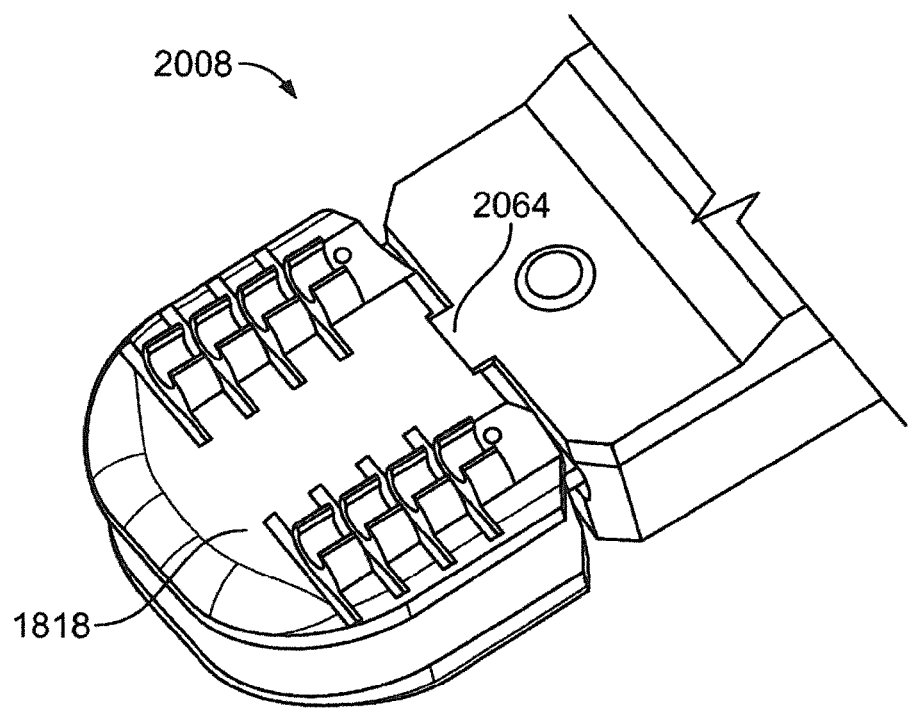
FIG. 111A is an enlarged perspective view of the implant and implant inserter tool of FIG. 108 illustrating the engagement of the implant and inserter tool.
Figure 111B:
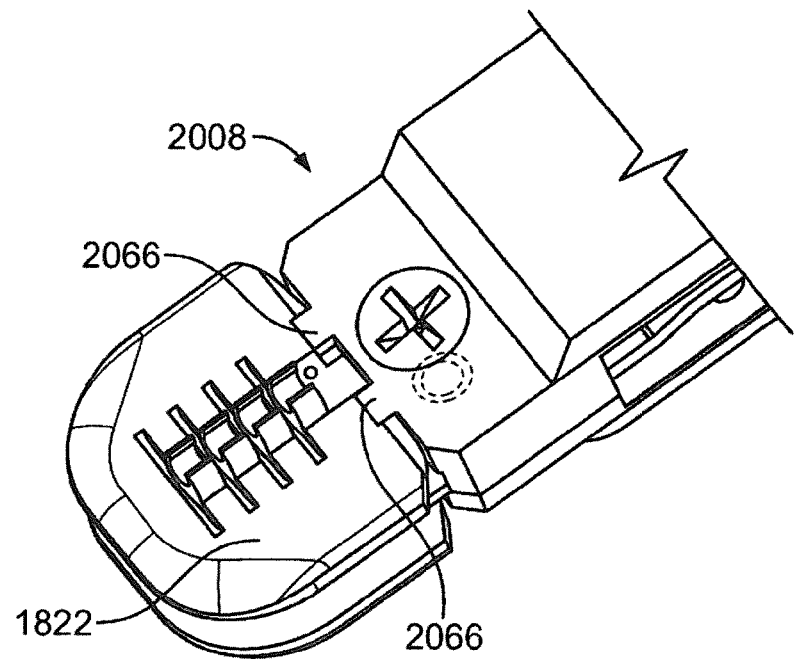
FIG. 111B is an enlarged perspective view of the underside of the implant and implant inserter tool of FIG. 108 illustrating the engagement of the implant and inserter tool.
Figure 112A:
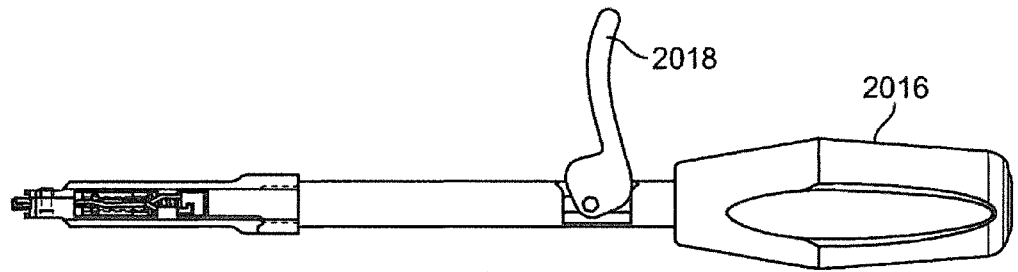
FIG. 112A is a side view of the implant inserter tool of FIG. 108 illustrating the initial disengaged position of the inserter tool.
Figure 112B:
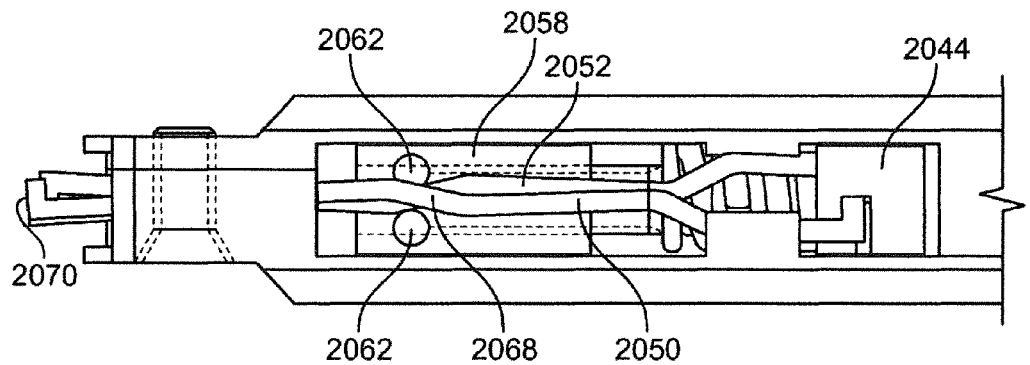
FIG. 112B is an enlarged side view of the gripping mechanism of the inserter tool of FIG. 108 illustrating the position of the gripping mechanism in the initial disengaged position.

The gripping mechanism 2020 includes two upper and two lower flexible prongs 2050, 2052 which operate in tandem with upper and lower tabs 2064, 2066 for gripping and holding the disc implant 1752 (shown in FIG. 111A-B). The prongs 2050, 2052 are made with a thin rectangular stainless steel shafts having a series of bends 2068, 2072. The upper prongs 2050 generally extend along the longitudinal axis of the insertion tool 2008 and have a series of two upward sloping bends 2068 so that the implant gripping end 2070 of the prong 2050 is vertically higher than the anchor end disposed in the prong holder 2044. The lower prongs 2052 are shaped in a similar manner, except that they have a series of two downward sloping bends 2072 so that the implant gripping end 2070 of the prong 2052 is vertically lower than the anchor end 2048 disposed in the prong holder 2044. The upper and lower prongs 2050, 2052 are paired adjacent each other and opposite the other pair along the outer lateral edges of the housing, such that the shaft 2026 and compression block 2058 may translate between the sets of prongs 2050, 2052. The upper and lower housing members 2036, 2038 have guide surfaces 2074 formed in the internal surfaces for guiding and securing the prongs 2050, 2052 to prevent them from becoming misaligned. The gripping ends 2070 of the prongs 2050, 2052 have an L-shape for being inserted into the recesses 2012 of the disc implant 1752.

Figure 113A:
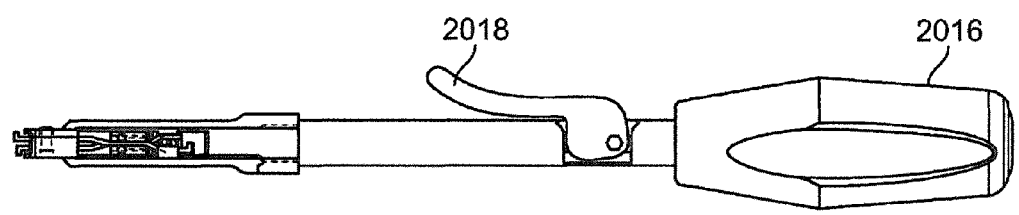
FIG. 113A is a side view of the implant inserter tool of FIG. 108 illustrating the engaged position of the inserter tool.
Figure 113B:
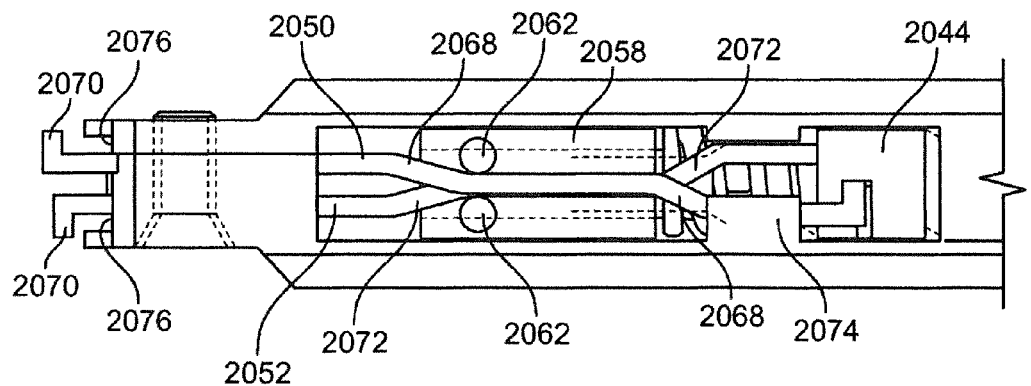
FIG. 113B is an enlarged side view of the gripping mechanism of the inserter tool of FIG. 108 illustrating the gripping mechanism in the engaged position.

In operation, the implant inserter tool prongs 2050, 2052 are movable in vertical and longitudinal directions to engage and disengage the disc implant 1752. In the initial disengaged position shown in FIG. 112A-B, the lever 2018 is in a released position. The compression block 2058 is pushed forward by the push rod 2026. The two opposed pins 2062 extending through the compression block 2058 are pushed over the sloping bends 2068, 2072 in the prongs 2050, 2052, which locally deform the prongs 2050, 2052 and forces the gripping ends 2070 of the prongs 2050, 2052 together, effectively lowering the gripping ends 2070 of the upper prongs 2050 and raising the gripping ends 2070 of the lower prongs 2052. In this manner, the forward portion of the inserter tool 2008 may be inserted between the upper and lower disc implant members 1818, 1822. To engage the implant 1752, the lever 2018 is pressed forwards, as shown in FIGS. 113A-B. This causes the push rod 2026 to pull the compression block 2058 rearwards. The opposed pins 2062 are thereby removed from the sloped portions 2068, 2072 of the prongs 2050, 2052, which allows the prongs 2050, 2052 to return to their original unflexed shape. In this manner, the gripping ends 2070 will spread vertically apart and engage the gripping recesses 2012 of the disc implant 1752. To provide a counteracting moment against the force imparted by the prongs 2050, 2052 on the implant 1752, tabs 2064, 2066 disposed on the forward ends of the housing members 2036, 2038 engage the implant 1752 on the shelves 2006, 2010 disposed on the rear portions of the disc members 1818, 1822, as shown in FIG. 111. In addition, as the lever 2018 is pushed forward, the compression block 2058 biases against the forward spring 2056, causing the prong holder 2044 to be biased rearwards against the rearward spring 2040. This causes the prong holder 2044 and the prongs 2050, 2052 to translate rearwards to pull the implant 1752 tight against the forward face of the housing members 2036, 2038. The limited range of motion of the lever 2018 prevents damage to the implant 1752 that may be caused by over-tightening the gripping mechanism 2020.

Once the implant 1752 is secured to the inserter 2008, the disc implant 1752 is then inserted into the intervertebral space 1330. The position of the implant 1752 may be determined using fluoroscopy to view the orientation of the implant 1752. Tantalum markers disposed in the frontal face of both the upper and lower disc members 1818, 1822 allow the surgeon to identify the position of the insertion end of the implant 1752. In addition, the cam shafts 1816, which are also radiopaque when made out of titanium or stainless steel, may be used to determine the orientation of the implant 1752. After the surgeon has placed the implant 1752 in the desired position, he releases the implant 1752 by lifting the lever 2018. The prongs 2050, 2052 are pushed forward and retracted vertically inwards, which releases the implant 1752. The surgeon then secures the implant 1752 in place by actuating the securing mechanism. Specifically, the surgeon turns each of the cams 1816 180 degrees using a driver, thereby deploying the cam members 1846 into the bone of the upper and lower vertebrae 1332, 1334. The surgeon can feel the resistance provided by the interaction between the camming surfaces of the cam shafts 1816 and the retainer member 1824 while deploying the cam members 1846. In this manner, he can determine when the cam members 1846 have been fully deployed. In addition, the camming surfaces of the cam shafts 1816 and the retainer members 1824 will prevent the cams 1816 from derotating and allowing the implant 1752 to migrate.

In a preferred embodiment, such as illustrated in FIGS. 114-134, an artificial disc device comprises an upper bearing member and lower bearing member. In FIGS. 114-121, only the upper bearing member 3008 is shown, although an implant according to the present invention preferably includes both upper and lower bearing members. The lower bearing member is preferably similar in structure to those illustrated in FIGS. 122-130. An implant according to the present invention includes one or more restraint portion(s) or structure located on one or both of the bearing members to help keep the bearing members from becoming dislodged or migrating across the inner surface or endplate of the vertebrae (not shown) after insertion. The restraint portion may take the form of a deployable securing member 3006, which is movable from an undeployed configuration, wherein the restraining portion is positioned remotely from the adjacent bone surface and a deployed configuration, wherein the restraining portion is positioned in contact with the adjacent bone for affixing the implant thereto. Described in this application are various securing members that can be used on the endplate facing surfaces of a vertebra to restrain an implant.

Figure 114:
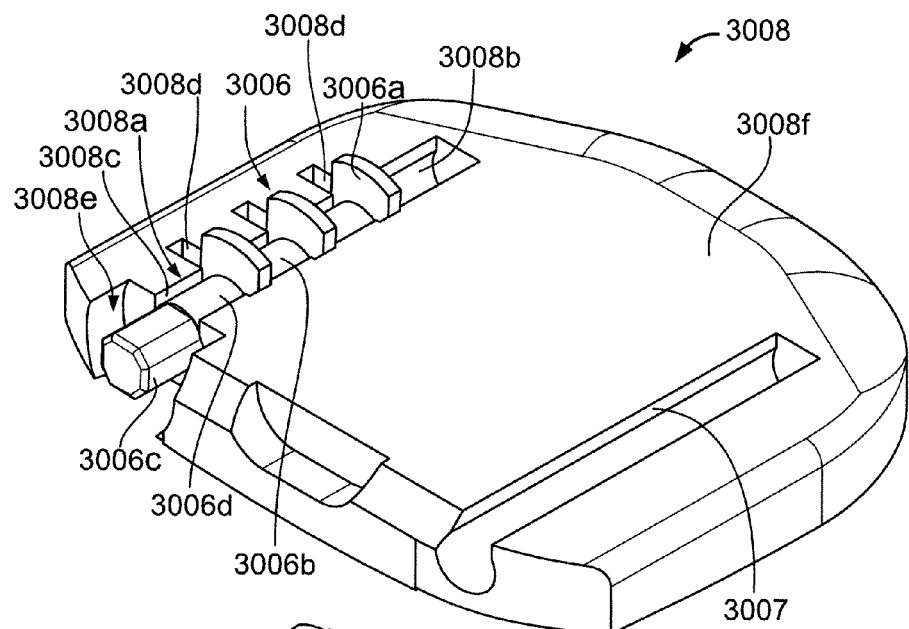
FIG. 114 is a anterolateral perspective view of a bearing member of an intervertebral implant according to the present invention illustrating a deployable securing member in a bone engaging orientation.

In the form shown in FIGS. 114-121, an upper bearing member 3008 is shown with a single securing member 3006. The elongate groove 3007 formed in the outer bearing surface 3008f of the upper bearing member 3008 shown on the right hand side in FIG. 114 is preferably replaced by a restraint portion similar to securing member 3006 to increase gripping engagement with the vertebra. Thus, the securing member 3006 shown serves as an example according to the present invention, and may be located on other portions of an implant, alone or in combination with other securing members 3006.

The securing member 3006 in the present form has restraint portions in the form of deployable bone engaging members 3006a. The bone engaging members 3006a are disposed on an elongate shaft 3006b housed within the body of the bearing member 3008. In a preferred orientation, the securing member 3006 is secured within a recess 3008b of the body of the bearing member 3008 by a securing member receiving portion 3008a in the form of a snap joint. A neck portion 3006d of the elongate shaft 3006b is held by opposing inner surfaces 3008c of the receiving portion 3008a via an interference or friction fit. In this regard, the preferred PEEK material from which the bearing members including the receiving portion 3008a thereof are formed provides the receiving portion 3008a with sufficient strength and resiliency to provide a secure friction fit with the shaft portions 3006b snap-fit therebetween while allowing for the shaft portions 3006b to be rotated to secure the bearing member 3008 to the corresponding adjacent vertebrae. This configuration is advantageous, because it requires no additional fasteners, pins, or supports, thereby reducing parts and increasing reliability and safety of the implant.

The elongate shaft 3006b is preferably configured with a profile suitable for rotation. The elongate shaft is 3006b provided with a drive head 3006c operable to mate with an actuator, such as a driver, operable to deploy the restraint portions via rotation of the elongate shaft 3006b. The securing member receiving portion 3008a includes an actuator receiving portion 3008e for receiving the actuator therein. In the form illustrated in FIGS. 114-121, the actuator receiving portion 3008e provides clearance for the driver to grasp the drive head 3006c, and keeps the drive head 3006c from protruding outside of the footprint of the implant body. This feature increases the safety and comfort of the implant over other known implants, because implants with projections that extend outside of the implant body and especially outside of the intervertebral space can interfere with adjacent vital tissues, nerves, blood vessels, and the digestive and respiratory tracts.

The bone engaging members 3006a take the form of lobe members that may be deployed into engagement with the endplate of the vertebrae upon rotation of a drive head 3006c of the elongate shaft 3006b using the proper instrument. The lobe members 3006a have bodies oriented generally transversely to a longitudinal axis of the elongate shaft 3006b. In this orientation, the lobe members 3006a keep the implant from migrating, particularly in the direction along the longitudinal axis. The lobe members 3006a may include a sharpened edge for easing the deployment of the lobe members 3006a into the adjacent bone. The lobe members 3006a may include apertures or slots to encourage bone growth therethrough. In addition, the lobe members 3006a may take a variety of sizes and shapes. Additional examples of securing members may be found in U.S. patent application Ser. No. 11/856,667, filed Sep. 17, 2007, which is incorporated herein in its entirety. Further, although the securing member 3006 is shown having three lobe members 3006a, different numbers of bone engaging members may be implemented. The securing member may be manufactured from an array of biocompatible materials, including, but not limited to polymers such as PEEK or metals such as titanium or stainless steel alloys, although radiolucent materials are preferred.

Figure 115:
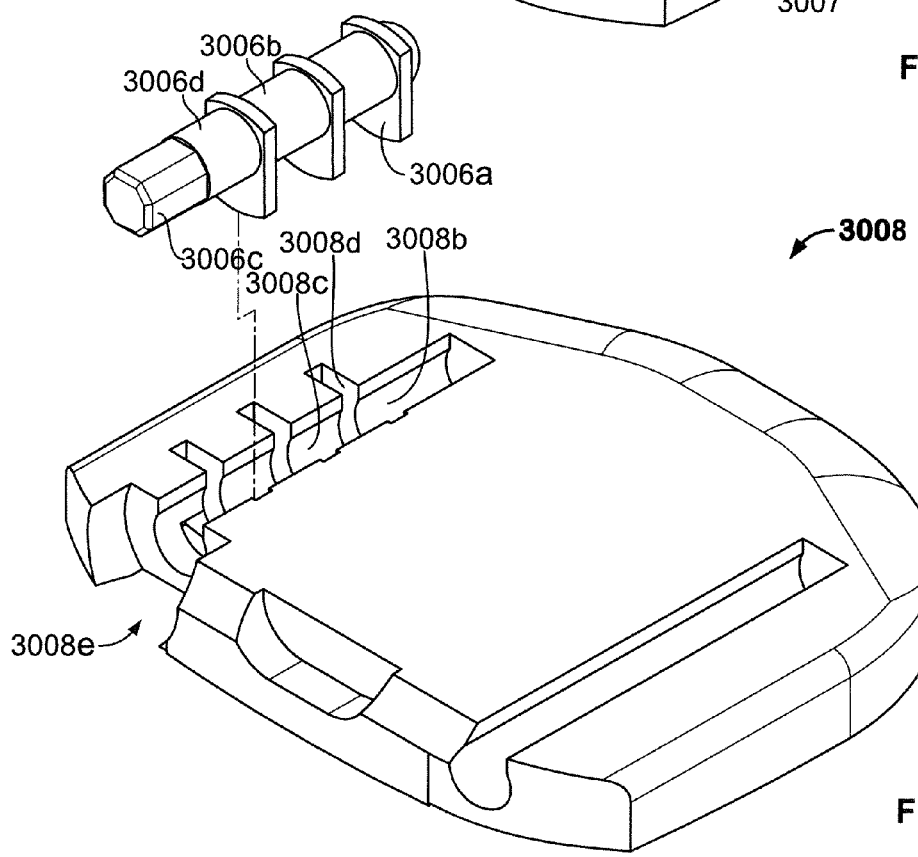
FIG. 115 is an exploded anterolateral perspective view of the bearing member of FIG. 114.
Figure 116:
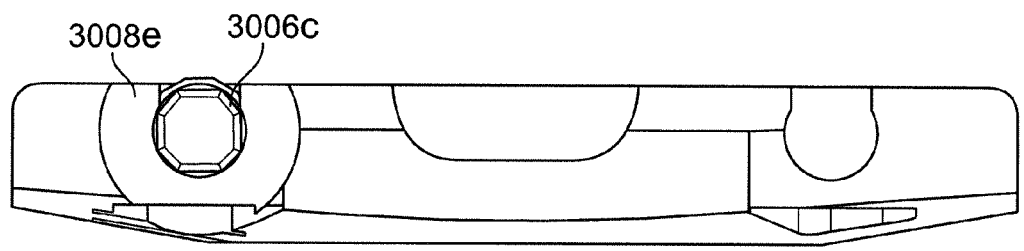
FIG. 116 is an anterior view of the bearing member of FIG. 114 illustrating the deployable securing member in an undeployed configuration, wherein the securing member is completely submerged within the bearing member so as to not protrude above the upper bearing surface.
Figure 117:
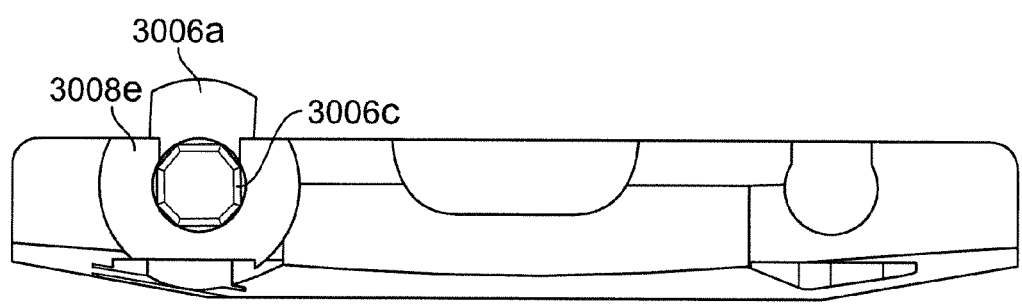
Figure 118:
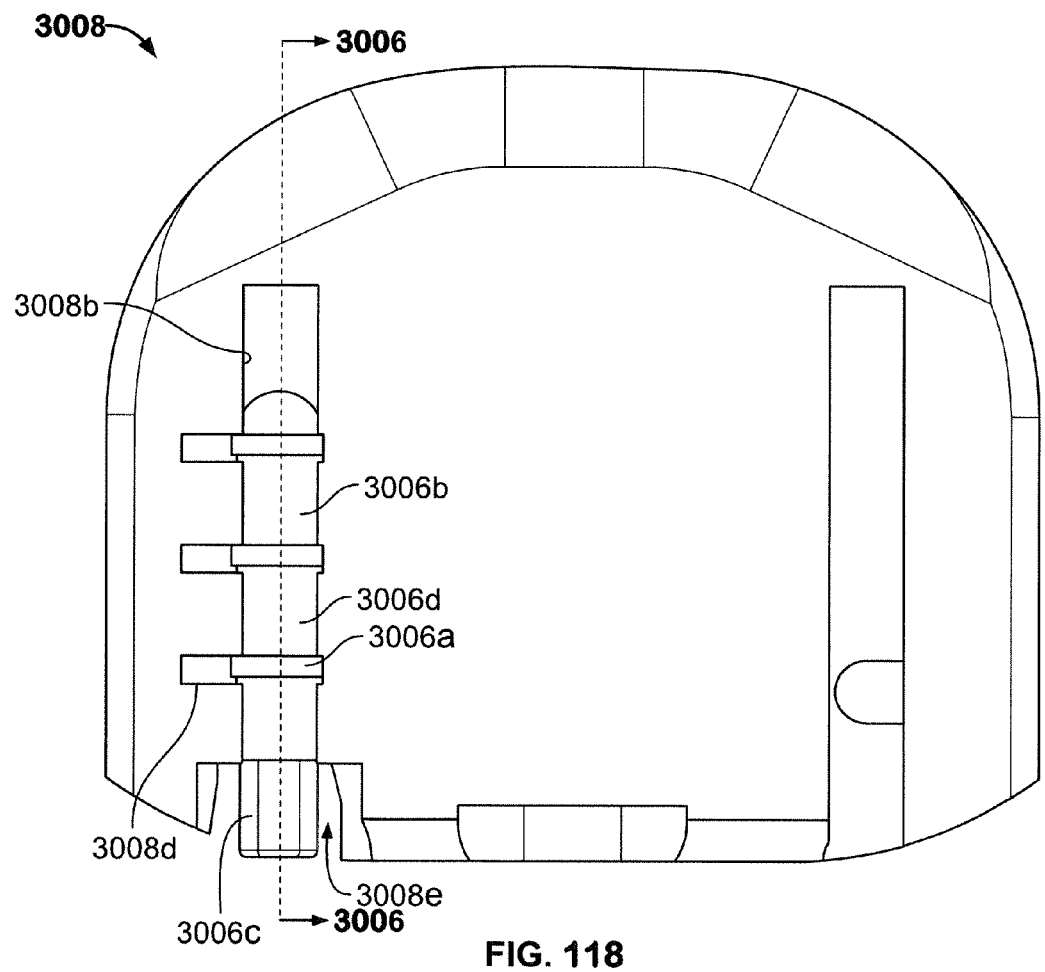
Figure 119:
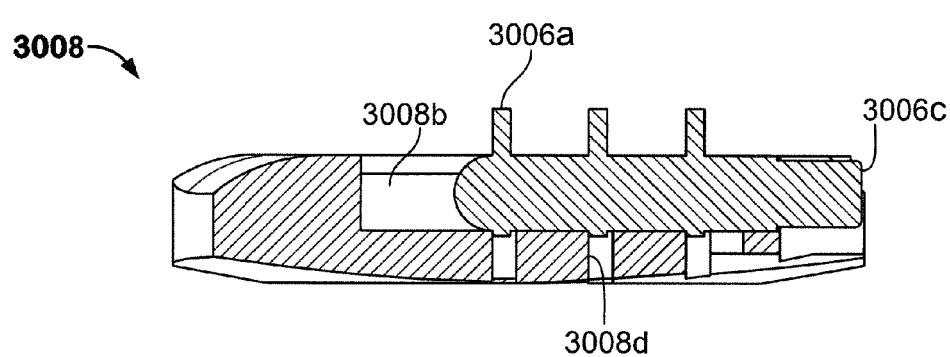
Figure 120:
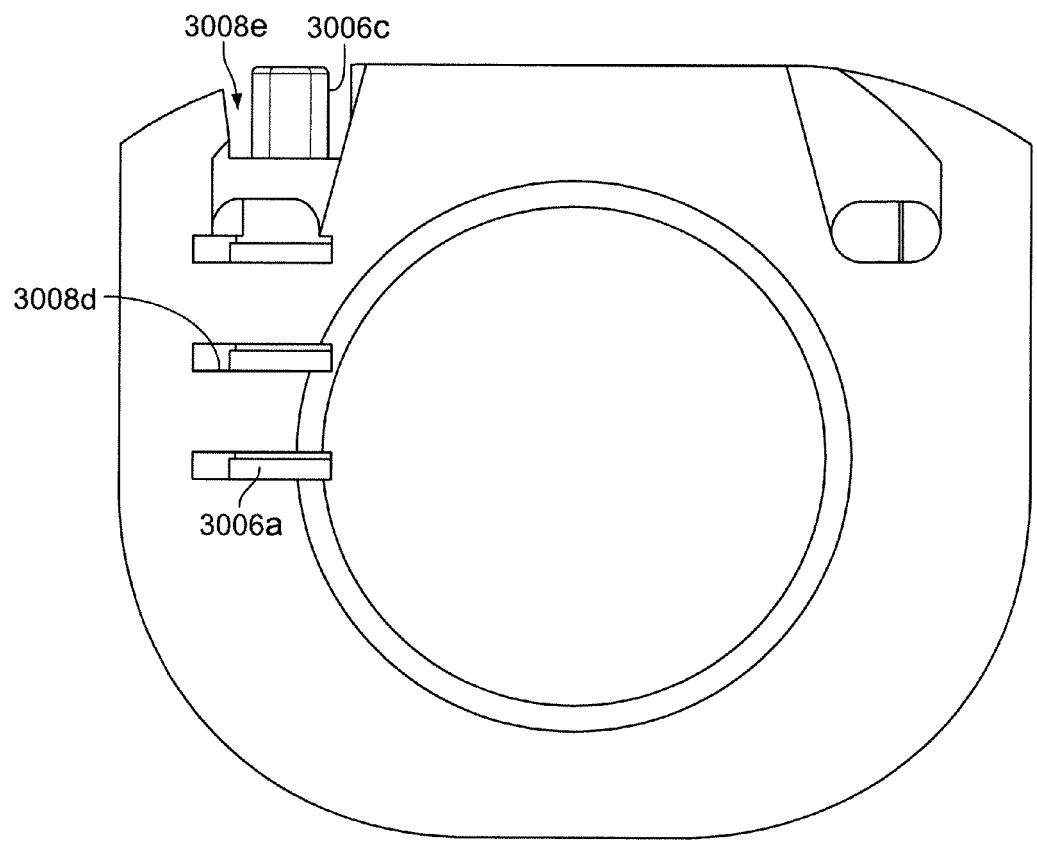
Figure 121:
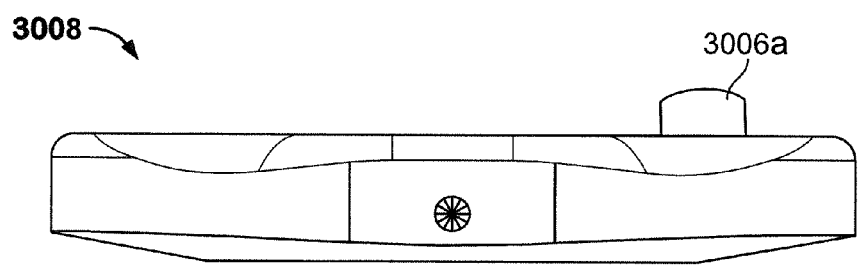

More specifically, the securing member 3006 includes several lobe members 3006a spaced along the length thereof. Initially, in an undeployed configuration, the securing member 3006 is oriented with the lobe members 3006a oriented downwards or towards the interior of the implant, as shown in FIGS. 115 and 116, for insertion of the implant into the intervertebral space. The lobe members 3006a are received in the restraint portion recesses 3008d formed in the upper surface 3008f of the upper bearing member 3008. Rotating the shaft 3006b 180 degrees via a driver from its undeployed insertion orientation to its deployed bone-engaging orientation shifts the lobes 3006a either into recesses cut into the vertebral body, if the vertebra has been prepared prior to insertion of the implant, or directly into the adjacent bone if the vertebra has not been prepared. In this manner, the artificial disc device may be secured in the intervertebral space against extrusion out therefrom during articulation of upper and lower bearing members relative to each other as the upper and lower vertebrae shift via an arcuate bearing interface formed between the members (see e.g., FIG. 123).

Once the disc device is inserted, the restraining portions may be deployed into the endplate to secure the artificial disc device in the desired location between the vertebrae. In the embodiment shown in FIGS. 114-121, the securing member is completely submerged within the body of the implant, such that the implant may be inserted without need for any preparation of the vertebral bodies prior to insertion. Thus, this embodiment is advantageous for ease of insertion and for reducing trauma to the implant site. However, in some cases it may be preferable to implement an implant having a securing member that protrudes outside of the bone engaging surface of the bearing member.

In the embodiments shown in FIGS. 122-134, the surgeon may be required to prepare the vertebral body to accept restraint portions that are intended to become integrated into the bone. In most cases, this preparation involves removing bone and creating restraint access portions typically in the form of a recess, channel, slot or profile similar to the restraint feature. Obviously, the size of the restraint portion will affect the size of the restraint access portion. Therefore, it is beneficial that restraint portions that interfere with the bone are suitably sized to prevent an oversized restraint access that compromises the vertebrae and risks vertebrae fracture. It is preferable that both the restraint access and restraint portion have radiused edges to reduce stress concentrations in the vertebral body.

The deployable securing member 3006, including the deployable bone engaging members 3006a may take on different geometries and orientations to improve performance of the securing member 3006. For example, the lobe members 3006a may include serrations, divots, or recesses to promote boney ingrowth. The serrations may also help to cut the bone when the securing member 3006 is rotated. In addition, the lobe members 3006a may be cupped or slanted to further promote anchoring of the implant to the vertebrae. Further, the lobe members 3006a may have an outside contour, such that shape or size of the lobe members 3006a varies from one end of the shaft 3006b to the other. The contour may match the profile of the endplates to take advantage of the softer bone in the center of the vertebrae as opposed to the harder-denser bone at the periphery of the vertebrae. Further, the shafts 3006b may have any number of lobe members 3006a. In a preferred embodiment, each shaft 3006b may have between three and five lobe members 3006a. Larger implants may have five members per shaft 3006b, while smaller implants may have only three. The shafts 3006b are preferably made from titanium or stainless steel, and may be coated with a bone-growth promoting substance, such as hydroxyapatite, tricalcium phosphates, or calcium phosphates.

In other forms, the shaft(s) 3006b on the upper or lower bearing members may be disposed at converging or diverging angles. This orientation prevents migration of the implant not only in an anterior/posterior direction, but also substantially in the lateral direction as well.

The securing members 3006 of the embodiment described in FIGS. 114-121 may provide tactile feedback regarding the position of the securing member 3006 to the surgeon as the securing member 3006 is deployed. Because the bone is relatively soft compared to the projections 3006a being deployed into the bone, the bone provides little resistance to the projections 3006a as they are deployed into the bone. Therefore, it is helpful to provide the surgeon with tactile feedback so that he does not over- or under-deploy the projections, causing the implant to be improperly affixed to the bone. In addition, the securing member may be provided with positive retraction blocking structure. Because the vertebral bone provides only a limited amount of resistance to the deployable projections, the projections may be prone to retract, derotate, or otherwise begin to return to their original undeployed position over time. Thus, retraction blocking structures may be provided on the disc implant to avoid this condition.

In another form in accordance with the present invention, an intervertebral implant 3102 with a deployable securing member 3106 is shown in FIGS. 122-126. Generally, the implant has upper and lower bearing members 3108, 3110, each having a plurality of deployable securing members 3106 disposed on the outer bearing surfaces 3108f, 3110a. Although the current embodiment is shown with a single securing member 3106 with a plurality of restraining portions disposed on the upper bearing member 3108, a preferred embodiment has at least one securing member 3106 on each bearing member 3108, 3110.

The securing member 3106 of FIGS. 122-126 includes a plurality of restraining portions in the form of deployable plate members 3106a. Each deployable plate member 3106a has a head portion 3106b and two opposing legs 3106c. The head portion 3106b is preferably provided with a blade or sharpened tip 3106d for easing the penetration of the adjacent bone when the plate member 3106a is deployed into engagement with the bone. The head 3106b also preferably has a tapered configuration, thickening from the tip 3106d down towards the legs 3106c. Opposing stops 3106e are provided at lower faces of the head portion 3106b to support the plate member 3106a against the body of the bearing member 3108 when the plate member 3106a is in an undeployed configuration. Similarly, at least one leg 3106c is provided with a stop 3106f with an abutment surface 3106g for interacting with an opposing abutment surface 3108b of the securing member receiving portion 3108a. Between the opposing legs 3106c is a gap 3106h for receiving an actuator. An actuator engagement portion in the form of an arcuate interior surface 3106i adjacent the gap 3106h interacts with the actuator during insertion of the actuator, which causes deployment of the plate member 3106a.

The deployable plate members 3106a are each received in the securing member receiving portion 3108a in restraint portion recesses in the form of generally rectangular openings 3108c (FIG. 124) in the bearing member 3108. The openings 3108c are disposed along the outer lateral side of the upper bearing member 3108 and are arranged in a row with the longitudinal aspect of the openings disposed transverse to an anterior-posterior axis 3118 of the implant 3102. The securing member receiving portion 3108a includes a raised ridge 3108e that protrudes outwardly beyond an outer bearing surface 3108f of the bearing member 3108. A cylindrical recess 3108g is disposed in the ridge 3108e with a longitudinal axis of the recess aligned along the anterior-posterior axis 3118 of the bearing member 3108 for receiving the actuator in the form of an elongate plunger 3112. Plate member gaps 3108h in the ridge portion 3108e are provided adjacent each opening 3108c to provide clearance for the plate members 3106a.

Figure 126:
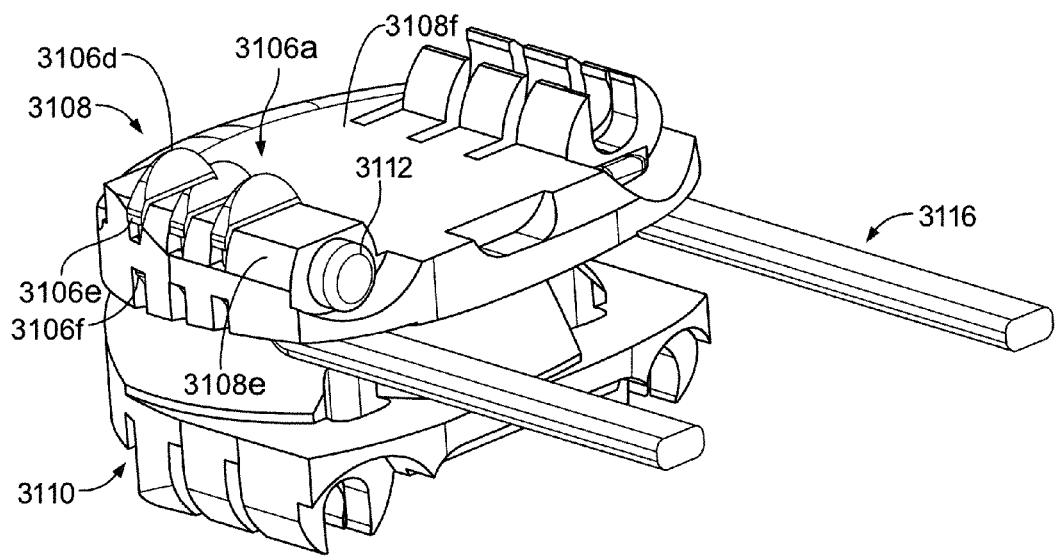

In operation, once the vertebrae have been prepared (if at all) to accept the implant 3102, the implant 3102 is inserted into the intervertebral space using an insertion tool. The deployable securing member 3106 is actuated by inserting the elongate plunger 3112 into the cylindrical recess 3108g of the actuator receiving portion 3108d, as shown in FIG. 126. The elongate plunger 3112 has a tapered tip 3112a to facilitate insertion thereof and gradual deployment of the deployable plate members 3106a. During insertion of the elongate plunger 3112, the tapered tip 3112a biases against the arcuate interior surface 3106i, which causes the plate member 3106a to be propelled outward towards the adjacent bone. Once the tip 3112a progresses past the plate member 3106a, the rest of the elongate shaft of the plunger 3112 is allowed to pass underneath the interior surface 3106i and through gap 3106h between the legs 3106c. The elongate plunger continues into the next portion of the ridge 3108e through cylindrical recess 3108g and similarly causes the other plate members 3106a to deploy. Once the elongate plunger 3112 is fully inserted, the enlarged head portion 3112b of the plunger will come into contact with an anterior facing surface 3108n of the ridge portion 3108e, which keeps the plunger 3112 from being inserted too far. Stop 3106f keeps the plate members 3106a from becoming loose or from being overextended via contact between abutment surface 3106g and opposing abutment surface 3108b. In the aforementioned configuration, the plate members are deployed straight up or linearly into the vertebrae, without any rotational displacement of the plate members 3106a. This embodiment is advantageous because the restraining portions do not pull the implant 3102 further into the intervertebral space, which can bring the implant out of the desired position, or cause trauma to the surrounding tissue and blood vessels. The plate members 3106a are allowed to be retracted by removing the plunger from the receiving portion 3108a.

The lateral orientation (i.e., transverse to the anterior-posterior axis) of the plate members 3106a is advantageous for providing superior resistance to migration in the anterior or posterior direction of the implant. However, the plate members 3106a may be oriented in other configurations.

The following description of the general features of a preferred embodiment of an intervertebral implant according to the present invention is described with respect to the embodiment in FIGS. 122-126. However, the general features described below may be implemented in any of the embodiments described herein.

It is preferred that the footprint of the artificial disc devices herein be similar to the footprint of the endplate although generally smaller to fit within the intervertebral space. The outer bearing surfaces 3108f are preferably contoured to match the contour of the endplates. For example, if the surgeon prepares the endplates to be flat, it is preferred that the outer bearing surfaces 3108f, 3110a are also flat. Likewise, if the endplates are prepared to be concave, it is preferred that the outer bearing surfaces 3108f, 3110a are similarly convex. It should be noted that endplates that are concave will generally retain the artificial disc device better since the device becomes cupped between the vertebrae.

Figure 122:
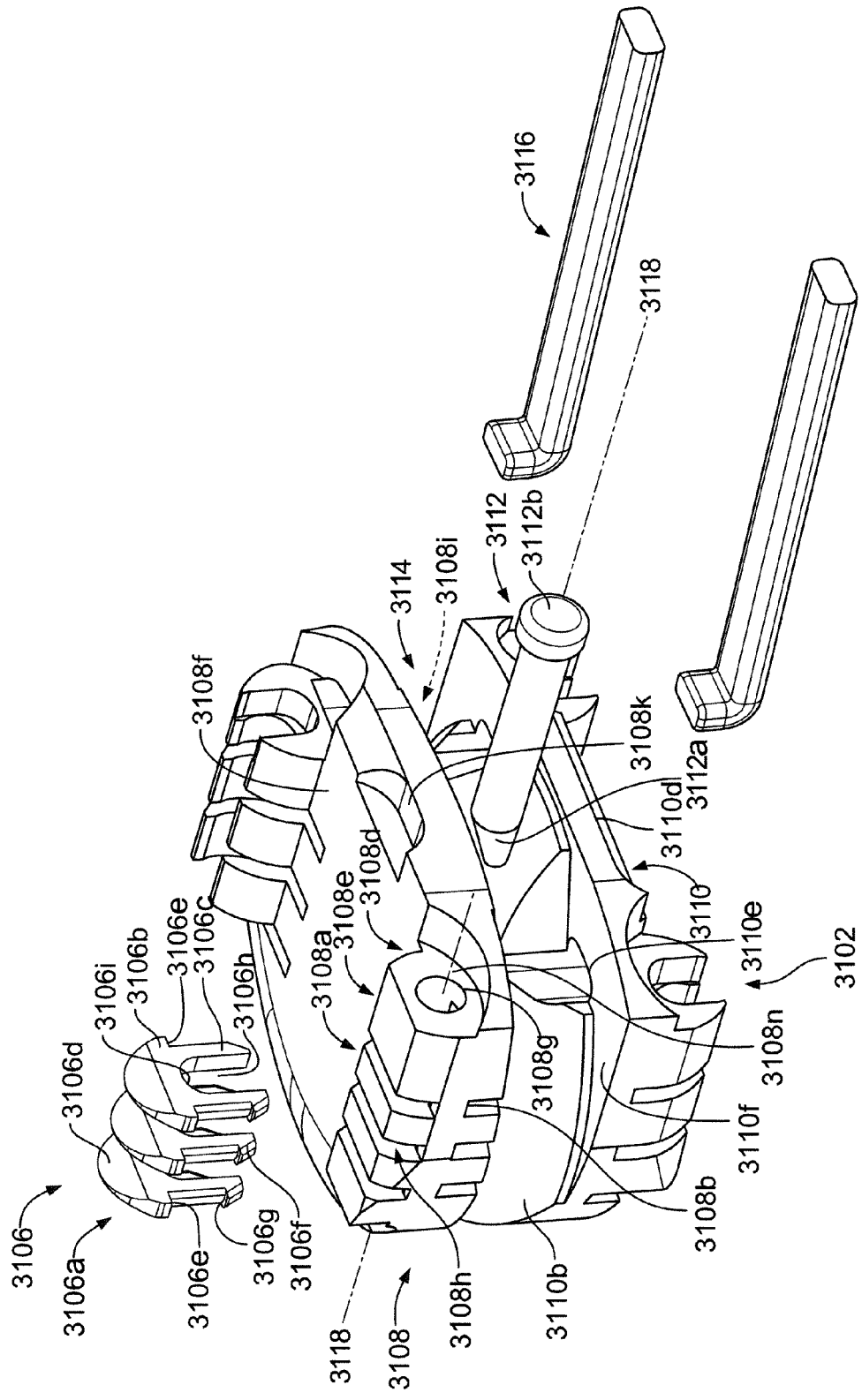

FIG. 122 shows an artificial disc implant 3102 with upper and lower bearing members 3108, 3110 having a bearing interface 3114 therebetween that allows the members 3108, 3110 to shift or articulate relative to each other when implanted and secured in an intervertebral space. The bearing interface 3114 includes concave recess 3108i (FIG. 123) formed in the inner or lower surface 3108p of the upper bearing member 3108 and a substantially convex portion 3110b that projects up from inner or upper surface 3110f of the lower bearing member 3110. Although not preferred, the concave and convex portions 3108i, 3110b may be switched such that the upper bearing member 3108 may alternatively comprise the convex portion 3110b. The securing members according to the present invention may be utilized with unitary implants, such as spinal cages and spacers, as well as multi-piece implants, such as the motion-preserving intervertebral implants disclosed in the drawings.

The convex portion 3110b comprises a convex articulation surface 3110c, and the concave portion 3108i comprises a concave articulation surface 3108j. It is preferred that the articulation surfaces 3110c and 3108j have substantially matching geometries or radii of curvature although some mismatch of curvature may be desired to provide a combination of rolling and sliding motion to occur between the articulation surfaces 3110c and 3108j. U.S. Provisional Application 61/050,612 filed May 5, 2008 discloses a "ball-in-bowl" configuration for the articulation surfaces, and is hereby incorporated by reference in its entirety. In particular, the concave articulation surface 3108j may have two different radii of curvature, such that one portion of the concave articulation surface 3108j has a first radius of curvature, and a second portion of the concave articulation surface 3108j has a second, larger radius of curvature. The first radius of curvature is preferably the same as the radius of curvature of the convex articulation surface 3110c, such that rotational sliding may occur between the articulation surfaces 3108j, 3110c. When the joint is extended, the concave articulation surface 3108j is allowed to translate slightly due to the mismatch in curvature between the first radius of curvature of the convex articulation surface 3110c and the second, larger radius of curvature of the concave articulation surface 3108j. This configuration allows for a greater range of motion and a more natural movement of the joint.

Figure 123:
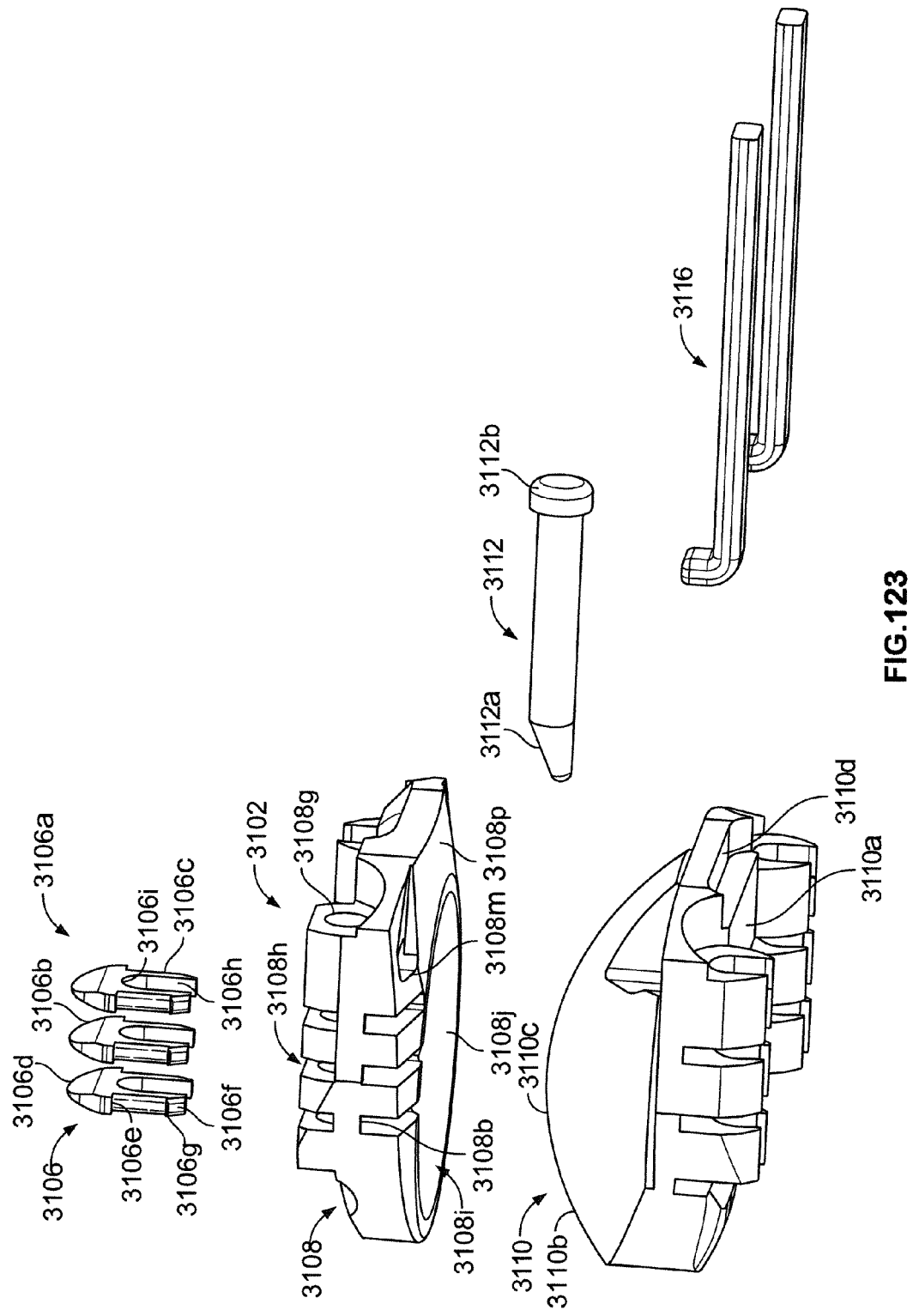

As discussed above, the geometries may be complex in nature but preferably are ball and socket style. The convex portion 3110b and concave portion 3108i may extend substantially to the outer perimeter of the bearing member 3108, 3110 as illustrated in FIGS. 122 and 123, or may be formed, typically with a smaller radius of curvature inward a predetermined distance from the outer perimeter of the bearing member 3108, 3110. Each bearing member 3108, 3110 is preferably manufactured from PEEK (polyetheretherketone) or fiber reinforced PEEK or other biocompatible polymer combination or radiolucent material demonstrating very low surface wear in high repetition wear testing.

The disc implant 3102 according to the present embodiment has docking features for attaching the implant 3102 to an insertion tool. The lower bearing member 3110 has a shelf-like platform 3110d along its anterior face for providing a contact surface for the implant insertion tool. Similarly, the upper bearing member 3108 has a shelf 3108k on its anterior face for providing a contact surface for the insertion tool. The internal facing surfaces 3108p, 3110f of both bearing members 3108, 3110 each have a pair of generally rectangular recesses 3108m, 3110e disposed thereon to accept gripping members of the insertion tool. Two of the gripping members, prongs 3116, are shown with the implant 3102 for reference. The prongs 3116 engage the upper bearing member 3108 within recesses 3108m during insertion of the implant 3102. Preferably, two additional prongs are provided with the insertion tool for engaging with recesses 3110e to work in tandem with prongs 3116. These docking features are advantageous because the insertion tool manipulates the implant 3102 substantially within the overall footprint of the implant 3102. This prevents trauma to the surrounding tissue and bone during insertion of the implant 3102 and removal of the inserter after the implant 3102 is inserted.

Once the implant 3102 is secured to the inserter, the disc implant 3102 is then inserted into the intervertebral space. The position of the implant 3102 may be determined using fluoroscopy to view the orientation of the implant 3102. Tantalum markers 3108q, 3110g (FIG. 124) disposed in the posterior face of both the upper and lower bearing members 3108, 3110 allow the surgeon to identify and position the posterior end of the implant 3102. In addition, the securing member(s) 3106, which are also radiopaque when made out of titanium or stainless steel, may be used to determine the orientation of the implant 3102.

In another form in accordance with the present invention illustrated in FIGS. 127-130, an intervertebral implant 3202 with a deployable securing member is disclosed. The implant body is similar to that of the embodiment shown in FIGS. 122-126. However, the securing member is comprised of deployable arms 3206a which may be rotated about a pivot into engagement with the bone. The arms 3206a are deployed via an elongate plunger 3212 similar to that of the embodiment disclosed in FIGS. 127-130. The deployable arms are preferably rotatable about an anterior-posterior axis such that the deployable arms 3206a are disposed transversely to the anterior-posterior axis and translation thereof into a deployed position does not cause shifting of the implant 3202.

The securing member is provided with three deployable arms 3206a having bone engaging head portions 3206b. The head portion 3206b preferably has a sharpened outer edge 3206c for easing penetration of the head portion 3206b into the bone. The head portions 3206b have a generally arcuate profile, with a convex outer edge 3206c and a concave inner surface 3206d for engaging with the arcuate outer surface of the elongate plunger 3212. Each head portion 3206b is connected to a transverse shaft 3206e via a neck portion 3206f. The transverse shaft 3206e is cylindrically shaped for being pivotally captured within similarly-shaped channel 3208b. The transverse shaft 3206e is held within the channel 3208b with a friction fit so that no additional fasteners or pieces are required to connect the restraining portions to the implant 3202. This construction simplifies manufacture and assembly, and increases the robustness of the implant. Because intervertebral implants in particular may be very small in many applications, it is desirable for such implants to have few components. For example, a cervical disc implant may only be 5 mm high. Thus, these kinds of implants must have components that are sturdy and robust enough to be functional on a very small scale.

The securing member receiving portion 3208a has a similar configuration to that of the embodiment described in FIGS. 122-126. A cylindrical ridge portion 3208e protrudes outwards from the outer bearing surface 3208f and contains a cylindrical recess 3208g for receiving the elongate plunger 3212. Lateral channels 3208h disposed in the bearing member and the cylindrical ridge portion 3208e extend transversely to the cylindrical recess 3208g for receiving the deployable arms 3206a. The lateral channels 3208h are in communication with channel 3208b. When the deployable arms 3206a are configured within the lateral channels 3208h in an undeployed orientation, the arms 3206a remain within the profile of the bearing member and the ridge 3208e for ease of insertion of the implant into the intervertebral space.

To actuate and deploy the deployable arms 3206a, the plunger 3212 is inserted into the cylindrical recess 3208g. The tapered tip 3212a interacts with the concave inner surface 3206d of the deployable arm 3206a, gradually biasing the arm 3206a upward, causing the arm 3206a to rotate about the transverse shaft portion 3206e. The deployable arm 3206a is deployed fully to its maximum height once the plunger tip extends beyond the concave inner surface 3206d, such that the deployable arm 3206a rests on top of and is supported by the shaft 3212b of the plunger 3212. As shown in FIGS. 129 and 130, the deployable arms protrude substantially above the ridge 3208e such that they are operable to engage with the adjacent bone for fixing the implant to the vertebra.

In another form in accordance with the present invention, an intervertebral implant 3302 having a deployable securing member 3306 for affixing the implant to the adjacent vertebra is disclosed in FIGS. 131-134. In the present form, the securing member 3306a takes the form of a deformable or bendable elongate member 3306a that may be inserted into the securing member receiving portion 3308a and bent into a form causing bone engaging projections to engage with the adjacent vertebra.

The bendable elongate member 3306a is preferably a flat elongate member having a longitudinal length between its ends and a width. The elongate member 3306a has a leading end 3306b with an enlarged width that is inserted first into the receiving portion 3308a. A trailing end 3306c is provided with a transverse tab portion 3306d transverse to the longitudinal length thereof for manipulating the elongate member 3306a and providing a stop to keep the elongate member 3306a from being inserted too far into the intervertebral space. The trailing end 3306c is also provided with a guide portion 3306e having an enlarged width for guiding the elongate member 3306a within the insertion instrument 3314 and the securing member receiving portion 3308a. In addition, a central guide portion 3306f is positioned between the two ends for guiding the elongate member 3306a. In between either end 3306b, 3306c and the central guide portion 3306f is a bending zone 3306g which is configured for being bent during insertion of the elongate member 3306a and protruding upwardly or outwardly into engagement with the adjacent bone. The bending zone 3306g preferably includes perforations or weakened portions 3306h to promote bending at a predetermined location on the elongate member 3306a. In a preferred embodiment, the bending zones 3306g include a preformed protrusion or spike 3306i which lies within the elongate member prior to bending thereof. When the elongate member 3306a is bent, the bending zones are forced into an inverse V shape, causing the spike 3306i to be deployed upwards into the adjacent bone. Although the elongate member 3306a is shown with two bending zones 3306g and spikes 3306i, the elongate member 3306a may be provided with different numbers of bending zones and spikes. Although the bendable elongate member has portions bent into a V shape, other shapes and configurations are contemplated.

Figure 124:
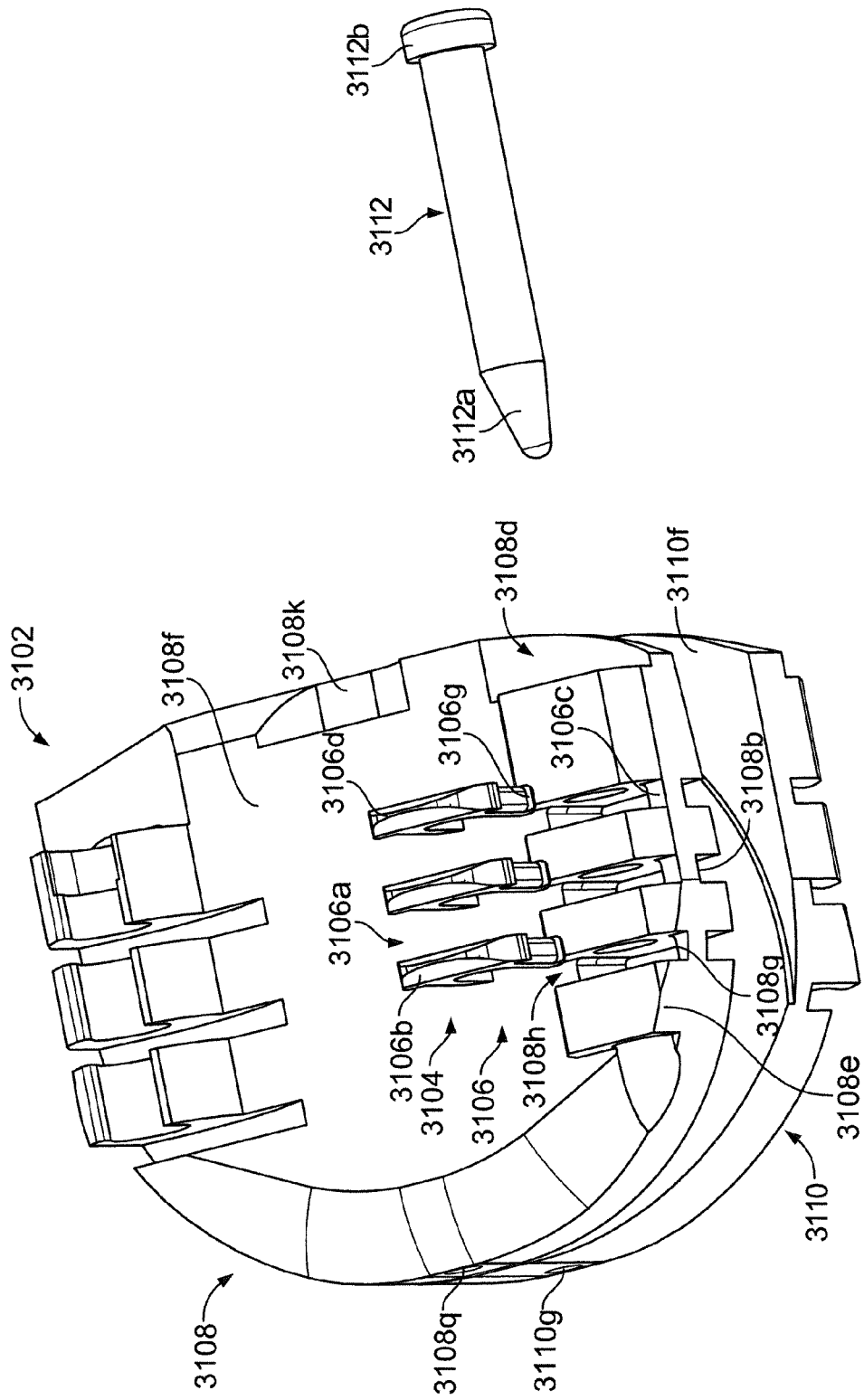
Figure 125:
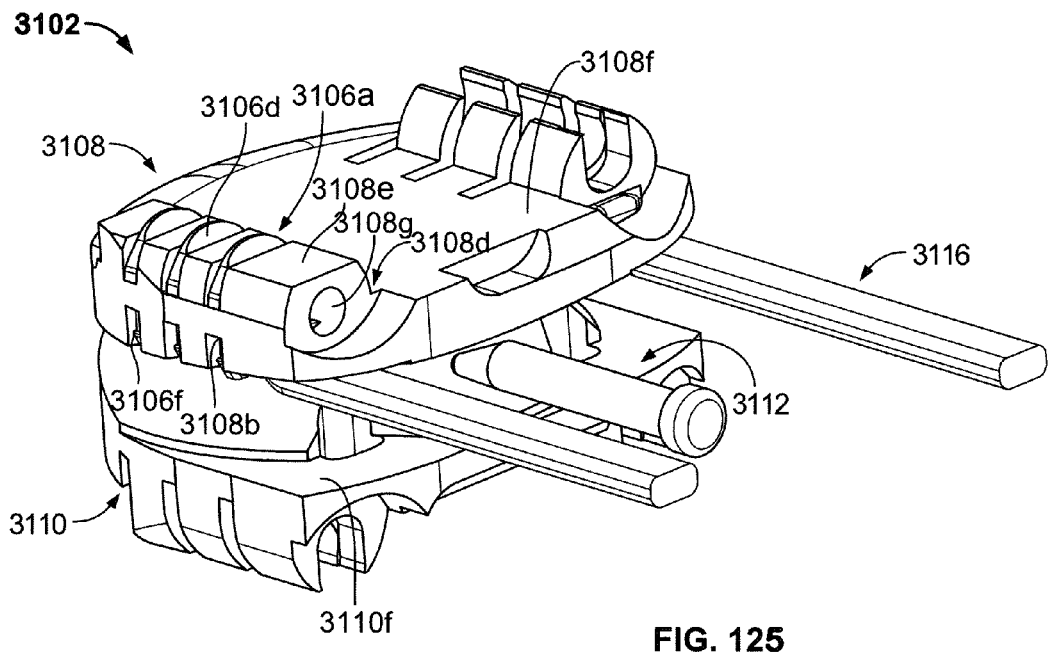

The securing member receiving portion 3308a takes the form of a generally U-shaped channel 3308b disposed along a lateral edge on the upper bearing member 3308. The channel 3308b has opposing side walls 3308c, 3308d and a bottom surface 3308e extending between the two side walls 3308c, 3308d. Extending between the side walls 3308c, 3308d are restraining members in the form of pins 3308f. The pins 3308f are operable to restrain the elongate bending member 3306a from bending at predetermined locations. Pins 3308f are preferably cylindrical or have radiused edges to prevent stress concentrations on the bending member 3306a and to reduce friction thereon during bending. Thus, the pins are located in positions corresponding to positions on the elongate bending member 3306a that are to remain unbent. The weakened portions 3306h on the elongate member 3306a are preferably aligned with the pins 3308f, such that when the bending member is inserted into the receiving portion 3308a, the bending member will bend in the open areas between the pins 3308f. As shown in FIG. 124, the pins 3308f are positioned above the bottom surface 3308e such that the elongate member 3306a is held relatively snug therebetween. The channel 3308b has an end wall 3308j operable to provide a stop for the bending member 3306a, as well as a surface to compress the bending member 3306a against to cause bending of the bending zones 3306g and deployment of spikes 3306i.

The insertion instrument 3314 comprises a generally C-shaped housing with opposing arms 3314a, 3314b to provide opposing grooves 3314c, 3314d in which the bending member may be inserted for guiding the bending member into the securing member receiving portion. The widened ends 3306b, 3306c and central portion 3306f fit within the grooves 3314c, 3314d. The transverse tab portion 3306d is sized and configured to fit between the opposing arms 3314a, 3314b such that it may pass therebetween. This way, the bending member 3306a may be pushed into the receiving portion via the transverse tab portion 3306d. The insertion instrument 3314 is also provided with an extended lip 3314e on the insertion end for providing the bending member 3306a with additional support to prevent bending of the member 3306a as it leaves the insertion instrument 3314 and prior to reaching the first pin 3308f at the entrance of the channel 3308b at the anterior side of the implant 3302.

In operation, the implant 3302 is first inserted into the prepared intervertebral space via an implant insertion instrument, which includes prongs 3316 which grasp the implant 3302 in opposing recesses on the inner facing surface of the upper bearing member 3308, as shown in FIG. 134. Next, the bending member 3306a is slid into the grooves 3314c, 3314d of the insertion instrument as shown in FIG. 132. Then, the insertion instrument 3314 is positioned adjacent the receiving portion 3308a such that the elongate member 3306a is aligned with the channel 3308b. The bending member 3306a is then pushed into the channel 3308b between the pins 3308f and the bottom surface of the channel 3308e via the transverse tab portion 3306d. Once the insertion end 3306b of the bending member 3306a reaches the abutment surface 3308j, further insertion of the bending member 3306a will cause compression and the bending member 3306a will begin to bend or deform. This deformation begins at the weakened portions 3306h and causes the bending zones 3306g to deform upwards into engagement with the adjacent bone. As the bending zone 3306g begins to bend at its peak, the barb or spike 3306i will be deployed upwards into the bone. Once the bending member 3306a has been fully inserted into the receiving portion, the insertion instrument 3314 may be removed from the implant site. Further details of the preparation of the vertebrae, insertion procedure and insertion tool may be found in U.S. patent application Ser. No. 11/856,667, which is incorporated by reference herein.

The securing member receiving portion 3308a for the elongate bending member 3306a is shown in FIGS. 131-134 in one location on the implant; however, it is contemplated that the upper and lower members 3308, 3310 may include securing members 3306 in more than one location. Further, all of the securing members shown and described herein may be implemented together with different types of securing members, such as those shown and described above or other securing members and restraining members known in the art. However, in a preferred form, an implant according to the present invention comprises two securing members of similar configurations on each bearing member.

In other forms of the invention, the implant may comprise a pharmacological agent used for treating various spinal conditions, including degenerative disc disease, spinal arthritis, spinal infection, spinal tumor and osteoporosis. Such agents include antibiotics, analgesics, anti-inflammatory drugs, including steroids, and combinations thereof. Other such agents are well known to the skilled artisan. These agents are also used in therapeutically effective amounts. Such amounts may be determined by the skilled artisan depending on the specific case.

The pharmacological agents, if any, are preferably dispersed within the implant for in vivo release. The pharmacological agents may be dispersed in the spacer by adding the agents to the implant when it is formed, by soaking a formed implant in an appropriate solution containing the agent, or by other appropriate methods known to the skilled artisan. In other forms of the invention, the pharmacological agents may be chemically or otherwise associated with the implant. For example, the agents may be chemically attached to the outer surface of the implant.

Although the securing members and insertion tools have been described with reference to a disc replacement implant, the securing members and tools may be easily adapted for use with other artificial implants, such as fusion promoting implants, including vertebral body replacements, spinal cages, and the like. In addition, the invention described herein may also be applied to other motion preserving implants, such as those with articulating surfaces, including nucleus replacement implants. Moreover, the securing members, insertion tools, and methods described herein may be implemented in other weight-bearing joint implants, such as ankle, knee, or hip joint implants.

While the invention has been described with respect to specific examples including presently preferred modes of carrying out the invention, those skilled in the art will appreciate that there are numerous variations and permutations of the above described systems and techniques that fall within the spirit and scope of the invention as set forth in the claims.

What is claimed is:

1. An intervertebral disc implant for being inserted between adjacent upper and lower vertebral bones, comprising:
an upper bearing member;
a lower bearing member;
a body of the upper bearing member having an outer bearing surface for being disposed adjacent the upper vertebral bone;
a body of the lower bearing member having an outer bearing surface for being disposed adjacent the lower vertebral bone;
an articulation interface between the upper and lower bearing members for allowing relative movement therebetween with the bearing members configured to fit in an intervertebral space between upper and lower vertebral bones;
a rotary securing member rotatably mounted to one of the bearing members to be carried by the one bearing member, so that the rotary securing member extends along the outer bearing surface of the one bearing member prior to being inserted into the intervertebral space, and is inserted together with the one bearing member into the intervertebral space, and after insertion of the rotary securing member and the one bearing member into the intervertebral space, the rotary securing member is arranged for being rotated for securing the one bearing member to the adjacent vertebral bone;
a rotary shaft of the securing member having a longitudinal axis; and
a plurality of spaced-apart plate-like bone-engaging portions extending generally transversely from the rotary shaft and each including a distal arc-shaped edge portion spaced from the rotary shaft such that rotation of the rotary shaft about the longitudinal axis causes a corresponding rotation of the bone-engaging portions about the longitudinal axis to allow the rotary shaft of the rotary securing member to be rotated from an undeployed orientation with the bone-engaging portions out of engagement with the adjacent vertebral bone and a deployed orientation with the bone-engaging portions including the distal arc-shaped edge portions thereof in imbedded engagement with the adjacent vertebral bone;
wherein each of the plurality of plate-like bone-engaging portions has opposing side face portions extending orthogonally from the rotary shaft relative to the longitudinal axis thereof and the distal arc-shaped edge portion spaced from the rotary shaft is disposed at an outermost extent of the opposing side portions.

2. The intervertebral disc implant of claim 1, wherein the plurality of spaced plate-like bone-engaging portions include first, second, and third bone-engaging portions each fixedly disposed on the rotary shaft and spaced apart along the longitudinal axis from the other bone engaging portions for engaging with the adjacent vertebral bone to secure the one bearing member relative thereto.

3. The intervertebral disc implant of claim 1, wherein when in the undeployed orientation, the plurality of bone-engaging portions are disposed within the body of the one bearing member such that they do not protrude outside of the outer bearing surface thereof.

4. The intervertebral disc implant of claim 1, wherein the body includes a plurality of spaced apart recesses sized and configured to receive the corresponding plurality of bone-engaging portions when the bone-engaging portions are in the undeployed orientation.

5. The intervertebral disc implant of claim 1, wherein the securing member is connected to the one bearing member via a friction fit.

6. The intervertebral disc implant of claim 1, wherein at least one securing member is disposed on each of the upper and lower bearing members for fixing the bearing members relative to the adjacent vertebral bones.

7. The intervertebral disc implant of claim 1, wherein the plurality of bone-engaging portions are formed on the rotary shaft, such that each rotary securing member is monolithic.

8. The intervertebral disc implant of claim 1, wherein the distal arc-shaped edge portion subtends an angle of at least 90 degrees.

9. An intervertebral disc implant for being inserted between adjacent upper and lower vertebral bones, comprising:
an upper bearing member;
a lower bearing member;
a body of the upper bearing member having an outer bearing surface for being disposed adjacent the upper vertebral bone;
a body of the lower bearing member having an outer bearing surface for being disposed adjacent the lower vertebral bone;
an articulation interface between the upper and lower bearing members for allowing relative movement therebetween with the bearing members configured to fit in an intervertebral space between upper and lower vertebral bones;
a rotary securing member rotatably mounted to one of the bearing members to be carried by the one bearing member, so that the rotary securing member extends along the outer bearing surface of the one bearing member prior to being inserted into the intervertebral space, and is inserted together with the one bearing member into the intervertebral space, and after insertion of the rotary securing member and the one bearing member into the intervertebral space, the rotary securing member is arranged for being rotated for securing the one bearing member to the adjacent vertebral bone;
a rotary shaft of the securing member having a longitudinal axis; and
a plurality of spaced-apart plate-like bone-engaging portions extending generally transversely from the rotary shaft and each including a distal arc-shaped edge portion spaced from the rotary shaft such that rotation of the rotary shaft about the longitudinal axis causes a corresponding rotation of the bone-engaging portions about the longitudinal axis to allow the rotary shaft of the rotary securing member to be rotated from an undeployed orientation with the bone-engaging portions out of engagement with the adjacent vertebral bone and a deployed orientation with the bone-engaging portions including the distal arc-shaped edge portions thereof in imbedded engagement with the adjacent vertebral bone;
wherein the plate-like bone-engaging portions each comprise a leading cutting edge that extends outwardly from the rotary shaft in a direction transverse to the longitudinal axis of the rotary shaft and terminates at the distal arc-shaped edge portion for cutting into the adjacent vertebral bone and leading the distal arc-shaped edge portion into the cut adjacent vertebral bone as the bone-engaging portion is rotated into the deployed orientation to create a groove in the adjacent vertebral bone sized to fit the bone-engaging portion therein.

10. The intervertebral disc implant of claim 9, wherein the plurality of plate-like bone-engaging portions extend transversely to the longitudinal axis of the rotary shaft and are parallel to one another.

11. An intervertebral disc implant for being inserted between adjacent upper and lower vertebral bones, comprising:
    an upper bearing member;
    a lower bearing member;
    a body of the upper bearing member having an outer bearing surface for being disposed adjacent the upper vertebral bone;
    a body of the lower bearing member having an outer bearing surface for being disposed adjacent the lower vertebral bone;
    an articulation interface between the upper and lower bearing members for allowing relative movement therebetween with the bearing members configured to fit in an intervertebral space between upper and lower vertebral bones;
    a rotary securing member rotatably mounted to one of the bearing members to be carried by the one bearing member, so that the rotary securing member extends along the outer bearing surface of the one bearing member prior to being inserted into the intervertebral space, and is inserted together with the one bearing member into the intervertebral space, and after insertion of the rotary securing member and the one bearing member into the intervertebral space, the rotary securing member is arranged for being rotated for securing the one bearing member to the adjacent vertebral bone;
    a rotary shaft of the securing member having a longitudinal axis;
    a plurality of spaced-apart plate-like bone-engaging portions extending generally transversely from the rotary shaft and each including a distal arc-shaped edge portion spaced from the rotary shaft such that rotation of the rotary shaft about the longitudinal axis causes a corresponding rotation of the bone-engaging portions about the longitudinal axis to allow the rotary shaft of the rotary securing member to be rotated from an undeployed orientation with the bone-engaging portions out of engagement with the adjacent vertebral bone and a deployed orientation with the bone-engaging portions including the distal arc-shaped edge portions thereof in imbedded engagement with the adjacent vertebral bone; and
    a securing member receiving portion extending outwardly from the outer bearing surface of the one bearing member having at least one pair of opposed arms that extend beyond the outer bearing surface and having opposing inner arcuate surface portions for retaining the rotary shaft therebetween with a friction fit.

12. The intervertebral disc implant of claim 11, wherein the securing member receiving portion includes at least two pairs of opposed arms for retaining the securing member therebetween, wherein one of the plurality of bone-engaging portions is disposed between the two pairs of opposed arms for providing a path for which the bone engaging member may travel between the undeployed and the deployed orientations.

13. An intervertebral disc implant, comprising:
    an upper bearing member;
    a lower bearing member;
    a body of the upper bearing member having an outer bearing surface for being disposed adjacent the upper vertebral bone;
    a body of the lower bearing member having an outer bearing surface for being disposed adjacent the lower vertebral bone;
    an articulation interface between the upper and lower bearing members for allowing relative movement therebetween;
    a rotary securing member rotatably mounted to one of the bearing members for being rotated for securing the one bearing member to the adjacent vertebral bone;
    a rotary shaft of the securing member having a longitudinal axis; and
    a securing member receiving portion of the one bearing member having at least one pair of opposed arms extending outwardly from so as to extend beyond the outer bearing surface, and the at least one pair of opposed arms having a gap therebetween for receiving the rotary shaft and the gap being sized so that the at least one pair of opposed arms have a friction fit with the rotary shaft to retain the rotary shaft therein with at least a portion of the securing member extending beyond the outer bearing surface prior to the rotary securing member being rotated for securing the one bearing member to the adjacent vertebral bone.

14. The intervertebral disc implant of claim 13, wherein the securing member includes a plate-like bone-engaging portion extending from the rotary shaft configured to be rotated from an undeployed orientation with the bone-engaging portion disposed within the body of the bearing member and out of engagement with the adjacent vertebral bone and a deployed orientation with the bone-engaging portion in engagement with the adjacent vertebral bone and the bone-engaging portion being configured such that rotation of the rotary shaft from the undeployed orientation to the deployed orientation does not cause the rotary shaft to advance along the longitudinal axis thereof and the outer bearing surface.

15. The intervertebral disc implant of claim 13, wherein the securing member receiving portion further comprises a second pair of opposed arms extending from the outer bearing surface having a gap therebetween for receiving the rotary shaft therein with the second pair of opposed arms retaining the securing member therebetween with a friction fit, the second pair of opposed arms spaced along the longitudinal axis of the rotary shaft from the at least one pair of opposed arms.

16. The intervertebral disc implant of claim 13, wherein the rotary shaft has a length, and the securing member receiving portion includes a channel defined in part by the gap between the at least one pair of opposed arms for receiving the rotary shaft, the rotary shaft being disposed at least partially within the channel with the channel extending along at least a majority of the length of the rotary shaft.

17. The intervertebral disc implant of claim 13, wherein the one bearing member has a transversely oriented recess in communication with the outer bearing surface thereof disposed generally transversely to the longitudinal axis of the rotary shaft for receiving a bone-engaging portion of the securing member in an undeployed orientation.

18. The intervertebral disc implant of claim 13, further comprising a plurality of spaced plate-like bone-engaging portions extending generally transversely from the rotary shaft such that rotation of the rotary shaft about the longitudinal axis causes a corresponding rotation of the bone engaging portions about the longitudinal axis to allow the rotary shaft of the rotary securing member to be rotated from an undeployed orientation with the bone-engaging portions out of engagement with the adjacent vertebral bone and a deployed orientation with the bone-engaging portions in imbedded engagement with the adjacent vertebral bone.

19. An intervertebral disc implant, comprising:
   an upper bearing member;
   a lower bearing member;
   a body of the upper bearing member having an outer bearing surface for being disposed adjacent the upper vertebral bone;
   a body of the lower bearing member having an outer bearing surface for being disposed adjacent the lower vertebral bone;
   an articulation interface between the upper and lower bearing members for allowing relative movement therebetween;
   a rotary securing member rotatably mounted to one of the bearing members for being rotated for securing the one bearing member to the adjacent vertebral bone;
   a rotary shaft of the securing member having a longitudinal axis; and
   a securing member receiving portion of the one bearing member having at least one pair of opposed arms extending outwardly from the outer bearing surface, and the at least one pair of opposed arms having a gap therebetween for receiving the rotary shaft and the gap being sized so that the at least one pair of opposed arms have a friction fit with the rotary shaft to retain the rotary shaft therein;
   wherein the rotary shaft is configured to be rotated approximately 180 degrees from an undeployed orientation to a deployed orientation.

* * * * *